United States Patent
Tafesse

(10) Patent No.: US 9,963,458 B2
(45) Date of Patent: May 8, 2018

(54) INDOLE AND INDOLINE-TYPE PIPERIDINE COMPOUNDS AND USES THEREOF

(71) Applicant: Laykea Tafesse, Robbinsville, NJ (US)

(72) Inventor: Laykea Tafesse, Robbinsville, NJ (US)

(73) Assignee: Purdue Pharma L.P., Stamford, CT (US)

(*) Notice: Subject to any disclaimer, the term of this patent is extended or adjusted under 35 U.S.C. 154(b) by 0 days. days.

(21) Appl. No.: 14/654,727

(22) PCT Filed: Dec. 23, 2013

(86) PCT No.: PCT/IB2013/002872
§ 371 (c)(1),
(2) Date: Jun. 22, 2015

(87) PCT Pub. No.: WO2014/102588
PCT Pub. Date: Jul. 3, 2014

(65) Prior Publication Data
US 2015/0315201 A1    Nov. 5, 2015

Related U.S. Application Data

(60) Provisional application No. 61/746,281, filed on Dec. 27, 2012.

(51) Int. Cl.
*C07D 487/08* (2006.01)
*C07D 471/08* (2006.01)

(52) U.S. Cl.
CPC ......... *C07D 487/08* (2013.01); *C07D 471/08* (2013.01)

(58) Field of Classification Search
CPC .......................... C07D 487/08; C07D 471/08
USPC ...................................................... 546/124
See application file for complete search history.

(56) References Cited

U.S. PATENT DOCUMENTS

| | | |
|---|---|---|
| 6,635,653 B2 | 10/2003 | Goehring et al. |
| 6,686,370 B2 | 2/2004 | Kyle |
| 6,828,440 B2 | 12/2004 | Goehring et al. |
| 6,861,421 B2 | 3/2005 | Goehring et al. |
| 6,867,222 B2 | 3/2005 | Sun et al. |
| 6,872,733 B2 | 3/2005 | Goehring et al. |
| 6,984,664 B2 | 1/2006 | Kyle et al. |
| 6,995,168 B2 | 2/2006 | Chen et al. |
| 7,414,062 B2 | 8/2008 | Chen et al. |
| 7,456,198 B2 | 11/2008 | Kyle et al. |
| 7,495,109 B2 | 2/2009 | Sun et al. |
| 7,563,809 B2 | 7/2009 | Goehring et al. |
| 7,678,809 B2 | 3/2010 | Kyle et al. |
| 7,939,670 B2 | 5/2011 | Sun et al. |
| 8,110,602 B2 | 2/2012 | Brown et al. |
| 8,252,815 B2 | 8/2012 | Sun et al. |
| 8,476,271 B2 | 7/2013 | Tsuno et al. |
| 8,637,502 B2 | 1/2014 | Brown et al. |
| 8,846,929 B2 | 9/2014 | Fuchino et al. |
| 2004/0132757 A1 | 7/2004 | Kyle et al. |
| 2004/0259775 A1 | 12/2004 | Kyle |
| 2005/0192307 A1 | 9/2005 | Goehring et al. |
| 2005/0256000 A1 | 11/2005 | Schaper et al. |
| 2005/0256103 A1 | 11/2005 | Suzuki et al. |
| 2006/0106114 A1 | 5/2006 | Kyle et al. |
| 2008/0214827 A1 | 9/2008 | Goehring et al. |
| 2011/0092704 A1 | 4/2011 | Gharagozloo et al. |
| 2013/0274265 A1 | 10/2013 | Fuchino et al. |
| 2014/0045830 A1 | 2/2014 | Tsuno et al. |
| 2014/0128346 A1 | 5/2014 | Tadesse et al. |
| 2014/0187535 A1 | 7/2014 | Tanaka et al. |
| 2014/0187544 A1 | 7/2014 | Marra et al. |
| 2015/0011529 A1 | 1/2015 | Tafesse et al. |
| 2015/0141643 A1 | 5/2015 | Fuchino et al. |
| 2016/0272640 A1 | 9/2016 | Brown |

FOREIGN PATENT DOCUMENTS

| | | |
|---|---|---|
| EP | 0470039 A2 | 2/1992 |
| EP | 0976732 A1 | 2/2000 |
| EP | 1123702 A1 | 8/2001 |
| FR | 2767827 A1 | 3/1999 |
| JP | 2008-007416 A | 1/2008 |
| WO | WO-1996/023784 A1 | 8/1995 |
| WO | WO-1996/023784 A1 | 8/1996 |
| WO | WO-1998/028293 A1 | 7/1998 |

(Continued)

OTHER PUBLICATIONS

Boss et al. "Orexin receptor . . . " Expert Opin. Ther. Patents 24(12):1367-1381 (2014).*
Jiang et al. "Nicotinic acetylcholine . . . " CA150:507051 (2009).*
Schulse et al. "Preparation of thiaz . . . " CA152:144693 (2010).*
Spear et al. "Preparation of piperi . . . " CA161:186466 (2014).*
Sun et al. "Preparation of piperidi . . . " CA137:337889 (2002).*
Zaveri et al. "Agonist and antag . . . " CA143:115435 (2005).*
Cai et al. "Antagonist of the oresin . . . " Exp. Opin. Ther. Patents 16(5) 631046 (2006).*
Lang et al. "Structure activity . . . " J. Med. Chem. 47, p. 1153-60 (2004).*
Smart et al. "Orexins and . . . " Eur. J. Pharm. 440, 199-212 (2002).*
Smith et al. "Evidence implicating . . . " Neurosci. Lett. 341, 256-258 (2003).*
Taheri et al. "The role of . . . " Ann. Rev. Neurosci. 25, 283-313 (2002).*
Henderson et al, "The Orphan Opioid Receptor and its Endogenous Ligand-Nociceptin/Orphanin FQ," Trends Pharmacol. Sci. 18(8):293-300 (1997).

(Continued)

*Primary Examiner* — Timothy R Rozof
(74) *Attorney, Agent, or Firm* — Purdue Pharma L.P.; Alan L. Koller; Weiying Yang

(57) ABSTRACT

The disclosure relates to indole-type piperidine compounds, indoline-type piperidine compounds and related piperidine-type bicyclic compounds containing a five-membered nitrogen-containing ring (e.g., pyrrole or dihydropyrrole) fused to a heteroaryl ring, compositions comprising an effective amount of such compounds, and methods to treat or prevent a condition, such as pain, comprising administering to an animal in need thereof an effective amount of an indole-type piperidine compound, indoline-type piperidine compound or related piperidine-type bicyclic compound containing a five-membered nitrogen-containing ring (e.g., pyrrole or dihydropyrrole) fused to a heteroaryl ring.

13 Claims, No Drawings

(56) References Cited

FOREIGN PATENT DOCUMENTS

| WO | WO-1999/046260 A1 | 9/1999 |
| WO | WO-1999/050254 A1 | 10/1999 |
| WO | WO-2001/090102 A2 | 11/2001 |
| WO | WO-2003/062234 A1 | 7/2003 |
| WO | WO-2005/028451 A1 | 3/2005 |
| WO | WO2005060947 * | 7/2005 |
| WO | WO-2012/103806 A1 | 8/2012 |
| WO | WO-2014/102589 A1 | 7/2014 |
| WO | WO-2014/102590 A1 | 7/2014 |

OTHER PUBLICATIONS

International Search Report dated Jul. 8, 2014 in corresponding International Application No. PCT/IB2013/002872.
Coe JW et al. "Convenient Preparation of N-Substituted Indoles by Modified Leimgruber-Batcho Indole Synthesis", Tetrahedron Letters, Pergamon, GB, vol. 37, No. 34, 6045-6048 (1996).
Henderson et al., "The Orphan Opioid Receptor and its Endogenous Ligand—Nociceptin/Orphanin FQ," Trends Pharmacol. Sci. 18(8):293-300 (1997).
International Search Report dated Jul. 8, 2014 in corresponding International Application No. PCT/IB2013/002672.

* cited by examiner

INDOLE AND INDOLINE-TYPE PIPERIDINE COMPOUNDS AND USES THEREOF

CROSS-REFERENCE TO RELATED APPLICATIONS

This application is the U.S. national phase, pursuant to 35 U.S.C. § 371, of PCT International Application Ser. No. PCT/IB2013/002872, filed Dec. 23, 2013, designating the United States and published in English on Jul. 3, 2014 as PCT Publication No. WO 2014/102588 A2, which claims priority to U.S. Provisional Application Ser. No. 61/746,281, filed Dec. 27, 2012. The contents of the afore-mentioned patent applications are incorporated herein by their entirety.

1. FIELD

The disclosure relates to indole-type piperidine compounds, indoline-type piperidine compounds and related piperidine-type bicyclic compounds containing a five-membered nitrogen-containing ring (e.g., pyrrole or dihydropyrrole) fused to a heteroaryl ring, compositions comprising an effective amount of such compounds, and methods to treat or prevent a condition, such as pain, comprising administering to an animal in need thereof an effective amount of indole-type piperidine compound, indoline-type piperidine compound or related piperidine-type bicyclic compound containing a five-membered nitrogen-containing ring (e.g., pyrrole or dihydropyrrole) fused to a heteroaryl ring.

2. BACKGROUND

Chronic pain is a major contributor to disability and is the cause of much suffering. The successful treatment of severe and chronic pain is a primary goal of the physician, with opioid analgesics being preferred drugs for doing so.

Three major classes of opioid receptors in the central nervous system (CNS) have long been known, with each class having subtype receptors. These receptor classes are known as $\mu$, $\kappa$ and $\delta$. As opiates have a high affinity for these receptors while not being endogenous to the body, research followed in order to identify and isolate the endogenous ligands to these receptors. These ligands were identified as endorphins, dynorphins and enkephalins, respectively.

Experimentation eventually led to the identification of an opioid receptor-like (ORL-1) receptor with a high degree of homology to the known receptor classes. The ORL-1 receptor was classified as an opioid receptor based only on structural grounds, as the receptor did not exhibit pharmacological homology. It was initially demonstrated that non-selective ligands having a high affinity for $\mu$, $\kappa$ and $\delta$ receptors had low affinity for the ORL-1 receptor. This characteristic, along with the fact that an endogenous ligand had not yet been discovered, led to the term "orphan receptor." See, e.g., Henderson et al., "The orphan opioid receptor and its endogenous ligand—nociceptin/orphanin FQ," *Trends Pharmacol. Sci.* 18(8):293-300 (1997).

Subsequent research led to the isolation and structure of the endogenous ligand of the ORL-1 receptor (i.e., nociceptin; also known as orphanin FQ (OFQ)). This ligand is a seventeen amino acid peptide structurally similar to members of the opioid peptide family.

The discovery of the ORL-1 receptor presents an opportunity in drug discovery for novel compounds that can be administered for pain management or other syndromes modulated by this receptor.

International PCT Publication Nos. WO 99/46260, WO 99/50254, WO 01/90102, WO 2005/028451, WO 2003/062234, and U.S. Pat. App. No. 2005/0256000, respectively, describe quinoxalines or derivatives thereof as (i) inhibitors of protein kinase C, (ii) serine protease inhibitors, (iii) herbicides, (iv) M2 acetylcholine receptor agonists, (v) medicaments for diseases involving poly(ADP-ribose) polymerase, and (vi) safeners for plants.

Citation of any reference in Section 2 of this application is not to be construed as an admission that such reference is prior art to the present application.

3. SUMMARY

In one aspect of the disclosure, new compounds that exhibit affinity for the ORL-1 receptor are described below (and referred to hereinafter as Compounds of Formula (I)).

In some embodiments, Compounds of Formula (I) exhibit agonist activity or partial agonist activity at the ORL-1 receptor. In other embodiments, Compounds of Formula (I) exhibit agonist activity at the ORL-1 receptor. In other embodiments, Compounds of Formula (I) exhibit partial agonist activity at the ORL-1 receptor. In yet other embodiments, Compounds of Formula (I) exhibit antagonist activity at the ORL-1 receptor.

In other embodiments of the disclosure, Compounds of Formula (I) exhibit agonistic or partial agonistic activity for the ORL-1 receptor, and also for one or more of the $\mu$, $\kappa$ and $\delta$ receptors. In other embodiments, Compounds of Formula (I) exhibit affinity for both the ORL-1 receptor and the $\mu$ receptor. In other embodiments, Compounds of Formula (I) act as ORL-1 receptor agonists or partial agonists and as $\mu$ receptor agonists or partial agonists. In other embodiments, Compounds of Formula (I) act as ORL-1 receptor agonists and as $\mu$ receptor agonists or partial agonists. In other embodiments, Compounds of Formula (I) act as ORL-1 receptor partial agonists and as $\mu$ receptor agonists or partial agonists. In other embodiments, Compounds of Formula (I) act as ORL-1 receptor agonists or partial agonists and as $\mu$ receptor agonists. In other embodiments, Compounds of Formula (I) act as ORL-1 receptor agonists or partial agonists and as $\mu$ receptor partial agonists. In other embodiments, Compounds of Formula (I) act as ORL-1 receptor agonists and as $\mu$ receptor agonists. In other embodiments, Compounds of Formula (I) act as ORL-1 receptor agonists and as $\mu$ receptor partial agonists. In other embodiments, Compounds of Formula (I) act as ORL-1 receptor partial agonists and as $\mu$ receptor agonists. In other embodiments, Compounds of Formula (I) act as ORL-1 receptor partial agonists and as $\mu$ receptor partial agonists. In other embodiments, Compounds of Formula (I) act as ORL-1 receptor agonists or partial agonists and as $\mu$ receptor antagonists. In other embodiments, Compounds of Formula (I) act as ORL-1 receptor agonist and as $\mu$ receptor antagonists. In other embodiments, Compounds of Formula (I) act as ORL-1 receptor partial agonists and as $\mu$ receptor antagonists. In other embodiments, Compounds of Formula (I) act as ORL-1 receptor antagonists and as $\mu$ receptor agonists or partial agonists. In other embodiments, Compounds of Formula (I) act as ORL-1 receptor antagonists and as $\mu$ receptor agonists. In other embodiments, Compounds of Formula (I) act as ORL-1 receptor antagonists and as $\mu$ receptor partial agonists.

Compounds of Formula (I) can be used to treat an animal suffering from chronic or acute pain.

Another aspect of the disclosure provides methods for treating chronic or acute pain in an animal by administering one or more Compounds of Formula (I) to an animal in need of such treatment. In certain embodiments, such compounds have a piperidine ring bonded to a bicyclic group containing a five-membered nitrogen-containing ring (e.g., pyrrole or dihydropyrrole) fused to a benzene ring or a heteroaryl ring. In other embodiments, the bicyclic compound is an indole (i.e., pyrrole fused to a benzo group). In other embodiments, the bicyclic compound is an indoline (i.e., pyrrolidine fused to a benzo group). In still other embodiments, the bicyclic portion of the molecule is comprised of a pyrolle or pyrrolidine ring fused to a pyridine ring. In certain embodiments, Compounds of Formula (I) effectively treat chronic or acute pain in the animal, while producing fewer or reduced side effects compared to previously available compounds.

Compounds of the disclosure include those of Formula (I):

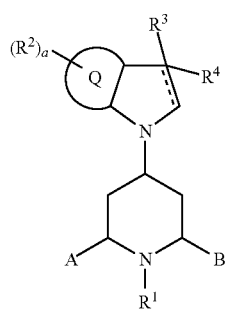

(I)

and the pharmaceutically acceptable salts and solvates thereof (collectively referred to hereinafter as "Compounds of Formula (I)"), wherein:

Q is fused benzo or fused (5- or 6-membered)heteroaryl;
each $R^2$ is independently selected from:
(a) -halo, —CN, —NO$_2$, —OT$^3$, —C(=O)T$^3$, —C(=O)OT$^3$, —C(=O)N(T$^1$)(T$^2$), —S(=O)$_2$OT$^3$, —S(=O)T$^3$, —S(=O)$_2$T$^3$, —O—S(=O)$_2$T$^3$, —S(=O)$_2$N(T$^1$)(T$^2$), —N(T$^1$)(T$^2$), —N(T$^3$)C(=O)T$^3$, —N(T$^3$)C(=O)N(T$^1$)(T$^2$), —N(T$^3$)S(=O)T$_3$, —N(T$^3$)S(=O)$_2$T$^3$, —N(T$^3$)C(=O)OT$^3$, and —N(T$^3$)S(=O)$_2$N(T$^1$)(T$^2$); and
(b) —(C$_1$-C$_6$)alkyl, —(C$_2$-C$_6$)alkenyl, —(C$_2$-C$_6$)alkynyl, and —(C$_1$-C$_6$)alkoxy, each of which is unsubstituted or substituted with 1, 2, or 3 independently selected $R^8$ groups; and
(c) -phenyl, -naphthalenyl, and -(5- or 6-membered)heteroaryl, each of which is unsubstituted or substituted with 1, 2, or 3 independently selected $R^7$ groups;
a is an integer selected from 0, 1, and 2;
the dashed line denotes the presence or absence of a bond provided that:
(a) when the dashed line denotes the presence of a double bond, then $R^4$ is absent, and
(b) when the dashed line denotes the presence of a single bond, then $R^4$ is present;
$R^3$ is:
(a) —X, —(C$_1$-C$_6$)alkyl-X, -(5- or 6-membered)heterocycle-X, or -(5- or 6-membered)heterocycle-(C$_1$-C$_6$)alkyl-X; or
(b) —(CH$_2$)$_d$—C(=Y)CN, —(CH$_2$)$_d$—C(=Y)X, —(CH$_2$)$_d$—C(=Y)T$^3$, —(CH$_2$)$_d$—C(=Y)YX, —(CH$_2$)$_d$—C(=Y)YT$^3$, —(CH$_2$)$_d$—C(=Y)YX, —(CH$_2$)$_d$—C(=Y)YT$^3$, —(CH$_2$)$_d$—C(=Y)N(T$^1$)(T$^2$), —(CH$_2$)$_d$—C(=Y)N(R$^9$)CN, —(CH$_2$)$_d$—C(=Y)N(R$^9$)X, —(CH$_2$)$_d$—C(=Y)N(R$^9$)YH, —(CH$_2$)$_d$—C(=Y)N(R$^9$)YX, —(CH$_2$)$_d$—C(=Y)N(R$^9$)YCH$_2$X, —(CH$_2$)$_d$—C(=Y)N(R$^9$)YCH$_2$CH$_2$X, or —(CH$_2$)$_d$—C(=Y)N(R$^9$)S(=O)$_2$T$^3$;

X is selected from:
(a) —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, and -(7- to 10-membered)bicycloheterocycle, each of which is unsubstituted or substituted with 1, 2, or 3 independently selected $R^8$ groups; and
(b) -phenyl, -naphthalenyl, —(C$_{14}$)aryl, and -(5- or 6-membered)heteroaryl, each of which is unsubstituted or substituted with 1, 2, or 3 independently selected $R^7$ groups;
each Y is independently O or S;
$R_4$ is:
(a) —H; or
(b) —(C$_1$-C$_4$)alkyl which is unsubstituted or substituted with 1, 2, or 3 groups independently selected from —OH, —(C$_1$-C$_4$)alkoxy, —N(R$_6$)$_2$, —C(=O)OR$_9$, and —C(=O)N(R$_6$)$_2$,
A and B are independently selected from:
(a) —H, —CN, —C(=O)OT$_3$, and —C(=O)N(T$^1$)(T$^2$); and
(b) —(C$_3$-C$_{12}$)cycloalkyl, —(C$_3$-C$_{12}$)cycloalkoxy, —(C$_1$-C$_6$)alkyl, —(C$_2$-C$_6$)alkenyl, —(C$_2$-C$_6$)alkynyl, and —(C$_1$-C$_6$)alkoxy, each of which is unsubstituted or substituted with 1 or 2 substituents independently selected from —OH, —S(=O)$_2$NH$_2$, —N(R$^6$)$_2$, =NR$^6$, —C(=O)OT$^3$, —C(=O)N(R$^6$)$_2$, —N(R$^6$)C(=O)R$^9$, and -(5- or 6-membered)heterocycle, or 1, 2, or 3 independently selected -halo; or
(c) A-B can together form a (C$_2$-C$_6$)bridge, which is unsubstituted or substituted with 1, 2, 3, 4, 5, 6, 7, or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the 5-membered, nitrogen-containing ring that is fused to the Q group can be in the endo- or exo-configuration with respect to the A-B bridge;
$R^1$ is selected from:
(a) —(C$_3$-C$_7$)cycloalkoxy, —(C$_3$-C$_{14}$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_4$)bicycloalkenyl, —(C$_8$-C$_{20}$)tricycloalkenyl, and -(3- to 8-membered)heterocycle, each of which is unsubstituted or substituted with 1, 2, 3, or 4 independently selected $R^8$ groups; and
(b)

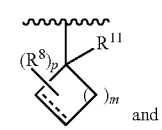

(i)

and

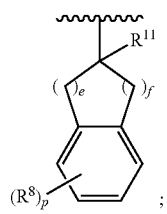

(ii)

;

and
(c) -phenyl, -naphthalenyl, —$(C_{14})$aryl, and -(5- to 10-membered)heteroaryl, each of which is unsubstituted or substituted with 1, 2, 3, or 4 independently selected $R^7$ groups; and
(d) —$(C_2-C_4)$alkyl substituted with one substituent selected from —$(C_6-C_{14})$bicycloalkyl, —$(C_8-C_{20})$tricycloalkyl, or phenyl, each of which is unsubstituted or substituted with 1, 2, 3, or 4 independently selected $R^7$ groups;

each $R_6$ is independently —H, —$(C_1-C_6)$alkyl, or —$(C_3-C_7)$cycloalkyl, or two $R^6$ groups attached to the same nitrogen atom can together form a 5- to 8-membered ring, wherein the number of atoms in the ring includes the nitrogen atom, and in which one of the 5- to 8-membered ring carbon atoms is optionally replaced by O, S, or $N(T^3)$, wherein the —$(C_1-C_6)$alkyl is unsubstituted or substituted with 1, 2, or 3 groups independently selected from —OH, —$(C_1-C_4)$alkoxy, —$N(R^9)_2$, —$C(=O)R^9$, and —$C(=O)NR^9$;

each $R^7$ is independently —$(C_1-C_4)$alkyl, —$(C_2-C_6)$alkenyl, —$(C_2-C_6)$alkynyl, —$OR^9$, —$SR^9$, —$C(halo)_3$, —$CH(halo)_2$, —$CH_2(halo)$, —CN, -halo, —$N_3$, —$NO_2$, —$CH=N(R^9)$, —$N(R^9)_2$, —$N(R^9)OH$, —$N(R^9)S(=O)R^{12}$, —$N(R^9)S(=O)_2R^{12}$, —$N(R^9)C(=O)R^{12}$, —$N(R^9)C(=O)N(T^1)(T^2)$, —$N(R^9)C(=O)OR^{12}$, —$C(=O)R^9$, —$C(=O)N(T^1)(T^2)$, —$C(=O)OR^9$, —$OC(=O)R^9$, —$OC(=O)N(T^1)(T^2)$, —$OC(=O)OR^9$, —$S(=O)R^9$, or —$S(=O)_2R^9$;

each $R^8$ is independently —$(C_1-C_4)$alkyl, —$(C_2-C_6)$alkenyl, —$(C_2-C_6)$alkynyl, -(5- or 6-membered)heteroaryl, —$(C_1-C_6)$alkyl, —$C(=O)OR^9$, —$N(R^9)(C_1-C_6)$alkyl-$C(=O)OR^9$, —$OR^9$, —$SR^9$, —$C(halo)_3$, —$CH(halo)_2$, —$CH_2(halo)$, —CN, =O, =S, -halo, —$N_3$, —$NO_2$, —$CH=N(R^9)$, —$N(R^9)_2$, —$N(R^9)OH$, —$N(R^9)S(=O)R^{12}$, —$N(R^9)S(=O)_2R^{12}$, —$N(R^9)C(=O)R^{12}$, —$N(R^9)C(=O)N(T^1)(T^2)$, —$N(R^9)C(=O)OR^{12}$, —$C(=O)R^9$, —$C(=O)N(T^1)(T^2)$, —$C(=O)OR^9$, —$OC(=O)R^9$, —$OC(=O)N(T^1)(T^2)$, —$OC(=O)OR^9$, —$S(=O)R^9$, or —$S(=O)_2R^9$;

each $R^9$ is independently —H, —$(C_1-C_6)$alkyl, —$(C_2-C_6)$alkenyl, —$(C_2-C_6)$alkynyl, —$(C_3-C_8)$cycloalkyl, —$(C_5-C_8)$cycloalkenyl, -phenyl, -benzyl, -(3- to 7-membered)heterocycle, —$C(halo)_3$, —$CH(halo)_2$, or —$CH_2(halo)$;

$R^{11}$ is —H, —CN, —$C(=O)OR^9$, or —$C(=O)N(R^6)_2$ or $R^{11}$ can be —$(C_1-C_4)$alkyl which is unsubstituted or substituted with —OH, —$(C_1-C_4)$alkoxy, —$N(R^6)_2$, —$C(=O)OR^9$, or —$C(=O)N(R^6)_2$; each $R^{12}$ is independently —H or —$(C_1-C_4)$alkyl;

each d is, independently, an integer selected from 0, 1, 2, and 3;

m is an integer selected from 0, 1, 2, 3, 4, 5, 6, 7, 8, 9, 10, and 11;

e and f are each an integer independently selected from 0, 1, 2, 3, 4, and 5 provided that 2≤(e+0≤5);

each p is an integer independently selected from 0, 1, 2, 3, and 4;

each $T^1$ and $T^2$ is independently —H or —$(C_1-C_{10})$alkyl which is unsubstituted or substituted with 1, 2, or 3 independently selected $R^5$ groups and, optionally, in which any —$(C_1-C_{10})$alkyl carbon atom except the carbon atom bonded directly to the atom to which $T^1$ or $T^2$ is attached is independently replaced by O, S, or $N(R^6)$, or $T_1$ and $T_2$ can together form a 5- to 8-membered ring wherein the number of atoms in the ring includes the nitrogen atom to which $T^1$ and $T^2$ are bonded, said 5- to 8-membered ring is unsubstituted or substituted with 1, 2, or 3 independently selected $R^5$ groups and, optionally, any carbon atom in said 5- to 8-membered ring is independently replaced by O, S, or $N(R^6)$;

each $T^3$ is independently —H or —$(C_1-C_{10})$alkyl which is unsubstituted or substituted with 1, 2, or 3 independently selected $R_5$ groups and, optionally, in which any —$(C_1-C_{10})$alkyl carbon atom except the carbon atom bonded directly to the atom to which $T^3$ is attached is independently replaced by O, S, or $N(R^{12})$;

each $R^5$ is independently —$(C_1-C_4)$alkyl, —$(C_2-C_6)$alkenyl, —$(C_2-C_6)$alkynyl, -(5- or 6-membered)heteroaryl, —$(C_1-C_6)$alkyl —$C(=O)OR^9$, —$OR^9$, —$SR^9$, —$C(halo)_3$, —$CH(halo)_2$, —$CH_2(halo)$, —CN, =O, =S, -halo, —$N_3$, —$NO_2$, —$CH=N(R^9)$, —$N(R^9)(C_1-C_6)$alkyl-$C(=O)OR^9$, —$N(R^9)_2$, —$N(R^9)OH$, —$N(R^9)S(=O)R^{12}$, —$N(R^9)S(=O)_2R^{12}$, —$N(R^9)C(=O)R^{12}$, —$N(R^9)C(=O)OR^{12}$, —$C(=O)R^9$, —$C(=O)OR^9$, —$OC(=O)R^9$, —$OC(=O)OR^9$, —$S(=O)R^9$, or —$S(=O)_2R^9$; and each halo is independently —F, —Cl, —Br, or —I.

Compounds of the disclosure include those of Formula (I*):

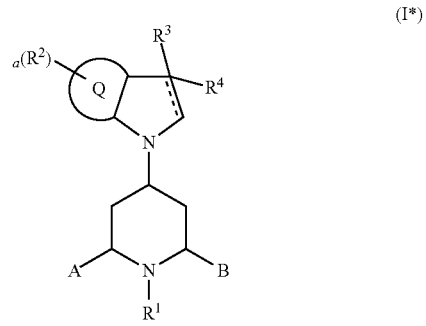

and the pharmaceutically acceptable salts and solvates thereof (collectively referred to hereinafter as "Compounds of Formula (I*)"), wherein:

Q is fused benzo or fused (5- or 6-membered)heteroaryl;

each $R^2$ is independently selected from:
(a) -halo, —CN, —$NO_2$, —$OT^3$, —$C(=O)T^3$, —$C(=O)OT^3$, —$C(=O)N(T^1)(T^2)$, —$S(=O)_2$, 0 $T^3$, —$S(=O)T^3$, —$S(=O)_2T^3$, —O—$S(=O)_2T^3$, —$S(=O)_2N(T^1)(T^2)$, —$N(T^1)(T^2)$, —$N(T^3)C(=O)T^3$, —$N(T^3)C(=O)N(T^1)(T^2)$, —$N(T^3)S(=O)T_3$, —$N(T^3)S(=O)_2T^3$, —$N(T^3)C(=O)OT^3$, and —$N(T^3)S(=O)_2N(T^1)(T^2)$; and
(b) —$(C_1-C_6)$alkyl, —$(C_2-C_6)$alkenyl, —$(C_2-C_6)$alkynyl, and —$(C_1-C_6)$alkoxy, each of which is unsubstituted or substituted with 1, 2, or 3 independently selected $R^8$ groups; and
(c) -phenyl, -naphthalenyl, and -(5- or 6-membered)heteroaryl, each of which is unsubstituted or substituted with 1, 2, or 3 independently selected $R^7$ groups;

a is an integer selected from 0, 1, and 2;

the dashed line denotes the presence or absence of a bond provided that:
(a) when the dashed line denotes the presence of a double bond, then $R^4$ is absent, and
(b) when the dashed line denotes the presence of a single bond, then $R^4$ is present;

$R^3$ is:
(a) —X, —$(C_1-C_6)$alkyl-X, -(5- or 6-membered)heterocycle-X, or -(5- or 6-membered)heterocycle-$(C_1-C_6)$alkyl-X; or (b) —(CH$_2$)$_d$—C(=Y)CN, —(CH$_2$)$_d$—C(=Y)X, —(CH$_2$)$_d$—C(=Y)T$^3$, —(CH$_2$)$_d$—C(=Y)YX, —(CH$_2$)$_d$—C(=Y)C(=Y)YX, —(CH$_2$)$_d$—C(=Y)YT$^3$, —(CH$_2$)$_d$—C(=Y)N(T$^1$)(T$^2$), —(CH$_2$)$_d$—C(=Y)N(R$^9$)CN, —(CH$_2$)$_d$—C(=Y)N(R$^9$)X, —(CH$_2$)$_d$—C(=Y)N(R$^9$)YH, —(CH$_2$)$_d$—C(=Y)N(R$^9$)YX, —(CH$_2$)$_d$—C(=Y)N(R$^9$)YCH$_2$X, —(CH$_2$)$_d$—C(=Y)N(R$^9$)YCH$_2$CH$_2$X, or —(CH$_2$)$_d$—C(=Y)N(R$^9$)S(=O)$_2$T$^3$;

X is selected from:
(a) —H, —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, and -(7- to 10-membered)bicycloheterocycle, each of which is unsubstituted or substituted with 1, 2, or 3 independently selected R$^8$ groups; and
(b) -phenyl, -naphthalenyl, —(C$_{14}$)aryl, and -(5- or 6-membered)heteroaryl, each of which is unsubstituted or substituted with 1, 2, or 3 independently selected R$^7$ groups;

each Y is independently O or S;

R$_4$ is:
(a) —H; or
(b) —(C$_1$-C$_4$)alkyl which is unsubstituted or substituted with 1, 2, or 3 groups independently selected from —OH, —(C$_1$-C$_4$)alkoxy, —N(R$_6$)$_2$, —C(=O)OR$_9$, and —C(=O)N(R$_6$)$_2$, A and B are independently selected from:
(a) —H, —CN, —C(=O)OT$_3$, and —C(=O)N(T$^1$)(T$^2$); and
(b) —(C$_3$-C$_{12}$)cycloalkyl, —(C$_3$-C$_{12}$)cycloalkoxy, —(C$_1$-C$_6$)alkyl, —(C$_2$-C$_6$)alkenyl, —(C$_2$-C$_6$)alkynyl, and —(C$_1$-C$_6$)alkoxy, each of which is unsubstituted or substituted with 1 or 2 substituents independently selected from —OH, —S(=O)$_2$NH$_2$, —N(R$_6$)$_2$, =NR$^6$, —C(=O)OT$^3$, —C(=O)N(R$^6$)$_2$, —N(R$^6$)C(=O)R$^9$, and -(5- or 6-membered)heterocycle, or 1, 2, or 3 independently selected -halo; or
(c) A-B can together form a (C$_2$-C$_6$)bridge, which is unsubstituted or substituted with 1, 2, 3, 4, 5, 6, 7, or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the 5-membered, nitrogen-containing ring that is fused to the Q group can be in the endo- or exo-configuration with respect to the A-B bridge;

R$^1$ is selected from:
(a) —(C$_3$-C$_7$)cycloalkoxy, —(C$_3$-C$_{14}$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, and -(3- to 8-membered)heterocycle, each of which is unsubstituted or substituted with 1, 2, 3, or 4 independently selected R$^8$ groups; and
(b)

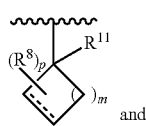

and

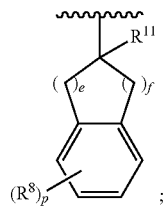

and
(c) -phenyl, -naphthalenyl, —(C$_{14}$)aryl, and -(5- to 10-membered)heteroaryl, each of which is unsubstituted or substituted with 1, 2, 3, or 4 independently selected R$^7$ groups; and
(d) —(C$_2$-C$_4$)alkyl substituted with —(C$_6$-C$_{14}$)bicycloalkyl, —(C$_8$-C$_{20}$)tricycloalkyl, or phenyl, each of which is unsubstituted or substituted with 1, 2, 3, or 4 independently selected R$^7$ groups;

each R$_6$ is independently —H, —(C$_1$-C$_6$)alkyl, or —(C$_3$-C$_7$)cycloalkyl, or two R$^6$ groups attached to the same nitrogen atom can together form a 5- to 8-membered ring, wherein the number of atoms in the ring includes the nitrogen atom, and in which one of the 5- to 8-membered ring carbon atoms is optionally replaced by O, S, or N(T$^3$), wherein the —(C$_1$-C$_6$)alkyl is unsubstituted or substituted with 1, 2, or 3 groups independently selected from —OH, —(C$_1$-C$_4$)alkoxy, —N(R$^9$)$_2$, —C(=O)OR$^9$ and —C(=O)NR$^9$;

each R$^7$ is independently —(C$_1$-C$_4$)alkyl, —(C$_2$-C$_6$)alkenyl, —(C$_2$-C$_6$)alkynyl, —OR$^9$, —SR$^9$, —C(halo)$_3$, —CH(halo)$_2$, —CH$_2$(halo), —CN, -halo, —N$_3$, —NO$_2$, —CH=N(R$^9$), —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each R$^8$ is independently —(C$_1$-C$_4$)alkyl, —(C$_2$-C$_6$)alkenyl, —(C$_2$-C$_6$)alkynyl, -(5- or 6-membered)heteroaryl, —(C$_1$-C$_6$)alkyl-C(=O)OR$^9$, —N(R$^9$)(C$_1$-C$_6$)alkyl-C(=O)OR$^9$, —OR$^9$, —SR$^9$, —C(halo)$_3$, —CH(halo)$_2$, —CH$_2$(halo), —CN, =O, =S, -halo, —N$_3$, —NO$_2$, —CH=N(R$^9$), —N(R$^9$)$_2$, —N(R$^9$)OH, —N(R$^9$)S(=O)R$^{12}$, —N(R$^9$)S(=O)$_2$R$^{12}$, —N(R$^9$)C(=O)R$^{12}$, —N(R$^9$)C(=O)N(T$^1$)(T$^2$), —N(R$^9$)C(=O)OR$^{12}$, —C(=O)R$^9$, —C(=O)N(T$^1$)(T$^2$), —C(=O)OR$^9$, —OC(=O)R$^9$, —OC(=O)N(T$^1$)(T$^2$), —OC(=O)OR$^9$, —S(=O)R$^9$, or —S(=O)$_2$R$^9$;

each R$^9$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -benzyl, -(3- to 7-membered)heterocycle, —C(halo)$_3$, —CH(halo)$_2$, or —CH$_2$(halo);

R$^{11}$ is —H, —CN, —C(=O)OR$^9$, or —C(=O)N(R$^6$)$_2$ or R$^{11}$ can be —(C$_1$-C$_4$)alkyl which is unsubstituted or substituted with —OH, —(C$_1$-C$_4$)alkoxy, —N(R$^6$)$_2$, —C(=O)OR$^9$, or —C(=O)N(R$^6$)$_2$; each R$^{12}$ is independently —H or —(C$_1$-C$_4$)alkyl;

each d is, independently, an integer selected from 0, 1, 2, and 3;

m is an integer selected from 0, 1, 2, 3, 4, 5, 6, 7, 8, 9, 10, and 11;

e and f are each an integer independently selected from 0, 1, 2, 3, 4, and 5 provided that 2≤(e+f)≤5;

each p is an integer independently selected from 0, 1, 2, 3, and 4;

each $T^1$ and $T^2$ is independently —H or —$(C_1$-$C_{10})$alkyl which is unsubstituted or substituted with 1, 2, or 3 independently selected $R^5$ groups and, optionally, in which any —$(C_1$-$C_{10})$alkyl carbon atom except the carbon atom bonded directly to the atom to which $T^1$ or $T^2$ is attached is independently replaced by O, S, or N($R^6$), or $T_1$ and $T_2$ can together form a 5- to 8-membered ring wherein the number of atoms in the ring includes the nitrogen atom to which $T^1$ and $T^2$ are bonded, said 5- to 8-membered ring is unsubstituted or substituted with 1, 2, or 3 independently selected $R^5$ groups and, optionally, any carbon atom in said 5- to 8-membered ring is independently replaced by O, S, or N($R^6$);

each $T^3$ is independently —H or —$(C_1$-$C_{10})$alkyl which is unsubstituted or substituted with 1, 2, or 3 independently selected $R_5$ groups and, optionally, in which any —$(C_1$-$C_{10})$ alkyl carbon atom except the carbon atom bonded directly to the atom to which $T^3$ is attached is independently replaced by O, S, or N($R^{12}$);

each $R^5$ is independently —$(C_1$-$C_4)$alkyl, —$(C_2$-$C_6)$alkenyl, —$(C_2$-$C_6)$alkynyl, -(5- or 6-membered)heteroaryl, —$(C_1$-$C_6)$alkyl-C(=O)O$R^9$, —O$R^9$, —S$R^9$, —C(halo)$_3$, —CH(halo)$_2$, —CH$_2$(halo), —CN, =O, =S, -halo, —N$_3$, —NO$_2$, —CH=N($R^9$), —N($R^9$)($C_1$-$C_6$)alkyl-C(=O)O$R^9$, —N($R^9$)$_2$, —N($R^9$)OH, —N($R^9$)S(=O)$R^{12}$, —N($R^9$)S(=O)$_2R^{12}$, —N($R^9$)C(=O)$R^{12}$, —N($R^9$)C(=O)O$R^{12}$, —C(=O)$R^9$, —C(=O)O$R^9$, —OC(=O)$R^9$, —OC(=O)O$R^9$, —S(=O)$R^9$, or —S(=O)$_2R^9$; and each halo is independently —F, —Cl, —Br, or —I.

Compounds of Formula (I) may alternatively be referred to herein as indole-type or indoline-type piperidine compounds. It will be understood, however, that ring Q, in addition to a benzene ring, can be a 5- or 6-membered heteroaryl, as defined herein.

Compounds of Formula (I) are useful for treating and/or preventing pain (see, for e.g; Courteix, et al. (2004). Evidence for an exclusive antinociceptive effect of nociceptin/orphanin FQ, an endogenous ligand for the ORL1 receptor, in two animal models of neuropathic pain. *Pain*, 110: 236-245; Reinscheid, et al. (1995). Orphanin FQ: a neuropeptide that activates an opioid-like G protein-coupled receptor. *Science*, 270: 792-794; Bignan et al. (2005). Recent advances towards the discovery of ORL-1 receptor agonists and antagonists. *Expert Opinion on Therapeutic Patents*, 15(4): 357-388; Meunier, et al. (1995). Isolation and structure of the endogenous agonist of opioid receptor-like ORL1 receptor. *Nature*, 377: 532-535; Briscini, et al (2002). Up-regulation of ORL-1 receptors in spinal tissue of allodynic rats after sciatic nerve injury. *Eur. J. Pharmacol.*, 447: 59-65; Li, et al. (2004). Role of nociceptin in the modulation of nociception in the arcuate nucleus of rats. *Brain Res.*, 1025: 67-74), anxiety (see for e.g., Jenck, et al. (1997). Orphanin FQ acts as an anxiolytic to attenuate behavioral responses to stress. *Proc. Natl. Acad. Sci., U.S.A.*, 94: 14854-14858; Koster, et al. (1999). Targeted disruption of the orphanin FQ/nociceptin gene increases stress susceptibility and impairs stress adaptation in mice. *Proc. Natl. Acad. Sci. U.S.A.*, 96: 10444-10449; Griebel, et al. (1999). Orphanin FQ, a novel neuropeptide with anti-stress-like activity. *Brain Res.*, 836: 221-224; Jenck, et al. (2000). A synthetic agonist at the orphanin FQ/nociceptin receptor ORL1: Anxiolytic profile in the rat. Proc. Natl. Acad. Sci., 97: 4938-4943), cough (see for e.g., Fischer, et al. (1998). Nociceptin-induced inhibition of tachykinergic neurotransmission in guinea pig bronchus. *J. Pharmacol. Ther.*, 285: 902-907; Rizzi, et al. (1999). Nociceptin receptor activation inhibits tachykinergic non adrenergic non cholinergic contraction of guinea pig isolated bronchus. *Life Sci.*, 64: L157-L163; Shah, et al. (1998). Nociceptin inhibits non-cholinergic contraction in guinea-pig airway. *Br. J. Pharmacol.*, 125: 510-516; Patel, et al., (1997). Naloxone-insensitive inhibition of acetylcholine release from parasympathetic nerves innervating guinea-pig trachea by the novel opioid, nociceptin. *Br. J. Pharmacol.*, 120: 735-736; Helyes, et al. (1997). Inhibition by nociceptin of neurogenic inflammation and the release of SP and CGRP from sensory nerve terminals. *Br. J. Pharmacol.*, 121: 613-615; Nemeth, et al., (1998). Inhibition of nociceptin on sensory neuropeptide release and mast cell-mediated plasma extravasation in rats. *Eur. J. Pharmacol.*, 347: 101-104; McLeod, et al. (2001). Nociceptin inhibits cough in the guinea-pig by activation of ORL1 receptors. *Br. J. Pharmacol.*, 132: 1175-1178; Corboz, et al. (2000). Nociceptin inhibits capsaicin-induced bronchoconstriction in isolated guinea pig lung. *Eur. J. Pharmacol.*, 402: 171-179), gut motility disorders (such as diarrhea and constipation) (see for e.g., Wang, et al. (1994). cDNA cloning of an orphan opiate receptor gene family member and its splice variant. *FEBS Lett.*, 348: 75-79; Calo', et al. (1996). The mouse deferens: a pharmacological preparation sensitive to nociceptin. *Eur. J. Pharmacol.*, 311: R3-R5; Zhang, et al. (1997). Orphanin FQ has an inhibitory effect on the guinea pig ileum and the mouse vas deferens. *Brain Res.*, 772: 102-106; Osinski, et al. (1999). Cloning, expression and functional role of a nociceptin/orphanin FQ receptor in the porcine gastrointestinal tract. *Eur. J. Pharmacol.*, 365: 281-289; Yasdani, et al. (1999). Functional significance of a newly discovered neuropeptide, orphanin FQ, in rat gastrointestinal motility. *Gastroenterology*, 116: 108-117; Corbett, et al. (1998). The pharmacological actions of nociceptin in the isolated colon of rat, mouse, and man. *Naunyn Schmiedebergs Arch. Pharmacol.*, 358(Suppl 1): P40.47; Osinski, et al. (1999). Peripheral and central actions of orphanin FQ (nociceptin) on murine colon. *Am. J. Physiol.*, 276: G125-G131; Rizzi, et al. (1999). [Nphe$^1$]nociceptin(1-13)NH$_2$ antagonizes nociceptin effects in the mouse colon. *Eur. J. Pharmacol.*, 285: R3-R5; Taniguchi, et al. (1998). The effect of nociceptin an endogenous ligand for the ORL1 receptor, on rat colonic contraction and transit. *Eur. J. Pharmacol.*, 353: 265-271; Pheng, et al. (2000). [Nphe$^1$]nociceptin(1-13) NH$_2$ selectively antagonizes nociceptin effects in the rabbit isolated ileum. *Eur. J. Pharmacol.*, 397: 383-388), high blood pressure (see for e.g., Champion & Kadowitz (1997). Nociceptin, an endogenous ligand for the ORL1 receptor, has novel hypotensive activity in the rat. *Life Sci.*, 60: PL 241-245; Giuliani, et al. (1997). Effect of nociceptin on heart rate and blood pressure in anaesthetized rats. *Eur. J Pharmacol.*, 333: 177-179; Kapusta, et al. (1997). Diuretic and antinatriuretic responses produced by the endogenous opioid-like peptide, noceptin (orphanin FQ). Life Sci., 60: PL15-PL21; Kapusta, et al. (1999). Central administration of [Phe1psi(CH$_2$—NH)Gly2]nociceptin(1-13)-NH$_2$ and orphanin FQ/nociceptin (OFQ/N) produce similar cardiovascular and renal responses in conscious rats. J. Pharmacol. Exp. Ther., 289: 173-180; Madeddu, et al. (1999). Cardiovascular effects of nociceptin in unanesthetized mice. *Hypertension*, 33: 914-919; Bigoni, et al. (1999). Characterization of nociceptin receptors in the periphery: in vitro and in vivo studies. *Naunyn Schmiedebergs Arch. Pharmacol.*, 359: 160-167; Chu, et al. (1999). Inhibition of cardiovascular activity following microinjection of novel opioid-like neuropeptide nociceptin (orphanin FQ) into the rat rostral ventrolateral medulla. *Brain Res.*, 829: 134-142; Chu, et al. (1999). The nociceptin receptor-mediated inhibition of the rat rostral ventrolateral medulla neurons in vitro. *Eur. J. Pharmacol.*, 364: 49-53; Arndt, et al. (1999). Nociceptin/orphanin FQ increases blood pressure and heart rate via sympathetic activation in sheep. *Peptides*, 20: 465-470; Gumusel, et al. (1997). Nociceptin: an endogenous agonist for central opioid-like1 (ORL1) receptors possesses systemic vasorelaxant properties. *Life Sci.*, 69: PLI41-PL145; Champion et al. (1998). Nociceptin, a novel endogenous ligand for the ORL1 receptor, dilates isolated resistance arteries from the rat. *Regul. Peptides*, 78: 69-74; Czapla, et al. (1997). Decreases in systemic arterial and hindquarters perfusion pressure in response to nociceptin are not inhibited by naloxone in the rat. *Peptides*, 18: 1197-1200; Armstead (1999), Nociceptin/orphanin FQ dilates pial arteries by K(ATP) and k(ca) channel activation. *Brain Res.*, 835: 315-323; Bucher (1998), ORL1 receptor-mediated inhibition by nociceptin of noradrenaline release from perivascular sympathetic nerve endings of the rat tail artery. *Naunyn Schmiedebergs Arch. Pharmacol.*, 358: 682-685; Champion et al. (1997). Nociceptin, a novel endogenous ligand for the ORL1 receptor, has potent erectile activity in the cat. *Am. J. Physiol.*, 73: E214-E219), epilepsy (see for e.g., Nicol, et al. (1996), Nociceptin induced inhibition of K+ evoked glutamate release from rat cerebrocortical slices. *Br. J. Pharmacol.*, 119: 1081-1083; Nicol, et al. (1998). Nociceptin inhibits glutamate release from rat cerebellar slices. *Br. J. Pharmacol.*, 123: 217P; Allen, et al. (1999). Orphanin-FQ/nociceptin (OFQ/N) modulates the activity of suprachiasmatic nucleus neurons. *J. Neurosci.*, 19: 2152-2160; Faber, et al. (1996). Depression of glutamatergic transmission by nociceptin in the neonatal rat hemisected spinal cord preparation in vitro. *Br. J Pharmacol.*, 119: 189-190; Vaughn, et al. (1997). Actions of the ORL1 receptor ligand nociceptin on membrane properties of rat periaqueductal gray neurons in vitro. *J. Neurosci.*, 17: 996-1003; Wang, et al. (1996). Nociceptin (orphanin FQ), and endogenous ligand for the ORL1 (opioid receptor-like1) receptor, modulates responses of trigeminal neurons evoked by excitatory amino acids and somatosensory stimuli. *J. Neurophysiol.*, 76: 3568-3572; Yu & Xie (1998). Orphanin FQ/nociceptin inhibits synaptic transmission and long-term potentiation in rat dentate gyrus through postsynaptic mechanisms. *J. Neurophysiol.*, 80: 1277-1284; Bregola, et al. (1999). Limbic seizures increase pronociceptin mRNA levels in the thalamic reticular nucleus. *Neuroreport*, 19: 541-546; Sieklucka-Dziuba, et al. (2002). Nociceptin, OP4 receptor ligand in different models of experimental epilepsy. *Peptides*, 23: 497-505; Gutierrez, et al, (2001). Orphanin FQ/nociceptin inhibits kindling epileptogenesis and enhances hippocampal feed-forward inhibition. Neuroscience, 105: 325-333; Tallent, et al. (2001). Nociceptin reduces epileptiform events in CA3 hippocampus via presynaptic and postsynaptic mechanisms. *J. Neurosci.*, 21: 6940-6948), eating-related disorders (such as anorexia/cachexia and obesity) (see for e.g., Pomonis, et al. (1996). Orphanin FQ, agonist of orphan opioid receptor ORL1, stimulates feeding in rats. *Neuroreport*, 8: 369-371; Stratford et al. (1997). Injections of nociceptin into nucleus accumbens shell of ventromedial hypothalamic nucleus increase food intake. *Neuroreport*, 8: 423-426; Lee, et al. (1997). Nociceptin hyperpolarises neurones in the rt ventromedial hypothalamus. *Neurosci. Lett.*, 239: 37-40; Polidori, et al. (1999). Sensitivity of brain sites to the orexigenic effect of nociceptin or of its analog [Phe]psi(CH$_2$—NH)Gly2]NC(1-13)NH$_2$. *Regul. Peptides*, 80:126; Polidori, et al. (2000). Pharmacological characterization of the nociceptin receptor mediating hyperphagia: indentification of a selective antagonist. *Psychopharmacology*, 148: 430-437; Rowland, et al. (1996). The physiology and brain mechanisms of feeding. *Nutrition*, 12: 626-639), urinary incontinence (see for e.g., Giuliani, et al. (1998). The inhibitory effect of nociceptin on the micturition reflex in anaesthetized. *Br. J. Pharmacol.*, 24: 1566-1572; Giuliani, et al. (1999). Nociceptin protects capsaicin-sensitive afferent fibers in the rat urinary bladder from desensitization. Nanyn Schmiedeberg's *Arch. Pharmacol.*, 360: 202-208; Lecci, et al. (2000). Multiple sites of action in the inhibitory effect of nociceptin on the micturition reflex. *J. Urology*, 163: 638-645), renal function (see for e.g., Kapusta, et al. (1997). Diuretic and antinatriuretic responses produced by the endogenous opioid-like peptide, noceptin (orphanin FQ). Life Sci., 60: PLI5-PL21; Kapusta, et al. (1999). Central administration of [Phe1psi(CH2-NH)Gly2]nociceptin(1-13)-NH2 and orphanin FQ/nociceptin (OFQ/N) produce similar cardiovascular and renal responses in conscious rats. J. Pharmacol. Exp. Ther., 289: 173-180; drug abuse (see for e.g., Devine et al. (1996). The novel neuropeptide orphanin FQ fails to produce conditioned place preference or aversion. *Brain Res.*, 727: 225-229; Ciccocioppo, et al. (1999). Effect of nociceptin on alcohol intake in alcohol-preferring rats. *Psychopharmacology*, 141: 220-224; Angeletti, et al., (1999). Effect of nociceptin on morphine-induced conditioned place preference in rats. *Regulatory Peptides*, 80: 122; Murphy et al. (1999). Orphanin FQ/nociceptin blocks acquisition of morphine place preference. *Brain Res.*, 832: 168-170; Pieretti & Di Giannuario (1999). Orphanin FQ effects on morphine-induced dopamine release in the accumbens of rats. *Regulatory Peptides*, 80: 126; Walker et al. (1998). Nociceptin fails to affect heroin self-administration in the rat. *Neuroreport*, 9: 2243-2247; Narayanan & Maidment (1999). Orphanin FQ and behavioral sensitization to cocaine. *Pharmacol. Biochem. Behav.*, 63: 271-277), memory disorders (see for e.g., Sandin, et al. (1997). Nociceptin/orphanin FQ microinjected into hippocampus impairs spatial learning in rats. *Eur. J. Neurosci.*, 9: 194-197; Yu, et al. (1997). Orphanin FQ inhibits synaptic transmission and long-term potentiation in rat hippocampus. *Hippocampus*, 7: 88-94; Yu & Xie (1998). Orphanin FQ/nociceptin inhibits synaptic transmission and long-term potentiation in rat dentate gyrus through postsynaptic mechanisms. *J. Neurophysiol.*, 80: 1277-1284; Manabe, et al. (1998). Facilitation of long-term potentiation and memory in mice lacking nociceptin receptors. *Nature*, 394: 577-581; Hiramatsu & Inoue (1999). Effects of nocistatin on nociceptin-induced impairment of learning and memory in mice. *Eur. J. Pharmacol.*, 367: 151-155; Mamiya, et al. (1999). Nociceptin system plays a role in the memory retention: involvement of naloxone benzoylhydrazone binding sites. *Neuroreport*, 10: 1171-1175; Hiramatsu & Inoue (2000). Improvement by low doses of nociceptin on scopolamine-induced impairment of learning and/or memory. *Eur. J. Pharmacol.*, 395: 149-156), depression (see for e.g. Rizzi, et al. (2011). Nociceptin/orphanin FQ receptor knockout rats: in vitro and in vivo studies. *Neuropharmacology*, 60: 572-579; Goeldner, et al. (2010). Endogenous nociceptin/orphanin-FQ in the dorsal hippocampus facilitates despair-related behavior. *Hippocampus*, 20: 911-916; Vitale, et al. (2009). Chronic treatment with the selective NOP receptor antagonist [Nphe 1, Arg 14, Lys 15]N/OFQ-NH2 (UFP-101) reverses the behavioural and biochemical effects of unpredictable chronic mild stress in rats. *Psychopharmacology*, 207: 173-189; Zambello, et al. (2008). Acute stress differentially affects corticotropin-releasing hormone mRNA expression in the central amygdala of the "expressed" flinders sensitive line and the control flinders resistant line rats. *Progress in Neuro-Psychopharmacology & Biological Psychiatry,* 32: 651-661; Gavioli & Calo' (2006). Antidepressant- an anxiolytic-like effects of nociceptin/orphanin FQ receptor ligands. *Naunyn-Schmiedebergs Arch. Pharmacol.,* 372: 319-330; Gavioli, et al. (2003). Blockade of nociceptin/orphanin FQ-NOP receptor signalling produces antidepressant-like effects: pharmacological and genetic evidences from the mouse forced swimming test. *Eur. J. Neurosci.,* 17: 1987-1990) or locomotor disorders (such as Parkinsonism) (see for e.g., Reinscheid, et al. (1995). Orphanin FQ: a neuropeptide that activates an opioidlike G protein-coupled receptor. *Science,* 270: 792-794; Calo' et al. (1999). Characterization of nociceptin receptors modulating locomotor activity in mice. *Fund. Clin. Pharmacol.,* 13-S1: S27.6; Devine, et al. (1996). Rats rapidly develop tolerance to the locomotor-inhibiting effects of the novel neuropeptide orphanin FQ. *Neurochem. Res.,* 21: 1387-1396; Noble & Roques (1997). Association of aminopeptidase N and endopeptidase 14.15 inhibitors potentiate behavioral effects mediated by nociceptin/orphanin FQ in mice. *FEBS Lett.,* 401: 227-229; Florin, et al. (1996). Nociceptin stimulates locomotion and exploratory behaviour in mice. *Eur. J Pharmacol.,* 317: 9-13) (each being a "Condition") in an animal. For a general discussion of ORL1 receptors see. Calo' et al. (2000). Pharmacology of nociceptin and its receptor: a novel therapeutic target. *Br. J. Pharmacol.* 129: 1261-1283.

In one aspect, the disclosure provides pharmaceutical compositions comprising an effective amount of a Compound of Formula (I) and a pharmaceutically acceptable carrier or excipient. Such compositions are useful for treating or preventing a Condition in an animal.

In another aspect, Compounds of Formula (I) may be used in the manufacture of a medicament useful for treating a Condition or for preventing a Condition.

In another aspect, the disclosure provides methods for treating or preventing a Condition in an animal, comprising administering an effective amount of a Compound of Formula (I) to an animal in need of said treatment or prevention.

In another aspect, the disclosure provides methods for inhibiting ORL-1 receptor function in a cell, comprising contacting a cell capable of expressing the ORL-1 receptor with an ORL-1 receptor function-inhibiting amount of a Compound of Formula (I). In another aspect, the disclosure provides methods for activating ORL-1 receptor function in a cell, comprising contacting a cell capable of expressing the ORL-1 receptor with an ORL-1 receptor function-activating amount of a Compound of Formula (I).

In yet another aspect, the disclosure provides methods for preparing a pharmaceutical composition, comprising the step of admixing a Compound of Formula (I) and a pharmaceutically acceptable carrier or excipient.

In yet another aspect, the disclosure provides a kit comprising a container containing an effective amount of a Compound of Formula (I).

In yet another aspect, the disclosure provides novel intermediates for use in making a Compound of Formula (I). In certain embodiments, the bicyclic compound is an indole.

The disclosure can be understood more fully by reference to the following detailed description and illustrative examples, which are intended to exemplify non-limiting embodiments of the disclosure.

4. DETAILED DESCRIPTION

The invention includes the following:
(1) A compound of Formula (I):

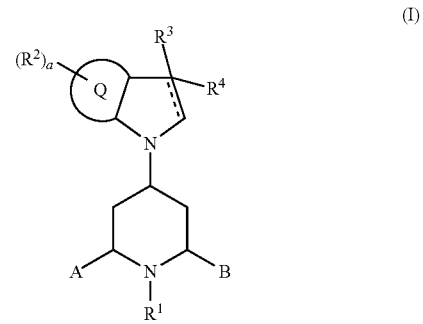

and the pharmaceutically acceptable salts and solvates thereof, wherein $R^1$, $R^2$, $R^3$, $R^4$, Q, A, B and a are as defined above.

(2) The compound of the above (1) or a pharmaceutically acceptable salt or solvate thereof, wherein Y is O.

(3) The compound of the above (1) or (2) or a pharmaceutically acceptable salt or solvate thereof, wherein $R^3$ is selected from —H, —C(=O)C(=O)OH, —C(=O)C(=O)NH$_2$, —CH$_2$C(=O)OH, —CH$_2$C(=O)NH$_2$, —CF$_2$C(=O)OH and —CF$_2$C(=O)NH$_2$.

(4) The compound of any one of the above (1) to (3) or a pharmaceutically acceptable salt or solvate thereof, wherein $R^3$ is selected from —C(=O)C(=O)OH, —C(=O)C(=O)NH$_2$, —CH$_2$C(=O)OH and —CH$_2$C(=O)NH$_2$.

(5) The compound of any one of the above (1) to (4) or a pharmaceutically acceptable salt or solvate thereof, wherein Q is benzo, pyridino, pyrimidino, pyrazino, or pyridazino, and preferably Q is benzo or pyridino, wherein preferably the 2- and 3-positions of the pyridino are fused to the 6-membered, nitrogen-containing ring.

(6) The compound of any one of the above (1) to (5) or a pharmaceutically acceptable salt or solvate thereof, wherein Q is fused benzo.

(7) The compound of any one of the above (1) to (5) or a pharmaceutically acceptable salt or solvate thereof, wherein Q is fused pyridyl.

(8) The compound of any one of the above (1) to (7) or a pharmaceutically acceptable salt or solvate thereof, wherein the dashed line is present.

(9) The compound of any one of the above (1) to (7) or a pharmaceutically acceptable salt or solvate thereof, wherein the dashed line is absent and $R^4$ is H.

(10) The compound of any one of the above (1) to (9) or a pharmaceutically acceptable salt or solvate thereof, wherein a is 0.

(11) The compound of any one of the above (1) to (10) or a pharmaceutically acceptable salt or solvate thereof, wherein $R^1$ is selected from ($C_3$-$C_7$)cycloalkoxy, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, and -(3- to 8-membered)heterocycle, each of which is unsubstituted or substituted with 1, 2, 3, or 4 independently selected $R^8$ groups.

(12) The compound of any one of the above (1) to (10) or a pharmaceutically acceptable salt or solvate thereof, wherein R¹ is —(C₃-C₄)cycloalkyl, which is unsubstituted or substituted with 1, 2, 3, or 4 independently selected R⁸ groups.

(13) The compound of any one of the above (1) to (10) or a pharmaceutically acceptable salt or solvate thereof, wherein R¹ is —(C₈-C₁₀)cycloalkyl, which is unsubstituted.

(14) The compound of any one of the above (1) to (10) or a pharmaceutically acceptable salt or solvate thereof, wherein R¹ is —(C₈-C₁₀)cycloalkyl, which is substituted with 1 R⁸ group.

(15) The compound of any one of the above (1) to (10) or a pharmaceutically acceptable salt or solvate thereof, wherein R¹ is —C₉-C₁₀ cycloalkyl, which is unsubstituted or substituted with 1 R⁸ group.

(16) The compound of any one of the above (1) to (10) or a pharmaceutically acceptable salt or solvate thereof, wherein R¹ is —C₁₀)cycloalkyl, which is unsubstituted.

(17) The compound of any one of the above (1) to (10) or a pharmaceutically acceptable salt or solvate thereof, wherein R¹ is —C₁₀ cycloalkyl, which is substituted with 1 R⁸ group.

(18) The compound of any one of the above (1) to (10) or a pharmaceutically acceptable salt or solvate thereof, wherein R¹ is:

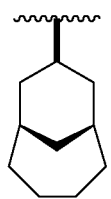

(19) The compound of any of the above (1) to (10) or a pharmaceutically acceptable salt or solvate thereof, wherein R¹ is:

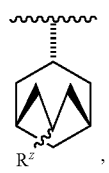

wherein R$^z$ is —H or —(C₁-C₆)alkyl.

(20) The compound of any one of the above (1) to (10) or a pharmaceutically acceptable salt or solvate thereof, wherein —R₁ is:

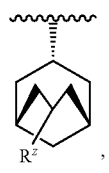

wherein R$_z$ is —H, —CH₃, or —CH₂CH₃.

(21) The compound of any one of the above (1) to (10) or a pharmaceutically acceptable salt or solvate thereof, wherein R¹ is:

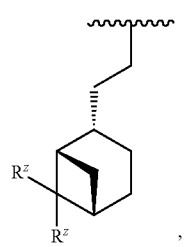

wherein each R$^z$ is independently —H, —(C₁-C₄)alkyl, —OH, or —CN and preferably each R$^z$ is independently —H, —CH₃, or —CH₂CH₃.

(22) The compound of any of the above (1) to (10) or a pharmaceutically acceptable salt or solvate thereof, where R¹ is

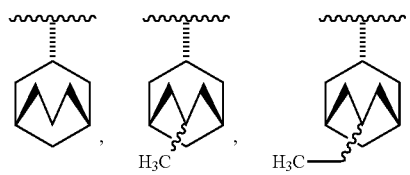

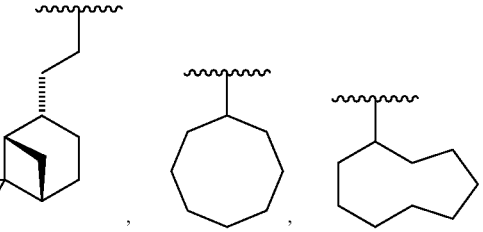

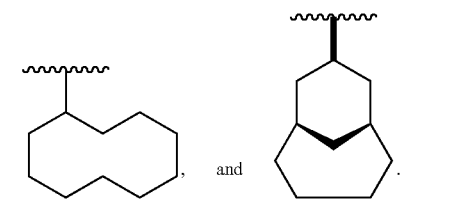

(23) The compound of any one of the above (1) to (10) or a pharmaceutically acceptable salt or solvate thereof, wherein R₁ is:

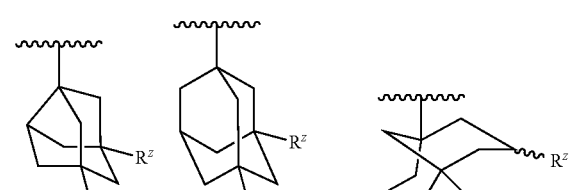

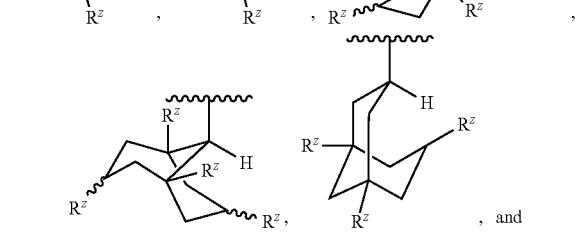

17

-continued

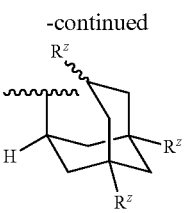

wherein each $R_z$ is independently —H, —(C$_1$-C$_4$)alkyl, —OH, or —CN and preferably each $R_z$ is independently —H, —CH$_3$, or —CH$_2$CH$_3$.

(24) The compound of any one of the above (1) to (10) or a pharmaceutically acceptable salt or solvate thereof, wherein —R$_1$ is:

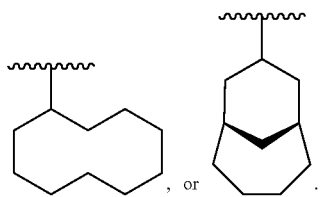

(25) The compound of any one of the above (1) to (24) or a pharmaceutically acceptable salt or solvate thereof, wherein A and B together form a bridge such that the bridged-piperidine is:

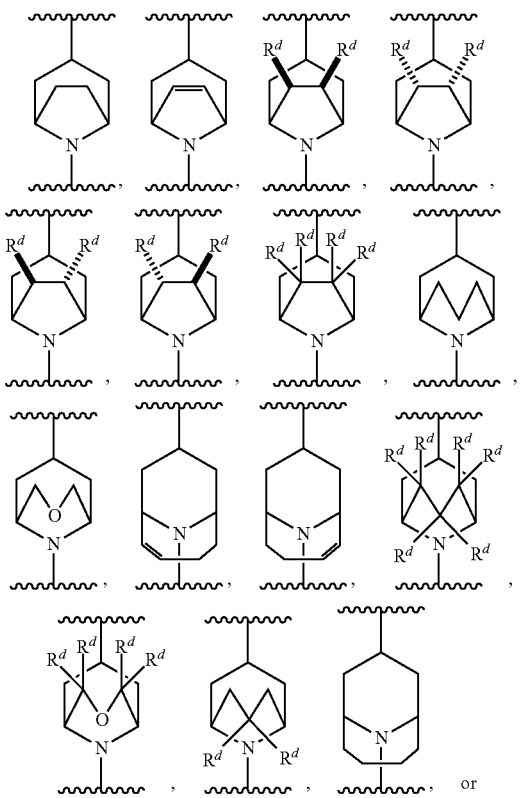

18

-continued

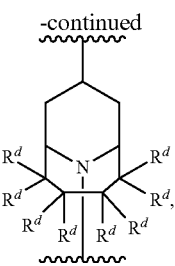

wherein each $R^d$ is independently selected from —H, —(C$_1$-C$_6$)alkyl, -halo, —C(halo)$_3$, —CH(halo)$_2$, and —CH$_2$(halo).

(26) The compound of any one of the above (1) to (24) or a pharmaceutically acceptable salt or solvate thereof, wherein A and B together form a bridge such that the bridged-piperidine is:

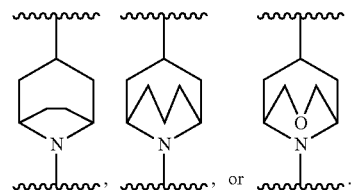

(27) The compound of any one of the above (1) to (24) or a pharmaceutically acceptable salt or solvate thereof, wherein A and B together form a bridge such that the bridged-piperidine is:

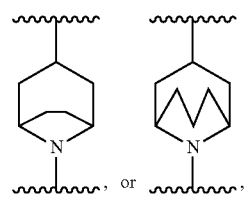

(28) The compound of any one of the above (1) to (24) or a pharmaceutically acceptable salt or solvate thereof, wherein the A-B bridge of the bridged-piperidine is in the endo-configuration with respect to the 5-membered, nitrogen-containing ring that is fused to the Q ring.

(29) The compound of any one of the above (1) to (28), or a pharmaceutically acceptable salt or solvate thereof, wherein a is 1 and R$^2$ is -halo.

(30) The compound of the above (1) or a pharmaceutically acceptable salt or solvate thereof, wherein:

Q is benzo;

a is 0;

A-B together form a (C$_2$-C$_6$)bridge, which is unsubstituted or substituted with 1, 2, 3, or 4 substituents independently selected from —OH, —(C$_1$-C$_4$)alkyl, -halo, and —C(halo)$_3$, and which bridge optionally contains —HC=CH— or —O— within the (C$_2$-C$_6$)bridge; wherein the A-B bridge can be in the endo- or exo-configuration with respect to the 5-membered, nitrogen-containing ring that is fused to the Q$_a$ ring; and R$^1$ is selected from (C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{4}$)bicycloalkenyl, —(C$_8$-C$_{20}$)tricycloalkenyl, and -(3- to 8-membered)heterocycle, each of which is unsubstituted or substituted with 1, 2, 3, or 4 independently selected R$^8$ groups.

(31) The compound of the above (1) or a pharmaceutically acceptable salt or solvate thereof, wherein:

Q is benzo;

a is 0;

A-B together form a ($C_2$-$C_6$)bridge, which is unsubstituted or substituted with 1, 2, 3, or 4 substituents independently selected from —OH, —($C_1$-$C_4$)alkyl, -halo, and —C(halo)$_3$, and which bridge optionally contains —HC=CH— or —O— within the ($C_2$-$C_6$)bridge; wherein the A-B bridge can be in the endo- or exo-configuration with respect to the 5-membered, nitrogen-containing ring that is fused to the $Q_a$ ring; and $R^1$ is ($C_8$-$C_{10}$)cycloalkyl, each of which is unsubstituted or unsubstituted with 1 or 2 independently selected $R^8$ groups.

(32) The compound of the above (30) or (31), wherein $R^3$ is selected from —C(=O)C(=O)OH, —C(=O)C(=O)NH$_2$, —CH$_2$C(=O)OH and —CH$_2$C(=O)NH$_2$.

(33) The compound of the above (1) or a pharmaceutically acceptable salt or solvate thereof, wherein the compound has the structure:

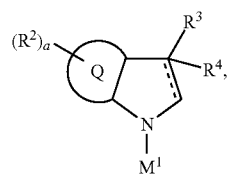

wherein $M^1$ is selected from:

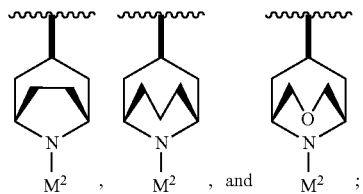

and $M^2$ is selected from:

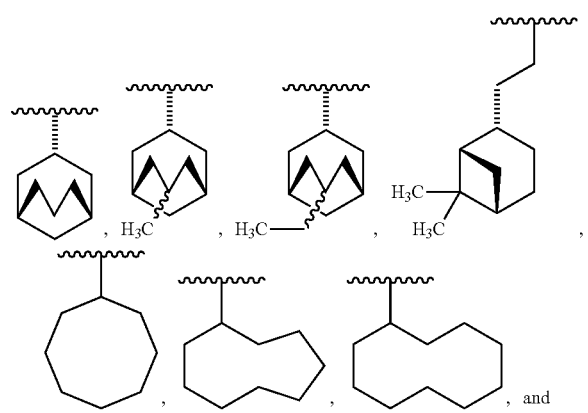

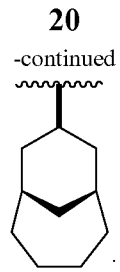

(34) The compound of (33), wherein the compound has the structure:

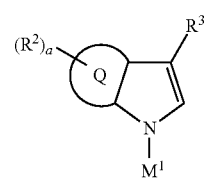

or a pharmaceutically acceptable salt or solvate thereof.

(35) The compound of (33), wherein the compound has the structure:

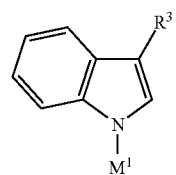

or a pharmaceutically acceptable salt or solvate thereof.

(36) The compound of any of the above (33) to (35) or a pharmaceutically acceptable salt or solvate thereof, wherein $R^3$ is selected from —H, —C(=O)C(=O)OH, —C(=O)C(=O)NH$_2$, —CH$_2$C(=O)OH, —CH$_2$C(=O)NH$_2$, —CF$_2$C(=O)OH and —CF$_2$C(=O)NH$_2$.

(37) The compound of any of the above (33) to (35) or a pharmaceutically acceptable salt or solvate thereof, wherein $R^3$ is selected from —C(=O)C(=O)OH, —C(=O)C(=O)NH$_2$, —CH$_2$C(=O)OH and —CH$_2$C(=O)NH$_2$.

(38) The compound of the above (1), wherein the compound is of Formula (IAE):

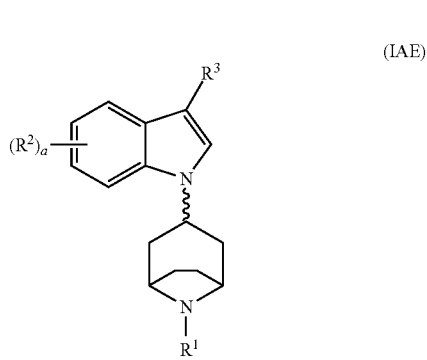

(IAE)

or a pharmaceutically acceptable salt or solvate thereof.

(39) The compound of the above (1), wherein the compound is of Formula (IAE$_1$):

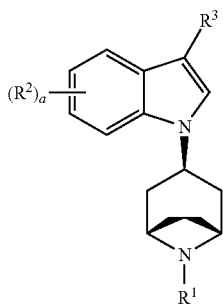

(IAE$_1$)

or a pharmaceutically acceptable salt or solvate thereof.

(40) The compound of the above (1), wherein the compound is of Formula (IAH):

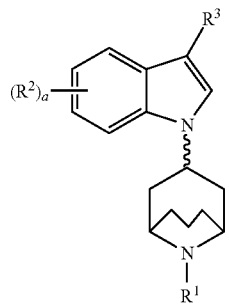

(IAH)

or a pharmaceutically acceptable salt or solvate thereof.

(41) The compound of (1), wherein the compound is of Formula (IAH$_1$):

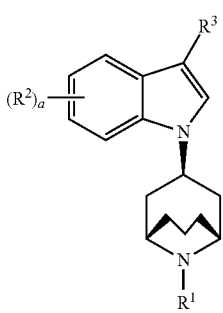

(IAH$_1$)

or a pharmaceutically acceptable salt or solvate thereof.

(42) The compound of the above (1), wherein the compound has the following chemical formula:

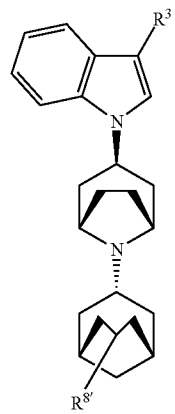

or a pharmaceutically acceptable salt or solvate thereof, wherein $R^{8'}$ is selected from the group consisting of —H, and —(C$_1$-C$_4$)alkyl.

(43) The compound of the above (1), wherein the compound has the following chemical formula:

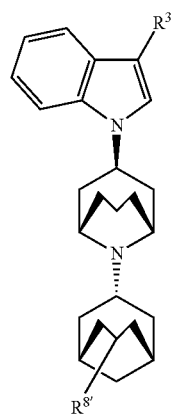

or a pharmaceutically acceptable salt or solvate thereof, wherein $R^{8'}$ is selected from the group consisting of —H, and —(C$_1$-C$_4$)alkyl.

(44) The compound of the above (1), wherein the compound has the following chemical formula:

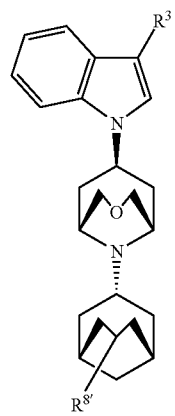

or a pharmaceutically acceptable salt or solvate thereof, wherein $R^{8t}$ is selected from the group consisting of —H, and —$(C_1$-$C_4)$alkyl.

(45) The compound of the above (1), wherein the compound has the following chemical formula:

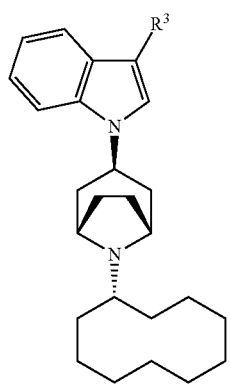

or a pharmaceutically acceptable salt or solvate thereof.

(46) The compound of the above (1), wherein the compound has the following chemical formula:

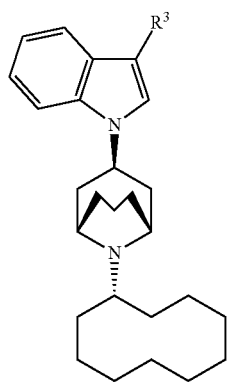

or a pharmaceutically acceptable salt or solvate thereof.

(47) The compound of any one of the above (38) to (46) or a pharmaceutically acceptable salt or solvate thereof, wherein $R^3$ is selected from —H, —C(=O)C(=O)OH, —C(=O)C(=O)NH$_2$, —CH$_2$C(=O)OH, —CH$_2$C(=O)NH$_2$, —CF$_2$C(=O)OH and —CF$_2$C(=O)NH$_2$.

(48) The compound of any one of the above (38) to (46) or a pharmaceutically acceptable salt or solvate thereof, wherein $R^3$ is selected from —C(=O)C(=O)OH, —C(=O)C(=O)NH$_2$, —CH$_2$C(=O)OH and —CH$_2$C(=O)NH$_2$.

(49) The compound of any one of the above (38) to (46) or a pharmaceutically acceptable salt or solvate thereof, wherein $R^3$ is selected from —C(=O)C(=O)OH, and —CH$_2$C(=O)OH.

(50) A compound selected from:

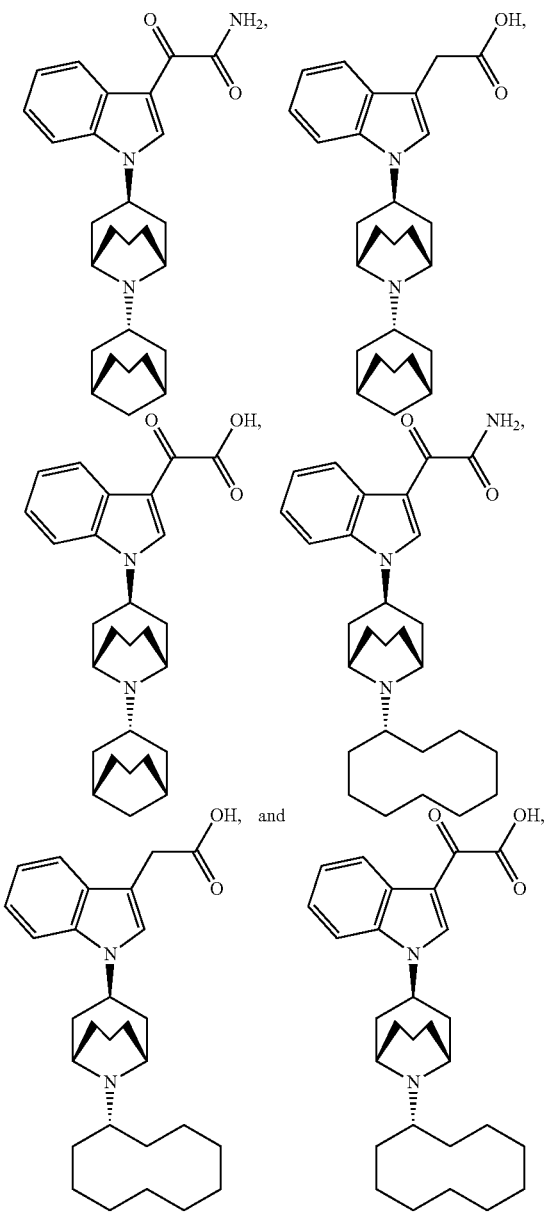

or a pharmaceutically acceptable salt or solvate thereof.

(51) A compound selected from:

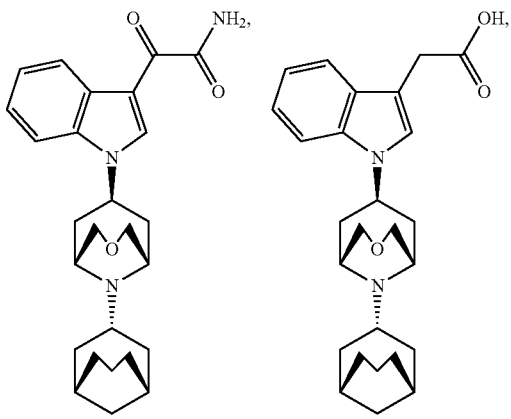

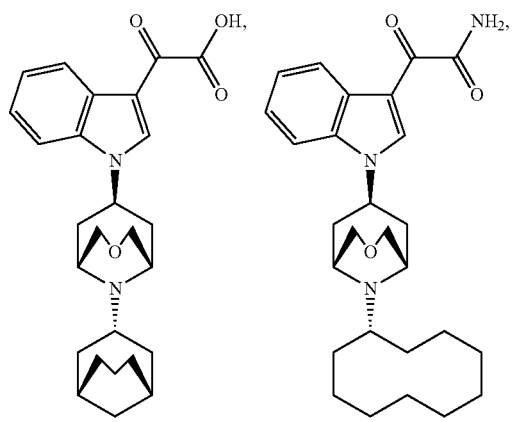
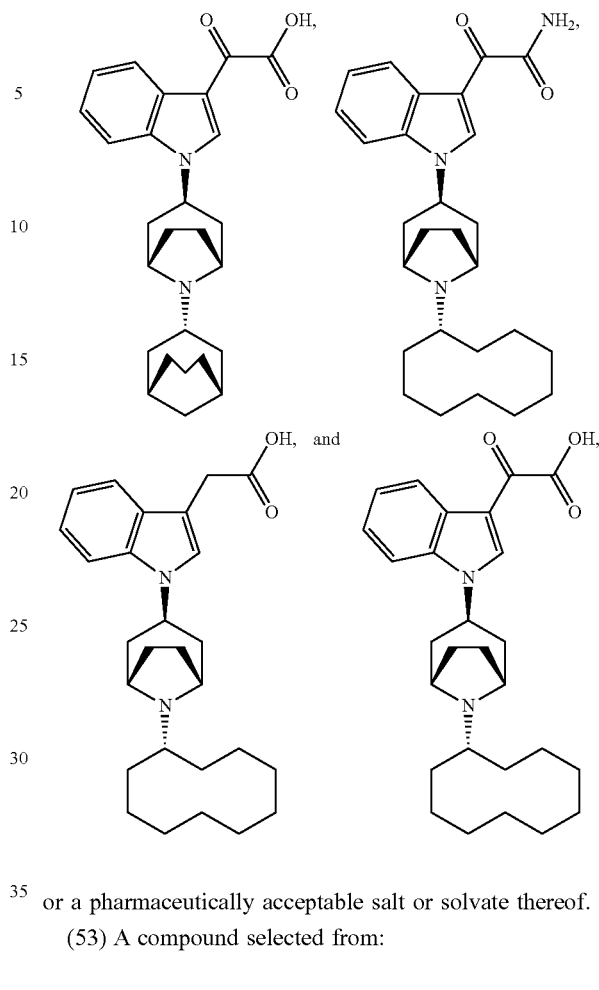
or a pharmaceutically acceptable salt or solvate thereof.
(52) A compound selected from:
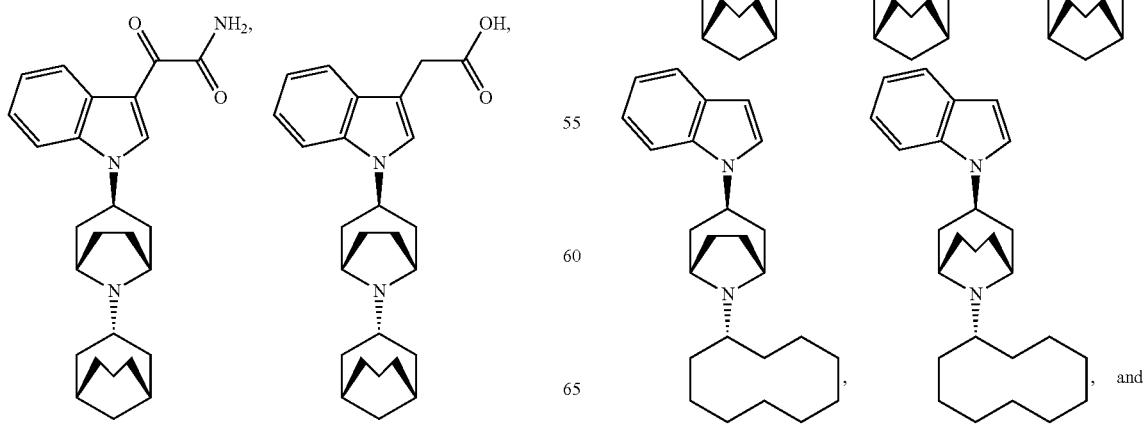
or a pharmaceutically acceptable salt or solvate thereof.
(53) A compound selected from:

-continued

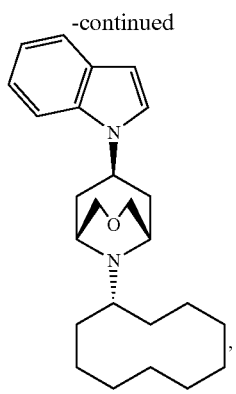

or a pharmaceutically acceptable salt or solvate thereof.

(54) A compound selected from:

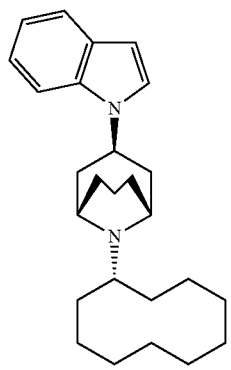

or a pharmaceutically acceptable salt thereof.

(55) The compound of any one of the above (1) to (54) or a pharmaceutically acceptable salt or solvate thereof, which is radiolabeled.

(56) The compound of any one of the above (1) to (55), wherein the pharmaceutically acceptable salt or solvate is a pharmaceutically acceptable salt, preferably a hydrochloride-salt, a sodium-salt, a potassium-salt, or a para-toluenesulfonic acid-salt.

(57) The compound of any one of the above (1) to (56) or a pharmaceutically acceptable salt or solvate thereof, wherein the % de of the compound is at least about 95%.

(58) The compound of the above (57) or a pharmaceutically acceptable salt or solvate thereof, wherein the % de of the compound is at least about 99%.

(59) A composition comprising an effective amount of the compound or a pharmaceutically acceptable salt or solvate of the compound of any one of the above (1) to (58) and a pharmaceutically acceptable carrier or excipient.

(60) A method for preparing a composition, comprising the step of admixing a compound or a pharmaceutically acceptable salt or solvate of the compound of any one of the above (1) to (58) and a pharmaceutically acceptable carrier or excipient.

(61) A method for modulating ORL-1 receptor function in a cell, comprising contacting a cell capable of expressing the ORL-1 receptor with an effective amount of the composition or the compound or a pharmaceutically acceptable salt or solvate of the compound of any one of the above (1) to (59).

(62) The method of the above (61), wherein the composition or the compound or the pharmaceutically acceptable salt or solvate of the compound acts as an agonist at the ORL-1 receptor.

(63) The method of the above (61), wherein the composition or the compound or the pharmaceutically acceptable salt or solvate of the compound acts as a partial agonist at the ORL-1 receptor.

(64) The method of the above (61), wherein the composition or the compound or the pharmaceutically acceptable salt or solvate of the compound acts as an antagonist at the ORL-1 receptor.

(65) A method for treating pain in an animal, comprising administering to an animal in need thereof an effective amount of the composition or the compound or a pharmaceutically acceptable salt or solvate of the compound of any one of the above (1) to (59).

(66) A method for treating a memory disorder, obesity, constipation, depression, Parkinsonism, anxiety, cough, diarrhea, high blood pressure, epilepsy, anorexia/cachexia, urinary incontinence, drug abuse, a sleep disorder, a metabolic disorder, a renal disorder, or a cardiovascular disorder in an animal, comprising administering to an animal in need thereof an effective amount of the composition or the compound or a pharmaceutically acceptable salt or solvate of the compound of any one of the above (1) to (59).

(67) Use of a compound or the pharmaceutically acceptable salt or solvate of the compound of any one of the above (1) to (58) for the manufacture of a medicament useful for treating pain, a memory disorder, obesity, constipation, depression, dementia, Parkinsonism, anxiety, cough, diarrhea, high blood pressure, epilepsy, anorexia/cachexia, urinary incontinence, drug abuse, a sleep disorder, a metabolic disorder, a renal disorder, or a cardiovascular disorder.

(68) The compound or the pharmaceutically acceptable salt or solvate of the compound of any one of the above (1) to (58) for use in the treatment of pain, a memory disorder, obesity, constipation, depression, dementia, Parkinsonism, anxiety, cough, diarrhea, high blood pressure, epilepsy, anorexia/cachexia, urinary incontinence, drug abuse, a sleep disorder, a metabolic disorder, a renal disorder, or a cardiovascular disorder.

(69) A kit, comprising a sterile container containing an effective amount of the composition or the compound or a pharmaceutically acceptable salt or solvate of the compound of any one of the above (1) to (59).

4.1. Bicyclic Pyrrole and Dihydropyrrole Containing Compounds of Formula (I)

As stated above, Compounds of Formula (I) encompass indole-type piperidine compounds, indoline-type piperidine compounds and related piperidine-type bicyclic compounds containing a five-membered nitrogen-containing ring (e.g., pyrrole or dihydropyrrole) fused to a benzo or heteroaryl ring. Such compounds are represented schematically in Formula (I):

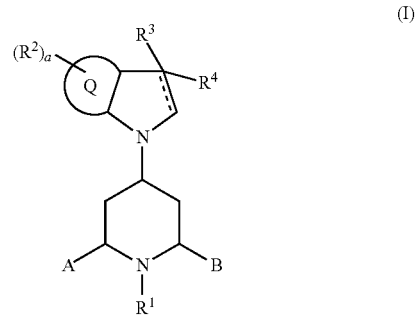

and include the pharmaceutically acceptable salts or solvates thereof, including pharmaceutically acceptable salts and solvates thereof, where $R^1$, $R^2$, $R^3$, $R^4$, Q, A, B and a are defined above.

In one embodiment, a is 0 or 1. In another embodiment, a is 0. In another embodiment, a is 1.

In another embodiment, a is 2.

In another embodiment, each $R^2$ is independently -halo, —OH, —NH$_2$, —CN, —(C$_1$-C$_6$)alkyl, —(C$_3$-C$_7$)cycloalkyl, -(5- or 6-membered)heterocycle, -phenyl, -naphthalenyl, or -(5- or 6-membered)heteroaryl.

In another embodiment, a is 1 and $R^2$ is -halo, —OH, —NH$_2$, —CN, —(C$_1$-C$_6$)alkyl, —(C$_3$-C$_7$)cycloalkyl, -(5- or 6-membered)heterocycle, -phenyl, -naphthalenyl, or -(5- or 6-membered)heteroaryl. In another embodiment, a is 1 and $R_2$ is -halo, —OH, —NH$_2$, —CN, methyl, ethyl, n-propyl, iso-propyl, cyclopentyl, cyclohexyl, cycloheptyl, or phenyl. In another embodiment, a is 1 and $R_2$ is -halo. In another embodiment, a is 1 and $R_2$ is —F or —Cl. In another embodiment, a is 1 and $R_2$ is —F. In another embodiment, a is 1 and $R_2$ is —Cl.

In another embodiment, a is 2 and each $R^2$ is independently -halo, —OH, —NH$_2$, —CN, —(C$_1$-C$_6$)alkyl, —(C$_3$-C$_7$)cycloalkyl, -(5- or 6-membered)heterocycle, -phenyl, -naphthalenyl, or -(5- or 6-membered)heteroaryl. In another embodiment, a is 2 and each $R^2$ is independently -halo, —OH, —NH$_2$, —CN, methyl, ethyl, n-propyl, iso-propyl, cyclopentyl, cyclohexyl, cycloheptyl, or phenyl. In another embodiment, a is 2 and each $R^2$ is -halo. In another embodiment, a is 2 and each $R^2$ is —F or —Cl. In another embodiment, a is 2 and each $R^2$ is —F. In another embodiment, a is 2 and each $R^2$ is —Cl.

In another embodiment, Q is benzo, pyridino, pyrimidino, pyrazino, pyridazino, pyrrolino, imidazolino, pyrazolino, triazolino, furano, oxazolino, isoxazolino, oxadiazolino, thiopheno, thiazolino, isothiazolino, or thiadiazolino. In another embodiment, Q is benzo, pyrrolino, imidazolino, pyrazolino, triazolino, furano, oxazolino, isoxazolino, oxadiazolino, thiopheno, thiazolino, isothiazolino, or thiadiazolino. In another embodiment, Q is benzo, imidazolino, pyrazolino, triazolino, oxazolino, isoxazolino, oxadiazolino, thiazolino, isothiazolino, or thiadiazolino. In another embodiment, $Q_a$ is benzo, pyrrolino, imidazolino, pyrazolino, or triazolino. In another embodiment, Q is benzo, furano, oxazolino, isoxazolino, or oxadiazolino. In another embodiment, Q is benzo, oxazolino, isoxazolino, or oxadiazolino. In another embodiment, Q is benzo, thiopheno, thiazolino, isothiazolino, or thiadiazolino. In another embodiment, Q is benzo, thiazolino, isothiazolino, or thiadiazolino. In another embodiment, Q is benzo, pyrrolino, furano, or thiopheno. In another embodiment, Q is pyridino, pyrimidino, pyrazino, pyridazino, pyrrolino, imidazolino, pyrazolino, triazolino, furano, oxazolino, isoxazolino, oxadiazolino, thiopheno, thiazolino, isothiazolino, or thiadiazolino. In another embodiment, Q is pyrrolino, imidazolino, pyrazolino, triazolino, furano, oxazolino, isoxazolino, oxadiazolino, thiopheno, thiazolino, isothiazolino, or thiadiazolino. In another embodiment, Q is imidazolino, pyrazolino, triazolino, oxazolino, isoxazolino, oxadiazolino, thiopheno, thiazolino, isothiazolino, or thiadiazolino. In another embodiment, Q is pyrrolino, imidazolino, pyrazolino, or triazolino. In another embodiment, Q is furano, oxazolino, isoxazolino, or oxadiazolino. In another embodiment, Q is oxazolino, isoxazolino, or oxadiazolino. In another embodiment, Q is thiopheno, thiazolino, isothiazolino, or thiadiazolino. In another embodiment, Q is thiazolino, isothiazolino, or thiadiazolino. In another embodiment, Q is pyrrolino, furano, or thiopheno. In another embodiment, Q, is benzo, pyridino, pyrimidino, pyrazino, or pyridazino. In another embodiment, Q is benzo, pyrimidino, pyrazino, or pyridazino. In another embodiment, Q is pyridino, pyrimidino, pyrazino, or pyridazino. In another embodiment, Q is pyrimidino, pyrazino, or pyridazino. In another embodiment, Q is benzo or pyridino. In another embodiment, Q is benzo. In another embodiment, Q is pyridino.

In another embodiment, $R^3$ is —H, —(C$_1$-C$_6$)alkyl-, —(CH$_2$)—C(=O)CN, —(CH$_2$)—C(=O)OH, —(CH$_2$)$_2$—C(=O)OH, —(CH$_2$)—C(=O)NH$_2$, —(CH$_2$)$_2$—C(=O)NH$_2$, —(CH$_2$)—C(=O)O(C$_1$-C$_6$)alkyl, —(CH$_2$)$_2$—C(=O)O(C$_1$-C$_6$)alkyl, —(CH$_2$)—C(=O)NH(C$_1$-C$_6$)alkyl, —(CH$_2$)$_2$—C(=O)NH(C$_1$-C$_6$)alkyl, —(CH$_2$)—C(=O)N((C$_1$-C$_6$)alkyl)$_2$, or —(CH$_2$)$_2$—C(=O)N((C$_1$-C$_6$)alkyl)$_2$.

In another embodiment, $R^3$ is —C(=O)C(=O)OH, —C(=O)C(=O)O(C$_1$-C$_6$)alkyl, —C(=O)C(=O)NH$_2$, —C(=O)C(=O)NH(C$_1$-C$_6$)alkyl, —C(=O)C(=O)N((C$_1$-C$_6$)alkyl)$_2$, C(=S)C(=S)OH, —C(=S)C(=S)O(C$_1$-C$_6$)alkyl, —C(=S)C(=S)NH$_2$, —C(=S)C(=S)NH(C$_1$-C$_6$)alkyl or —C(=S)C(=S)N((C$_1$-C$_6$)alkyl)$_2$.

In another embodiment, $R^1$ is (C$_3$-C$_7$)cycloalkoxy, —(C$_3$-C$_{14}$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, and -(3- to 8-membered)heterocycle, each of which is unsubstituted or substituted with 1, 2, 3, or 4 independently selected $R^8$ groups. In another embodiment, $R^1$ is (C$_3$-C$_7$)cycloalkoxy, —(C$_3$-C$_4$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, and -(3- to 8-membered)heterocycle and $R^8$ is —(C$_1$-C$_4$)alkyl.

In another embodiment, $R^1$ is optionally substituted cyclooctyl. In another embodiment, $R_1$ is optionally substituted cyclooctenyl. In another embodiment, $R_1$ is optionally substituted anthryl. In another embodiment, $R^1$ is —C$_8$ bicycloalkyl. In another embodiment, $R^1$ is —C$_9$ bicycloalkyl. In another embodiment, $R^1$ is —C$_8$ bicycloalkyl and $R^8$ is —CH$_3$. In another embodiment, $R^1$ is —C$_9$ bicycloalkyl and $R^8$ is —CH$_3$. In another embodiment, $R_1$ is optionally substituted noradamantyl.

In another embodiment, $R^1$ is:

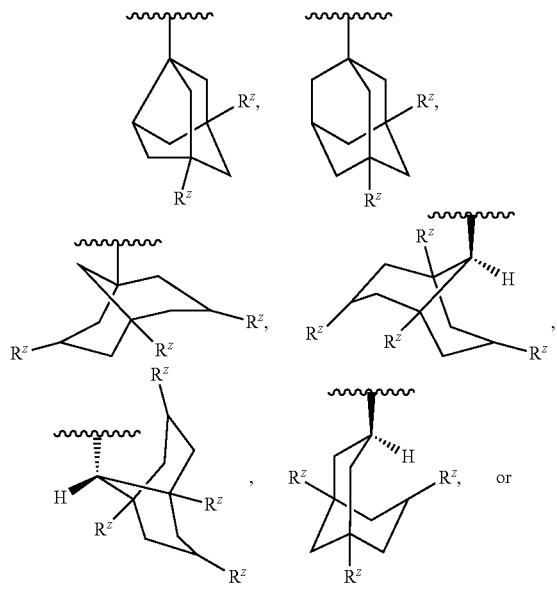

-continued

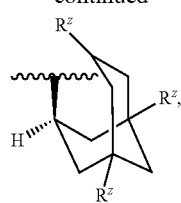

where each $R^z$ is independently —H, —$(C_1$-$C_4)$alkyl, —OH, or —CN and preferably each $R^z$ is independently —H, —$CH_3$, or —$CH_2CH_3$.

In another embodiment, $R^1$ is:

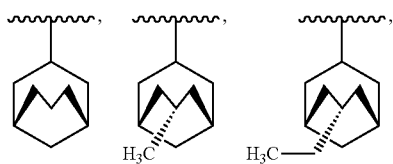

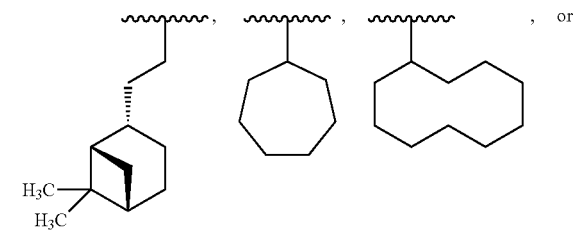

In another embodiment, $R^1$ is:

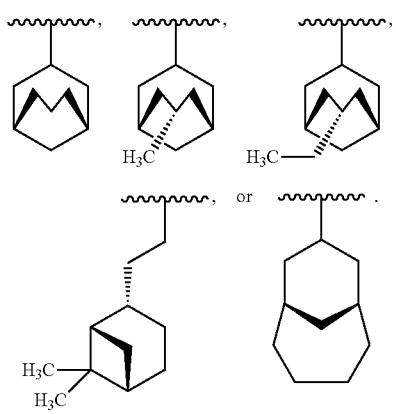

In another embodiment, $R^1$ is:

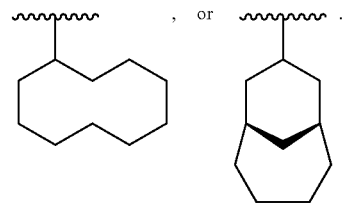 [SMILES: *C1CCCCCCCCC1 ; *C1C[C@H]2CCCC[C@@H](C1)C2]

In another embodiment, $R^1$ is:

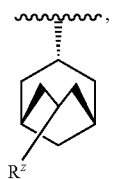

where $R^z$ is —H, —$CH_3$, or —$CH_2CH_3$.

In another embodiment, $R^1$ is:

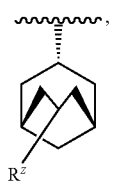

where $R^z$ is —H, or —$(C_1$-$C_4)$alkyl.

In another embodiment. $R_1$ is

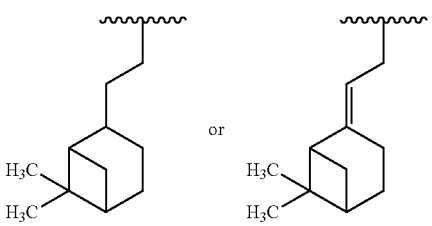

In another embodiment, A and B are independently selected from:
(a) —H, —CN, —C(=O)$OT_3$, and —C(=O)N($T_1$)($T_2$); and
(b) —$(C_3$-$C_2)$cycloalkyl, —$(C_3$-$C_1$2)cycloalkoxy, —$(C_1$-$C_6)$alkyl, —$(C_2$-$C_6)$alkenyl, —$(C_2$-$C_6)$alkynyl, and —$(C_1$-$C_6)$alkoxy, each of which is unsubstituted or substituted with 1 or 2 substituents independently selected from —OH, —S(=O)$_2$$NH_2$, —N($R_6$)$_2$, =$NR_6$, —C(=O)$OT_3$, —C(=O)N($R_6$)$_2$, —N($R_6$)C(=O)$R_9$, and -(5- or 6-membered)heterocycle, or 1, 2, or 3 independently selected -halo; or (c) A-B can together form a $(C_2$-$C_6)$bridge, which is unsubstituted or substituted with 1, 2, 3, 4, 5, 6, 7 or 8 substituents independently selected from —OH, —$(C_1$-$C_4)$alkyl, -halo, and —C(halo)$_3$, and which bridge optionally contains —HC=CH— or —O— within the $(C_2$-$C_6$)

bridge; wherein the 5-membered, nitrogen-containing ring that is fused to the $Q_a$ ring can be in the endo- or exo-configuration with respect to the A-B bridge.

In another embodiment, A and B are each independently —H or —($C_1$-$C_6$)alkyl. In another embodiment, A is —($C_1$-$C_6$)alkyl. In another embodiment, B is —($C_1$-$C_6$)alkyl. In another embodiment, A and B are each independently —($C_1$-$C_6$)alkyl. In another embodiment, A is —($C_1$-$C_6$)alkyl and B is H. In another embodiment, A is —H and B is —($C_1$-$C_6$)alkyl. In another embodiment, A and B are each independently —H or —$CH_3$. In another embodiment, A is —$CH_3$. In another embodiment, B is —$CH_3$. In another embodiment, A and B are each —$CH_3$. In another embodiment, A is —$CH_3$ and B is H. In another embodiment, A is —H and B is —$CH_3$. In another embodiment, A is —H. In another embodiment, B is H. In another embodiment, A and B are each —H.

In another embodiment, A-B together form a ($C_2$)bridge which bridge is substituted or unsubstituted. In another embodiment, A-B together form a ($C_2$)bridge which bridge is unsubstituted. In another embodiment, A-B together form a ($C_2$)bridge which bridge is substituted by one or two methyl groups. In another embodiment, A-B together form a ($C_3$)bridge which bridge is substituted or unsubstituted. In another embodiment, A-B together form a ($C_3$)bridge which bridge is unsubstituted. In another embodiment, A-B together form a ($C_3$)bridge which bridge is substituted by one or two methyl groups. In another embodiment, A-B together form a ($C_4$)bridge which bridge is substituted or unsubstituted. In another embodiment, A-B together form a ($C_4$)bridge which bridge is unsubstituted. In another embodiment, A-B together form a ($C_4$)bridge which bridge is substituted by one or two methyl groups. In another embodiment, A-B together form a ($C_5$)bridge which bridge is substituted or unsubstituted. In another embodiment, A-B together form a ($C_5$)bridge which bridge is unsubstituted. In another embodiment, A-B together form a ($C_5$)bridge which bridge is substituted by one or two methyl groups. In another embodiment, A-B together form a ($C_6$)bridge which bridge is substituted or unsubstituted. In another embodiment, A-B together form a ($C_6$)bridge which bridge is unsubstituted. In another embodiment, A-B together form a ($C_6$)bridge which bridge is substituted by one or two methyl groups.

In another embodiment, A-B together form a ($C_2$)bridge which bridge is —HC=CH— and is substituted or unsubstituted. In another embodiment, A-B together form a ($C_2$) bridge which bridge is —HC=CH— and is unsubstituted. In another embodiment, A-B together form a ($C_2$)bridge which is —HC=CH— and is substituted by one or two methyl groups. In another embodiment, A-B together form a ($C_3$)bridge which is —$CH_2$—HC=CH— or —HC=CH—$CH_2$— and is substituted or unsubstituted. In another embodiment, A-B together form a ($C_3$)bridge which is —$CH_2$—HC=CH— or —HC=CH—$CH_2$— and is unsubstituted. In another embodiment, A-B together form a ($C_3$)bridge which is —$CH_2$—HC=CH— or —HC=CH—$CH_2$— and is substituted by one or two methyl groups. In another embodiment, A-B together form a ($C_4$)bridge which is —$CH_2$—$CH_2$—HC=CH—, —$CH_2$—HC=CH—$CH_2$—, or —HC=CH—$CH_2$—$CH_2$— and is substituted or unsubstituted. In another embodiment, A-B together form a ($C_4$)bridge which is —$CH_2$—$CH_2$—HC=CH—, —$CH_2$—HC=CH—$CH_2$—, or —HC=CH—$CH_2$—$CH_2$— and is unsubstituted. In another embodiment, A-B together form a ($C_4$)bridge which is —$CH_2$—$CH_2$—HC=CH—, —$CH_2$—HC=CH—$CH_2$—, or —HC=CH—$CH_2$—$CH_2$— and is substituted by one or two methyl groups.

In another embodiment, A-B together form a ($C_2$)bridge which is —$CH_2$—O—$CH_2$— and is substituted or unsubstituted. In another embodiment, A-B together form a ($C_2$) bridge which is —$CH_2$—O—$CH_2$— and is unsubstituted. In another embodiment, A-B together form a ($C_2$)bridge which is —$CH_2$—O—$CH_2$— and is substituted by one or two methyl groups. In another embodiment, A-B together form a ($C_3$)bridge which is —$CH_2$—O—$CH_2$—$CH_2$— or —$CH_2$—$CH_2$—O—$CH_2$— and is substituted or unsubstituted.

In another embodiment, A-B together form a ($C_3$)bridge which is —$CH_2$—O—$CH_2$—$CH_2$— or —$CH_2$—$CH_2$—O—$CH_2$— and is unsubstituted. In another embodiment, A-B together form a ($C_3$)bridge which is —$CH_2$—O—$CH_2$—$CH_2$— or —$CH_2$—$CH_2$—O—$CH_2$— and is substituted by one or two methyl groups. In another embodiment, A-B together form a ($C_4$)bridge which is —$CH_2$—O—$CH_2$—$CH_2$—$CH_2$—, —$CH_2$—$CH_2$—O—$CH_2$—$CH_2$—, or —$CH_2$—$CH_2$—$CH_2$—O—$CH_2$— and is substituted or unsubstituted. In another embodiment, A-B together form a ($C_4$)bridge which is —$CH_2$—O—$CH_2$—$CH_2$—$CH_2$—, —$CH_2$—$CH_2$—O—$CH_2$—$CH_2$—, or —$CH_2$—$CH_2$—$CH_2$—O—$CH_2$— and is unsubstituted. In another embodiment, A-B together form a ($C_4$)bridge which is —$CH_2$—O—$CH_2$—$CH_2$—$CH_2$—, —$CH_2$—$CH_2$—O—$CH_2$—$CH_2$—, or —$CH_2$—$CH_2$—$CH_2$—O—$CH_2$— and is substituted by one or two methyl groups.

In another embodiment, A-B together form a —$CH_2$—NH—$CH_2$— bridge. In another embodiment, A-B together form a —$CH_2$—N($CH_3$)—$CH_2$— bridge. In another embodiment, A-B together form a —$CH_2$—N(cyclohexyl)-$CH_2$— bridge. In another embodiment, A-B together form a —$CH_2$—N($CH_2$—$CH_2$—OH)—$CH_2$— bridge.

In another embodiment, A-B together form a

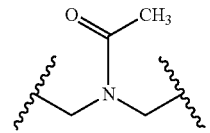 [SMILES: *CN(C*)C(C)=O]

bridge. In another embodiment, A-B together form a

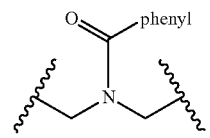

bridge. In another embodiment, A-B together form a

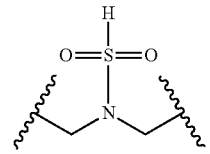 [SMILES: *CN(C*)[SH](=O)=O]

bridge. In another embodiment, A-B together form a

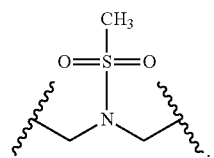 [SMILES: *CN(C*)S(C)(=O)=O]

bridge.

In another embodiment, A and B together form a bridge such that the bridged-piperidine is:

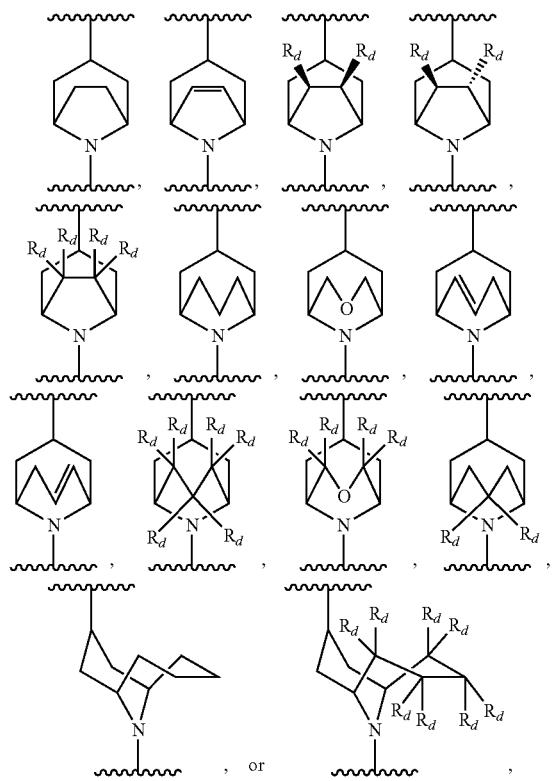

wherein each $R_d$ is independently —H, —($C_1$-$C_4$)alkyl, -halo, or —C(halo)$_3$.

In another embodiment, A and B together form a bridge such that the bridged-piperidine is:

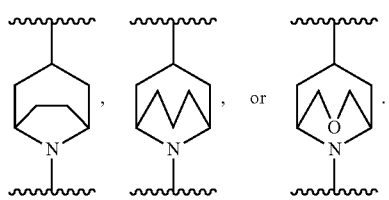

In another embodiment, A and B together form a bridge such that the bridged-piperidine is:

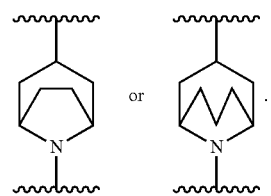 [SMILES: *C1CC2CCC(C1)N2* ; *C1CC2CCCC(C1)N2*]

In another embodiment, the A-B bridge of the bridged-piperidine is in the endo-configuration with respect to the pyrrole ring of the bicyclic ring.

In another embodiment, the bicyclic compound is:

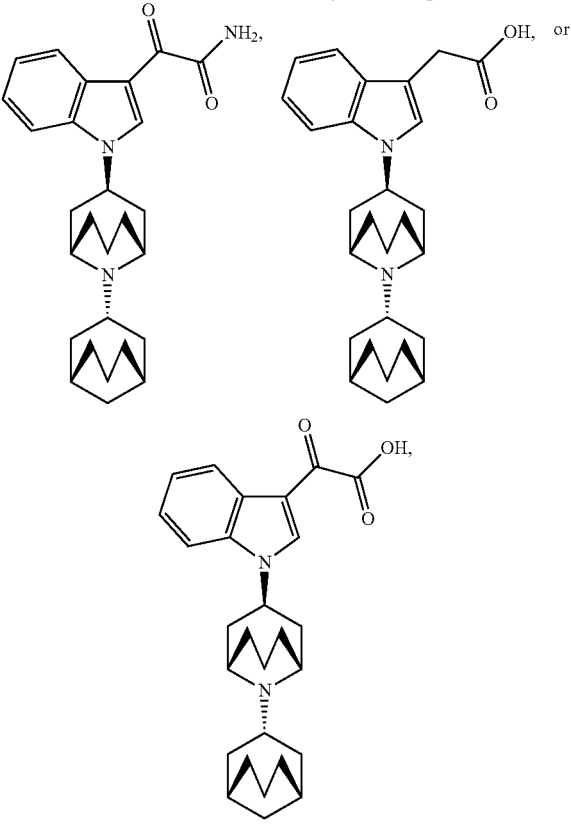

or a pharmaceutically acceptable salt or solvate thereof.

In another embodiment, the bicyclic compound is:

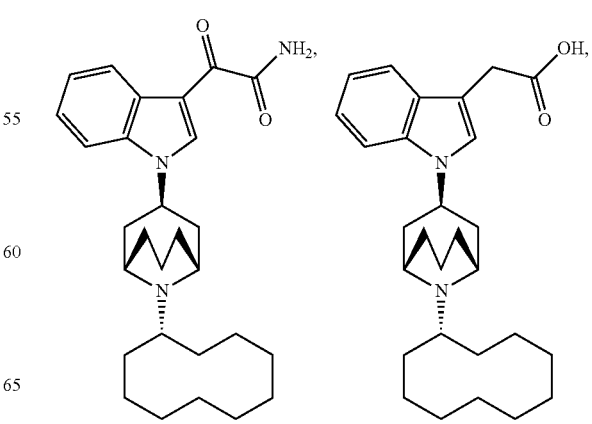

-continued

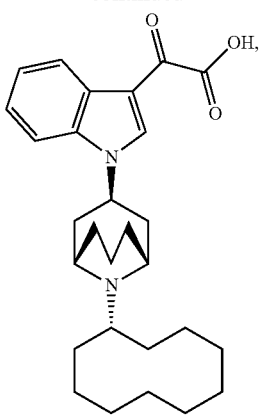

or a pharmaceutically acceptable salt or solvate thereof.

In another embodiment, the Compound of Formula (I) is in the form of a pharmaceutically acceptable salt. In another embodiment, the pharmaceutically acceptable salt is a hydrochloride salt. In another embodiment, the pharmaceutically acceptable salt is a sodium salt. In another embodiment, the pharmaceutically acceptable salt is a potassium salt. In another embodiment, the pharmaceutically acceptable salt is a para-toluenesulfonic acid salt.

In other embodiments, the Compound of Formula (I) has one of the formulae of Table 1.

TABLE 1

| Formula | Compound |
|---|---|
| IA | 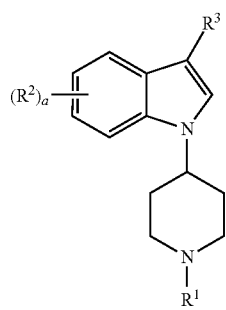 |
| IB | 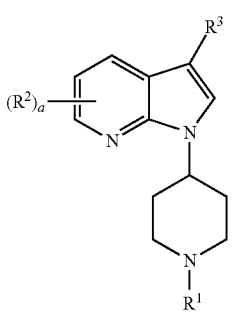 |

TABLE 1-continued

| Formula | Compound |
|---|---|
| IC | 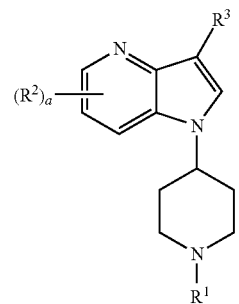 |
| ID | 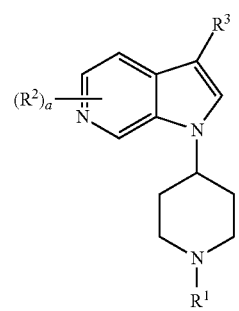 |
| IE |  |
| IE$_1$[††] |  |
| IE$_2$[†] | 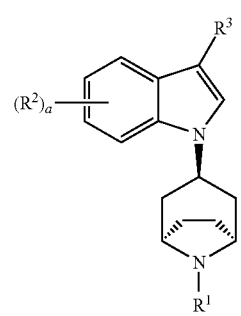 |

TABLE 1-continued

| Formula | Compound |
|---|---|
| IF | *(structure: 7-azaindole with R³ at 3-position, (R²)ₐ on pyridine ring, N-linked to tropane/azabicyclic system with wavy bond, N-R¹)* |
| IF₁† | *(structure: 7-azaindole with R³, (R²)ₐ, N-linked to azabicyclic system with defined stereochemistry, N-R¹)* |
| IF₂†† | *(structure: 7-azaindole with R³, (R²)ₐ, N-linked to azabicyclic system with opposite stereochemistry, N-R¹)* |
| IG | *(structure: 4-azaindole with R³, (R²)ₐ, N-linked to azabicyclic system with wavy bond, N-R¹)* |
| IG₁† | *(structure: 4-azaindole with R³, (R²)ₐ, N-linked to azabicyclic system with defined stereochemistry, N-R¹)* |

TABLE 1-continued

| Formula | Compound |
|---|---|
| IG2†† | *(structure: 4-azaindole with R³, (R²)ₐ, N-linked to azabicyclic system with opposite stereochemistry, N-R¹)* |
| IH | *(structure: indole with R³, (R²)ₐ, N-linked to azabicyclic system with wavy bond, N-R¹)* |
| IH₁† | *(structure: indole with R³, (R²)ₐ, N-linked to azabicyclic system with defined stereochemistry, N-R¹)* |
| IH₂†† | *(structure: indole with R³, (R²)ₐ, N-linked to azabicyclic system with opposite stereochemistry, N-R¹)* |
| II | *(structure: indole with R³, (R²)ₐ, N-linked to azabicyclic system with wavy bond, N-R¹)* |

TABLE 1-continued
| Formula | Compound |
|---|---|
| II₁† | 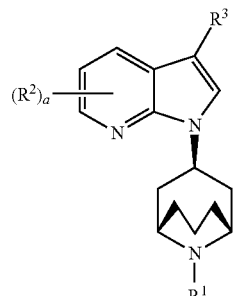 |
| II₂†† | 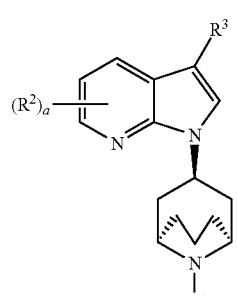 |
| IJ | 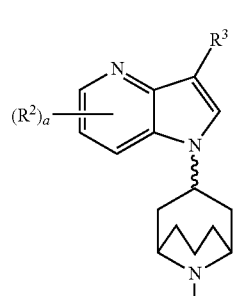 |
| IJ₁† | 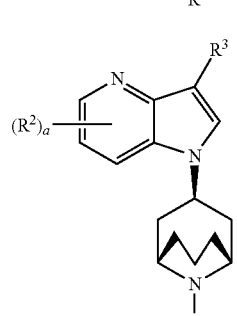 |
| IJ₂†† | 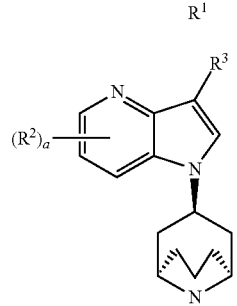 |
TABLE 1-continued
| Formula | Compound |
|---|---|
| IK |  |
| IK₁† | 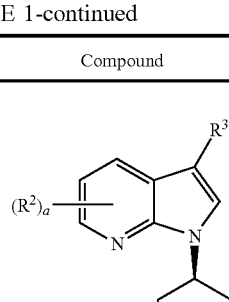 |
| IK₂†† | 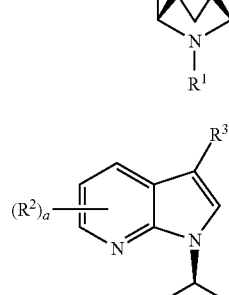 |
| IL | 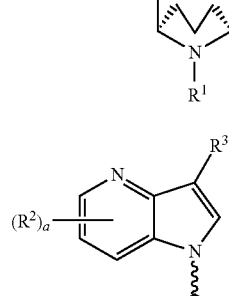 |
| IL₁† | 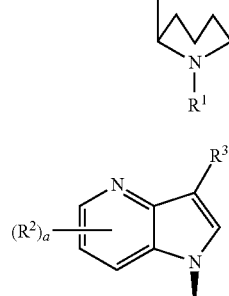 |

TABLE 1-continued
| Formula | Compound |
|---|---|
| IL₂†† | 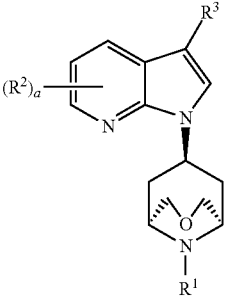 |
| IM | 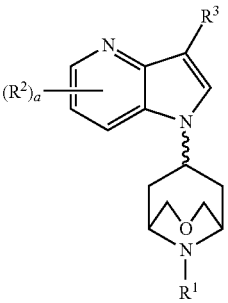 |
| IM₁† | 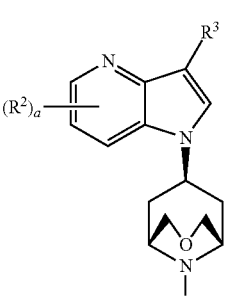 |
| IM₂†† | 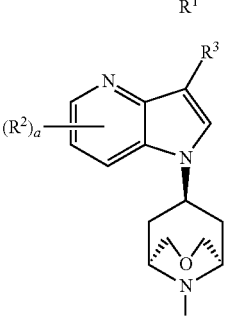 |
| IN | 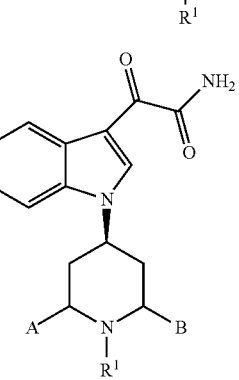 |
| IO | 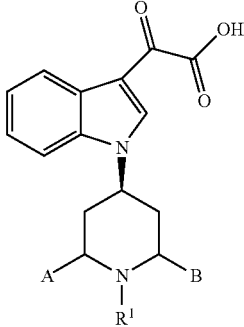 |
| IP | 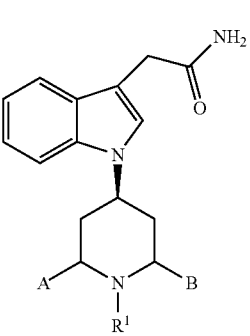 |
| IQ | 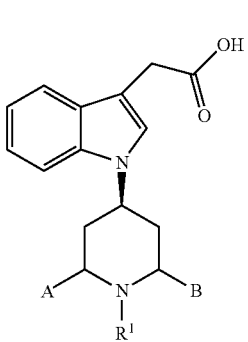 |
| IR | 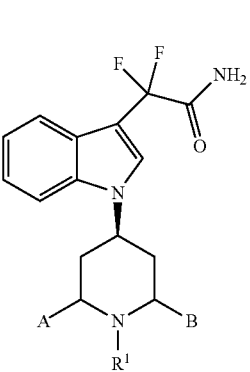 |

TABLE 1-continued
| Formula | Compound |
|---|---|
| IS† | 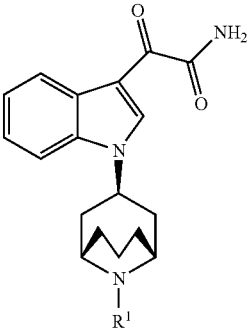 |
| IT† | 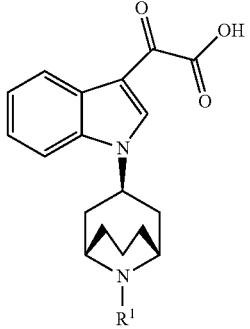 |
| IU† | 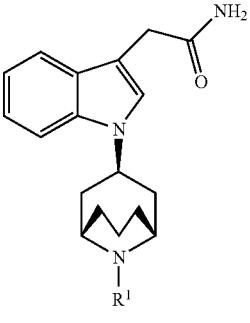 |
| IV† | 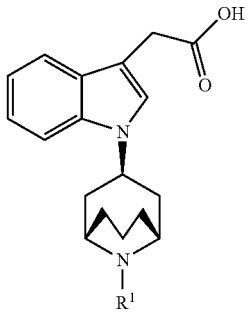 |
| IW† | 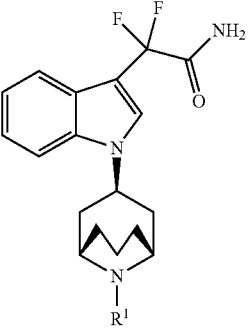 |
| IX† | 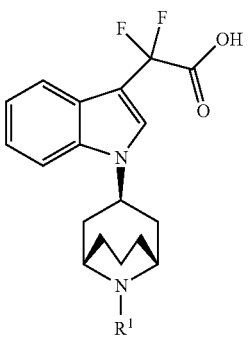 |
| IY† | 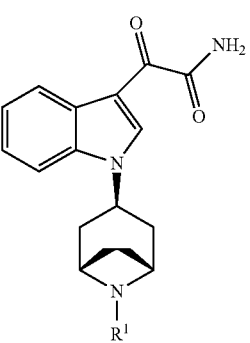 |
| IZ† | 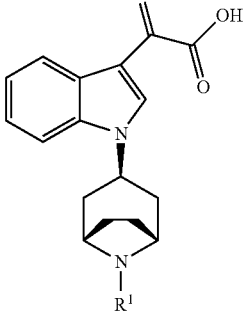 |

TABLE 1-continued

| Formula | Compound |
|---|---|
| IAA† | 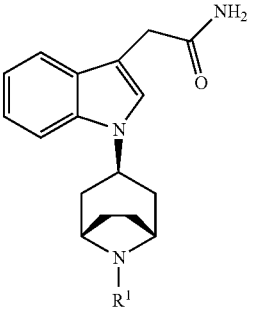 |
| IAB† | 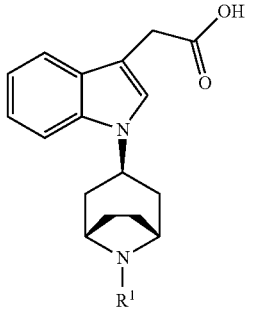 |
| IAC† | 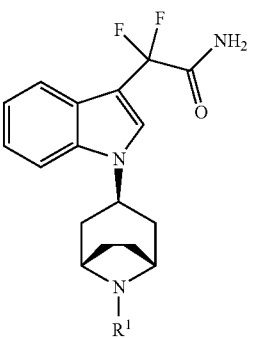 |
| IAD† | 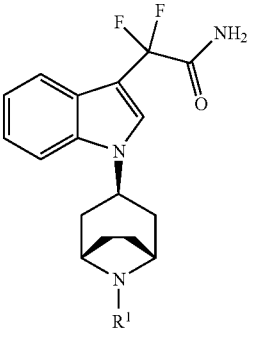 |

†indicates the 5-membered, nitrogen-containing ring 5to the benzo or pyridino is in the endo-configuration with respect to the alkyl or —CH₂—O—CH₂— bridge.
††indicates the 5-membered, nitrogen-containing ring that is fused to the benzo or pyridino is in the exo-configuration with respect to the alkyl or —CH₂—O—CH₂— bridge.

where $R^1$, $R^2$, $R^3$, A, B and a are as defined above for the Compounds of Formula (I).

Illustrative compounds of Formula (I) are listed below in Tables 2-21.

TABLE 2

(a)

(b)

and pharmaceutically acceptable salts and solvates thereof, where:

| Compound | $R^3$ | $R^{8'}$ |
|---|---|---|
| A1 a or b | H | H |
| A2 a or b | C(=O)C(=O)OH | H |
| A3 a or b | C(=O)C(=O)NH₂ | H |
| A4 a or b | C(=O)C(=O)OCH₃ | H |
| A5 a or b | C(=O)C(=O)OCH₂CH₃ | H |
| A6 a or b | C(=O)H | H |
| A7 a or b | C(=O)CH₃ | H |
| A8 a or b | C(=O)CH₂CH₃ | H |
| A9 a or b | C(=O)NH₂ | H |
| A10 a or b | C(=O)NHCH₃ | H |
| A11 a or b | C(=O)N(CH₃)₂ | H |
| A12 a or b | C(=O)CH₂NH₂ | H |
| A13 a or b | C(=O)OCH₂CH₃ | H |
| A14 a or b | C(=O)OCH₂OH | H |
| A15 a or b | CH₂C(=O)OH | H |
| A16 a or b | CF₂C(=O)OH | H |
| A17 a or b | CHFC(=O)OH | H |
| A18 a or b | CH₂C(=O)OCH₃ | H |
| A19 a or b | CH₂C(=O)OCH₂CH₃ | H |
| A20 a or b | CH₂C(=O)NH₂ | H |
| A21 a or b | CF₂C(=O)NH₂ | H |
| A22 a or b | CHFC(=O)NH₂ | H |
| A23 a or b | CH₂C(=O)NHCH₃ | H |
| A24 a or b | CH₂C(=O)NH(CH₃)₂ | H |
| A25 a or b | C(=O)OH | H |
| A26 a or b | C(=O)OCH₃ | H |
| A27 a or b | CH₂C(=O)NHCH₂C(=O)OH | H |
| A28 a or b | CH₂C(=O)NHCH₂C(=O)OCH₃ | H |
| A29 a or b | H | CH₃ |
| A30 a or b | C(=O)C(=O)OH | CH₃ |
| A31 a or b | C(=O)C(=O)NH₂ | CH₃ |
| A32 a or b | C(=O)C(=O)OCH₃ | CH₃ |
| A33 a or b | C(=O)C(=O)OCH₂CH₃ | CH₃ |

TABLE 2-continued

| Compound | R³ | |
|---|---|---|
| A34 a or b | C(=O)H | CH₃ |
| A35 a or b | C(=O)CH₃ | CH₃ |
| A36 a or b | C(=O)CH₂CH₃ | CH₃ |
| A37 a or b | C(=O)NH₂ | CH₃ |
| A38 a or b | C(=O)NHCH₃ | CH₃ |
| A39 a or b | C(=O)N(CH₃)₂ | CH₃ |
| A40 a or b | C(=O)CH₂NH₂ | CH₃ |
| A41 a or b | C(=O)OCH₂CH₃ | CH₃ |
| A42 a or b | C(=O)OCH₂OH | CH₃ |
| A43 a or b | CH₂C(=O)OH | CH₃ |
| A44 a or b | CH₂C(=O)OCH₃ | CH₃ |
| A45 a or b | CH₂C(=O)OCH₂CH₃ | CH₃ |
| A46 a or b | CH₂C(=O)NH₂ | CH₃ |
| A47 a or b | CH₂C(=O)NHCH₃ | CH₃ |
| A48 a or b | CH₂C(=O)NH(CH₃)₂ | CH₃ |
| A49 a or b | C(=O)OH | CH₃ |
| A50 a or b | C(=O)OCH₃ | CH₃ |
| A51 a or b | CH₂C(=O)NHCH₂C(=O)OH | CH₃ |
| A52 a or b | CH₂C(=O)NHCH₂C(=O)OCH₃ | CH₃ |
| A53 a or b | H | CH₂CH₃ |
| A54 a or b | C(=O)C(=O)OH | CH₂CH₃ |
| A55 a or b | C(=O)C(=O)NH₂ | CH₂CH₃ |
| A56 a or b | C(=O)C(=O)OCH₃ | CH₂CH₃ |
| A57 a or b | C(=O)C(=O)OCH₂CH₃ | CH₂CH₃ |
| A58 a or b | C(=O)H | CH₂CH₃ |
| A59 a or b | C(=O)CH₃ | CH₂CH₃ |
| A60 a or b | C(=O)CH₂CH₃ | CH₂CH₃ |
| A61 a or b | C(=O)NH₂ | CH₂CH₃ |
| A62 a or b | C(=O)NHCH₃ | CH₂CH₃ |
| A63 a or b | C(=O)N(CH₃)₂ | CH₂CH₃ |
| A64 a or b | C(=O)CH₂NH₂ | CH₂CH₃ |
| A65 a or b | C(=O)OCH₂CH₃ | CH₂CH₃ |
| A66 a or b | C(=O)OCH₂OH | CH₂CH₃ |
| A67 a or b | CH₂C(=O)OH | CH₂CH₃ |
| A68 a or b | CH₂C(=O)OCH₃ | CH₂CH₃ |
| A69 a or b | CH₂C(=O)OCH₂CH₃ | CH₂CH₃ |
| A70 a or b | CH₂C(=O)NH₂ | CH₂CH₃ |
| A71 a or b | CH₂C(=O)NHCH₃ | CH₂CH₃ |
| A72 a or b | CH₂C(=O)NH(CH₃)₂ | CH₂CH₃ |
| A73 a or b | C(=O)OH | CH₂CH₃ |
| A74 a or b | C(=O)OCH₃ | CH₂CH₃ |
| A75 a or b | CH₂C(=O)NHCH₂C(=O)OH | CH₂CH₃ |
| A76 a or b | CH₂C(=O)NHCH₂C(=O)OCH₃ | CH₂CH₃ |

TABLE 3

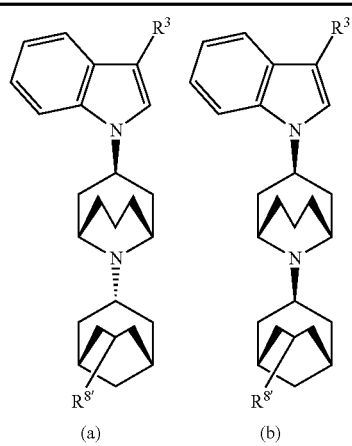

(a)  (b)

and pharmaceutically acceptable salts and solvates thereof, where:

| Compound | R³ | R⁸' |
|---|---|---|
| A77 a or b | H | H |
| A78 a or b | C(=O)C(=O)OH | H |
| A79 a or b | C(=O)C(=O)NH₂ | H |
| A80 a or b | C(=O)C(=O)OCH₃ | H |
| A81 a or b | C(=O)C(=O)OCH₂CH₃ | H |
| A82 a or b | C(=O)H | H |

TABLE 3-continued

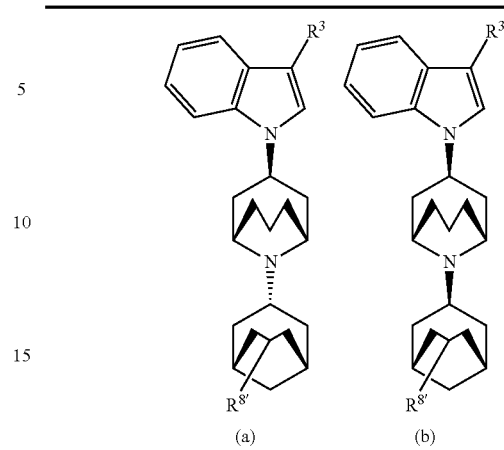

(a)  (b)

and pharmaceutically acceptable salts and solvates thereof, where:

| Compound | R³ | R⁸' |
|---|---|---|
| A83 a or b | C(=O)CH₃ | H |
| A84 a or b | C(=O)CH₂CH₃ | H |
| A85 a or b | C(=O)NH₂ | H |
| A86 a or b | C(=O)NHCH₃ | H |
| A87 a or b | C(=O)N(CH₃)₂ | H |
| A88 a or b | C(=O)CH₂NH₂ | H |
| A89 a or b | C(=O)OCH₂CH₃ | H |
| A90 a or b | C(=O)OCH₂OH | H |
| A91 a or b | CH₂C(=O)OH | H |
| A92 a or b | CF₂C(=O)OH | H |
| A93 a or b | CHFC(=O)OH | H |
| A94 a or b | CH₂C(=O)OCH₃ | H |
| A95 a or b | CH₂C(=O)OCH₂CH₃ | H |
| A96 a or b | CH₂C(=O)NH₂ | H |
| A97 a or b | CF₂C(=O)OCH₂CH₃ | H |
| A98 a or b | CHFC(=O)OCH₂CH₃ | H |
| A99 a or b | CH₂C(=O)NHCH₃ | H |
| A100 a or b | CH₂C(=O)NH(CH₃)₂ | H |
| A101 a or b | C(=O)OH | H |
| A102 a or b | C(=O)OCH₃ | H |
| A103 a or b | CH₂C(=O)NHCH₂C(=O)OH | H |
| A104 a or b | CH₂C(=O)NHCH₂C(=O)OCH₃ | H |
| A105 a or b | H | CH₃ |
| A106 a or b | C(=O)C(=O)OH | CH₃ |
| A107 a or b | C(=O)C(=O)NH₂ | CH₃ |
| A108 a or b | C(=O)C(=O)OCH₃ | CH₃ |
| A109 a or b | C(=O)C(=O)OCH₂CH₃ | CH₃ |
| A110 a or b | C(=O)H | CH₃ |
| A111 a or b | C(=O)CH₃ | CH₃ |
| A112 a or b | C(=O)CH₂CH₃ | CH₃ |
| A113 a or b | C(=O)NH₂ | CH₃ |
| A114 a or b | C(=O)NHCH₃ | CH₃ |
| A115 a or b | C(=O)N(CH₃)₂ | CH₃ |
| A116 a or b | C(=O)CH₂NH₂ | CH₃ |
| A117 a or b | C(=O)OCH₂CH₃ | CH₃ |
| A118 a or b | C(=O)OCH₂OH | CH₃ |
| A119 a or b | CH₂C(=O)OH | CH₃ |
| A120 a or b | CH₂C(=O)OCH₃ | CH₃ |
| A121 a or b | CH₂C(=O)OCH₂CH₃ | CH₃ |
| A122 a or b | CH₂C(=O)NH₂ | CH₃ |
| A123 a or b | CH₂C(=O)NHCH₃ | CH₃ |
| A124 a or b | CH₂C(=O)NH(CH₃)₂ | CH₃ |
| A125 a or b | C(=O)OH | CH₃ |
| A126 a or b | C(=O)OCH₃ | CH₃ |
| A127 a or b | CH₂C(=O)NHCH₂C(=O)OH | CH₃ |
| A128 a or b | CH₂C(=O)NHCH₂C(=O)OCH₃ | CH₃ |
| A129 a or b | H | CH₂CH₃ |
| A130 a or b | C(=O)C(=O)OH | CH₂CH₃ |
| A131 a or b | C(=O)C(=O)NH₂ | CH₂CH₃ |
| A132 a or b | C(=O)C(=O)OCH₃ | CH₂CH₃ |
| A133 a or b | C(=O)C(=O)OCH₂CH₃ | CH₂CH₃ |
| A134 a or b | C(=O)H | CH₂CH₃ |
| A135 a or b | C(=O)CH₃ | CH₂CH₃ |
| A136 a or b | C(=O)CH₂CH₃ | CH₂CH₃ |

TABLE 3-continued

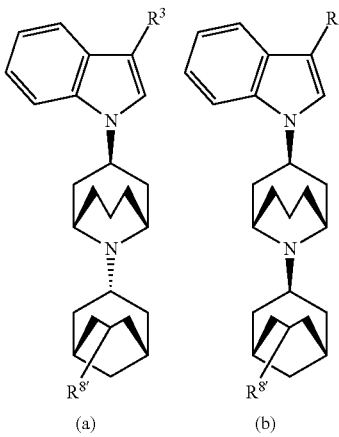

(a) (b)

and pharmaceutically acceptable salts and solvates thereof, where:

| Compound | R³ | R⁸' |
|---|---|---|
| A137 a or b | C(=O)NH₂ | CH₂CH₃ |
| A138 a or b | C(=O)NHCH₃ | CH₂CH₃ |
| A139 a or b | C(=O)N(CH₃)₂ | CH₂CH₃ |
| A140 a or b | C(=O)CH₂NH₂ | CH₂CH₃ |
| A141 a or b | C(=O)OCH₂CH₃ | CH₂CH₃ |
| A142 a or b | C(=O)OCH₂OH | CH₂CH₃ |
| A143 a or b | CH₂C(=O)OH | CH₂CH₃ |
| A144 a or b | CH₂C(=O)OCH₃ | CH₂CH₃ |
| A145 a or b | CH₂C(=O)OCH₂CH₃ | CH₂CH₃ |
| A146 a or b | CH₂C(=O)NH₂ | CH₂CH₃ |
| A147 a or b | CH₂C(=O)NHCH₃ | CH₂CH₃ |
| A148 a or b | CH₂C(=O)NH(CH₃)₂ | CH₂CH₃ |
| A149 a or b | C(=O)OH | CH₂CH₃ |
| A150 a or b | C(=O)OCH₃ | CH₂CH₃ |
| A151 a or b | CH₂C(=O)NHCH₂C(=O)OH | CH₂CH₃ |
| A152 a or b | CH₂C(=O)NHCH₂C(=O)OCH₃ | CH₂CH₃ |

TABLE 4

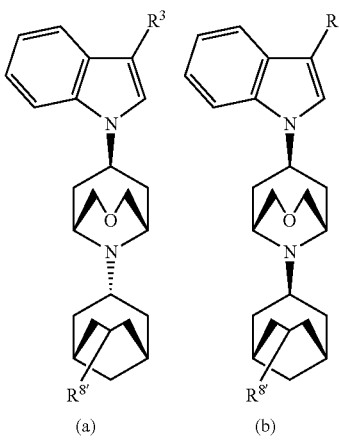

(a) (b)

and pharmaceutically acceptable salts and solvates thereof, where:

| Compound | R³ | R⁸' |
|---|---|---|
| A153 a or b | H | H |
| A154 a or b | C(=O)C(=O)OH | H |
| A155 a or b | C(=O)C(=O)NH₂ | H |
| A156 a or b | C(=O)C(=O)OCH₃ | H |
| A157 a or b | C(=O)C(=O)OCH₂CH₃ | H |
| A158 a or b | C(=O)H | H |
| A159 a or b | C(=O)CH₃ | H |
| A160 a or b | C(=O)CH₂CH₃ | H |

TABLE 4-continued

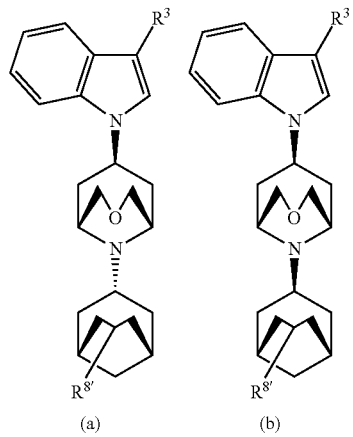

(a) (b)

and pharmaceutically acceptable salts and solvates thereof, where:

| Compound | R³ | R⁸' |
|---|---|---|
| A161 a or b | C(=O)NH₂ | H |
| A162 a or b | C(=O)NHCH₃ | H |
| A163 a or b | C(=O)N(CH₃)₂ | H |
| A164 a or b | C(=O)CH₂NH₂ | H |
| A165 a or b | C(=O)OCH₂CH₃ | H |
| A166 a or b | C(=O)OCH₂OH | H |
| A167 a or b | CH₂C(=O)OH | H |
| A168 a or b | CF₂C(=O)OH | H |
| A169 a or b | CHFC(=O)OH | H |
| A170 a or b | CH₂C(=O)OCH₃ | H |
| A171 a or b | CH₂C(=O)OCH₂CH₃ | H |
| A172 a or b | CH₂C(=O)NH₂ | H |
| A173 a or b | CF₂C(=O)OH | H |
| A174 a or b | CHFC(=O)OH | H |
| A175 a or b | CH₂C(=O)NHCH₃ | H |
| A176 a or b | CH₂C(=O)NH(CH₃)₂ | H |
| A177 a or b | C(=O)OH | H |
| A178 a or b | C(=O)OCH₃ | H |
| A179 a or b | CH₂C(=O)NHCH₂C(=O)OH | H |
| A180 a or b | CH₂C(=O)NHCH₂C(=O)OCH₃ | H |
| A181 a or b | H | CH₃ |
| A182 a or b | C(=O)C(=O)OH | CH₃ |
| A183 a or b | C(=O)C(=O)NH₂ | CH₃ |
| A184 a or b | C(=O)C(=O)OCH₃ | CH₃ |
| A185 a or b | C(=O)C(=O)OCH₂CH₃ | CH₃ |
| A186 a or b | C(=O)H | CH₃ |
| A187 a or b | C(=O)CH₃ | CH₃ |
| A188 a or b | C(=O)CH₂CH₃ | CH₃ |
| A189 a or b | C(=O)NH₂ | CH₃ |
| A190 a or b | C(=O)NHCH₃ | CH₃ |
| A191 a or b | C(=O)N(CH₃)₂ | CH₃ |
| A192 a or b | C(=O)CH₂NH₂ | CH₃ |
| A193 a or b | C(=O)OCH₂CH₃ | CH₃ |
| A194 a or b | C(=O)OCH₂OH | CH₃ |
| A195 a or b | CH₂C(=O)OH | CH₃ |
| A196 a or b | CH₂C(=O)OCH₃ | CH₃ |
| A197 a or b | CH₂C(=O)OCH₂CH₃ | CH₃ |
| A198 a or b | CH₂C(=O)NH₂ | CH₃ |
| A199 a or b | CH₂C(=O)NHCH₃ | CH₃ |
| A200 a or b | CH₂C(=O)NH(CH₃)₂ | CH₃ |
| A201 a or b | C(=O)OH | CH₃ |
| A202 a or b | C(=O)OCH₃ | CH₃ |
| A203 a or b | CH₂C(=O)NHCH₂C(=O)OH | CH₃ |
| A204 a or b | CH₂C(=O)NHCH₂C(=O)OCH₃ | CH₃ |
| A205 a or b | H | CH₂CH₃ |
| A206 a or b | C(=O)C(=O)OH | CH₂CH₃ |
| A207 a or b | C(=O)C(=O)NH₂ | CH₂CH₃ |
| A208 a or b | C(=O)C(=O)OCH₃ | CH₂CH₃ |
| A209 a or b | C(=O)C(=O)OCH₂CH₃ | CH₂CH₃ |
| A210 a or b | C(=O)H | CH₂CH₃ |
| A211 a or b | C(=O)CH₃ | CH₂CH₃ |
| A212 a or b | C(=O)CH₂CH₃ | CH₂CH₃ |
| A213 a or b | C(=O)NH₂ | CH₂CH₃ |
| A214 a or b | C(=O)NHCH₃ | CH₂CH₃ |

TABLE 4-continued

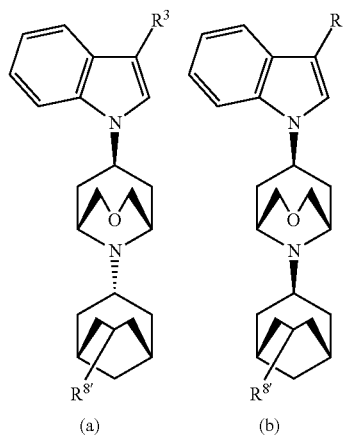

(a)     (b)

and pharmaceutically acceptable salts and solvates thereof, where:

| Compound | $R^3$ | $R^{8'}$ |
|---|---|---|
| A215 a or b | $C(=O)N(CH_3)_2$ | $CH_2CH_3$ |
| A216 a or b | $C(=O)CH_2NH_2$ | $CH_2CH_3$ |
| A217 a or b | $C(=O)OCH_2CH_3$ | $CH_2CH_3$ |
| A218 a or b | $C(=O)OCH_2OH$ | $CH_2CH_3$ |
| A219 a or b | $CH_2C(=O)OH$ | $CH_2CH_3$ |
| A220 a or b | $CH_2C(=O)OCH_3$ | $CH_2CH_3$ |
| A221 a or b | $CH_2C(=O)OCH_2CH_3$ | $CH_2CH_3$ |
| A222 a or b | $CH_2C(=O)NH_2$ | $CH_2CH_3$ |
| A223 a or b | $CH_2C(=O)NHCH_3$ | $CH_2CH_3$ |
| A224 a or b | $CH_2C(=O)NH(CH_3)_2$ | $CH_2CH_3$ |
| A225 a or b | $C(=O)OH$ | $CH_2CH_3$ |
| A226 a or b | $C(=O)OCH_3$ | $CH_2CH_3$ |
| A227 a or b | $CH_2C(=O)NHCH_2C(=O)OH$ | $CH_2CH_3$ |
| A228 a or b | $CH_2C(=O)NHCH_2C(=O)OCH_3$ | $CH_2CH_3$ |

TABLE 5

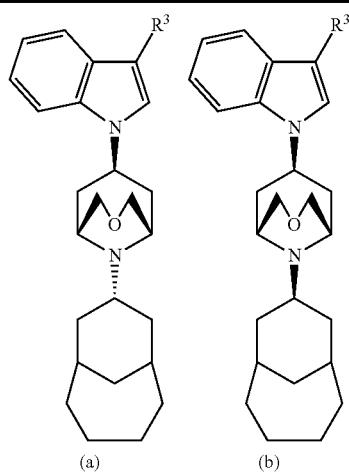

(a)     (b)

and pharmaceutically acceptable salts and solvates thereof, where:

| Compound | $R^3$ |
|---|---|
| A229 a or b | H |
| A230 a or b | $C(=O)C(=O)OH$ |
| A231 a or b | $C(=O)C(=O)NH_2$ |
| A232 a or b | $C(=O)C(=O)OCH_3$ |
| A233 a or b | $C(=O)C(=O)OCH_2CH_3$ |
| A234 a or b | $C(=O)H$ |
| A235 a or b | $C(=O)CH_3$ |
| A236 a or b | $C(=O)CH_2CH_3$ |

TABLE 5-continued

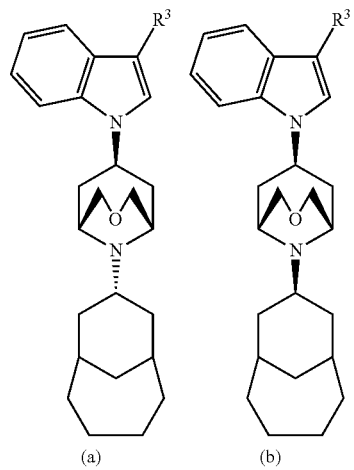

(a)     (b)

and pharmaceutically acceptable salts and solvates thereof, where:

| Compound | $R^3$ |
|---|---|
| A237 a or b | $C(=O)NH_2$ |
| A238 a or b | $C(=O)NHCH_3$ |
| A239 a or b | $C(=O)N(CH_3)_2$ |
| A240 a or b | $C(=O)CH_2NH_2$ |
| A241 a or b | $C(=O)OCH_2CH_3$ |
| A242 a or b | $C(=O)OCH_2OH$ |
| A243 a or b | $CH_2C(=O)OH$ |
| A244 a or b | $CH_2C(=O)OCH_3$ |
| A245 a or b | $CF_2C(=O)OH$ |
| A246 a or b | $CHFC(=O)OH$ |
| A247 a or b | $CH_2C(=O)OCH_2CH_3$ |
| A248 a or b | $CH_2C(=O)NH_2$ |
| A249 a or b | $CF_2C(=O)NH_2$ |
| A250 a or b | $CHFC(=O)NH_2$ |
| A251 a or b | $CH_2C(=O)NHCH_3$ |
| A252 a or b | $CH_2C(=O)NH(CH_3)_2$ |
| A253 a or b | $C(=O)OH$ |
| A254 a or b | $C(=O)OCH_3$ |
| A255 a or b | $CH_2C(=O)NHCH_2C(=O)OH$ |
| A256 a or b | $CH_2C(=O)NHCH_2C(=O)OCH_3$ |

TABLE 6

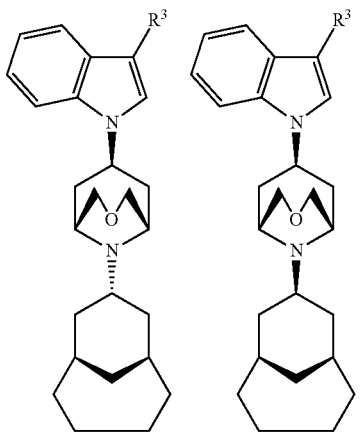

(a)     (b)

and pharmaceutically acceptable salts and solvates thereof, where:

| Compound | $R^3$ |
|---|---|
| A257 a or b | H |
| A258 a or b | $C(=O)C(=O)OH$ |

TABLE 6-continued

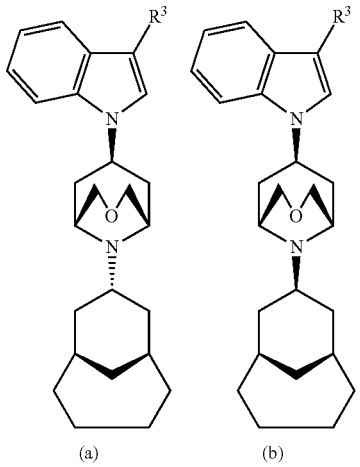

(a)     (b)

and pharmaceutically acceptable salts and solvates thereof, where:

| Compound | $R^3$ |
|---|---|
| A259 a or b | C(=O)C(=O)NH$_2$ |
| A260 a or b | C(=O)C(=O)OCH$_3$ |
| A261 a or b | C(=O)C(=O)OCH$_2$CH$_3$ |
| A262 a or b | C(=O)H |
| A263 a or b | C(=O)CH$_3$ |
| A264 a or b | C(=O)CH$_2$CH$_3$ |
| A265 a or b | C(=O)NH$_2$ |
| A266 a or b | C(=O)NHCH$_3$ |
| A267 a or b | C(=O)N(CH$_3$)$_2$ |
| A268 a or b | C(=O)CH$_2$NH$_2$ |
| A269 a or b | C(=O)OCH$_2$CH$_3$ |
| A270 a or b | C(=O)OCH$_2$OH |
| A271 a or b | CH$_2$C(=O)OH |
| A272 a or b | CF$_2$C(=O)OH |
| A273 a or b | CHFC(=O)OH |
| A274 a or b | CH$_2$C(=O)OCH$_3$ |
| A275 a or b | CH$_2$C(=O)OCH$_2$CH$_3$ |
| A276 a or b | CH$_2$C(=O)NH$_2$ |
| A277 a or b | CH$_2$C(=O)NHCH$_3$ |
| A278 a or b | CH$_2$C(=O)NH(CH$_3$)$_2$ |
| A279 a or b | C(=O)OH |
| A280 a or b | C(=O)OCH$_3$ |
| A281 a or b | CH$_2$C(=O)NHCH$_2$C(=O)OH |
| A282 a or b | CH$_2$C(=O)NHCH$_2$C(=O)OCH$_3$ |

TABLE 7

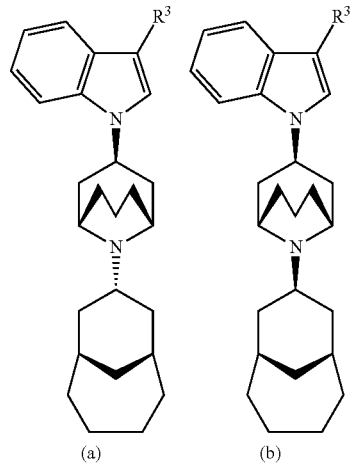

(a)     (b)

and pharmaceutically acceptable salts and solvates thereof, where:

| Compound | $R^3$ |
|---|---|
| A283 a or b | H |
| A284 a or b | C(=O)C(=O)OH |
| A285 a or b | C(=O)C(=O)NH$_2$ |
| A286 a or b | C(=O)C(=O)OCH$_3$ |
| A287 a or b | C(=O)C(=O)OCH$_2$CH$_3$ |
| A288 a or b | C(=O)H |
| A289 a or b | C(=O)CH$_3$ |
| A290 a or b | C(=O)CH$_2$CH$_3$ |
| A291 a or b | C(=O)NH$_2$ |
| A292 a or b | C(=O)NHCH$_3$ |
| A293 a or b | C(=O)N(CH$_3$)$_2$ |
| A294 a or b | C(=O)CH$_2$NH$_2$ |
| A295 a or b | C(=O)OCH$_2$CH$_3$ |
| A296 a or b | C(=O)OCH$_2$OH |
| A297 a or b | CH$_2$C(=O)OH |
| A298 a or b | CF$_2$C(=O)OH |
| A299 a or b | CHFC(=O)OH |
| A300 a or b | CH$_2$C(=O)OCH$_3$ |
| A301 a or b | CH$_2$C(=O)OCH$_2$CH$_3$ |
| A302 a or b | CH$_2$C(=O)NH$_2$ |
| A303 a or b | CH$_2$C(=O)NHCH$_3$ |
| A304 a or b | CH$_2$C(=O)NH(CH$_3$)$_2$ |
| A305 a or b | C(=O)OH |
| A306 a or b | C(=O)OCH$_3$ |
| A307 a or b | CH$_2$C(=O)NHCH$_2$C(=O)OH |
| A308 a or b | CH$_2$C(=O)NHCH$_2$C(=O)OCH$_3$ |

TABLE 8

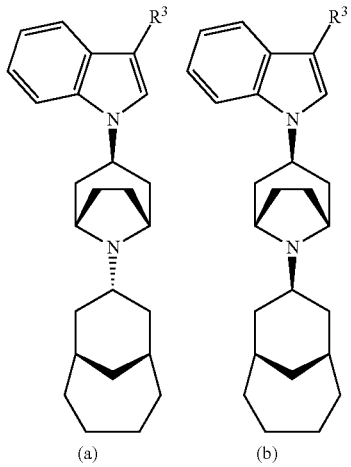

(a)     (b)

and pharmaceutically acceptable salts and solvates thereof, where:

| Compound | $R^3$ |
|---|---|
| A309 a or b | H |
| A310 a or b | C(=O)C(=O)OH |
| A311 a or b | C(=O)C(=O)NH$_2$ |
| A312 a or b | C(=O)C(=O)OCH$_3$ |
| A313 a or b | C(=O)C(=O)OCH$_2$CH$_3$ |
| A314 a or b | C(=O)H |
| A315 a or b | C(=O)CH$_3$ |
| A316 a or b | C(=O)CH$_2$CH$_3$ |
| A317 a or b | C(=O)NH$_2$ |
| A318 a or b | C(=O)NHCH$_3$ |
| A319 a or b | C(=O)N(CH$_3$)$_2$ |
| A320 a or b | C(=O)CH$_2$NH$_2$ |
| A321 a or b | C(=O)OCH$_2$CH$_3$ |
| A322 a or b | C(=O)OCH$_2$OH |
| A323 a or b | CH$_2$C(=O)OH |
| A324 a or b | CF$_2$C(=O)OH |
| A325 a or b | CHFC(=O)OH |
| A326 a or b | CH$_2$C(=O)OCH$_3$ |
| A327 a or b | CH$_2$C(=O)OCH$_2$CH$_3$ |
| A328 a or b | CH$_2$C(=O)NH$_2$ |
| A329 a or b | CH$_2$C(=O)NHCH$_3$ |
| A330 a or b | CH$_2$C(=O)NH(CH$_3$)$_2$ |
| A331 a or b | C(=O)OH |
| A332 a or b | C(=O)OCH$_3$ |
| A333 a or b | CH$_2$C(=O)NHCH$_2$C(=O)OH |
| A334 a or b | CH$_2$C(=O)NHCH$_2$C(=O)OCH$_3$ |

TABLE 9

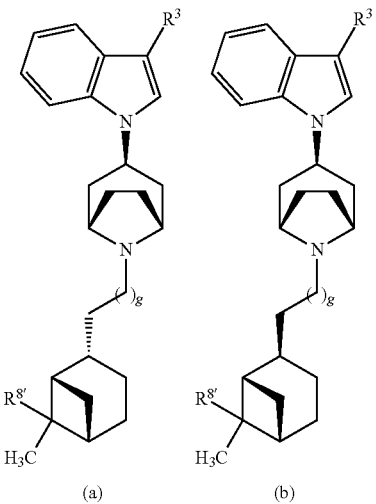

(a)     (b)

and pharmaceutically acceptable salts and solvates thereof, where:

| Compound | $R^3$ | $R^{8'}$ | g |
|---|---|---|---|
| A335 a or b | H | H | 0 |
| A336 a or b | C(=O)C(=O)OH | H | 0 |
| A337 a or b | C(=O)C(=O)NH$_2$ | H | 0 |
| A338 a or b | C(=O)C(=O)OCH$_3$ | H | 0 |
| A339 a or b | C(=O)C(=O)OCH$_2$CH$_3$ | H | 0 |
| A340 a or b | C(=O)H | H | 0 |
| A341 a or b | C(=O)CH$_3$ | H | 0 |
| A342 a or b | C(=O)CH$_2$CH$_3$ | H | 0 |
| A343 a or b | C(=O)NH$_2$ | H | 0 |
| A344 a or b | C(=O)NHCH$_3$ | H | 0 |
| A345 a or b | C(=O)N(CH$_3$)$_2$ | H | 0 |
| A346 a or b | C(=O)CH$_2$NH$_2$ | H | 0 |
| A347 a or b | C(=O)OCH$_2$CH$_3$ | H | 0 |
| A348 a or b | C(=O)OCH$_2$OH | H | 0 |
| A349 a or b | CH$_2$C(=O)OH | H | 0 |
| A350 a or b | CF$_2$C(=O)OH | H | 0 |
| A351 a or b | CHFC(=O)OH | H | 0 |
| A352 a or b | CH$_2$C(=O)OCH$_3$ | H | 0 |
| A353 a or b | CH$_2$C(=O)OCH$_2$CH$_3$ | H | 0 |
| A354 a or b | CH$_2$C(=O)NH$_2$ | H | 0 |
| A355 a or b | CF$_2$C(=O)OCH$_2$CH$_3$ | H | 0 |
| A356 a or b | CHFC(=O)OCH$_2$CH$_3$ | H | 0 |
| A357 a or b | CH$_2$C(=O)NHCH$_3$ | H | 0 |
| A358 a or b | CH$_2$C(=O)NH(CH$_3$)$_2$ | H | 0 |
| A359 a or b | C(=O)OH | H | 0 |
| A360 a or b | C(=O)OCH$_3$ | H | 0 |
| A361 a or b | CH$_2$C(=O)NHCH$_2$C(=O)OH | H | 0 |
| A362 a or b | CH$_2$C(=O)NHCH$_2$C(=O)OCH$_3$ | H | 0 |
| A363 a or b | H | CH$_3$ | 0 |
| A364 a or b | C(=O)C(=O)OH | CH$_3$ | 0 |
| A365 a or b | C(=O)C(=O)NH$_2$ | CH$_3$ | 0 |
| A366 a or b | C(=O)C(=O)OCH$_3$ | CH$_3$ | 0 |
| A367 a or b | C(=O)C(=O)OCH$_2$CH$_3$ | CH$_3$ | 0 |
| A368 a or b | C(=O)H | CH$_3$ | 0 |
| A369 a or b | C(=O)CH$_3$ | CH$_3$ | 0 |
| A370 a or b | C(=O)CH$_2$CH$_3$ | CH$_3$ | 0 |
| A371 a or b | C(=O)NH$_2$ | CH$_3$ | 0 |
| A372 a or b | C(=O)NHCH$_3$ | CH$_3$ | 0 |
| A373 a or b | C(=O)N(CH$_3$)$_2$ | CH$_3$ | 0 |
| A374 a or b | C(=O)CH$_2$NH$_2$ | CH$_3$ | 0 |
| A375 a or b | C(=O)OCH$_2$CH$_3$ | CH$_3$ | 0 |
| A376 a or b | C(=O)OCH$_2$OH | CH$_3$ | 0 |
| A377 a or b | CH$_2$C(=O)OH | CH$_3$ | 0 |
| A378 a or b | CF$_2$C(=O)OH | CH$_3$ | 0 |
| A379 a or b | CFHC(=O)OH | CH$_3$ | 0 |
| A380 a or b | CH$_2$C(=O)OCH$_3$ | CH$_3$ | 0 |
| A381 a or b | CH$_2$C(=O)OCH$_2$CH$_3$ | CH$_3$ | 0 |
| A382 a or b | CH$_2$C(=O)NH$_2$ | CH$_3$ | 0 |
| A383 a or b | CH$_2$C(=O)NHCH$_3$ | CH$_3$ | 0 |
| A384 a or b | CH$_2$C(=O)NH(CH$_3$)$_2$ | CH$_3$ | 0 |
| A385 a or b | C(=O)OH | CH$_3$ | 0 |

TABLE 9-continued

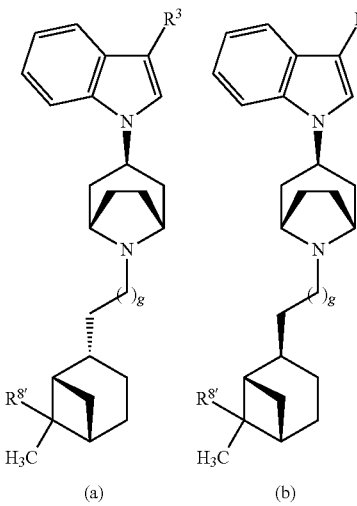

and pharmaceutically acceptable salts and solvates thereof, where:

| Compound | R³ | R⁸' | g |
|---|---|---|---|
| A386 a or b | C(=O)OCH₃ | CH₃ | 0 |
| A387 a or b | CH₂C(=O)NHCH₂C(=O)OH | CH₃ | 0 |
| A388 a or b | CH₂C(=O)NHCH₂C(=O)OCH₃ | CH₃ | 0 |
| A389 a or b | H | H | 1 |
| A390 a or b | C(=O)C(=O)OH | H | 1 |
| A391 a or b | C(=O)C(=O)NH₂ | H | 1 |
| A392 a or b | C(=O)C(=O)OCH₃ | H | 1 |
| A393 a or b | C(=O)C(=O)OCH₂CH₃ | H | 1 |
| A394 a or b | C(=O)H | H | 1 |
| A395 a or b | C(=O)CH₃ | H | 1 |
| A396 a or b | C(=O)CH₂CH₃ | H | 1 |
| A397 a or b | C(=O)NH₂ | H | 1 |
| A398 a or b | C(=O)NHCH₃ | H | 1 |
| A399 a or b | C(=O)N(CH₃)₂ | H | 1 |
| A400 a or b | C(=O)CH₂NH₂ | H | 1 |
| A401 a or b | C(=O)OCH₂CH₃ | H | 1 |
| A402 a or b | C(=O)OCH₂OH | H | 1 |
| A403 a or b | CH₂C(=O)OH | H | 1 |
| A404 a or b | CF₂C(=O)OH | H | 1 |
| A405 a or b | CFHC(=O)OH | H | 1 |
| A406 a or b | CH₂C(=O)OCH₃ | H | 1 |
| A407 a or b | CH₂C(=O)OCH₂CH₃ | H | 1 |
| A408 a or b | CH₂C(=O)NH₂ | H | 1 |
| A409 a or b | CH₂C(=O)NHCH₃ | H | 1 |
| A410 a or b | CH₂C(=O)NH(CH₃)₂ | H | 1 |
| A411 a or b | C(=O)OH | H | 1 |
| A412 a or b | C(=O)OCH₃ | H | 1 |
| A413 a or b | CH₂C(=O)NHCH₂C(=O)OH | H | 1 |
| A414 a or b | CH₂C(=O)NHCH₂C(=O)OCH₃ | H | 1 |
| A415 a or b | H | CH₃ | 1 |
| A416 a or b | C(=O)C(=O)OH | CH₃ | 1 |
| A417 a or b | C(=O)C(=O)NH₂ | CH₃ | 1 |
| A418 a or b | C(=O)C(=O)OCH₃ | CH₃ | 1 |
| A419 a or b | C(=O)C(=O)OCH₂CH₃ | CH₃ | 1 |
| A420 a or b | C(=O)H | CH₃ | 1 |
| A421 a or b | C(=O)CH₃ | CH₃ | 1 |
| A422 a or b | C(=O)CH₂CH₃ | CH₃ | 1 |
| A423 a or b | C(=O)NH₂ | CH₃ | 1 |
| A424 a or b | C(=O)NHCH₃ | CH₃ | 1 |
| A425 a or b | C(=O)N(CH₃)₂ | CH₃ | 1 |
| A426 a or b | C(=O)CH₂NH₂ | CH₃ | 1 |
| A427 a or b | C(=O)OCH₂CH₃ | CH₃ | 1 |
| A428 a or b | C(=O)OCH₂OH | CH₃ | 1 |
| A429 a or b | CH₂C(=O)OH | CH₃ | 1 |
| A430 a or b | CF₂C(=O)OH | CH₃ | 1 |
| A431 a or b | CHFC(=O)OH | CH₃ | 1 |
| A432 a or b | CH₂C(=O)OCH₃ | CH₃ | 1 |
| A433 a or b | CH₂C(=O)OCH₂CH₃ | CH₃ | 1 |
| A434 a or b | CH₂C(=O)NH₂ | CH₃ | 1 |
| A435 a or b | CH₂C(=O)NHCH₃ | CH₃ | 1 |
| A436 a or b | CH₂C(=O)NH(CH₃)₂ | CH₃ | 1 |

TABLE 9-continued

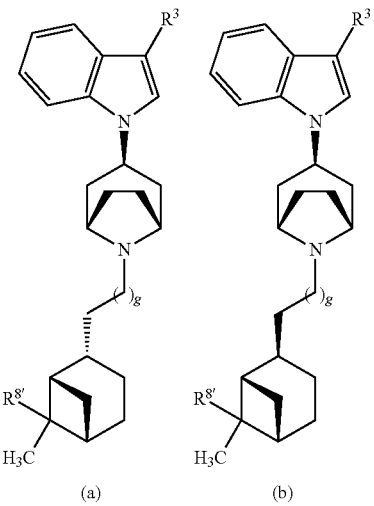

and pharmaceutically acceptable salts and solvates thereof, where:

| Compound | R³ | R⁸' | g |
|---|---|---|---|
| A437 a or b | C(=O)OH | CH₃ | 1 |
| A438 a or b | C(=O)OCH₃ | CH₃ | 1 |
| A439 a or b | CH₂C(=O)NHCH₂C(=O)OH | CH₃ | 1 |
| A440 a or b | CH₂C(=O)NHCH₂C(=O)OCH₃ | CH₃ | 1 |
| A441 a or b | H | H | 2 |
| A442 a or b | C(=O)C(=O)OH | H | 2 |
| A443 a or b | C(=O)C(=O)NH₂ | H | 2 |
| A444 a or b | C(=O)C(=O)OCH₃ | H | 2 |
| A445 a or b | C(=O)C(=O)OCH₂CH₃ | H | 2 |
| A446 a or b | C(=O)H | H | 2 |
| A447 a or b | C(=O)CH₃ | H | 2 |
| A448 a or b | C(=O)CH₂CH₃ | H | 2 |
| A449 a or b | C(=O)NH₂ | H | 2 |
| A450 a or b | C(=O)NHCH₃ | H | 2 |
| A451 a or b | C(=O)N(CH₃)₂ | H | 2 |
| A452 a or b | C(=O)CH₂NH₂ | H | 2 |
| A453 a or b | C(=O)OCH₂CH₃ | H | 2 |
| A454 a or b | C(=O)OCH₂OH | H | 2 |
| A455 a or b | CH₂C(=O)OH | H | 2 |
| A456 a or b | CH₂C(=O)OCH₃ | H | 2 |
| A457 a or b | CH₂C(=O)OCH₂CH₃ | H | 2 |
| A458 a or b | CH₂C(=O)NH₂ | H | 2 |
| A459 a or b | CH₂C(=O)NHCH₃ | H | 2 |
| A460 a or b | CH₂C(=O)NH(CH₃)₂ | H | 2 |
| A461 a or b | C(=O)OH | H | 2 |
| A462 a or b | C(=O)OCH₃ | H | 2 |
| A463 a or b | CH₂C(=O)NHCH₂C(=O)OH | H | 2 |
| A464 a or b | CH₂C(=O)NHCH₂C(=O)OCH₃ | H | 2 |
| A465 a or b | H | CH₃ | 2 |
| A466 a or b | C(=O)C(=O)OH | CH₃ | 2 |
| A467 a or b | C(=O)C(=O)NH₂ | CH₃ | 2 |
| A468 a or b | C(=O)C(=O)OCH₃ | CH₃ | 2 |
| A469 a or b | C(=O)C(=O)OCH₂CH₃ | CH₃ | 2 |
| A470 a or b | C(=O)H | CH₃ | 2 |
| A471 a or b | C(=O)CH₃ | CH₃ | 2 |
| A472 a or b | C(=O)CH₂CH₃ | CH₃ | 2 |
| A473 a or b | C(=O)NH₂ | CH₃ | 2 |
| A474 a or b | C(=O)NHCH₃ | CH₃ | 2 |
| A475 a or b | C(=O)N(CH₃)₂ | CH₃ | 2 |
| A476 a or b | C(=O)CH₂NH₂ | CH₃ | 2 |
| A477 a or b | C(=O)OCH₂CH₃ | CH₃ | 2 |
| A478 a or b | C(=O)OCH₂OH | CH₃ | 2 |
| A479 a or b | CH₂C(=O)OH | CH₃ | 2 |
| A480 a or b | CH₂C(=O)OCH₃ | CH₃ | 2 |
| A481 a or b | CH₂C(=O)OCH₂CH₃ | CH₃ | 2 |
| A482 a or b | CH₂C(=O)NH₂ | CH₃ | 2 |
| A483 a or b | CF₂C(=O)NH₂ | CH₃ | 2 |
| A484 a or b | CHFC(=O)NH₂ | CH₃ | 2 |
| A485 a or b | CH₂C(=O)NHCH₃ | CH₃ | 2 |
| A486 a or b | CH₂C(=O)NH(CH₃)₂ | CH₃ | 2 |
| A487 a or b | C(=O)OH | CH₃ | 2 |

TABLE 9-continued

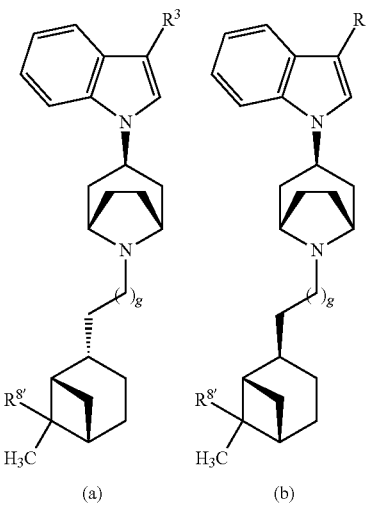

(a)     (b)

and pharmaceutically acceptable salts and solvates thereof, where:

| Compound | $R^3$ | $R^{8'}$ | g |
|---|---|---|---|
| A488 a or b | C(=O)OCH$_3$ | CH$_3$ | 2 |
| A489 a or b | CH$_2$C(=O)NHCH$_2$C(=O)OH | CH$_3$ | 2 |
| A490 a or b | CH$_2$C(=O)NHCH$_2$C(=O)OCH$_3$ | CH$_3$ | 2 |

TABLE 10

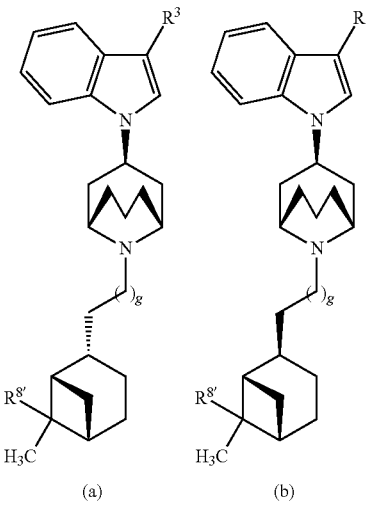

(a)     (b)

and pharmaceutically acceptable salts and solvates thereof, where:

| Compound | $R^3$ | $R^{8'}$ | g |
|---|---|---|---|
| A491 a or b | H | H | 0 |
| A492 a or b | C(=O)C(=O)OH | H | 0 |
| A493 a or b | C(=O)C(=O)NH$_2$ | H | 0 |
| A494 a or b | C(=O)C(=O)OCH$_3$ | H | 0 |
| A495 a or b | C(=O)C(=O)OCH$_2$CH$_3$ | H | 0 |
| A496 a or b | C(=O)H | H | 0 |
| A497 a or b | C(=O)CH$_3$ | H | 0 |
| A498 a or b | C(=O)CH$_2$CH$_3$ | H | 0 |
| A499 a or b | C(=O)NH$_2$ | H | 0 |
| A500 a or b | C(=O)NHCH$_3$ | H | 0 |
| A501 a or b | C(=O)N(CH$_3$)$_2$ | H | 0 |
| A502 a or b | C(=O)CH$_2$NH$_2$ | H | 0 |
| A503 a or b | C(=O)OCH$_2$CH$_3$ | H | 0 |
| A504 a or b | C(=O)OCH$_2$OH | H | 0 |

TABLE 10-continued

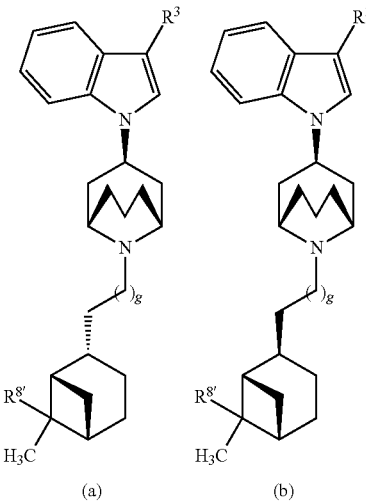

(a)     (b)

and pharmaceutically acceptable salts and solvates thereof, where:

| Compound | $R^3$ | $R^{8'}$ | g |
|---|---|---|---|
| A505 a or b | CH$_2$C(=O)OH | H | 0 |
| A506 a or b | CF$_2$C(=O)OH | H | 0 |
| A507 a or b | CHFC(=O)OH | H | 0 |
| A508 a or b | CH$_2$C(=O)OCH$_3$ | H | 0 |
| A509 a or b | CH$_2$C(=O)OCH$_2$CH$_3$ | H | 0 |
| A510 a or b | CH$_2$C(=O)NH$_2$ | H | 0 |
| A511 a or b | CF$_2$C(=O)NH$_2$ | H | 0 |
| A512 a or b | CHFC(=O)NH$_2$ | H | 0 |
| A513 a or b | CH$_2$C(=O)NHCH$_3$ | H | 0 |
| A514 a or b | CH$_2$C(=O)NH(CH$_3$)$_2$ | H | 0 |
| A515 a or b | C(=O)OH | H | 0 |
| A516 a or b | C(=O)OCH$_3$ | H | 0 |
| A517 a or b | CH$_2$C(=O)NHCH$_2$C(=O)OH | H | 0 |
| A518 a or b | CH$_2$C(=O)NHCH$_2$C(=O)OCH$_3$ | H | 0 |
| A519 a or b | H | CH$_3$ | 0 |
| A520 a or b | C(=O)C(=O)OH | CH$_3$ | 0 |
| A521 a or b | C(=O)C(=O)NH$_2$ | CH$_3$ | 0 |
| A522 a or b | C(=O)C(=O)OCH$_3$ | CH$_3$ | 0 |
| A523 a or b | C(=O)C(=O)OCH$_2$CH$_3$ | CH$_3$ | 0 |
| A524 a or b | C(=O)H | CH$_3$ | 0 |
| A525 a or b | C(=O)CH$_3$ | CH$_3$ | 0 |
| A526 a or b | C(=O)CH$_2$CH$_3$ | CH$_3$ | 0 |
| A527 a or b | C(=O)NH$_2$ | CH$_3$ | 0 |
| A528 a or b | C(=O)NHCH$_3$ | CH$_3$ | 0 |
| A529 a or b | C(=O)N(CH$_3$)$_2$ | CH$_3$ | 0 |
| A530 a or b | C(=O)CH$_2$NH$_2$ | CH$_3$ | 0 |
| A531 a or b | C(=O)OCH$_2$CH$_3$ | CH$_3$ | 0 |
| A532 a or b | C(=O)OCH$_2$OH | CH$_3$ | 0 |
| A533 a or b | CH$_2$C(=O)OH | CH$_3$ | 0 |
| A534 a or b | CF$_2$C(=O)OH | CH$_3$ | 0 |
| A535 a or b | CHFC(=O)OH | CH$_3$ | 0 |
| A536 a or b | CH$_2$C(=O)OCH$_3$ | CH$_3$ | 0 |
| A537 a or b | CH$_2$C(=O)OCH$_2$CH$_3$ | CH$_3$ | 0 |
| A538 a or b | CH$_2$C(=O)NH$_2$ | CH$_3$ | 0 |
| A539 a or b | CH$_2$C(=O)NHCH$_3$ | CH$_3$ | 0 |
| A540 a or b | CH$_2$C(=O)NH(CH$_3$)$_2$ | CH$_3$ | 0 |
| A541 a or b | C(=O)OH | CH$_3$ | 0 |
| A542 a or b | C(=O)OCH$_3$ | CH$_3$ | 0 |
| A543 a or b | CH$_2$C(=O)NHCH$_2$C(=O)OH | CH$_3$ | 0 |
| A544 a or b | CH$_2$C(=O)NHCH$_2$C(=O)OCH$_3$ | CH$_3$ | 0 |
| A545 a or b | H | H | 1 |
| A546 a or b | C(=O)C(=O)OH | H | 1 |
| A547 a or b | C(=O)C(=O)NH$_2$ | H | 1 |
| A548 a or b | C(=O)C(=O)OCH$_3$ | H | 1 |
| A549 a or b | C(=O)C(=O)OCH$_2$CH$_3$ | H | 1 |
| A550 a or b | C(=O)H | H | 1 |
| A551 a or b | C(=O)CH$_3$ | H | 1 |
| A552 a or b | C(=O)CH$_2$CH$_3$ | H | 1 |
| A553 a or b | C(=O)NH$_2$ | H | 1 |
| A554 a or b | C(=O)NHCH$_3$ | H | 1 |
| A555 a or b | C(=O)N(CH$_3$)$_2$ | H | 1 |

TABLE 10-continued

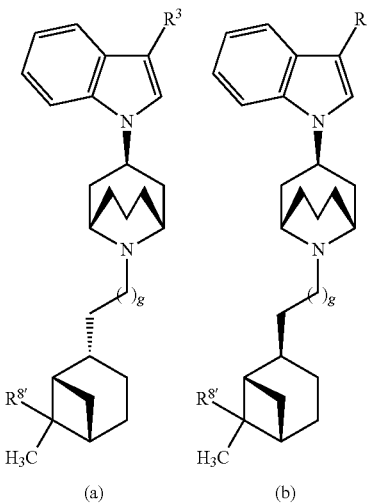

(a) (b)

and pharmaceutically acceptable salts and solvates thereof, where:

| Compound | R³ | R⁸' | g |
|---|---|---|---|
| A556 a or b | C(=O)CH₂NH₂ | H | 1 |
| A557 a or b | C(=O)OCH₂CH₃ | H | 1 |
| A558 a or b | C(=O)OCH₂OH | H | 1 |
| A559 a or b | CH₂C(=O)OH | H | 1 |
| A560 a or b | CF₂C(=O)OH | H | 1 |
| A561 a or b | CHFC(=O)OH | H | 1 |
| A562 a or b | CH₂C(=O)OCH₃ | H | 1 |
| A563 a or b | CH₂C(=O)OCH₂CH₃ | H | 1 |
| A564 a or b | CH₂C(=O)NH₂ | H | 1 |
| A565 a or b | CH₂C(=O)NHCH₃ | H | 1 |
| A566 a or b | CH₂C(=O)NH(CH₃)₂ | H | 1 |
| A567 a or b | C(=O)OH | H | 1 |
| A568 a or b | C(=O)OCH₃ | H | 1 |
| A569 a or b | CH₂C(=O)NHCH₂C(=O)OH | H | 1 |
| A570 a or b | CH₂C(=O)NHCH₂C(=O)OCH₃ | H | 1 |
| A571 a or b | H | CH₃ | 1 |
| A572 a or b | C(=O)C(=O)OH | CH₃ | 1 |
| A573 a or b | C(=O)C(=O)NH₂ | CH₃ | 1 |
| A574 a or b | C(=O)C(=O)OCH₃ | CH₃ | 1 |
| A575 a or b | C(=O)C(=O)OCH₂CH₃ | CH₃ | 1 |
| A576 a or b | C(=O)H | CH₃ | 1 |
| A577 a or b | C(=O)CH₃ | CH₃ | 1 |
| A578 a or b | C(=O)CH₂CH₃ | CH₃ | 1 |
| A579 a or b | C(=O)NH₂ | CH₃ | 1 |
| A580 a or b | C(=O)NHCH₃ | CH₃ | 1 |
| A581 a or b | C(=O)N(CH₃)₂ | CH₃ | 1 |
| A582 a or b | C(=O)CH₂NH₂ | CH₃ | 1 |
| A583 a or b | C(=O)OCH₂CH₃ | CH₃ | 1 |
| A584 a or b | C(=O)OCH₂OH | CH₃ | 1 |
| A585 a or b | CH₂C(=O)OH | CH₃ | 1 |
| A586 | CF₂C(=O)OH | CH₃ | 1 |
| A587 | CHFC(=O)OH | CH₃ | 1 |
| A588 a or b | CH₂C(=O)OCH₃ | CH₃ | 1 |
| A589 a or b | CH₂C(=O)OCH₂CH₃ | CH₃ | 1 |
| A590 a or b | CH₂C(=O)NH₂ | CH₃ | 1 |
| A591 | CF₂C(=O)OCH₂CH₃ | CH₃ | 1 |
| A592 | CHFC(=O)OCH₂CH₃ | CH₃ | 1 |
| A593 a or b | CH₂C(=O)NHCH₃ | CH₃ | 1 |
| A594 a or b | CH₂C(=O)NH(CH₃)₂ | CH₃ | 1 |
| A595 a or b | C(=O)OH | CH₃ | 1 |
| A596 a or b | C(=O)OCH₃ | CH₃ | 1 |
| A597 a or b | CH₂C(=O)NHCH₂C(=O)OH | CH₃ | 1 |
| A598 a or b | CH₂C(=O)NHCH₂C(=O)OCH₃ | CH₃ | 1 |
| A599 a or b | H | H | 2 |
| A600 a or b | C(=O)C(=O)OH | H | 2 |
| A601 a or b | C(=O)C(=O)NH₂ | H | 2 |
| A602 a or b | C(=O)C(=O)OCH₃ | H | 2 |
| A603 a or b | C(=O)C(=O)OCH₂CH₃ | H | 2 |
| A604 a or b | C(=O)H | H | 2 |
| A605 a or b | C(=O)CH₃ | H | 2 |
| A606 a or b | C(=O)CH₂CH₃ | H | 2 |
| A607 a or b | C(=O)NH₂ | H | 2 |
| A608 a or b | C(=O)NHCH₃ | H | 2 |
| A609 a or b | C(=O)N(CH₃)₂ | H | 2 |
| A610 a or b | C(=O)CH₂NH₂ | H | 2 |
| A611 a or b | C(=O)OCH₂CH₃ | H | 2 |
| A612 a or b | C(=O)OCH₂OH | H | 2 |
| A613 a or b | CH₂C(=O)OH | H | 2 |
| A614 | CH₂C(=O)OH | H | 2 |
| A615 | CF₂C(=O)OH | H | 2 |
| A616 a or b | CHFC(=O)OCH₃ | H | 2 |
| A617 a or b | CH₂C(=O)OCH₂CH₃ | H | 2 |
| A618 a or b | CH₂C(=O)NH₂ | H | 2 |
| A619 | CF₂C(=O)NH₂ | H | 2 |
| A620 | CHFC(=O)NH₂ | H | 2 |
| A621 a or b | CH₂C(=O)NHCH₃ | H | 2 |
| A622 a or b | CH₂C(=O)NH(CH₃)₂ | H | 2 |
| A623 a or b | C(=O)OH | H | 2 |
| A624 a or b | C(=O)OCH₃ | H | 2 |
| A625 a or b | CH₂C(=O)NHCH₂C(=O)OH | H | 2 |
| A626 a or b | CH₂C(=O)NHCH₂C(=O)OCH₃ | H | 2 |
| A627 a or b | H | CH₃ | 2 |
| A628 a or b | C(=O)C(=O)OH | CH₃ | 2 |
| A629 a or b | C(=O)C(=O)NH₂ | CH₃ | 2 |
| A630 a or b | C(=O)C(=O)OCH₃ | CH₃ | 2 |
| A631 a or b | C(=O)C(=O)OCH₂CH₃ | CH₃ | 2 |
| A632 a or b | C(=O)H | CH₃ | 2 |
| A633 a or b | C(=O)CH₃ | CH₃ | 2 |
| A634 a or b | C(=O)CH₂CH₃ | CH₃ | 2 |
| A635 a or b | C(=O)NH₂ | CH₃ | 2 |
| A636 a or b | C(=O)NHCH₃ | CH₃ | 2 |
| A637 a or b | C(=O)N(CH₃)₂ | CH₃ | 2 |
| A638 a or b | C(=O)CH₂NH₂ | CH₃ | 2 |
| A639 a or b | C(=O)OCH₂CH₃ | CH₃ | 2 |
| A640 a or b | C(=O)OCH₂OH | CH₃ | 2 |
| A641 a or b | CH₂C(=O)OH | CH₃ | 2 |
| A642 | CF₂C(=O)OH | CH₃ | 2 |
| A643 | CHFC(=O)OH | CH₃ | 2 |
| A644 a or b | CH₂C(=O)OCH₃ | CH₃ | 2 |
| A645 a or b | CH₂C(=O)OCH₂CH₃ | CH₃ | 2 |
| A646 a or b | CH₂C(=O)NH₂ | CH₃ | 2 |
| A647 a or b | CH₂C(=O)NHCH₃ | CH₃ | 2 |
| A648 a or b | CH₂C(=O)NH(CH₃)₂ | CH₃ | 2 |
| A649 a or b | C(=O)OH | CH₃ | 2 |
| A650 a or b | C(=O)OCH₃ | CH₃ | 2 |
| A651 a or b | CH₂C(=O)NHCH₂C(=O)OH | CH₃ | 2 |
| A652 a or b | CH₂C(=O)NHCH₂C(=O)OCH₃ | CH₃ | 2 |

TABLE 11

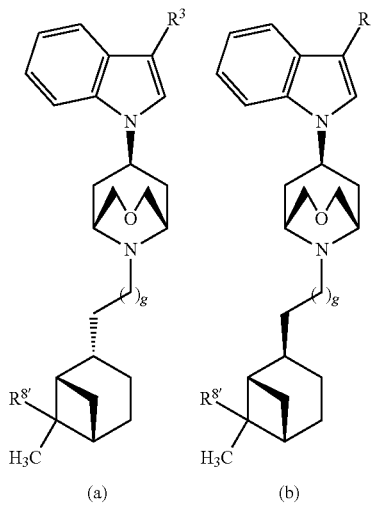

(a)   (b)

and pharmaceutically acceptable salts and solvates thereof, where:

| Compound | $R^3$ | $R^{8'}$ | g |
|---|---|---|---|
| A653 a or b | H | H | 0 |
| A654 a or b | C(=O)C(=O)OH | H | 0 |
| A655 a or b | C(=O)C(=O)NH$_2$ | H | 0 |
| A656 a or b | C(=O)C(=O)OCH$_3$ | H | 0 |
| A657 a or b | C(=O)C(=O)OCH$_2$CH$_3$ | H | 0 |
| A658 a or b | C(=O)H | H | 0 |
| A659 a or b | C(=O)CH$_3$ | H | 0 |
| A660 a or b | C(=O)CH$_2$CH$_3$ | H | 0 |
| A661 a or b | C(=O)NH$_2$ | H | 0 |
| A662 a or b | C(=O)NHCH$_3$ | H | 0 |
| A663 a or b | C(=O)N(CH$_3$)$_2$ | H | 0 |
| A664 a or b | C(=O)CH$_2$NH$_2$ | H | 0 |
| A665 a or b | C(=O)OCH$_2$CH$_3$ | H | 0 |
| A666 a or b | C(=O)OCH$_2$OH | H | 0 |
| A667 a or b | CH$_2$C(=O)OH | H | 0 |
| A668 a or b | CF$_2$C(=O)OH | H | 0 |
| A669 a or b | CHFC(=O)OH | H | 0 |
| A670 a or b | CH$_2$C(=O)OCH$_3$ | H | 0 |
| A671 a or b | CH$_2$C(=O)OCH$_2$CH$_3$ | H | 0 |
| A672 a or b | CH$_2$C(=O)NH$_2$ | H | 0 |
| A673 a or b | CF$_2$C(=O)NH$_2$ | H | 0 |
| A674 a or b | CHFC(=O)NH$_2$ | H | 0 |
| A675 a or b | CH$_2$C(=O)NHCH$_3$ | H | 0 |
| A676 a or b | CH$_2$C(=O)NH(CH$_3$)$_2$ | H | 0 |
| A677 a or b | C(=O)OH | H | 0 |
| A678 a or b | C(=O)OCH$_3$ | H | 0 |
| A679 a or b | CH$_2$C(=O)NHCH$_2$C(=O)OH | H | 0 |
| A680 a or b | CH$_2$C(=O)NHCH$_2$C(=O)OCH$_3$ | H | 0 |
| A681 a or b | H | CH$_3$ | 0 |
| A682 a or b | C(=O)C(=O)OH | CH$_3$ | 0 |
| A683 a or b | C(=O)C(=O)NH$_2$ | CH$_3$ | 0 |
| A684 a or b | C(=O)C(=O)OCH$_3$ | CH$_3$ | 0 |
| A685 a or b | C(=O)C(=O)OCH$_2$CH$_3$ | CH$_3$ | 0 |
| A686 a or b | C(=O)H | CH$_3$ | 0 |
| A687 a or b | C(=O)CH$_3$ | CH$_3$ | 0 |
| A688 a or b | C(=O)CH$_2$CH$_3$ | CH$_3$ | 0 |
| A689 a or b | C(=O)NH$_2$ | CH$_3$ | 0 |
| A690 a or b | C(=O)NHCH$_3$ | CH$_3$ | 0 |
| A691 a or b | C(=O)N(CH$_3$)$_2$ | CH$_3$ | 0 |
| A692 a or b | C(=O)CH$_2$NH$_2$ | CH$_3$ | 0 |
| A693 a or b | C(=O)OCH$_2$CH$_3$ | CH$_3$ | 0 |
| A694 a or b | C(=O)OCH$_2$OH | CH$_3$ | 0 |
| A695 a or b | CH$_2$C(=O)OH | CH$_3$ | 0 |
| A696 a or b | CF$_2$C(=O)OH | CH$_3$ | 0 |
| A697 a or b | CHFC(=O)OH | CH$_3$ | 0 |
| A698 a or b | CH$_2$C(=O)OCH$_3$ | CH$_3$ | 0 |
| A699 a or b | CH$_2$C(=O)OCH$_2$CH$_3$ | CH$_3$ | 0 |
| A700 a or b | CH$_2$C(=O)NH$_2$ | CH$_3$ | 0 |
| A701 a or b | CH$_2$C(=O)NHCH$_3$ | CH$_3$ | 0 |
| A702 a or b | CH$_2$C(=O)NH(CH$_3$)$_2$ | CH$_3$ | 0 |
| A703 a or b | C(=O)OH | CH$_3$ | 0 |

TABLE 11-continued

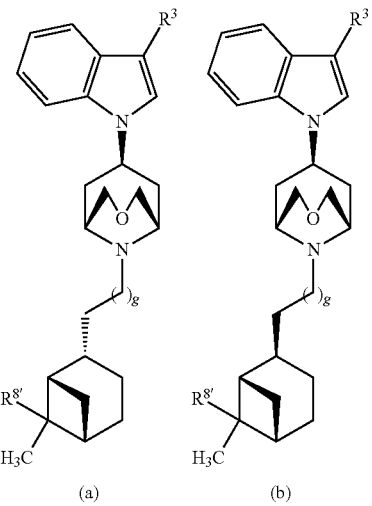

(a)   (b)

and pharmaceutically acceptable salts and solvates thereof, where:

| Compound | $R^3$ | $R^{8'}$ | g |
|---|---|---|---|
| A704 a or b | C(=O)OCH$_3$ | CH$_3$ | 0 |
| A705 a or b | CH$_2$C(=O)NHCH$_2$C(=O)OH | CH$_3$ | 0 |
| A706 a or b | CH$_2$C(=O)NHCH$_2$C(=O)OCH$_3$ | CH$_3$ | 0 |
| A707 a or b | H | H | 1 |
| A708 a or b | C(=O)C(=O)OH | H | 1 |
| A709 a or b | C(=O)C(=O)NH$_2$ | H | 1 |
| A710 a or b | C(=O)C(=O)OCH$_3$ | H | 1 |
| A711 a or b | C(=O)C(=O)OCH$_2$CH$_3$ | H | 1 |
| A712 a or b | C(=O)H | H | 1 |
| A713 a or b | C(=O)CH$_3$ | H | 1 |
| A714 a or b | C(=O)CH$_2$CH$_3$ | H | 1 |
| A715 a or b | C(=O)NH$_2$ | H | 1 |
| A716 a or b | C(=O)NHCH$_3$ | H | 1 |
| A717 a or b | C(=O)N(CH$_3$)$_2$ | H | 1 |
| A718 a or b | C(=O)CH$_2$NH$_2$ | H | 1 |
| A719 a or b | C(=O)OCH$_2$CH$_3$ | H | 1 |
| A720 a or b | C(=O)OCH$_2$OH | H | 1 |
| A721 a or b | CH$_2$C(=O)OH | H | 1 |
| A722 a or b | CF$_2$C(=O)OH | H | 1 |
| A723 a or b | CHFC(=O)OH | H | 1 |
| A724 a or b | CH$_2$C(=O)OCH$_3$ | H | 1 |
| A725 a or b | CH$_2$C(=O)OCH$_2$CH$_3$ | H | 1 |
| A726 a or b | CH$_2$C(=O)NH$_2$ | H | 1 |
| A727 a or b | CH$_2$C(=O)NHCH$_3$ | H | 1 |
| A728 a or b | CH$_2$C(=O)NH(CH$_3$)$_2$ | H | 1 |
| A729 a or b | C(=O)OH | H | 1 |
| A730 a or b | C(=O)OCH$_3$ | H | 1 |
| A731 a or b | CH$_2$C(=O)NHCH$_2$C(=O)OH | H | 1 |
| A732 a or b | CH$_2$C(=O)NHCH$_2$C(=O)OCH$_3$ | H | 1 |
| A733 a or b | H | CH$_3$ | 1 |
| A734 a or b | C(=O)C(=O)OH | CH$_3$ | 1 |
| A735 a or b | C(=O)C(=O)NH$_2$ | CH$_3$ | 1 |
| A736 a or b | C(=O)C(=O)OCH$_3$ | CH$_3$ | 1 |
| A737 a or b | C(=O)C(=O)OCH$_2$CH$_3$ | CH$_3$ | 1 |
| A738 a or b | C(=O)H | CH$_3$ | 1 |
| A739 a or b | C(=O)CH$_3$ | CH$_3$ | 1 |
| A740 a or b | C(=O)CH$_2$CH$_3$ | CH$_3$ | 1 |
| A741 a or b | C(=O)NH$_2$ | CH$_3$ | 1 |
| A742 a or b | C(=O)NHCH$_3$ | CH$_3$ | 1 |
| A743 a or b | C(=O)N(CH$_3$)$_2$ | CH$_3$ | 1 |
| A744 a or b | C(=O)CH$_2$NH$_2$ | CH$_3$ | 1 |
| A745 a or b | C(=O)OCH$_2$CH$_3$ | CH$_3$ | 1 |
| A746 a or b | C(=O)OCH$_2$OH | CH$_3$ | 1 |
| A747 a or b | CH$_2$C(=O)OH | CH$_3$ | 1 |
| A748 a or b | CF$_2$C(=O)OH | CH$_3$ | 1 |
| A749 a or b | CHFC(=O)OH | CH$_3$ | 1 |
| A750 a or b | CH$_2$C(=O)OCH$_3$ | CH$_3$ | 1 |
| A751 a or b | CH$_2$C(=O)OCH$_2$CH$_3$ | CH$_3$ | 1 |
| A752 a or b | CH$_2$C(=O)NH$_2$ | CH$_3$ | 1 |
| A753 a or b | CH$_2$C(=O)NHCH$_3$ | CH$_3$ | 1 |
| A754 a or b | CH$_2$C(=O)NH(CH$_3$)$_2$ | CH$_3$ | 1 |

TABLE 11-continued

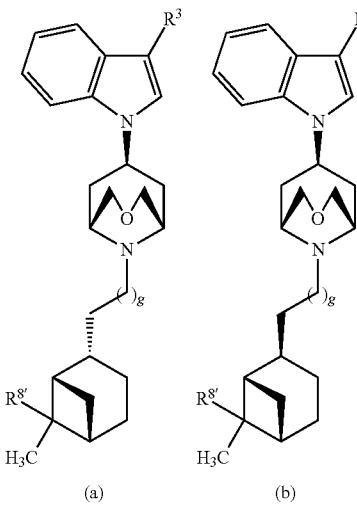

(a)   (b)

and pharmaceutically acceptable salts and solvates thereof, where:

| Compound | R³ | R⁸' | g |
|---|---|---|---|
| A755 a or b | C(=O)OH | CH₃ | 1 |
| A756 a or b | C(=O)OCH₃ | CH₃ | 1 |
| A757 a or b | CH₂C(=O)NHCH₂C(=O)OH | CH₃ | 1 |
| A758 a or b | CH₂C(=O)NHCH₂C(=O)OCH₃ | CH₃ | 1 |
| A759 a or b | H | H | 2 |
| A760 a or b | C(=O)C(=O)OH | H | 2 |
| A761 a or b | C(=O)C(=O)NH₂ | H | 2 |
| A762 a or b | C(=O)C(=O)OCH₃ | H | 2 |
| A763 a or b | C(=O)C(=O)OCH₂CH₃ | H | 2 |
| A764 a or b | C(=O)H | H | 2 |
| A765 a or b | C(=O)CH₃ | H | 2 |
| A766 a or b | C(=O)CH₂CH₃ | H | 2 |
| A767 a or b | C(=O)NH₂ | H | 2 |
| A768 a or b | C(=O)NHCH₃ | H | 2 |
| A769 a or b | C(=O)N(CH₃)₂ | H | 2 |
| A770 a or b | C(=O)CH₂NH₂ | H | 2 |
| A771 a or b | C(=O)OCH₂CH₃ | H | 2 |
| A772 a or b | C(=O)OCH₂OH | H | 2 |
| A773 a or b | CH₂C(=O)OH | H | 2 |
| A774 a or b | CF₂C(=O)OH | H | 2 |
| A775 a or b | CHFC(=O)OH | H | 2 |
| A776 a or b | CH₂C(=O)OCH₃ | H | 2 |
| A777 a or b | CH₂C(=O)OCH₂CH₃ | H | 2 |
| A778 a or b | CH₂C(=O)NH₂ | H | 2 |
| A779 a or b | CH₂C(=O)NHCH₃ | H | 2 |
| A780 a or b | CH₂C(=O)NH(CH₃)₂ | H | 2 |
| A781 a or b | C(=O)OH | H | 2 |
| A782 a or b | C(=O)OCH₃ | H | 2 |
| A783 a or b | CH₂C(=O)NHCH₂C(=O)OH | H | 2 |
| A784 a or b | CH₂C(=O)NHCH₂C(=O)OCH₃ | H | 2 |
| A785 a or b | H | CH₃ | 2 |
| A786 a or b | C(=O)C(=O)OH | CH₃ | 2 |
| A787 a or b | C(=O)C(=O)NH₂ | CH₃ | 2 |
| A788 a or b | C(=O)C(=O)OCH₃ | CH₃ | 2 |
| A789 a or b | C(=O)C(=O)OCH₂CH₃ | CH₃ | 2 |
| A790 a or b | C(=O)H | CH₃ | 2 |
| A791 a or b | C(=O)CH₃ | CH₃ | 2 |
| A792 a or b | C(=O)CH₂CH₃ | CH₃ | 2 |
| A793 a or b | C(=O)NH₂ | CH₃ | 2 |
| A794 a or b | C(=O)NHCH₃ | CH₃ | 2 |
| A795 a or b | C(=O)N(CH₃)₂ | CH₃ | 2 |
| A796 a or b | C(=O)CH₂NH₂ | CH₃ | 2 |
| A797 a or b | C(=O)OCH₂CH₃ | CH₃ | 2 |
| A798 a or b | C(=O)OCH₂OH | CH₃ | 2 |
| A799 a or b | CH₂C(=O)OH | CH₃ | 2 |
| A800 a or b | CF₂C(=O)OH | CH₃ | 2 |
| A801 a or b | CHFC(=O)OH | CH₃ | 2 |
| A802 a or b | CH₂C(=O)OCH₃ | CH₃ | 2 |
| A803 a or b | CH₂C(=O)OCH₂CH₃ | CH₃ | 2 |

TABLE 11-continued

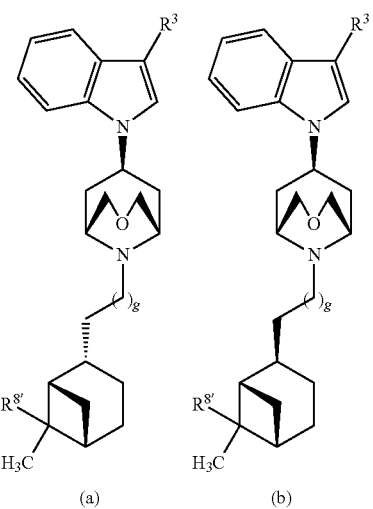

(a)   (b)

and pharmaceutically acceptable salts and solvates thereof, where:

| Compound | R³ | R⁸' | g |
|---|---|---|---|
| A804 a or b | CH₂C(=O)NH₂ | CH₃ | 2 |
| A805 a or b | CF₂C(=O)NH₂ | CH₃ | 2 |
| A806 a or b | CHFC(=O)NH₂ | CH₃ | 2 |
| A807 a or b | CH₂C(=O)NHCH₃ | CH₃ | 2 |
| A808 a or b | CH₂C(=O)NH(CH₃)₂ | CH₃ | 2 |
| A809 a or b | C(=O)OH | CH₃ | 2 |
| A810 a or b | C(=O)OCH₃ | CH₃ | 2 |
| A811 a or b | CH₂C(=O)NHCH₂C(=O)OH | CH₃ | 2 |
| A812 a or b | CH₂C(=O)NHCH₂C(=O)OCH₃ | CH₃ | 2 |

TABLE 12

(a)

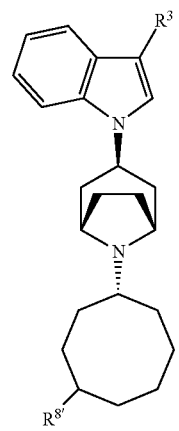

(b)

TABLE 12-continued

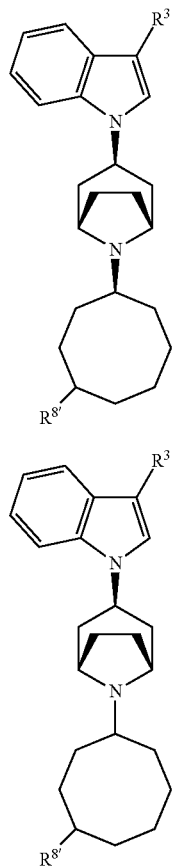

(c)

and pharmaceutically acceptable salts and solvates thereof, where:

| Compound | $R^3$ | $R^{8'}$ |
|---|---|---|
| A813 c | H | H |
| A814 c | C(=O)C(=O)OH | H |
| A815 c | C(=O)C(=O)NH$_2$ | H |
| A816 c | C(=O)C(=O)OCH$_3$ | H |
| A817 c | C(=O)C(=O)OCH$_2$CH$_3$ | H |
| A818 c | C(=O)H | H |
| A819 c | C(=O)CH$_3$ | H |
| A820 c | C(=O)CH$_2$CH$_3$ | H |
| A821 c | C(=O)NH$_2$ | H |
| A822 c | C(=O)NHCH$_3$ | H |
| A823 c | C(=O)N(CH$_3$)$_2$ | H |
| A824 c | C(=O)CH$_2$NH$_2$ | H |
| A825 c | C(=O)OCH$_2$CH$_3$ | H |
| A826 c | C(=O)OCH$_2$OH | H |
| A827 c | CH$_2$C(=O)OH | H |
| A828 c | CF$_2$C(=O)OH | H |
| A829 c | CHFC(=O)OH | H |
| A830 c | CH$_2$C(=O)OCH$_3$ | H |
| A831 c | CH$_2$C(=O)OCH$_2$CH$_3$ | H |
| A832 c | CH$_2$C(=O)NH$_2$ | H |
| A833 c | CF$_2$C(=O)NH$_2$ | H |
| A834 c | CHFC(=O)NH$_2$ | H |
| A835 c | CH$_2$C(=O)NHCH$_3$ | H |
| A836 c | CH$_2$C(=O)NH(CH$_3$)$_2$ | H |
| A837 c | C(=O)OH | H |
| A838 c | C(=O)OCH$_3$ | H |
| A839 c | CH$_2$C(=O)NHCH$_2$C(=O)OH | H |
| A840 c | CH$_2$C(=O)NHCH$_2$C(=O)OCH$_3$ | H |
| A841 a or b | H | CH$_3$ |
| A842 a or b | C(=O)C(=O)OH | CH$_3$ |
| A843 a or b | C(=O)C(=O)NH$_2$ | CH$_3$ |
| A844 a or b | C(=O)C(=O)OCH$_3$ | CH$_3$ |
| A845 a or b | C(=O)C(=O)OCH$_2$CH$_3$ | CH$_3$ |
| A846 a or b | C(=O)H | CH$_3$ |
| A847 a or b | C(=O)CH$_3$ | CH$_3$ |
| A848 a or b | C(=O)CH$_2$CH$_3$ | CH$_3$ |
| A849 a or b | C(=O)NH$_2$ | CH$_3$ |
| A850 a or b | C(=O)NHCH$_3$ | CH$_3$ |
| A851 a or b | C(=O)N(CH$_3$)$_2$ | CH$_3$ |
| A852 a or b | C(=O)CH$_2$NH$_2$ | CH$_3$ |
| A853 a or b | C(=O)OCH$_2$CH$_3$ | CH$_3$ |
| A854 a or b | C(=O)OCH$_2$OH | CH$_3$ |
| A855 a or b | CH$_2$C(=O)OH | CH$_3$ |
| A856 a or b | CF$_2$C(=O)OH | CH$_3$ |
| A857 a or b | CHFC(=O)OH | CH$_3$ |
| A858 a or b | CH$_2$C(=O)OCH$_3$ | CH$_3$ |
| A859 a or b | CH$_2$C(=O)OCH$_2$CH$_3$ | CH$_3$ |
| A860 a or b | CH$_2$C(=O)NH$_2$ | CH$_3$ |
| A861 a or b | CH$_2$C(=O)NHCH$_3$ | CH$_3$ |
| A862 a or b | CH$_2$C(=O)NH(CH$_3$)$_2$ | CH$_3$ |
| A863 a or b | C(=O)OH | CH$_3$ |
| A864 a or b | C(=O)OCH$_3$ | CH$_3$ |
| A865 a or b | CH$_2$C(=O)NHCH$_2$C(=O)OH | CH$_3$ |
| A866 a or b | CH$_2$C(=O)NHCH$_2$C(=O)OCH$_3$ | CH$_3$ |
| A867 a or b | CH$_2$C(=O)NHCH$_2$C(=O)OCH$_3$ | CH$_2$CH$_3$ |

TABLE 13

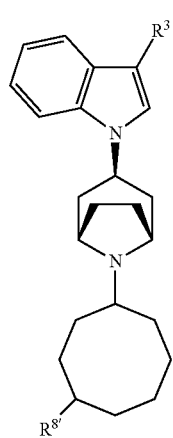

(a)

(b)

TABLE 13-continued

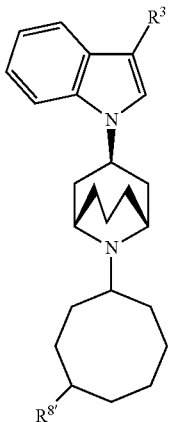

(c)

and pharmaceutically acceptable salts and solvates thereof, where:

| Compound | R³ | R⁸' |
|---|---|---|
| A868 c | H | H |
| A869 c | C(=O)C(=O)OH | H |
| A870 c | C(=O)C(=O)NH₂ | H |
| A871 c | C(=O)C(=O)OCH₃ | H |
| A872 c | C(=O)C(=O)OCH₂CH₃ | H |
| A873 c | C(=O)H | H |
| A874 c | C(=O)CH₃ | H |
| A875 c | C(=O)CH₂CH₃ | H |
| A876 c | C(=O)NH₂ | H |
| A877 c | C(=O)NHCH₃ | H |
| A878 c | C(=O)N(CH₃)₂ | H |
| A879 c | C(=O)CH₂NH₂ | H |
| A880 c | C(=O)OCH₂CH₃ | H |
| A881 c | C(=O)OCH₂OH | H |
| A882 c | CH₂C(=O)OH | H |
| A883 c | CF₂C(=O)OH | H |
| A884 c | CHFC(=O)OH | H |
| A885 c | CH₂C(=O)OCH₃ | H |
| A886 c | CH₂C(=O)OCH₂CH₃ | H |
| A887 c | CH₂C(=O)NH₂ | H |
| A888 c | CF₂C(=O)NH₂ | H |
| A889 c | CHFC(=O)NH₂ | H |
| A890 c | CH₂C(=O)NHCH₃ | H |
| A891 c | CH₂C(=O)NH(CH₃)₂ | H |
| A892 c | C(=O)OH | H |
| A893 c | C(=O)OCH₃ | H |
| A894 c | CH₂C(=O)NHCH₂C(=O)OH | H |
| A895 c | CH₂C(=O)NHCH₂C(=O)OCH₃ | H |
| A896 a or b | H | CH₃ |
| A897 a or b | C(=O)C(=O)OH | CH₃ |
| A898 a or b | C(=O)C(=O)NH₂ | CH₃ |
| A899 a or b | C(=O)C(=O)OCH₃ | CH₃ |
| A900 a or b | C(=O)C(=O)OCH₂CH₃ | CH₃ |
| A901 a or b | C(=O)H | CH₃ |
| A902 a or b | C(=O)CH₃ | CH₃ |
| A903 a or b | C(=O)CH₂CH₃ | CH₃ |
| A904 a or b | C(=O)NH₂ | CH₃ |
| A905 a or b | C(=O)NHCH₃ | CH₃ |
| A906 a or b | C(=O)N(CH₃)₂ | CH₃ |
| A907 a or b | C(=O)CH₂NH₂ | CH₃ |
| A908 a or b | C(=O)OCH₂CH₃ | CH₃ |
| A909 a or b | C(=O)OCH₂OH | CH₃ |
| A910 a or b | CH₂C(=O)OH | CH₃ |
| A911 a or b | CF₂C(=O)OH | CH₃ |
| A912 a or b | CHFC(=O)OH | CH₃ |
| A913 a or b | CH₂C(=O)OCH₃ | CH₃ |
| A914 a or b | CH₂C(=O)OCH₂CH₃ | CH₃ |
| A915 a or b | CH₂C(=O)NH₂ | CH₃ |
| A916 a or b | CF₂C(=O)NH₂ | CH₃ |
| A917 a or b | CHFC(=O)NH₂ | CH₃ |
| A918 a or b | CH₂C(=O)NHCH₃ | CH₃ |
| A919 a or b | CH₂C(=O)NH(CH₃)₂ | CH₃ |
| A920 a or b | C(=O)OH | CH₃ |
| A921 a or b | C(=O)OCH₃ | CH₃ |
| A922 a or b | CH₂C(=O)NHCH₂C(=O)OH | CH₃ |
| A923 a or b | CH₂C(=O)NHCH₂C(=O)OCH₃ | CH₃ |
| A924 a or b | CH₂C(=O)NHCH₂C(=O)OCH₃ | CH₂CH₃ |

TABLE 14

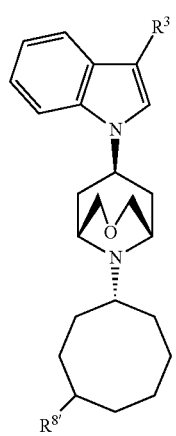

(a)

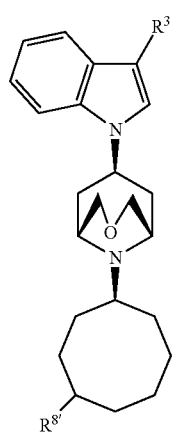

(b)

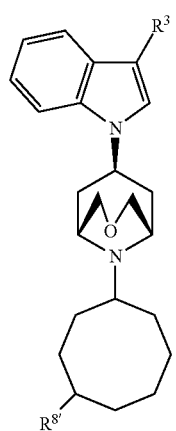

(c)

and pharmaceutically acceptable salts and solvates thereof, where:

| Compound | R3 | R⁸' |
|---|---|---|
| A925 c | H | H |
| A926 c | C(=O)C(=O)OH | H |
| A927 c | C(=O)C(=O)NH₂ | H |
| A928 c | C(=O)C(=O)OCH₃ | H |

TABLE 14-continued

| | | | |
|---|---|---|---|
| A929 | c | C(=O)C(=O)OCH₂CH₃ | H |
| A930 | c | C(=O)H | H |
| A931 | c | C(=O)CH₃ | H |
| A932 | c | C(=O)CH₂CH₃ | H |
| A933 | c | C(=O)NH₂ | H |
| A934 | c | C(=O)NHCH₃ | H |
| A935 | c | C(=O)N(CH₃)₂ | H |
| A936 | c | C(=O)CH₂NH₂ | H |
| A937 | c | C(=O)OCH₂CH₃ | H |
| A938 | c | C(=O)OCH₂OH | H |
| A939 | c | CH₂C(=O)OH | H |
| A940 | c | CF₂C(=O)OH | H |
| A941 | c | CHFC(=O)OH | H |
| A942 | c | CH₂C(=O)OCH₃ | H |
| A943 | c | CH₂C(=O)OCH₂CH₃ | H |
| A944 | c | CH₂C(=O)NH₂ | H |
| A945 | c | CF₂C(=O)NH₂ | H |
| A946 | c | CHFC(=O)NH₂ | H |
| A947 | c | CH₂C(=O)NHCH₃ | H |
| A948 | c | CH₂C(=O)NH(CH₃)₂ | H |
| A949 | c | C(=O)OH | H |
| A950 | c | C(=O)OCH₃ | H |
| A951 | c | CH₂C(=O)NHCH₂C(=O)OH | H |
| A952 | c | CH₂C(=O)NHCH₂C(=O)OCH₃ | H |
| A953 | a or b | H | CH₃ |
| A954 | a or b | C(=O)C(=O)OH | CH₃ |
| A955 | a or b | C(=O)C(=O)NH₂ | CH₃ |
| A956 | a or b | C(=O)C(=O)OCH₃ | CH₃ |
| A957 | a or b | C(=O)C(=O)OCH₂CH₃ | CH₃ |
| A958 | a or b | C(=O)H | CH₃ |
| A959 | a or b | C(=O)CH₃ | CH₃ |
| A960 | a or b | C(=O)CH₂CH₃ | CH₃ |
| A961 | a or b | C(=O)NH₂ | CH₃ |
| A962 | a or b | C(=O)NHCH₃ | CH₃ |
| A963 | a or b | C(=O)N(CH₃)₂ | CH₃ |
| A964 | a or b | C(=O)CH₂NH₂ | CH₃ |
| A965 | a or b | C(=O)OCH₂CH₃ | CH₃ |
| A966 | a or b | C(=O)OCH₂OH | CH₃ |
| A967 | a or b | CH₂C(=O)OH | CH₃ |
| A968 | a or b | CF₂C(=O)OH | CH₃ |
| A969 | a or b | CHFC(=O)OH | CH₃ |
| A970 | a or b | CH₂C(=O)OCH₃ | CH₃ |
| A971 | a or b | CH₂C(=O)OCH₂CH₃ | CH₃ |
| A972 | a or b | CH₂C(=O)NH₂ | CH₃ |
| A973 | a or b | CH₂C(=O)NHCH₃ | CH₃ |
| A974 | a or b | CH₂C(=O)NH(CH₃)₂ | CH₃ |
| A975 | a or b | C(=O)OH | CH₃ |
| A976 | a or b | C(=O)OCH₃ | CH₃ |
| A977 | a or b | CH₂C(=O)NHCH₂C(=O)OH | CH₃ |
| A978 | a or b | CH₂C(=O)NHCH₂C(=O)OCH₃ | CH₃ |
| A979 | a or b | CH₂C(=O)NHCH₂C(=O)OCH₃ | CH₂CH₃ |

TABLE 15

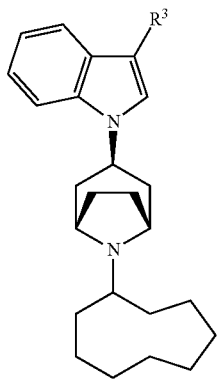

and pharmaceutically acceptable salts and solvates thereof, where:

| Compound | R³ |
|---|---|
| A980 | H |
| A981 | C(=O)C(=O)OH |
| A982 | C(=O)C(=O)NH₂ |

TABLE 15-continued

| Compound | R³ |
|---|---|
| A983 | C(=O)C(=O)OCH₃ |
| A984 | C(=O)C(=O)OCH₂CH₃ |
| A985 | C(=O)H |
| A986 | C(=O)CH₃ |
| A987 | C(=O)CH₂CH₃ |
| A988 | C(=O)NH₂ |
| A989 | C(=O)NHCH₃ |
| A990 | C(=O)N(CH₃)₂ |
| A991 | C(=O)CH₂NH₂ |
| A992 | C(=O)OCH₂CH₃ |
| A993 | C(=O)OCH₂OH |
| A994 | CH₂C(=O)OH |
| A995 | CF₂C(=O)OH |
| A996 | CHFC(=O)OH |
| A997 | CH₂C(=O)OCH₃ |
| A998 | CH₂C(=O)OCH₂CH₃ |
| A999 | CH₂C(=O)NH₂ |
| A1000 | CF₂C(=O)NH₂ |
| A1001 | CHFC(=O)NH₂ |
| A1002 | CH₂C(=O)NHCH₃ |
| A1003 | CH₂C(=O)NH(CH₃)₂ |
| A1004 | C(=O)OH |
| A1005 | C(=O)OCH₃ |
| A1006 | CH₂C(=O)NHCH₂C(=O)OH |
| A1007 | CH₂C(=O)NHCH₂C(=O)OCH₃ |

TABLE 16

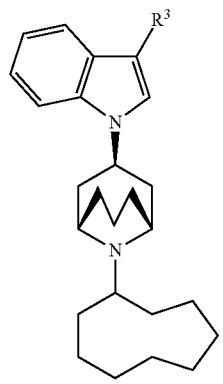

and pharmaceutically acceptable salts and solvates thereof, where:

| Compound | R³ |
|---|---|
| A1008 | H |
| A1009 | C(=O)C(=O)OH |
| A1010 | C(=O)C(=O)NH₂ |
| A1011 | C(=O)C(=O)OCH₃ |
| A1012 | C(=O)C(=O)OCH₂CH₃ |
| A1013 | C(=O)H |
| A1014 | C(=O)CH₃ |
| A1015 | C(=O)CH₂CH₃ |
| A1016 | C(=O)NH₂ |
| A1017 | C(=O)NHCH₃ |
| A1018 | C(=O)N(CH₃)₂ |
| A1019 | C(=O)CH₂NH₂ |
| A1020 | C(=O)OCH₂CH₃ |
| A1021 | C(=O)OCH₂OH |
| A1022 | CH₂C(=O)OH |
| A1023 | CF₂C(=O)OH |
| A1024 | CHFC(=O)OH |
| A1025 | CH₂C(=O)OCH₃ |
| A1026 | CH₂C(=O)OCH₂CH₃ |
| A1027 | CH₂C(=O)NH₂ |
| A1028 | CF₂C(=O)NH₂ |
| A1029 | CHFC(=O)NH₂ |
| A1030 | CH₂C(=O)NHCH₃ |
| A1031 | CH₂C(=O)NH(CH₃)₂ |
| A1032 | C(=O)OH |
| A1033 | C(=O)OCH₃ |
| A1034 | CH₂C(=O)NHCH₂C(=O)OH |
| A1035 | CH₂C(=O)NHCH₂C(=O)OCH₃ |

TABLE 17

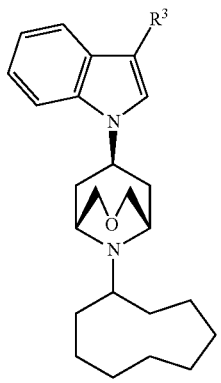

and pharmaceutically acceptable salts and solvates thereof, where:

| Compound | R³ |
| --- | --- |
| A1036 | H |
| A1037 | C(=O)C(=O)OH |
| A1038 | C(=O)C(=O)NH₂ |
| A1039 | C(=O)C(=O)OCH₃ |
| A1040 | C(=O)C(=O)OCH₂CH₃ |
| A1041 | C(=O)H |
| A1042 | C(=O)CH₃ |
| A1043 | C(=O)CH₂CH₃ |
| A1044 | C(=O)NH₂ |
| A1045 | C(=O)NHCH₃ |
| A1046 | C(=O)N(CH₃)₂ |
| A1047 | C(=O)CH₂NH₂ |
| A1048 | C(=O)OCH₂CH₃ |
| A1049 | C(=O)OCH₂OH |
| A1050 | CH₂C(=O)OH |
| A1051 | CF₂C(=O)OH |
| A1052 | CHFC(=O)OH |
| A1053 | CH₂C(=O)OCH₃ |
| A1054 | CH₂C(=O)OCH₂CH₃ |
| A1055 | CH₂C(=O)NH₂ |
| A1056 | CF₂C(=O)NH₂ |
| A1057 | CHFC(=O)NH₂ |
| A1058 | CH₂C(=O)NHCH₃ |
| A1059 | CH₂C(=O)NH(CH₃)₂ |
| A1060 | C(=O)OH |
| A1061 | C(=O)OCH₃ |
| A1062 | CH₂C(=O)NHCH₂C(=O)OH |
| A1063 | CH₂C(=O)NHCH₂C(=O)OCH₃ |

TABLE 18

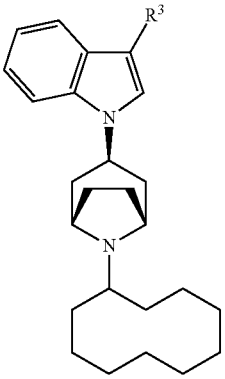

and pharmaceutically acceptable salts and solvates thereof, where:

| Compound | R³ |
| --- | --- |
| A1064 | H |
| A1065 | C(=O)C(=O)OH |
| A1066 | C(=O)C(=O)NH₂ |
| A1067 | C(=O)C(=O)OCH₃ |
| A1068 | C(=O)C(=O)OCH₂CH₃ |
| A1069 | C(=O)H |
| A1070 | C(=O)CH₃ |
| A1071 | C(=O)CH₂CH₃ |
| A1072 | C(=O)NH₂ |
| A1073 | C(=O)NHCH₃ |
| A1074 | C(=O)N(CH₃)₂ |
| A1075 | C(=O)CH₂NH₂ |
| A1076 | C(=O)OCH₂CH₃ |
| A1077 | C(=O)OCH₂OH |
| A1078 | CH₂C(=O)OH |
| A1079 | CF₂C(=O)OH |
| A1080 | CHFC(=O)OH |
| A1081 | CH₂C(=O)OCH₃ |
| A1082 | CH₂C(=O)OCH₂CH₃ |
| A1083 | CH₂C(=O)NH₂ |
| A1084 | CF₂C(=O)NH₂ |
| A1085 | CHFC(=O)NH₂ |
| A1086 | CH₂C(=O)NHCH₃ |
| A1087 | CH₂C(=O)NH(CH₃)₂ |
| A1088 | C(=O)OH |
| A1089 | C(=O)OCH₃ |
| A1090 | CH₂C(=O)NHCH₂C(=O)OH |
| A1091 | CH₂C(=O)NHCH₂C(=O)OCH₃ |

TABLE 19

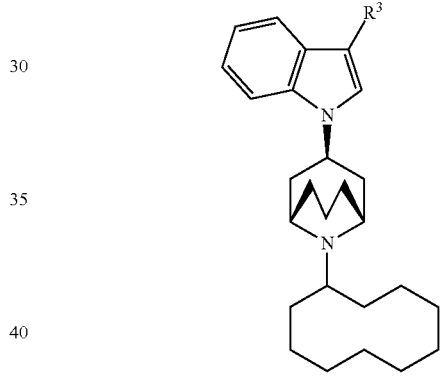

and pharmaceutically acceptable salts and solvates thereof, where:

| Compound | R³ |
| --- | --- |
| A1092 | H |
| A1093 | C(=O)C(=O)OH |
| A1094 | C(=O)C(=O)NH₂ |
| A1095 | C(=O)C(=O)OCH₃ |
| A1096 | C(=O)C(=O)OCH₂CH₃ |
| A1097 | C(=O)H |
| A1098 | C(=O)CH₃ |
| A1099 | C(=O)CH₂CH₃ |
| A1100 | C(=O)NH₂ |
| A1101 | C(=O)NHCH₃ |
| A1102 | C(=O)N(CH₃)₂ |
| A1103 | C(=O)CH₂NH₂ |
| A1104 | C(=O)OCH₂CH₃ |
| A1105 | C(=O)OCH₂OH |
| A1106 | CH₂C(=O)OH |
| A1107 | CF₂C(=O)OH |
| A1108 | CHFC(=O)OH |
| A1109 | CH₂C(=O)OCH₃ |
| A1110 | CH₂C(=O)OCH₂CH₃ |
| A1111 | CH₂C(=O)NH₂ |
| A1112 | CF₂C(=O)NH₂ |
| A1113 | CHFC(=O)NH₂ |
| A1114 | CH₂C(=O)NHCH₃ |
| A1115 | CH₂C(=O)NH(CH₃)₂ |
| A1116 | C(=O)OH |
| A1117 | C(=O)OCH₃ |

TABLE 19-continued

| | |
|---|---|
| A1118 | CH₂C(=O)NHCH₂C(=O)OH |
| A1119 | CH₂C(=O)NHCH₂C(=O)OCH₃ |

TABLE 20

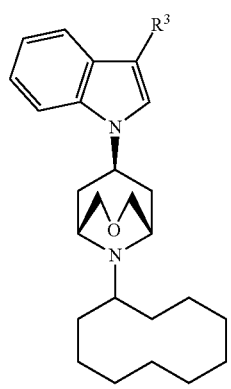

and pharmaceutically acceptable salts and solvates thereof, where:

| Compound | R³ |
|---|---|
| A1120 | H |
| A1121 | C(=O)C(=O)OH |
| A1122 | C(=O)C(=O)NH₂ |
| A1123 | C(=O)C(=O)OCH₃ |
| A1124 | C(=O)C(=O)OCH₂CH₃ |
| A1125 | C(=O)H |
| A1126 | C(=O)CH₃ |
| A1127 | C(=O)CH₂CH₃ |
| A1128 | C(=O)NH₂ |
| A1129 | C(=O)NHCH₃ |
| A1130 | C(=O)N(CH₃)₂ |
| A1131 | C(=O)CH₂NH₂ |
| A1132 | C(=O)OCH₂CH₃ |
| A1133 | C(=O)OCH₂OH |
| A1134 | CH₂C(=O)OH |
| A1135 | CF₂C(=O)OH |
| A1136 | CHFC(=O)OH |
| A1137 | CH₂C(=O)OCH₃ |
| A1138 | CH₂C(=O)OCH₂CH₃ |
| A1139 | CH₂C(=O)NH₂ |
| A1140 | CF₂C(=O)NH₂ |
| A1141 | CHFC(=O)NH₂ |
| A1142 | CH₂C(=O)NHCH₃ |
| A1143 | CH₂C(=O)NH(CH₃)₂ |
| A1144 | C(=O)OH |
| A1145 | C(=O)OCH₃ |
| A1146 | CH₂C(=O)NHCH₂C(=O)OH |
| A1147 | CH₂C(=O)NHCH₂C(=O)OCH₃ |

TABLE 21

(a)

(b)

and pharmaceutically acceptable salts and solvates thereof, where:

| Compound | R³ | R⁸' |
|---|---|---|
| A1148 a or b | H | H |
| A1149 a or b | C(=O)C(=O)OH | H |
| A1150 a or b | C(=O)C(=O)NH₂ | H |
| A1151 a or b | C(=O)C(=O)OCH₃ | H |
| A1152 a or b | C(=O)C(=O)OCH₂CH₃ | H |
| A1153 a or b | C(=O)H | H |
| A1154 a or b | C(=O)CH₃ | H |
| A1155 a or b | C(=O)CH₂CH₃ | H |
| A1156 a or b | C(=O)NH₂ | H |
| A1157 a or b | C(=O)NHCH₃ | H |
| A1158 a or b | C(=O)N(CH₃)₂ | H |
| A1159 a or b | C(=O)CH₂NH₂ | H |
| A1160 a or b | C(=O)OCH₂CH₃ | H |
| A1161 a or b | C(=O)OCH₂OH | H |
| A1162 a or b | CH₂C(=O)OH | H |
| A1163 a or b | CF₂C(=O)OH | H |
| A1164 a or b | CHFC(=O)OH | H |
| A1165 a or b | CH₂C(=O)OCH₃ | H |
| A1166 a or b | CH₂C(=O)OCH₂CH₃ | H |
| A1167 a or b | CH₂C(=O)NH₂ | H |
| A1168 a or b | CF₂C(=O)NH₂ | H |
| A1169 a or b | CHFC(=O)NH₂ | H |
| A1170 a or b | CH₂C(=O)NHCH₃ | H |
| A1171 a or b | CH₂C(=O)NH(CH₃)₂ | H |
| A1172 a or b | C(=O)OH | H |
| A1173 a or b | C(=O)OCH₃ | H |
| A1174 a or b | CH₂C(=O)NHCH₂C(=O)OH | H |
| A1175 a or b | CH₂C(=O)NHCH₂C(=O)OCH₃ | H |
| A1176 a or b | H | CH₃ |
| A1177 a or b | C(=O)C(=O)OH | CH₃ |
| A1178 a or b | C(=O)C(=O)NH₂ | CH₃ |
| A1179 a or b | C(=O)C(=O)OCH₃ | CH₃ |
| A1180 a or b | C(=O)C(=O)OCH₂CH₃ | CH₃ |
| A1181 a or b | C(=O)H | CH₃ |
| A1182 a or b | C(=O)CH₃ | CH₃ |

TABLE 21-continued

| | | |
|---|---|---|
| A1183 a or b | C(=O)CH$_2$CH$_3$ | CH$_3$ |
| A1184 a or b | C(=O)NH$_2$ | CH$_3$ |
| A1185 a or b | C(=O)NHCH$_3$ | CH$_3$ |
| A1186 a or b | C(=O)N(CH$_3$)$_2$ | CH$_3$ |
| A1187 a or b | C(=O)CH$_2$NH$_2$ | CH$_3$ |
| A1188 a or b | C(=O)OCH$_2$CH$_3$ | CH$_3$ |
| A1189 a or b | C(=O)OCH$_2$OH | CH$_3$ |
| A1190 a or b | CH$_2$C(=O)OH | CH$_3$ |
| A1191 a or b | CF$_2$C(=O)OH | CH$_3$ |
| A1192 a or b | CHFC(=O)OH | CH$_3$ |
| A1193 a or b | CH$_2$C(=O)OCH$_3$ | CH$_3$ |
| A1194 a or b | CH$_2$C(=O)OCH$_2$CH$_3$ | CH$_3$ |
| A1195 a or b | CH$_2$C(=O)NH$_2$ | CH$_3$ |
| A1196 a or b | CH$_2$C(=O)NHCH$_3$ | CH$_3$ |
| A1197 a or b | CH$_2$C(=O)NH(CH$_3$)$_2$ | CH$_3$ |
| A1198 a or b | C(=O)OH | CH$_3$ |
| A1199 a or b | C(=O)OCH$_3$ | CH$_3$ |
| A1200 a or b | CH$_2$C(=O)NHCH$_2$C(=O)OH | CH$_3$ |
| A1201 a or b | CH$_2$C(=O)NHCH$_2$C(=O)OCH$_3$ | CH$_3$ |
| A1202 a or b | H | CH$_2$CH$_3$ |
| A1203 a or b | C(=O)C(=O)OH | CH$_2$CH$_3$ |
| A1204 a or b | C(=O)C(=O)NH$_2$ | CH$_2$CH$_3$ |
| A1205 a or b | C(=O)C(=O)OCH$_3$ | CH$_2$CH$_3$ |
| A1206 a or b | C(=O)C(=O)OCH$_2$CH$_3$ | CH$_2$CH$_3$ |
| A1207 a or b | C(=O)H | CH$_2$CH$_3$ |
| A1208 a or b | C(=O)CH$_3$ | CH$_2$CH$_3$ |
| A1209 a or b | C(=O)CH$_2$CH$_3$ | CH$_2$CH$_3$ |
| A1210 a or b | C(=O)NH$_2$ | CH$_2$CH$_3$ |
| A1211 a or b | C(=O)NHCH$_3$ | CH$_2$CH$_3$ |
| A1212 a or b | C(=O)N(CH$_3$)$_2$ | CH$_2$CH$_3$ |
| A1213 a or b | C(=O)CH$_2$NH$_2$ | CH$_2$CH$_3$ |
| A1214 a or b | C(=O)OCH$_2$CH$_3$ | CH$_2$CH$_3$ |
| A1215 a or b | C(=O)OCH$_2$OH | CH$_2$CH$_3$ |
| A1216 a or b | CH$_2$C(=O)OH | CH$_2$CH$_3$ |
| A1217 a or b | CF$_2$C(=O)OH | CH$_2$CH$_3$ |
| A1218 a or b | CHFC(=O)OH | CH$_2$CH$_3$ |
| A1219 a or b | CH$_2$C(=O)OCH$_3$ | CH$_2$CH$_3$ |
| A1220 a or b | CH$_2$C(=O)OCH$_2$CH$_3$ | CH$_2$CH$_3$ |
| A1221 a or b | CH$_2$C(=O)NH$_2$ | CH$_2$CH$_3$ |
| A1222 a or b | CF$_2$C(=O)NH$_2$ | CH$_2$CH$_3$ |
| A1223 a or b | CHFC(=O)NH$_2$ | CH$_2$CH$_3$ |
| A1224 a or b | CH$_2$C(=O)NHCH$_3$ | CH$_2$CH$_3$ |
| A1225 a or b | CH$_2$C(=O)NH(CH$_3$)$_2$ | CH$_2$CH$_3$ |
| A1226 a or b | C(=O)OH | CH$_2$CH$_3$ |
| A1227 a or b | C(=O)OCH$_3$ | CH$_2$CH$_3$ |
| A1228 a or b | CH$_2$C(=O)NHCH$_2$C(=O)OH | CH$_2$CH$_3$ |
| A1229 a or b | CH$_2$C(=O)NHCH$_2$C(=O)OCH$_3$ | CH$_2$CH$_3$ |

4.2 Definitions

As used in connection with the Compounds of Formula (I), the terms used herein have the following meaning:

"—($C_1$-$C_{10}$)alkyl" means a straight chain or branched non-cyclic hydrocarbon having 1, 2, 3, 4, 5, 6, 7, 8, 9, or 10 carbon atoms. Representative straight chain —($C_1$-$C_{10}$)alkyls include -methyl, -ethyl, -n-propyl, -n-butyl, -n-pentyl, -n-hexyl, -n-heptyl, -n-octyl, -n-nonyl, and -n-decyl. A branched alkyl means that one or more straight chain —($C_1$-$C_8$)alkyl groups, such as methyl, ethyl or propyl, replace one or both hydrogens in a —CH$_2$— group of a straight chain alkyl. A branched non-cyclic hydrocarbon means that one or more straight chain —($C_1$-$C_{10}$)alkyl groups, such as methyl, ethyl or propyl, replace one or both hydrogens in a —CH$_2$— group of a straight chain non-cyclic hydrocarbon. Representative branched —($C_1$-$C_{10}$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

"—($C_1$-$C_6$)alkyl" means a straight chain or branched non-cyclic hydrocarbon having 1, 2, 3, 4, 5, or 6 carbon atoms. Representative straight chain —($C_1$-$C_6$)alkyls include -methyl, -ethyl, -n-propyl, -n-butyl, -n-pentyl, and -n-hexyl. Representative branched —($C_1$-$C_6$)alkyls include -iso-propyl, -sec-butyl, -iso-butyl, -tert-butyl, -iso-pentyl, -neopentyl, 1-methylbutyl, 2-methylbutyl, 3- methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethtylbutyl, 1,2-dimethylbutyl, 1,3-dimethylbutyl, 2,2-dimethylbutyl, 2,3-dimethylbutyl, and 3,3-dimethylbutyl.

"—($C_1$-$C_4$)alkyl" means a straight chain or branched non-cyclic hydrocarbon having 1, 2, 3, or 4 carbon atoms. Representative straight chain —($C_1$-$C_4$)alkyls include -methyl, -ethyl, -n-propyl, and -n-butyl. Representative branched —($C_1$-$C_4$)alkyls include -iso-propyl, -sec-butyl, -iso-butyl, and -tert-butyl.

"—($C_1$-$C_3$)alkyl" means a straight chain or branched non-cyclic hydrocarbon having 1, 2, or 3 carbon atoms. Representative straight chain —($C_1$-$C_3$)alkyls include -methyl, -ethyl, -n-propyl. Representative branched —($C_1$-$C_3$)alkyls include -iso-propyl.

"—($C_1$-$C_2$)alkyl" means a straight chain non-cyclic hydrocarbon having 1 or 2 carbon atoms. Representative —($C_1$-$C_2$)alkyls include -methyl and -ethyl.

"—($C_2$-$C_{10}$)alkenyl" means a straight chain or branched non-cyclic hydrocarbon having 2, 3, 4, 5, 6, 7, 8, 9, or 10 carbon atoms and including at least one carbon-carbon double bond. A branched alkenyl means that one or more straight chain —($C_1$-$C_8$)alkyl groups, such as methyl, ethyl or propyl, replace one or both hydrogens in a —CH$_2$— or —CH= group of a straight chain alkenyl. Representative straight chain and branched ($C_2$-$C_{10}$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl, and the like.

"—($C_2$-$C_6$)alkenyl" means a straight chain or branched non-cyclic hydrocarbon having 2, 3, 4, 5, or 6 carbon atoms and including at least one carbon-carbon double bond. Representative straight chain and branched ($C_2$-$C_6$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, and the like.

"—($C_2$-$C_3$)alkenyl" means a straight chain non-cyclic hydrocarbon having 2 or 3 carbon atoms and including at least one carbon-carbon double bond. Representative ($C_2$-$C_3$)alkenyls include -vinyl, -allyl, and 1-prop-1-enyl.

"—($C_2$-$C_{10}$)alkynyl" means a straight chain or branched non-cyclic hydrocarbon having 2, 3, 4, 5, 6, 7, 8, 9, or 10 carbon atoms and including at least one carbon-carbon triple bond. A branched alkynyl means that one or more straight chain —($C_1$-$C_8$)alkyl groups, such as methyl, ethyl or propyl, replace one or both hydrogens in a —CH$_2$— group of a straight chain alkynyl. Representative straight chain and branched —($C_2$-$C_{10}$)alkynyls include -ethynyl (-acetylenyl), -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like.

"—$(C_2-C_6)$alkynyl" means a straight chain or branched non-cyclic hydrocarbon having 2, 3, 4, 5, or 6 carbon atoms and including at least one carbon-carbon triple bond. Representative straight chain and branched $(C_2-C_6)$alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, and the like.

"—$(C_1-C_6)$alkoxy" means a straight chain or branched non-cyclic hydrocarbon having one or more ether groups and 1, 2, 3, 4, 5, or 6 carbon atoms. Representative straight chain and branched $(C_1-C_6)$alkoxys include -methoxy, -ethoxy, -methoxymethyl, -2-methoxyethyl, -5-methoxypentyl, -3-ethoxybutyl, (methoxymethoxy)methyl-, 1-(methoxy)-1-methoxyethyl-, trimethoxymethyl-, 2-((methoxy)methoxy)-2-methylpropyl-, 3-(1,1,1-trimethoxypropane), (methoxy)trimethoxymethyl-, (2,2,2-trimethoxyethoxy)-, and the like.

"—$(C_1-C_4)$alkoxy" means a straight chain or branched non-cyclic hydrocarbon having one or more ether groups and 1, 2, 3, or 4 carbon atoms. Representative straight chain and branched $(C_1-C_4)$alkoxys include -methoxy, -ethoxy, -methoxymethyl, -2-methoxyethyl, (methoxymethoxy)methyl-, 1-(methoxy)-1-methoxyethyl-, trimethoxymethyl-, and the like.

"—$(C_3-C_{14})$cycloalkyl" means a saturated monocyclic hydrocarbon having 3, 4, 5, 6, 7, 8, 9, 10, 11, 12, 13, or 14 carbon atoms. Representative $(C_3-C_{14})$cycloalkyls are -cyclopropyl, -cyclobutyl, -cyclopentyl, -cyclohexyl, -cycloheptyl, -cyclooctyl, -cyclononyl, -cyclodecyl, cycloundecyl, -cyclododecyl, and -cyclotetradecyl.

"—$(C_3-C_{12})$cycloalkyl" means a saturated monocyclic hydrocarbon having 3, 4, 5, 6, 7, 8, 9, 10, 11, or 12 carbon atoms. Representative $(C_3-C_{12})$cycloalkyls are -cyclopropyl, -cyclobutyl, -cyclopentyl, -cyclohexyl, -cycloheptyl, -cyclooctyl, -cyclononyl, -cyclodecyl, -cycloundecyl, and -cyclododecyl.

"—$(C_6-C_{12})$cycloalkyl" means a saturated monocyclic hydrocarbon having 6, 7, 8, 9, 10, 11, or 12 carbon atoms. Representative $(C_6-C_{12})$cycloalkyls are -cyclohexyl, -cycloheptyl, -cyclooctyl, -cyclononyl, -cyclodecyl, -cycloundecyl, and -cyclododecyl.

"—$(C_4-C_8)$cycloalkyl" or "4- to 8-member cycloalkyl ring" means a saturated monocyclic hydrocarbon having 4, 5, 6, 7, or 8 carbon atoms. Representative —$(C_4-C_8)$cycloalkyls are -cyclobutyl, -cyclopentyl, -cyclohexyl, -cycloheptyl, and -cyclooctyl.

"—$(C_3-C_8)$cycloalkyl" means a saturated monocyclic hydrocarbon having 3, 4, 5, 6, 7, or 8 carbon atoms. Representative $(C_3-C_8)$cycloalkyls include -cyclopropyl, -cyclobutyl, -cyclopentyl, -cyclohexyl, -cycloheptyl, and -cyclooctyl.

"—$(C_3-C_7)$cycloalkyl" means a saturated monocyclic hydrocarbon having 3, 4, 5, 6, or 7 carbon atoms. Representative $(C_3-C_7)$cycloalkyls include cyclopropyl, -cyclobutyl, -cyclopentyl, -cyclohexyl, and -cycloheptyl.

"—$(C_1-C_{14})$bicycloalkyl" means a bicyclic hydrocarbon ring system having 6, 7, 8, 9, 10, 11, 12, 13, or 14 carbon atoms and at least one saturated cyclic alkyl ring. In one embodiment, the —$(C_6-C_{14})$bicycloalkyl has one saturated cyclic alkyl ring. In another embodiment, the —$(C_6-C_{14})$bicycloalkyl has two saturated cyclic alkyl rings. Representative —$(C_6-C_{14})$bicycloalkyls include -indanyl, -norbornyl, -1,2,3,4-tetrahydronaphthalenyl, -5,6,7,8-tetrahydronaphthalenyl, -perhydronaphthalenyl, -bicyclo[2.2.1]hexyl, bicyclo[2.2.1.]heptyl, -bicyclo[2.2.2]octyl, -bicyclo[3.3.1]heptyl, -bicyclo[3.2.1]octyl, -bicyclo[3.3.1]nonyl, -bicyclo[3.3.2]decyl, -bicyclo[3.3.3]undecyl, -bicyclo[4.2.2]decyl, -bicyclo[4.3.2]undecyl, -bicyclo[4.3.1]decyl, and the like.

"—$(C_8-C_{20})$tricycloalkyl" means a tri-cyclic hydrocarbon ring system having 8, 9, 10, 11, 12, 13, 14, 15, 16, 17, 18, 19, or 20 carbon atoms and at least one saturated cyclic alkyl ring; thus, one of the rings can comprise, e.g., benzo. In one embodiment, the —$(C_8-C_{20})$tricycloalkyl has one saturated cyclic alkyl ring. In another embodiment, the —$(C_8-C_{20})$tricycloalkyl has two saturated cyclic alkyl rings. In another embodiment, the —$(C_8-C_{20})$tricycloalkyl has three saturated cyclic alkyl rings. Representative —$(C_8-C_{20})$tricycloalkyls include -pyrenyl, -adamantyl, -noradamantyl, -1,2,3,4-tetrahydroanthracenyl, -1,2,3,4,4a,9,9a,10-octahydroanthracenyl, -perhydroanthracenyl -aceanthrenyl, -1,2,3,4-tetrahydropenanthrenyl, -5,6,7,8-tetrahydrophenanthrenyl, -1,2,3,4,4a,9,10,10a-octahydrophenanthrenyl, -perhydrophenanthrenyl, -tetradecahydro-1H-cyclohepta[a]naphthalenyl, -tetradecahydro-1H-cycloocta[e]indenyl, -tetradecahydro-1H-cyclohepta[e]azulenyl, -hexadecahydrocycloocta[b]naphthalenyl, -hexadecahydrocyclohepta[a]heptalenyl, -tricyclo-pentadecanyl, -tricyclo-octadecanyl, -tricyclo-nonadecanyl, -tricyclo-icosanyl, -2,3-benzobicyclo [2.2.2]octanyl, -6,7-benzobicyclo[3.2.1]octanyl, -9,10-benzobicyclo[3.3.2]decanyl, -2,3,4,4a,9,9a-hexahydro-1H-fluorenyl, -1,2,3,4,4a,8b-hexahydrobiphenylenyl, and the like.

"—$(C_5-C_{14})$cycloalkenyl" means a cyclic non-aromatic hydrocarbon having at least one carbon-carbon double bond in the cyclic system and 5, 6, 7, 8, 9, 10, 11, 12, 13, or 14 carbon atoms. Representative $(C_5-C_{14})$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclononatrienyl, -cyclodecenyl, -cyclodecadienyl, -cyclotetradecenyl, -cyclododecadienyl, and the like.

"—$(C_5-C_{10})$cycloalkenyl" means a cyclic non-aromatic hydrocarbon having at least one carbon-carbon double bond in the cyclic system and 5, 6, 7, 8, 9, or 10 carbon atoms. Representative $(C_5-C_{10})$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclononatrienyl, -cyclodecenyl, -cyclodecadienyl, -cyclotetradecenyl, and the like.

"—$(C_1-C_8)$cycloalkenyl" means a cyclic non-aromatic hydrocarbon having at least one carbon-carbon double bond in the cyclic system and 5, 6, 7, or 8 carbon atoms. Representative $(C_5-C_8)$cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, and the like.

"—$(C_7-C_{14})$bicycloalkenyl" means a bicyclic hydrocarbon ring system having at least one carbon-carbon double bond in each ring and 7, 8, 9, 10, 11, 12, 13, or 14 carbon atoms. Representative —$(C_7-C_{14})$bicycloalkenyls include -bicyclo[3.2.0]hept-2-enyl, -indenyl, -pentalenyl, -naphthalenyl, -azulenyl, -heptalenyl, -1,2,7,8-tetrahydronaphthalenyl, -norbornenyl, and the like.

"—$(C_8-C_{20})$tricycloalkenyl" means a tricyclic hydrocarbon ring system having at least one carbon-carbon double bond in each ring and 8, 9, 10, 11, 12, 13, 14, 15, 16, 17, 18, 19, or 20 carbon atoms. Representative —$(C_8-C_{20})$tricycloalkenyls include -anthracenyl, -phenanthrenyl, -phenalenyl, -acenaphthalenyl, -as-indacenyl, -s-indacenyl, -2,3,6,7,8,9,10,11-octahydro-1H-cycloocta[e]indenyl, 2,3,4,7,8,9,10,11-octahydro-1H-cyclohepta[a]naphthalenyl, -8,9,10,11-tetrahydro-7H-cyclohepta[a]naphthalenyl, -2,3,4,5,6,7,8,9,10,11,12,13-dodecahydro-1H-cyclohepta[a]heptalenyl, -1,2,3,4,5,6,7,8,9,10,11,12,13,14-tetradecahydro-dicyclohepta[a,c]cyclooctenyl, -2,3,4,5,6,7,8,9,10,11,12,13-dodecahydro-1H-dibenzo[a,d]cyclononenyl, and the like.

"-(3- to 7-membered)heterocycle" or "-(3- to 7-membered)heterocyclo" means a 3- to 7-membered monocyclic heterocyclic ring, i.e., a monocyclic ring comprising at least one heteroatom, which is either saturated, unsaturated non-aromatic or aromatic. A 3-membered heterocycle contains 1 heteroatom, a 4-membered heterocycle can contain 1 or 2 heteroatoms, a 5-membered heterocycle can contain 1, 2, 3, or 4 heteroatoms, a 6-membered heterocycle can contain 1, 2, 3, or 4 heteroatoms, and a 7-membered heterocycle can contain 1, 2, 3, 4, or 5 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"-(5- or 6-membered)heterocycle" or "-(5- or 6-membered)heterocyclo" means a 5- or 6-membered monocyclic heterocyclic ring, i.e., a monocyclic ring comprising at least one heteroatom, which is either saturated, unsaturated non-aromatic or aromatic. A 5-membered heterocycle can contain 1, 2, 3, or 4 heteroatoms and a 6-membered heterocycle can contain 1, 2, 3, or 4 heteroatoms. Each heteroatom is independently selected from nitrogen, which can be quaternized; oxygen; and sulfur, including sulfoxide and sulfone. The -(5- or 6-membered)heterocycle can be attached via a nitrogen or carbon atom. Representative -(5- or 6-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, tetrahydrofuranyl, tetrahydropyranyl, dihydropyridinyl, tetrahydropyridinyl, tetrahydropyrimidinyl, tetrahydrothiophenyl, tetrahydrothiopyranyl, tetrazolyl, and the like.

"-(7- to 10-membered)bicycloheterocycle" or "-(7- to 10-membered)bicycloheterocyclo" means a 7- to 10-membered bicyclic, heterocyclic ring, each ring of which is independently either saturated, unsaturated non-aromatic or aromatic, i.e., where at least one ring comprises at least one heteroatom. A -(7- to 10-membered)bicycloheterocycle contains 1, 2, 3, or 4 heteroatoms independently selected from nitrogen, which can be quaternized; oxygen; and sulfur, including sulfoxide and sulfone. The -(7- to 10-membered) bicycloheterocycle can be attached via a nitrogen or carbon atom. Representative -(7- to 10-membered)bicycloheterocycles include -quinolinyl, -isoquinolinyl, -2,3-dihydrobenzofuranyl, -1,3-dihydroisobenzofuranyl, -benzo[d][1,3]dioxolyl, -2,3-dihydrobenzo[b]thiophenyl, -1,3-dihydrobenzo[c]thiophenyl, -benzo[d][,3]dithiolyl, -chromonyl, -chromanyl, -2,3-dihydrobenzo[b][1,4]dioxinyl, -thiochromonyl, -thiochromanyl, -2,3-dihydrobenzo[b][1,4]dithiinyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -indolinyl, -isoindolinyl, -1,2,3,4-tetrahydroquinolinyl, -1,2,3,4-tetrahydroisoquinolinyl, and the like.

"—$(C_3-C_{12})$cycloalkoxy" means a saturated monocyclic hydrocarbon having 3, 4, 5, 6, 7, 8, 9, 10, 11, or 12 carbon atoms where at least one of the carbon atoms is replaced by an oxygen atom. Representative $(C_3-C_{12})$cycloalkoxy are -oxiranyl, -oxetanyl, -tetrahydrofuranyl, -tetrahydro-2H-pyranyl, -1,4-dioxanyl, -oxepanyl, -1,4-dioxepanyl, -oxocanyl, -1,5-dioxocanyl, -1,3,5-trioxocanyl, -oxonanyl, -1,5-dioxonanyl, -1,4,7-trioxonanyl, -oxacyclododecanyl, -1,7-dioxacyclododecanyl, and -1,5,9-trioxacyclododecanyl.

"—$(C_3-C_7)$cycloalkoxy" means a saturated monocyclic hydrocarbon having 3, 4, 5, 6, or 7 carbon atoms where at least one of the carbon atoms is replaced by an oxygen atom. Representative $(C_3-C_7)$cycloalkoxy are -oxiranyl, -oxetanyl, -tetrahydrofuranyl, -tetrahydro-2H-pyranyl, -1,4-dioxanyl, -oxepanyl, and -1,4-dioxepanyl.

"—$(C_{14})$aryl" means a 14-membered aromatic carbocyclic moiety such as -anthryl or -phenanthryl.

"-(5- to 10-membered)heteroaryl" means an aromatic heterocycle ring of 5 to 10 members, including both mono- and bicyclic ring systems, i.e., a monocyclic aromatic ring comprising at least one heteroatom independently selected from nitrogen, oxygen, and sulfur or a bicyclic aromatic ring where at least one ring comprises at least one heteroatom independently selected from nitrogen, oxygen, and sulfur. In one embodiment, a monocyclic -(5- to 10-membered)heteroaryl comprises at least two heteroatoms independently selected from nitrogen, oxygen, and sulfur. In another embodiment, a bicyclic -(5- to 10-membered)heteroaryl comprises at least two heteroatoms, present in the same or in different rings, each heteroatom being independently selected from nitrogen, oxygen, and sulfur. In another embodiment, one of the -(5- to 10-membered)heteroaryl's rings contain at least one carbon atom. In another embodiment, both of the bicyclic -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, cinnolinyl, phthalazinyl, and quinazolinyl.

"-(5- or 6-membered)heteroaryl" means a monocyclic aromatic heterocycle ring of 5 or 6 members, i.e., a monocyclic aromatic ring comprising at least one heteroatom independently selected from nitrogen, oxygen, and sulfur. In one embodiment, the -(5- or 6-membered)heteroaryl ring contains at least one carbon atom. Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"—$CH_2$(halo)" means a methyl group where one of the hydrogens of the methyl group has been replaced with a halogen. Representative —$CH_2$(halo) groups include —$CH_2F$, —$CH_2Cl$, —$CH_2Br$, and —$CH_2I$.

"—$CH(halo)_2$" means a methyl group where two of the hydrogens of the methyl group have each been independently replaced with a halogen. Representative —CH(halo)₂ groups include —CHF₂, —CHCl₂, —CHBr₂, —CHBrCl, —CHClI, and —CHI₂.

"—C(halo)₃" means a methyl group where each of the hydrogens of the methyl group has been independently replaced with a halogen. Representative —C(halo)₃ groups include —CF₃, —CCl₃, —CBr₃, —Cl₃, —CF₂Br, —CF₂Cl, —CCl₂F, and —CFClBr.

"-Halogen" or "-halo" means —F, —Cl, —Br, or —F.

"Oxo", "=O", and the like as used herein mean an oxygen atom doubly bonded to carbon or another element.

"Thiooxo", "thioxo", "=S", and the like as used herein mean a sulfur atom doubly bonded to carbon or another element.

"(C₂-C₆)bridge" as used herein means a hydrocarbon chain containing 2 to 6 carbon atoms joining two atoms of the piperidine ring of Formula (I) to form a fused bicyclic ring system. For example, compounds of the disclosure can comprise a (C₂-C₆)bridge joining positions 2 and 6 of the piperidine ring (A-B can together form a (C₂-C₆)bridge). Exemplary compounds of the disclosure include those with an unsubstituted (C₂)bridge, —CH₂—CH₂—, joining positions 2 and 6 of the piperidine ring (A-B can together form a (C₂)bridge); an unsubstituted (C₃)bridge, —CH₂—CH₂—CH₂—, joining positions 2 and 6 of the piperidine ring (A-B can together form a (C₃)bridge); an unsubstituted (C₄) bridge, —CH₂—CH₂—CH₂—CH₂—, joining positions 2 and 6 of the piperidine ring (A-B can together form a (C₄)bridge); an unsubstituted (C₅)bridge, —CH₂—CH₂—CH₂—CH₂—CH₂—, joining positions 2 and 6 of the piperidine ring (A-B can together form a (C₅)bridge); or an unsubstituted (C₆)bridge, —CH₂—CH₂—CH₂—CH₂—CH₂—CH₂—, joining positions 2 and 6 of the piperidine ring (A-B can together form a (C₆)bridge). Examples of compounds where A-B can together form a (C₂-C₆)bridge include compounds comprising the following ring systems: 8-aza-bicyclo[3.2.1]octane; 9-aza-bicyclo[3.3.1]nonane; 10-aza-bicyclo[4.3.1]decane; 11-aza-bicyclo[5.3.1]undecane; and 12-aza-bicyclo[6.3.1]dodecane. Examples of a (C₂-C₆)bridge which contains —HC=CH— within the (C₂-C₆)bridge include —HC=CH—, —CH₂—HC=CH—, —HC=CH—CH₂—, —CH₂—HC=CH—CH₂—, and the like. Examples of a (C₂-C₆)bridge which contains —O— within the (C₂-C₆)bridge include —CH₂—O—CH₂-(containing 2 carbon atoms), —CH₂—O—CH₂—CH₂— and —CH₂—CH₂—O—CH₂— (each containing 3 carbon atoms), —CH₂—CH₂—O—CH₂—CH₂—, —CH₂—O—CH₂—CH₂—CH₂— and —CH₂—CH₂—CH₂—O—CH₂— (each containing 4 carbon atoms), and the like.

In compounds of the disclosure comprising a bridge joining positions 2 and 6 of the piperidine ring (e.g., A-B can together form a (C₂-C₆)bridge), for, e.g., a compound of Formula (I), the exemplary endo bridge:

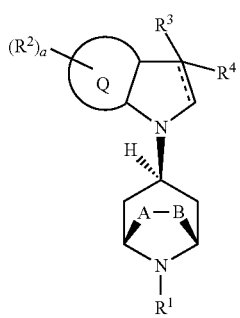

is equivalent to

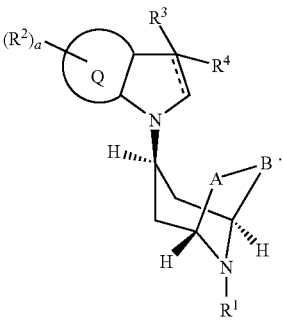

In compounds of the disclosure comprising a bridge joining positions 2 and 6 of the piperidine ring (e.g., A-B can together form a (C₂-C₆)bridge), for, e.g., a compound of Formula (I), the exemplary exo bridge:

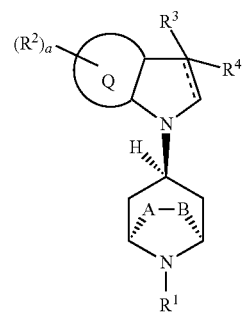

is equivalent to

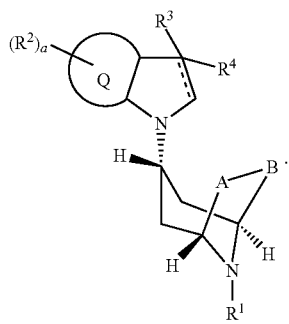

In compounds of the disclosure where the —R¹ group comprises a bicyclic group, that bicyclic group can have two orientations. For example, for a —R¹ group that is a —(C₆-C₁₄)bicycloalkyl, e.g., bicyclo[3.3.1]nonanyl, attached directly to the piperidine ring nitrogen, the following orientations are possible:

Endo:

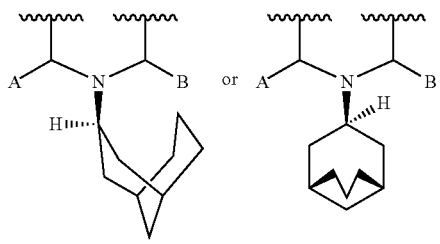

Exo:

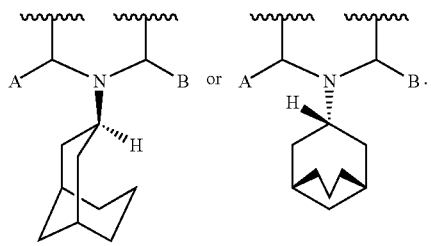

As used herein in connection with formula (i) of $R^1$, when the dashed line denotes the presence of a double bond at that position, then formula (i) is understood to appear as follows

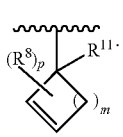

(i)

As used herein in connection with formula (i) of $R^1$, when the dashed line denotes the absence of a double bond at that position, then formula (i) is understood to appear as follows

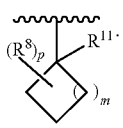

(i)

The terms "benzo", "benzo group" and the like, when used in connection with the Q ring, means

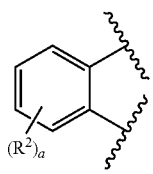

where $R_2$, and a are defined above for the Compounds of Formula (I).

The terms "pyridyl", "pyridino", "pyridino group" and the like, when used in connection with the Q ring, means

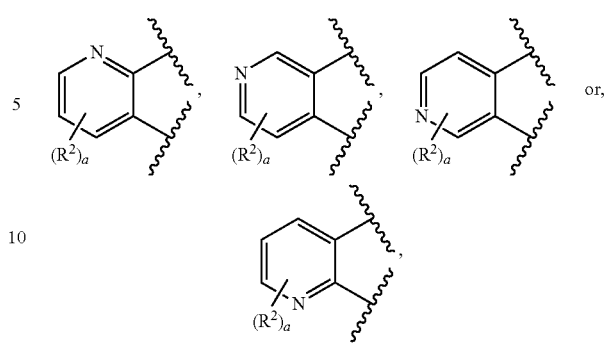

where $R^2$, and a are defined above for the compounds of Formula (I). In one embodiment, the optionally-substituted pyridino Q ring is

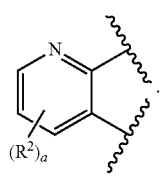

In another embodiment, the optionally-substituted pyridino Q ring is

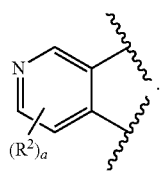

In another embodiment, the optionally-substituted pyridino Q ring is

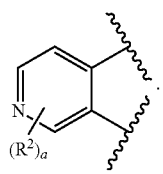

In another embodiment, the optionally-substituted pyridino Q ring is

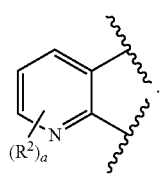

The terms "pyrimidyl", "pyrimidino", "pyrimidino group" and the like, when used in connection with the optionally-substituted Q ring, means

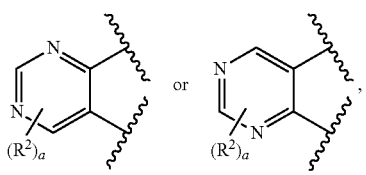 or , where $R_2$ and a are defined above for the Compounds of Formula (I). In one embodiment, the optionally-substituted pyrimidino Q ring is

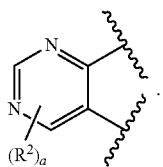

In another embodiment, the optionally-substituted pyrimidino Q ring is

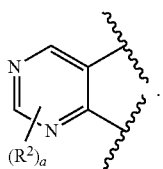

The terms "pyrazinyl", "pyrazino", "pyrazino group" and the like, when used in connection with the optionally-substituted Q ring, means

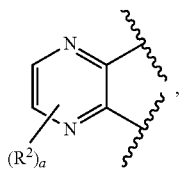

where $R^2$ and a are defined above for the compounds of Formula (I).

The terms "pyridazino", "pyridazino group" and the like, when used in connection with the optionally-substituted Q ring, means

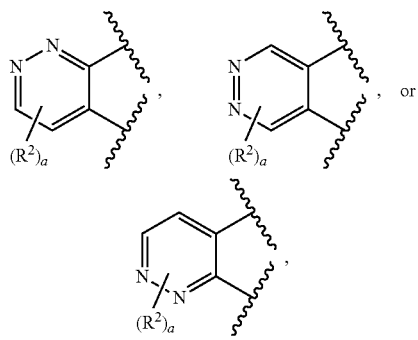

where $R_2$ and a are defined above for the Compounds of Formula (I). In one embodiment, the optionally-substituted pyridazino Q ring is

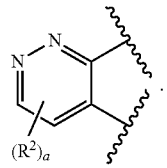

In another embodiment, the optionally-substituted pyridazino Q ring is

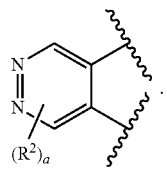

In another embodiment, the optionally-substituted pyridazino Q ring is

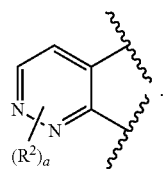

The terms "pyrrolininyl", ""pyrrolino", "pyrrolino group" and the like, when used in connection with the optionally-substituted Q ring, means

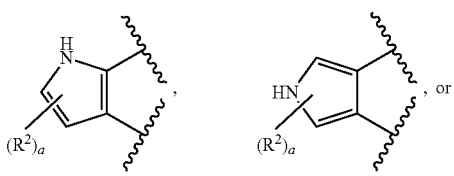

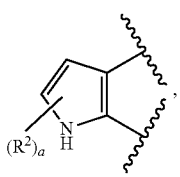

where $R^2$ and a are defined above for the compounds of Formula (I). In one embodiment, the optionally-substituted pyrrolino Q ring is

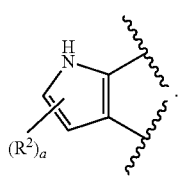

In another embodiment, the optionally-substituted pyrrolino Q ring is

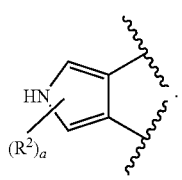

In another embodiment, the optionally-substituted pyrrolino Q ring is

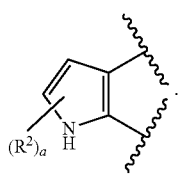

The terms "imidazolyl", "imidazolino", "imidazolino group" and the like, when used in connection with the optionally-substituted $_a$ ring, means

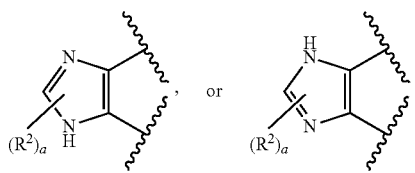

where $R^2$ and a are defined above for the compounds of Formula (I). In one embodiment, the optionally-substituted imidazolino $Q_a$ ring is

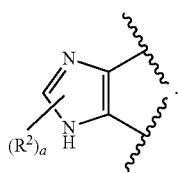

In another embodiment, the optionally-substituted imidazolino Q ring is

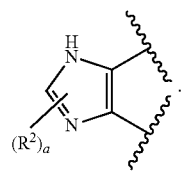

The terms "pyrazoyyl", pyrazolino", "pyrazolino group" and the like, when used in connection with the optionally-substituted Q ring, means

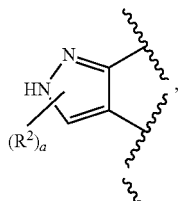 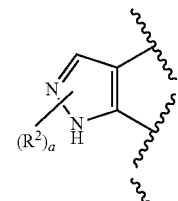

where $R_2$ and a are defined above for the compounds of Formula (I). In one embodiment, the optionally-substituted pyrazolino Q ring is

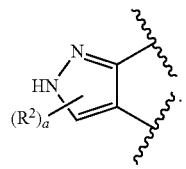

In another embodiment, the optionally-substituted pyrazolino Q ring is

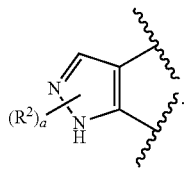

In another embodiment, the optionally-substituted pyrazolino Q ring is

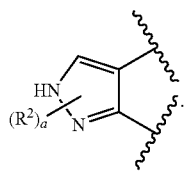

In another embodiment, the optionally-substituted pyrazolino Q ring is

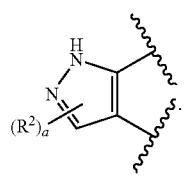

The terms "triazolyl","triazolino", "triazolino group" and the like, when used in connection with the optionally-substituted Q ring, means

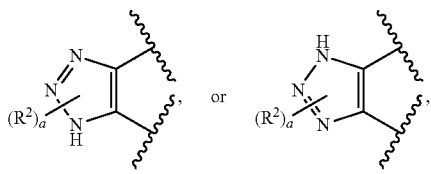

where R₂ and a are defined above for the compounds of Formula (I). In one embodiment, the optionally-substituted triazolino Q ring is

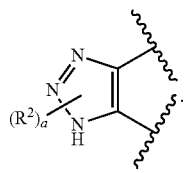

In another embodiment, the optionally-substituted triazolino Q ring is

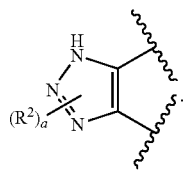

The terms "furano", "furano group" and the like, when used in connection with the optionally-substituted Q ring, means

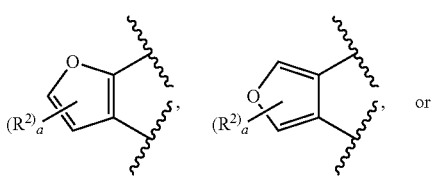

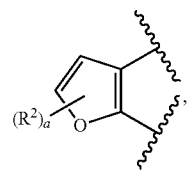

where $R^2$ and a are defined above for the Compounds of Formula (I). In one embodiment, the optionally-substituted furano Q ring is

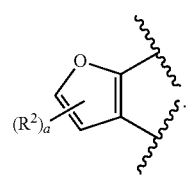

In another embodiment, the optionally-substituted furano Q ring is

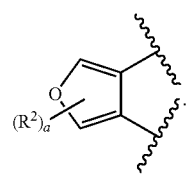

In another embodiment, the optionally-substituted furano Q ring is

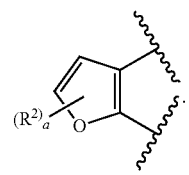

The terms "oxazolyl", "oxazolino", "oxazolino group" and the like, when used in connection with the optionally-substituted Q ring, means

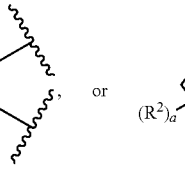 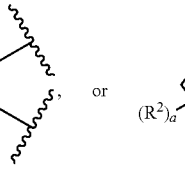

where $R^2$ and a are defined above for the Compounds of Formula (I). In one embodiment, the optionally-substituted oxazolino Q ring is

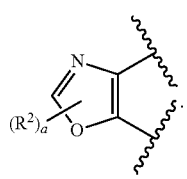

In another embodiment, the optionally-substituted oxazolino Q ring is

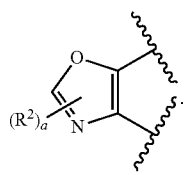

The terms "isooxazolyl", "isoxazolino", "isoxazolino group" and the like, when used in connection with the optionally-substituted Q ring, means

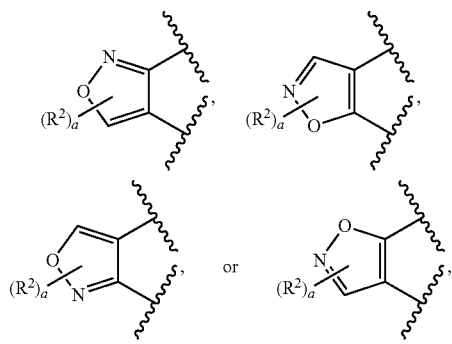

where $R^2$ and a are defined above for the compounds of Formula (I). In one embodiment, the optionally-substituted isoxazolino Q ring is

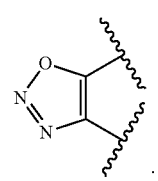

In another embodiment, the optionally-substituted isoxazolino Q ring is

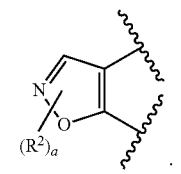

In another embodiment, the optionally-substituted isoxazolino Q ring is

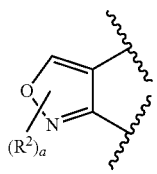

In another embodiment, the optionally-substituted isoxazolino Q ring is

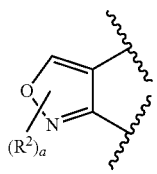

In another embodiment, the optionally-substituted isoxazolino Q ring is

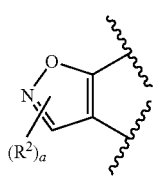

The terms "oxadiazolino", "oxadiazolino group" and the like, when used in connection with the optionally-substituted Q ring, means

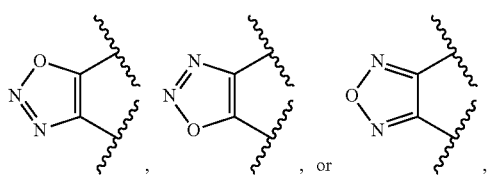

where $R_2$ and a are defined above for the compounds of Formula (I). In one embodiment, the optionally-substituted oxadiazolino Q ring is

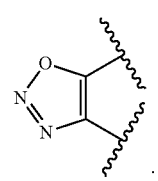

In another embodiment, the optionally-substituted oxadiazolino Q ring is

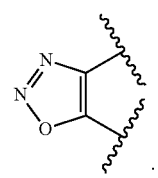

In another embodiment, the optionally-substituted oxadiazolino Q ring is

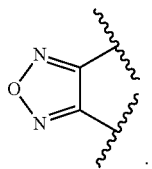

The terms "thienyl", "thiopheno", "thiopheno group" and the like, when used in connection with the optionally-substituted Q ring, means

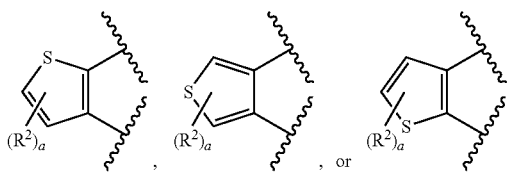

where $R^2$ and a are defined above for compounds of Formula (I). In one embodiment, the optionally-substituted thiopheno Q ring is

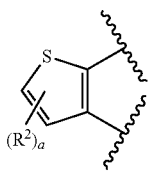

In another embodiment, the optionally-substituted thiopheno Q ring is

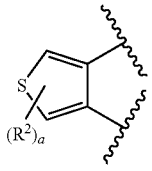

In another embodiment, the optionally-substituted thiopheno Q ring is

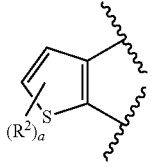

The terms "thiazolyl", "thiazolino", "thiazolino group" and the like, when used in connection with the optionally-substituted Q ring, means

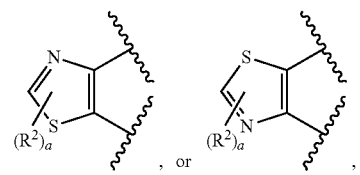

where $R_2$ and a are defined above for the compounds of Formula (I). In one embodiment, the optionally-substituted thiazolino Q ring is

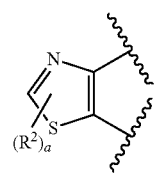

In another embodiment, the optionally-substituted thiazolino Q ring is

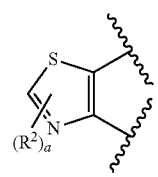

The terms "isothiazolyl", "isothiazolino", "isothiazolino group" and the like, when used in connection with the optionally-substituted Q ring, means

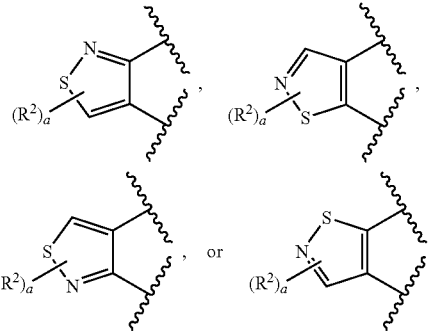

where $R^2$ and a are defined above for the compounds of Formula (I). In one embodiment, the optionally-substituted isothiazolino $Q_n$ ring is

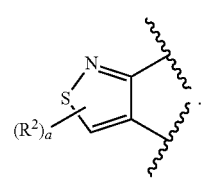

In another embodiment, the optionally-substituted isothiazolino Q ring is

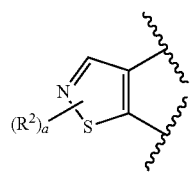

In another embodiment, the optionally-substituted isothiazolino Q ring is

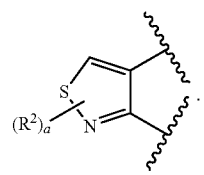

In another embodiment, the optionally-substituted isothiazolino Q ring is

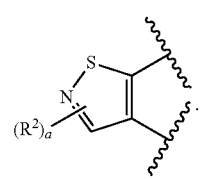

The terms "thiadiazolyl", "thiadiazolino", "thiadiazolino group" and the like, when used in connection with the optionally-substituted Q ring, means

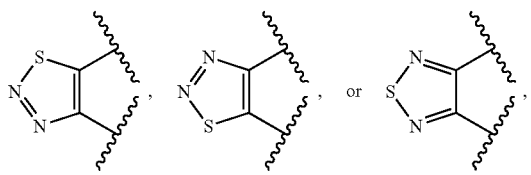

where $R^2$ and a are defined above for the compounds of Formula (I). In one embodiment, the optionally-substituted thiadiazolino Q ring is

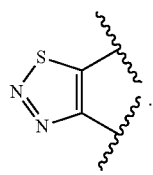 [SMILES: *c1nnsc1*]

In another embodiment, the optionally-substituted thiadiazolino Q ring is

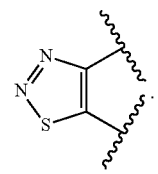

In another embodiment, the optionally-substituted thiadiazolino Q ring is

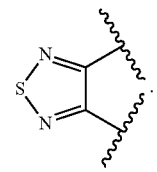 [SMILES: *c1nsnc1*]

In one embodiment, the term "optionally substituted bicyclo[3.3.1]nonyl" and the like when used in connection with the optionally-substituted $R^1$ group is understood to refer to one of the structures below:

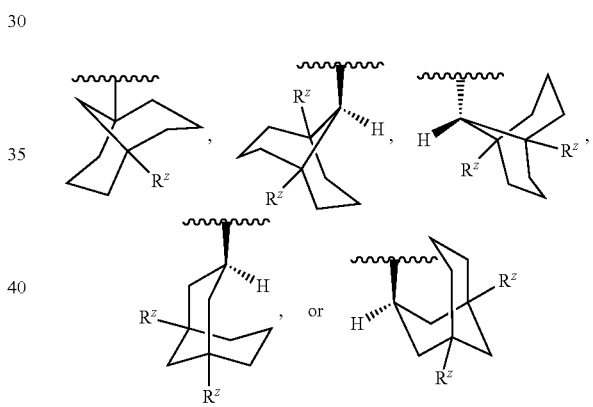

where the substituents are as defined above for the Compounds of Formula (I); and where in one or more embodiments, the optionally substituted $R^1$ group comprises one or more of the above-recited optionally substituted bicycle [3.3.1]nonyl structures.

In one embodiment, the term "optionally substituted —($C_6$-$C_{14}$)bicycloalkyl" means

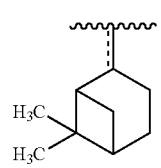

where the dashed line denotes the presence or absence of a bond. When the dashed line is present as a bond to provide one bond of a double bond, then the group above is understood to appear as follows

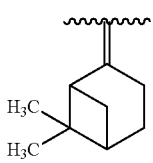

and when the dashed line is absent, then the optionally substituted —(C$_6$-C$_{14}$)bicycloalkyl group above is understood to appear as follows

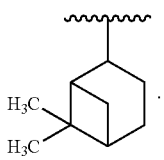

The term "tetrazolyl group" means

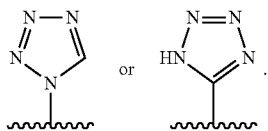 [SMILES: *n1cnnn1 ; *c1nnn[nH]1]

In one embodiment, the tetrazolyl group is

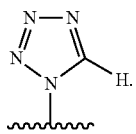

In another embodiment, the tetrazolyl group is

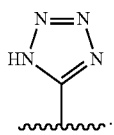

When a first group is "substituted with one or more" second groups, one or more hydrogen atoms of the first group is replaced with a corresponding number of second groups. When the number of second groups is two or greater, each second group can be the same or different. In one embodiment, a first group is substituted with up to three second groups. In another embodiment, a first group is substituted with one or two second groups. In another embodiment, a first group is substituted with two second groups. In another embodiment, a first group is substituted with two second groups and each second group is identical. In another embodiment, a first group is substituted with only one second group.

The term "animal" includes, but is not limited to, a human or a non-human animal, such as a companion animal or livestock, e.g., a cow, monkey, baboon, chimpanzee, horse, sheep, pig, chicken, turkey, quail, cat, dog, mouse, rat, rabbit or guinea pig.

Compounds of Formula (I) include all pharmaceutically acceptable salts, solvates, radiolabeled forms, stereoisomers, enantiomers, diastereomers, other stereoisomeric forms, racemic mixtures, and tautomers thereof.

In one embodiment, a Compound of Formula (I) is in the form of a pharmaceutically acceptable salt or solvate thereof.

The term "pharmaceutically acceptable salt", as used herein, is any pharmaceutically acceptable salt that can be prepared from a compound of the disclosure including a salt formed from an acid and a basic functional group, such as a nitrogen group of an indole-type or indoline-type piperidine e compound (i.e., an acid addition salt). Illustrative salts include, but are not limited to, sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. For example, for a Indole compound where J is N(R$_{90}$), a chloride salt can be formed by reacting the compound with HCl to provide the hydrochloride of the Indole compound, e.g., J is N(H)(R$_{90}$). The term "pharmaceutically acceptable salt" also includes a salt prepared from a an indole-type or indoline-type piperidine compound of the disclosure having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl-N-ethylamine; diethylamine; triethylamine; mono-, bis-, or tris-(2-hydroxy-(C$_1$-C$_3$)alkyl amines), such as mono-, bis-, or tris-(2-hydroxyethyl)amine, 2-hydroxy-tert-butylamine, or tris-(hydroxymethyl)methylamine, N,N-di-[(C$_1$-C$_3$)alkyl]-(hydroxy-(C$_1$-C$_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. In one embodiment, the pharmaceutically acceptable salt is a hydrochloride-salt, a sulfate-salt, a sodium-salt, a potassium-salt, a benzene sulfonic acid-salt, a para-toluenesulfonic acid-salt, or a fumaric acid-salt. In another embodiment, the pharmaceutically acceptable salt is a hydrochloride-salt or a sulfate-salt. In another embodiment, the pharmaceutically acceptable salt is a hydrochloride-salt. In another embodiment, the pharmaceutically acceptable salt is a sulfate-salt. In another embodiment, the pharmaceutically acceptable salt is a sodium-salt. In another embodiment, the pharmaceutically acceptable salt is a potassium-salt. In another embodiment, the pharmaceutically acceptable salt is a para-toluenesulfonic acid-salt. In another embodiment, the pharmaceutically acceptable salt is a fumaric acid-salt. In another embodiment, the pharmaceutically acceptable fumaric acid-salt contains about one equivalent of an indole-type or indoline-type piperidine compound of the disclosure compound and about 0.5 equivalents of fumaric acid, e.g., from about 0.3 to about 0.7 equivalents of fumaric acid in one embodiment, from about 0.4 to about 0.6 equivalents of fumaric acid in another embodiment, from about 0.44 to about 0.56 equivalents of fumaric acid in another embodiment, or from about 0.47 to about 0.53 equivalents of fumaric acid in another embodiment. In another embodiment, the pharmaceutically acceptable fumaric acid-salt contains one equivalent of an indole-type or indoline-type piperidine compound of the disclosure and 0.5 equivalents of fumaric acid. One skilled in the art will recognize that, e.g., acid addition salts, of an indole-type or indoline-type piperidine compound of the disclosure can be prepared by reaction of the compounds with the appropriate acid by a variety of known methods.

In certain embodiments, the pharmaceutically acceptable salt includes two or more salt groups, such as two halide salt groups, and/or a combination of salt types, such as a chloride salt group and a bromide salt group. For example, in some embodiments, the pharmaceutically acceptable salt includes both a base addition salt group and an acid addition salt group. In certain embodiments, the pharmaceutically acceptable salt is a zwitterion.

The compounds of the disclosure provided herein also encompass all solvates of the indole-type or indoline-type piperidine compound of the disclosure. "Solvates" are known in the art and are considered in view of this disclosure to be a combination, physical association and/or solvation of an indole-type or indoline-type piperidine compound of the disclosure with a solvent molecule. This physical association can involve varying degrees of ionic and covalent bonding, including hydrogen bonding. When the solvate is of the stoichiometric type, there is a fixed ratio of the solvent molecule to an indole-type or indoline-type piperidine compound, e.g., a disolvate, monosolvate or hemisolvate when the solvent molecule: an indole-type or indoline-type piperidine compound has molecule molar ratio is 2:1, 1:1 or 1:2, respectively. In other embodiments, the solvate is of the nonstoichiometric type. For example, the indole-type or indoline-type piperidine compound crystal can contain solvent molecules in the structural voids, e.g., channels, of the crystal lattice. In certain instances, the solvate can be isolated, for example when one or more solvent molecules are incorporated into the crystal lattice of a crystalline solid. Thus, "solvate", as used herein, encompasses both solution-phase and isolatable solvates. As the crystalline form of a solvate can also be referred to as a "pseudopolymorph", the compounds of the disclosure provided herein also encompass all pseudopolymorphs of the indole-type or indoline-type piperidine compound of the disclosure. An indole-type or indoline-type piperidine compound of the disclosure can be present as a solvated form with a pharmaceutically acceptable solvent, such as water, methanol, ethanol, and the like, and it is intended that the disclosure include both solvated and unsolvated indole-type or indoline-type piperidine compounds. As "hydrate" relates to a particular subgroup of solvates, i.e., where the solvent molecule is water, hydrates are included within the solvates of the disclosure. In one embodiment, the indole-type or indoline-type piperidine compound of the disclosure is present as a monohydrate, i.e., as a free base where the water:Indole compound molar ratio is about 1:1, e.g., from 0.91:1 to 1.09:1 in one embodiment, from 0.94:1 to 1.06:1 in another embodiment, from 0.97:1 to 1.03:1 in another embodiment, and from 0.985:1 to 1.015:1 in another embodiment, each said embodiment taking no account of surface water that might be present, if any.

Preparation of solvates is known in the art. For example, Caira et al., "Preparation and Crystal Characterization of a Polymorph, a Monohydrate, and an Ethyl Acetate Solvate of the Antifungal Fluconazole," *J. Pharmaceut. Sci.,* 93(3): 601-611 (2004), describes the preparation of solvates of fluconazole with ethyl acetate and with water. Similar preparations of solvates, hemisolvate, hydrates, and the like are described by Van Tonder et al., "Preparation and Physicochemical Characterization of 5 Niclosamide Solvates and 1 Hemisolvate," *AAPS Pharm. Sci. Tech.,* 5(1):Article 12 (2004), and Bingham et al., "Over one hundred solvates of sulfathiazole," *Chem. Comm.,* pp. 603-604 (2001). In one embodiment, a non-limiting, process involves dissolving the Indole compound in a desired amount of the desired solvent (organic, water or mixtures thereof) at temperatures above about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

In addition, one or more hydrogen, carbon or other atoms of an indole-type or indoline-type piperidine compound of the disclosure can be replaced by a radioactive isotope of the hydrogen, carbon or other atoms. Such a "radiolabeled", "radiolabeled form", and the like of an indole-type or indoline-type piperidine compound of the disclosure, each of which is encompassed by the disclosure, is useful as a research and/or diagnostic tool in metabolism pharmacokinetic studies and in binding assays. "Radioactive", as used herein with respect to an atom, means an atom that comprises a radioactive atom and therefore the specific radioactivity thereof is above the background level of radioactivity. Examples of radioactive isotopes that can be incorporated into an indole-type or indoline-type piperidine compound of the disclosure include isotopes of hydrogen, carbon, nitrogen, oxygen, phosphorous, sulfur, fluorine, chlorine, bromine, and iodine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I, respectively. In one embodiment, a radiolabeled indole-type or indoline-type piperidine compound of the disclosure contains 1, 2, 3, 4, or more radioactive isotopes, each of which is independently selected from hydrogen, carbon, nitrogen, oxygen, phosphorous, sulfur, fluorine, chlorine, bromine, and iodine. In another embodiment, a radiolabeled indole-type or indoline-type piperidine compound of the disclosure contains 1 or 2 radioactive isotopes, each of which is independently selected from hydrogen, carbon, nitrogen, oxygen, phosphorous, sulfur, fluorine, chlorine, bromine, and iodine. In another embodiment, a radiolabeled an indole-type or indoline-type piperidine compound of the disclosure contains 1 radioactive isotope which is selected from hydrogen, carbon, nitrogen, oxygen, phosphorous, sulfur, fluorine, chlorine, bromine, and iodine. In another embodiment, a radiolabeled an indole-type or indoline-type piperidine compound of the disclosure contains 1, 2, 3, 4, or more radioactive isotopes, each of which is independently selected from $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, a radiolabeled indole-type or indoline-type piperidine compound of the disclosure contains 1 or 2 radioactive isotopes, each of which is independently selected from $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, an indole-type or indoline-type piperidine compound of the disclosure contains 1 radioactive isotope which is selected from $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, a radiolabeled indole-type or indoline-type piperidine compound of the disclosure contains 1, 2, 3, 4, or more radioactive isotopes, each of which is independently selected from $^2$H, $^3$H, $^{13}$C, $^{14}$C, $^{15}$N, $^{18}$O, $^{32}$P, and $^{125}$I. In another embodiment, a radiolabeled indole-type or indoline-type piperidine compound of the disclosure contains 1 or 2 radioactive isotopes, each of which is independently selected from $^3$H, $^{14}$C, $^{15}$N, $^{18}$O, $^{32}$P, and $^{125}$I. In another embodiment, a radiolabeled an indole-type or indoline-type piperidine compound of the disclosure contains 1 radioactive isotope which is selected from $^3$H, $^{14}$C, $^{15}$N, $^{18}$O, $^{32}$P, and $^{125}$I.

Radiolabeled compounds of the disclosure can be prepared by methods known in the art. For example, a tritiated indole-type or indoline-type piperidine compound of the disclosure can be prepared by introducing tritium into the particular indole-type or indoline-type piperidine compound, for example, by catalytic dehalogenation with tritium. This method can include reacting a suitably halogen-substituted precursor of an indole-type or indoline-type piperidine compound of the disclosure with tritium gas in the presence of a suitable catalyst, for example, Pd/C, in the presence or absence of a base. Other suitable methods for preparing tritiated compounds can be found in Filer, "The Preparation and Characterization of Tritiated Neurochemicals," *Isotopes in the Physical and Biomedical Sciences*, Vol. 1, *Labeled Compounds* (Part A), E. Buncel et al, eds., Chapter 6, pp. 155-192 (1987). $^{14}$C-labeled compounds can be prepared by employing starting materials having a $^{14}$C carbon. Compounds containing piperazine isotopically enriched with $^{13}$C and/or $^{15}$N can be prepared as described in, e.g., FIG. 5A and the associated description, of U.S. Pat. No. 7,355,045 B2. Radiolabeled compounds containing $^{18}$F at the 6-position of an aniline ring can be prepared as described in column 27 of U.S. Pat. No. 6,562,319 B2.

A Compound of Formula (I) can contain one or more asymmetric centers and can thus give rise to enantiomers, diastereomers, and other stereoisomeric forms. Unless specifically otherwise indicated, the disclosure encompasses compounds with all such possible forms as well as their racemic and resolved forms or any mixture thereof. When an indole-type or indoline-type piperidine compound of the disclosure contains an olefinic double bond or other center of geometric asymmetry, and unless specifically otherwise indicated, it is intended to include all "geometric isomers", e.g., both E and Z geometric isomers. Unless specifically otherwise indicated, all "tautomers", e.g., lactam-lactim, urea-isourea, ketone-enol, amide-imidic acid, enamine-imine, amine-imine, and enamine-enimine tautomers, are intended to be encompassed by the disclosure as well.

As used herein, the terms "stereoisomer", "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "stereogenic center","chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule. Optical isomers of an indole-type or indoline-type piperidine compound of the disclosure can be obtained by known techniques such as chiral chromatography or formation of diastereomeric salts from an optically active acid or base.

Optical purity can be stated in terms of enantiomeric excess (% ee) and/or diastereomeric excess (% de), each which is determined by the appropriate formula below:

$$\% \ ee = \left[ \frac{\text{major enantiomer(mol)} - \text{minor enantiomer(mol)}}{\text{major enantiomer(mol)} + \text{minor enantiomer(mol)}} \right] \times 100\%$$

$$\% \ de = \left[ \frac{\text{major diastereomer(mol)} - \text{minor diastereomers(mol)}}{\text{major diastereomer(mol)} + \text{minor diastereomers(mol)}} \right] \times 100\%.$$

The term "MeOH" means methanol, i.e., methyl alcohol. The term "EtOH" means ethanol, i.e., ethyl alcohol. The term "Et$_2$O" means diethyl ether, i.e., ethoxyethane. The term "THF" means tetrahydrofuran. The term "DMF" means N,N-dimethylformamide. The term "DCM" means methylene chloride, i.e., dichloromethane or CH$_2$Cl$_2$. The term "DCE" means 1,2-dichloroethane. The term "EtOAc" means ethyl acetate. The term "MeCN" means acetonitrile. The term "DMSO" means dimethylsulfoxide, i.e., methylsulfinylmethane. The term "NMP" means N-methylpyrrolidinone, i.e., 1-methylpyrrolidin-2-one. The term "DMA" means N,N-dimethylacetamide. The term "MTBE" means tert-butyl methyl ether, i.e., 2-methoxy-2-methylpropane. The term "AcOH" means acetic acid. The term "TFA" means 2,2,2-trifluoroacetic acid. The term "TEA" means triethylamine. The term "DIEA" means diisopropylethylamine, i.e., N-ethyl-N-isopropylpropan-2-amine. The term "Bn" means benzyl, i.e.:

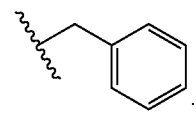

The term "BOC" means tert-butyloxycarbonyl, i.e.:

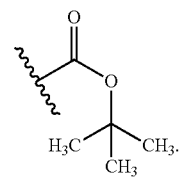

The term "IBD" means inflammatory-bowel disease. The term "IBS" means irritable-bowel syndrome. The term "ALS" means amyotrophic lateral sclerosis.

The term "effective amount", when used in connection with a Indole compound, means an amount effective for: (a) treating or preventing a Condition or symptom thereof; (b) detectably inhibiting ORL-1 receptor function in a cell; or (c) detectably activating ORL-1 receptor function in a cell.

The term "effective amount", when used in connection with a second therapeutic agent means an amount for providing the therapeutic effect of the second therapeutic agent.

The terms "modulate", "modulating", and the like as used herein with respect to the ORL-1 receptor mean the mediation of a pharmacodynamic response (e.g., analgesia) in an animal from (i) inhibiting or activating the receptor, or (ii) directly or indirectly affecting the normal regulation of the receptor activity. Compounds that modulate the receptor activity include agonists, partial agonists, antagonists, mixed agonists/antagonists, mixed partial agonists/antagonists and compounds which directly or indirectly affect regulation of the receptor activity.

As used herein, a compound that binds to a receptor and mimics the regulatory effect(s) of an endogenous ligand is defined as an "agonist". As used herein, a compound that binds to a receptor and is only partly effective as an agonist is defined as a "partial agonist". As used herein, a compound that binds to a receptor but produces no regulatory effect, but rather blocks binding of another agent to the receptor is defined as an "antagonist". (See Ross et al., "Pharmacodynamics: Mechanisms of Drug Action and the Relationship Between Drug Concentration and Effect," in *Goodman & Gilman's The Pharmacological Basis of Therapeutics* pp. 31-43 (Goodman et al., eds., 10$^{th}$ Ed., McGraw-Hill, New York 2001)).

The terms "treatment of", "treating", and the like include the amelioration or cessation of a Condition or a symptom thereof. In one embodiment, treating includes inhibiting, for example, decreasing the overall frequency of episodes of a Condition or a symptom thereof.

The terms "prevention of", "preventing", and the like include the avoidance of the onset of a Condition or a symptom thereof.

A "disorder" includes, but is not limited to, the Conditions defined above.

In the event of doubt as to the agreement of a depicted chemical structure and a chemical name, the depicted chemical structure governs.

It is appreciated that various features of the disclosure which are, for clarity, described in the context of separate embodiments, can also be provided in combination in a single embodiment unless otherwise specifically herein excluded. Conversely, various features of the disclosure which are, for brevity, described in the context of a single embodiment, can also be provided separately and/or in any suitable subcombination unless otherwise specifically herein excluded.

4.3 Methods for Making Indole-Type or Indoline-Type Piperidine Compounds

Indole-type or indoline-type piperidine compound of the disclosure can be made using conventional organic synthesis, in view of the present disclosure, and including the following illustrative methods shown in the schemes below where $R^1$, $R^2$, $R^3$, a, A, B, Q, X and a are defined above, L is a halogen leaving group such as Br or I, and R is —($C_1$-$C_4$)alkyl or —$CF_3$.

4.3.1 Methods for Making Indoline-Type Piperidine Compounds of Formula I' and Indole-Type Piperidine Compounds of Formula I"

Scheme A

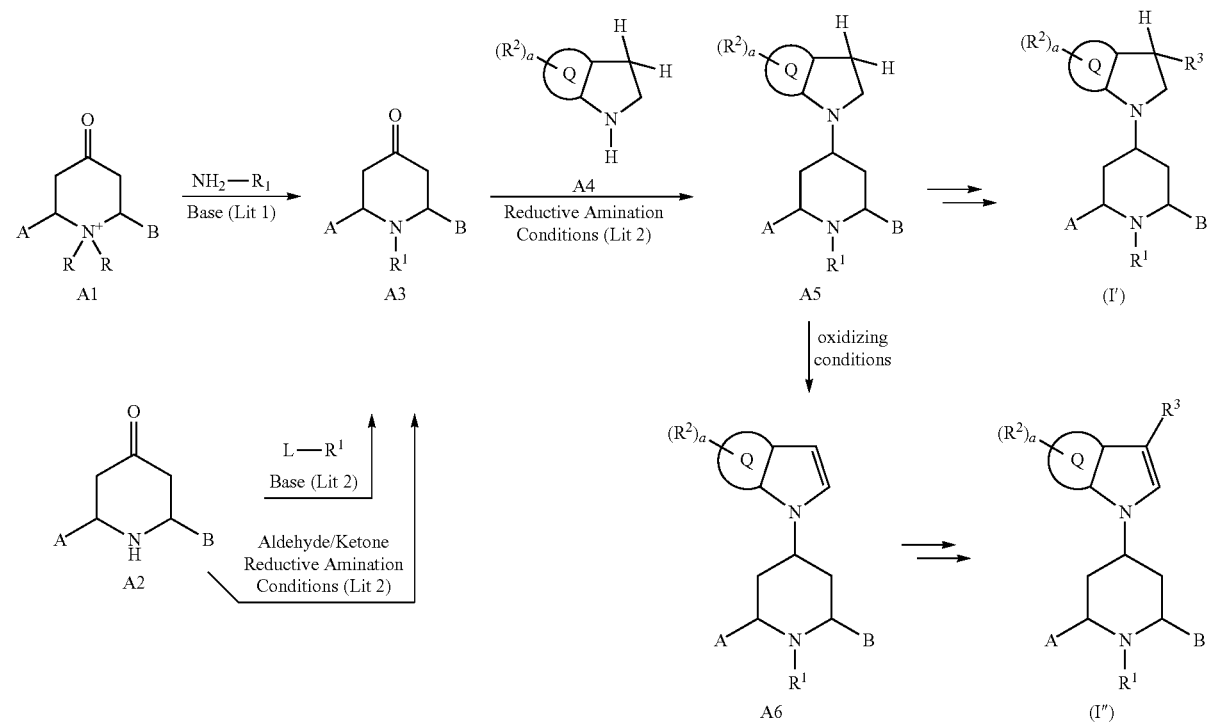

In Scheme A and the other schemes, "Lit 1" refers to the procedures described in the publications Tortolani et al., "A Convenient Synthesis to N-Aryl-Substituted 4-Piperidones," *Org. Lett.* 1:1261-1262 (1999) and/or International PCT Publication No. WO 2005/075459 A1 of Euro-Celtique S.A., "Lit 2" refers to the procedures described in U.S. Pat. No. 6,635,653 by Goehring et al., and "Lit 3" refers to the procedures described in the publication Dudash et al., "Synthesis and evaluation of 3-anilino-quinoxalinones as glycogen phosphorylase inhibitors," *Bioorg. Med. Chem. Lett.*, 15(21:4790-4793 (2005).

Compounds A1 and A2 are commercially available or can be prepared by methods known to the art.

A piperidinium salt of structure A1 can be reacted with a primary amine in a suitable solvent, such as EtOH, under reflux conditions in the presence of a base, such as potassium carbonate, as described in reference "Lit 1" to provide the 1-(substituted)piperidine-4-one Compound A3. As described in reference "Lit 2," Compound A3 can also be prepared by alkylation of a piperidine-4-one of structure A2 with an alkyl bromide or alkyl iodide in a suitable solvent, such as dimethyl formamide, MeCN or DMSO, in the presence of an inorganic base, such as potassium carbonate, or an organic base, such as DIEA. As described in reference "Lit 2," Compound A3 can also be prepared by reductive amination of Compound A2 with an aldehyde or ketone using either sodium triacetoxyborohydride or sodium cyanoborohydride in a suitable solvent, such as DCM or MeOH, respectively. Compound A3 can then be reacted with Compound A4 under reductive amination conditions using sodium triacetoxyborohydride or sodium cyanoborohydride in a suitable solvent, such as DCM or MeOH, respectively, to provide Compound A5, as described in reference "Lit 2." Compound A5 can be oxidized in the presence of a suitable oxidizing agent such as DDQ to provide Compound A6. As described below, Compound A5 or Compound A6 can be used as a precursor to synthesize (in several steps) particular compounds of Formula (I') or Formula (I"), which represent different embodiments of the compound of Formula (I).

4.3.2 Methods for Making Acylated Indole-Type Piperidine Compounds

Scheme B

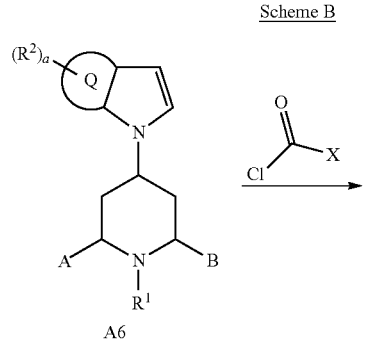

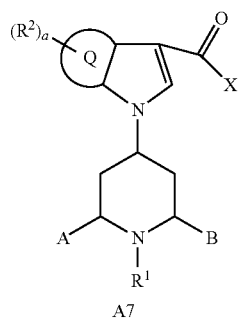

In Scheme B, Compound A6 is reacted with an acid chloride in a suitable organic solvent to provide Compound A7. In particular embodiments, the reaction can be carried out in the presence of a Lewis acid. In other embodiments, the reaction can be carried out in the presence of diethylaluminum chloride or dimethyl aluminum chloride. See *Org. Lett.*, 2(10):1485-1487 (2000). In alternative embodiments, 3-acylation of Compound A6 can be reaction can be carried out using acidic imidazolium chloroaluminate as an ionic liquid. See, for example, *Tet. Lett.* 43:5793-5795 (2002).

4.3.2.1 Methods for Acylating Indole-Type Piperidine Compounds with Oxalyl Chloride Scheme C

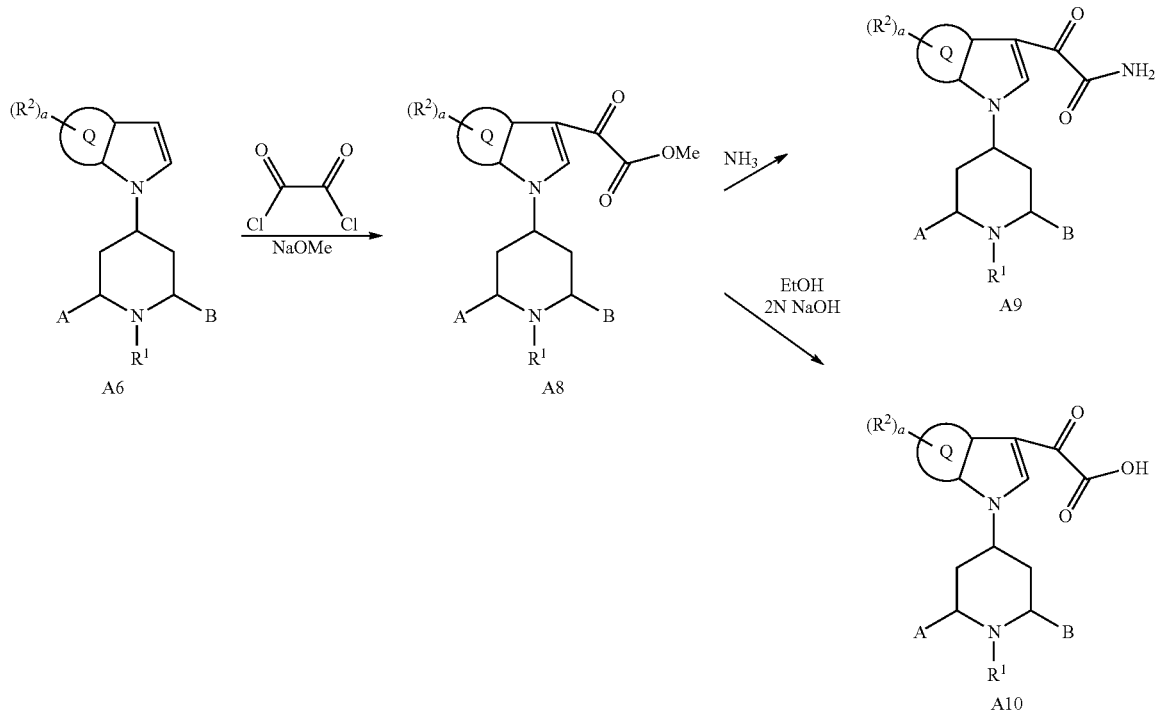

In Scheme C, Compound A6 is acylated with oxalyl chloride in a suitable organic solvent (e.g., dichloromethane) at ambient temperature. After 2-4 hours, the reaction mixture is cooled to about −70° C. and sodium methoxide is added to afford Compound A8. Compound A8 can be hydrolyzed with ammonia to produce Compound A9. Alternatively, Compound A8 can be dissolved in ethanol and 2N sodium hydroxide to produce Compound A10.

4.3.2.2 Alternative Methods for Making Compound A10

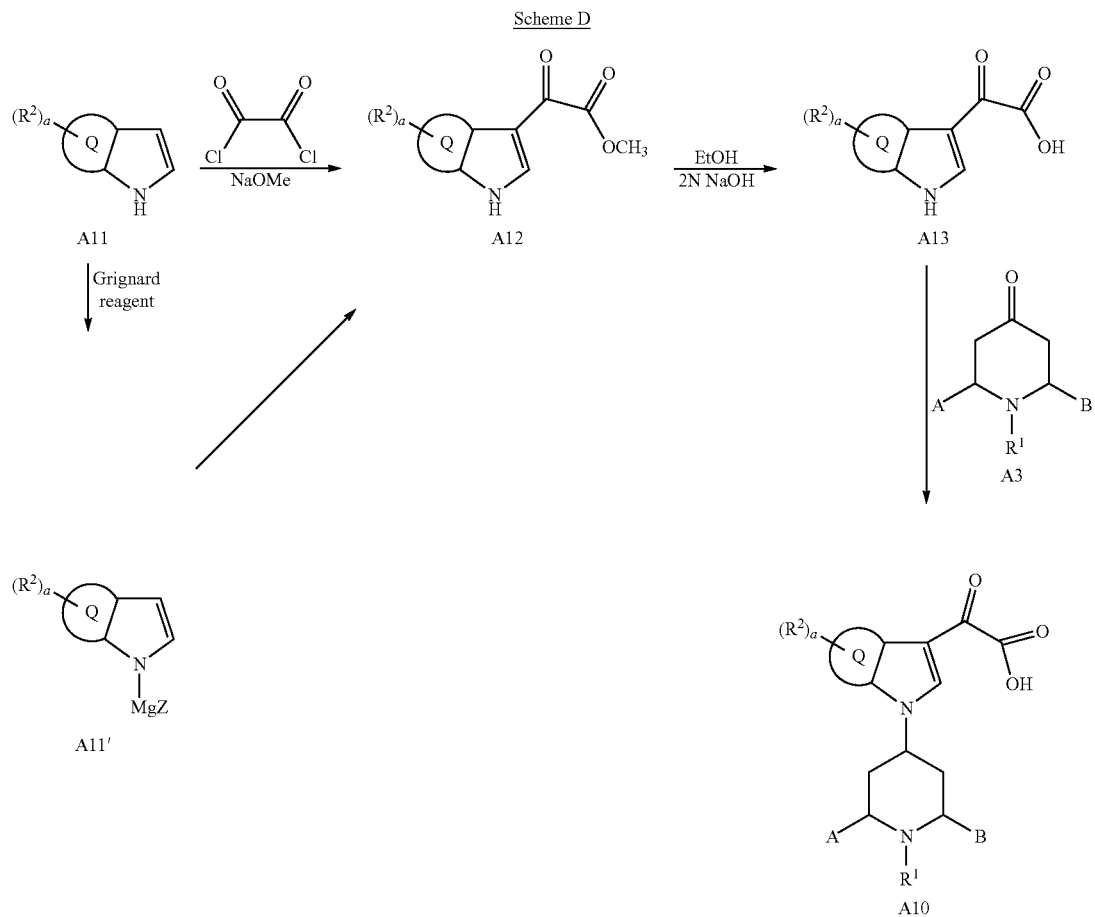

In Scheme D, compound A11 is reacted with oxalyl chloride reacting with oxalyl chloride in a suitable organic solvent (e.g., dichloromethane) at ambient temperature. After 2-4 hours, the reaction mixture is cooled to about −70° C. and sodium methoxide is added to afford Compound A12. In an alternative embodiment, Compound A11 is reacted with a Grignard reagent, preferably ethyl magnesium bromide, in diethyl ether or tetrahydrofuran at a temperature between −50° C. and 60° C. to afford Compound A 11'. Compound A11' is converted to Compound A12 through the addition of oxalyl chloride followed by addition of sodium methoxide to afford Compound A12. Compound A12 is then hydrolyzed to compound A13 through the addition of ethanol and sodium hydroxide. Compound A13 is then converted to Compound A10 through the addition of Compound A3 under the reductive amination conditions described in Section 4.3.1.

4.3.3 Reduction of Acylated Indole-Type Piperidine Compounds

Scheme E

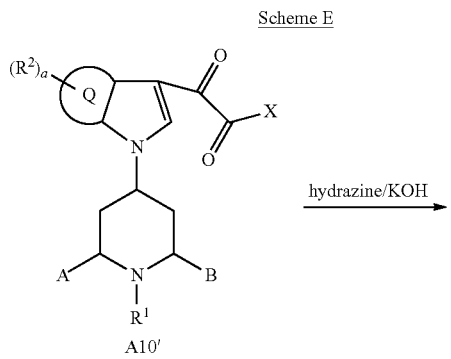

-continued
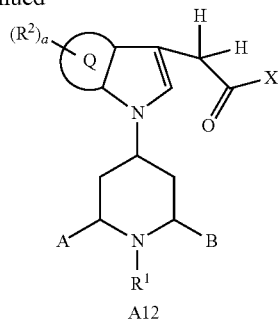
A12
In Scheme E, Compound A10' is reduced to Compound A12 by adding hydrazine in the presence of potassium hydroxide. The reaction can be carried out under standard Wolff-Kishner conditions at elevated temperatures (e.g., about 180° C.) in diethylene glycol or ethylene glycol. See *Comp. Org. Syn.* 8:372-343 (1991).
4.3.4 Alternative Method for Making Compound A12
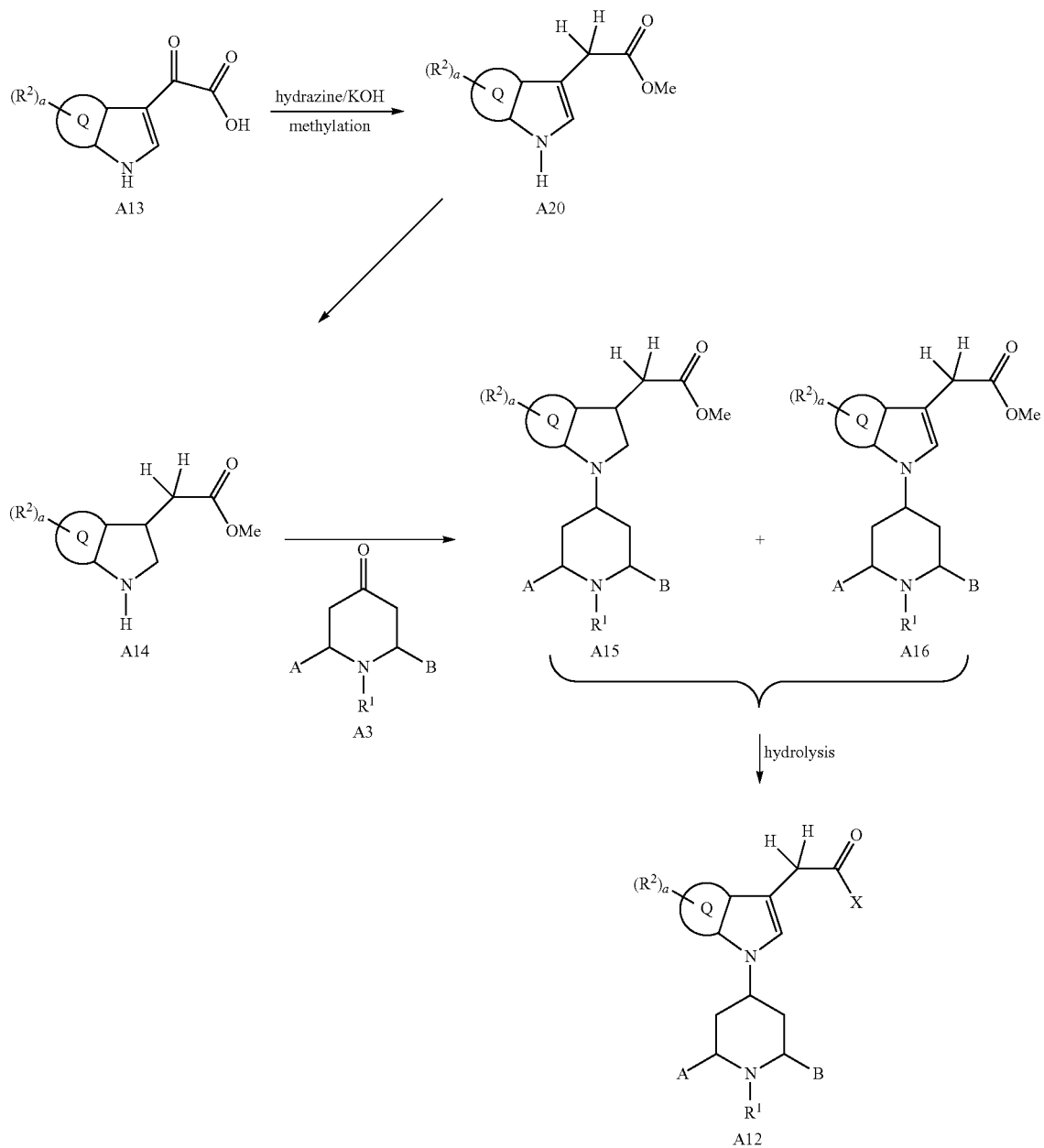

In Scheme F, Compound A13 is reduced under Wolff Kishner conditions and the resulting compound is methylated to afford Compound A20. Compound A20 is reduced to indoline Compound A14. The reaction can be carried out by adding a borane-pyridine complex to a suspension of Compound A13 in methanol and 12 N HCl (or trifluoroacetic acid) at a temperature between 0° C. and 25° C. See, for example, U.S. Pat. No. 4,210,590. After stirring for 1 to 3 hours, water is added slowly and the solution is basified to about a pH of 8 through the addition of sodium hydroxide. Indoline Compound A14 is then added to A3 under reductive amination conditions described in Section 4.3.1 to provide Compound A15 and Compound A16. Compound A16 can then be converted into compound A12 through methods known in the art (e.g., basic hydrolysis).

4.3.5. Method for Making Indoline-Type Piperidine Compound A18

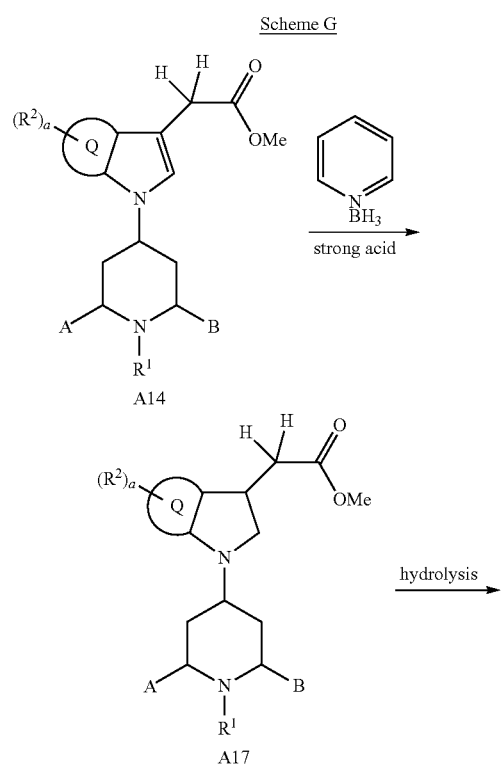

4,210,590. Compound A17 can then be converted into compound A18 through methods known in the art (e.g., basic hydrolysis).

4.3.6. Method for Making Fluorine Substituted Compound A19

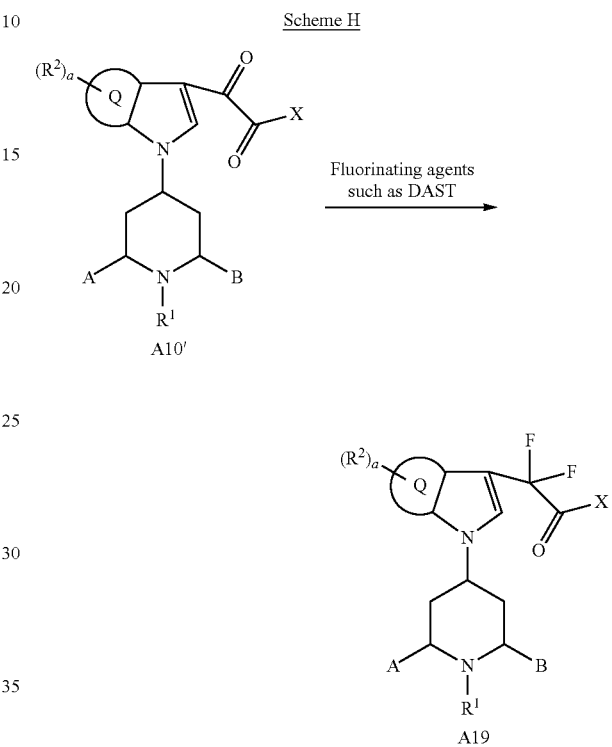

In Scheme H, Compound A0' is converted to Compound A19 through the addition of a fluorinating reagent such as ((diethylamino)sulfur trifluoride) (DAST). See, for example, *J. Org. Chem.*, 45(14), 2883-2887, (1980). The reaction can be carried out at room temperature or mild heating can be applied.

4.3.7 Method for Making Stereoselective Indole-Type Piperidine Compounds

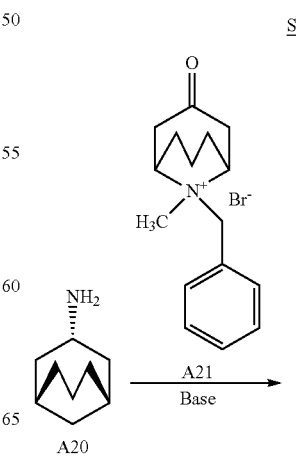

In Scheme G, Compound A14 is reduced to indoline Compound A17 through the addition of a borane-pyridine complex and a strong acid. See, for example, U.S. Pat. No.

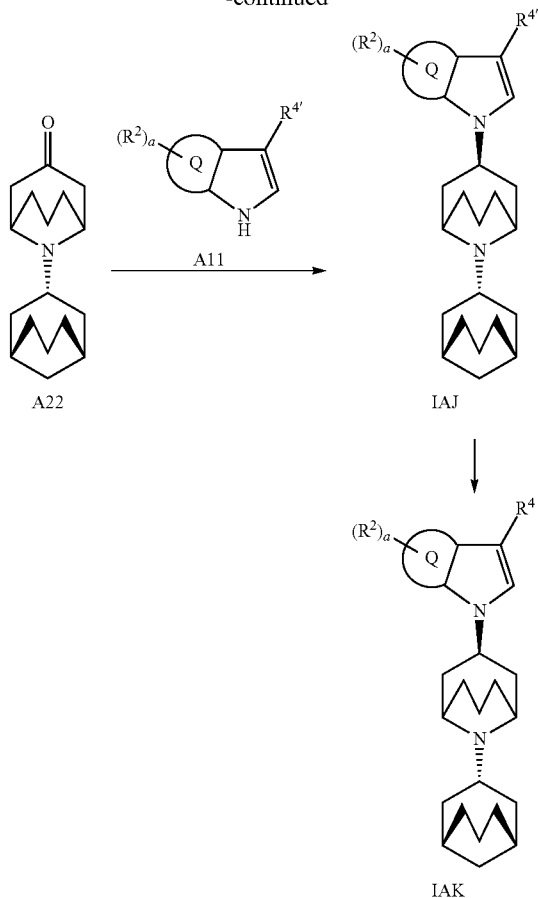

As shown in Scheme 1, an exemplary substituted indole-type piperidine Compound comprising an $R_1$ group formed from compound A20 can be prepared by a number of synthetic routes. For purposes of exemplification only, while the product illustrated in Scheme I is substituted indole-type piperidine compound IAJ or compound IAK, as those in the art will recognize this scheme is of course non-limiting and applicable to the preparation of other substituted indole-type piperidine compounds. Compound A22 can be prepared by methods described in WO 2009/027820, WO 2010/010458 or WO 2012/085648. For instance, in Scheme I, Compound A22 is formed by reacting Compound A20 and Compound A21 in the presence of a base. Compound A22, its hydrochloride, or its diphenylphosphate salt can then be reacted with Compound A11 to provide Compound Ic, where $R^{4'}$ represents a group that will ultimately be converted to $R^4$ in the final product. Multiple isomers of Compound IAJ can be purified purify by chromatography. Compound IAJ can be converted to Compound IAK in the presence of base.

4.4 Therapeutic Uses of Indole-Type or Indoline-Type Piperidine Compound of the Disclosure In accordance with the disclosure, the indole-type or indoline-type piperidine compounds are are administered to an animal in need of treatment or prevention of a Condition.

In one embodiment, an effective amount of certain indole-type or indoline-type piperidine compounds of the disclosure can be used to treat or prevent any condition treatable or preventable by inhibiting the activity of the ORL-1 receptor. Examples of Conditions that are treatable or preventable by inhibiting the activity of the ORL-1 receptor include, but are not limited to: pain (CNS effect), memory disorders, obesity, constipation, depression, dementia, and Parkinsonism.

In another embodiment, an effective amount of certain other indole-type or indoline-type piperidine compounds of the disclosure can be used to treat or prevent any condition treatable or preventable by activating the ORL-1 receptor. Examples of Conditions that are treatable or preventable by activating the ORL-1 receptor include, but are not limited to, pain, anxiety, cough, diarrhea, blood pressure disorder (via vasodilation and via diuresis), epilepsy, anorexia/cachexia, urinary incontinence, and drug abuse.

The indole-type or indoline-type piperidine compounds of the disclosure can be used to treat or prevent acute or chronic pain. Examples of pain that can be treated or prevented using a indole-type or indoline-type piperidine compound of the disclosure include, but are not limited to, cancer pain, neuropathic pain, labor pain, myocardial infarction pain, pancreatic pain, colic pain, post-operative pain, headache pain, muscle pain, arthritic pain, and pain associated with a periodontal disease, including gingivitis and periodontitis.

The indole-type or indoline-type piperidine compounds of the disclosure can also be used to treat or prevent pain associated with inflammation or with an inflammatory disease in an animal. Such pain can arise where there is an inflammation of the body tissue which can be a local inflammatory response or a systemic inflammation. For example, an indole-type or indoline-type piperidine compounds of the disclosure can be used to treat or prevent pain associated with inflammatory diseases including, but not limited to, organ transplant rejection; reoxygenation injury resulting from organ transplantation (see Grupp et al., "Protection against Hypoxia-reoxygenation in the Absence of Poly (ADP-ribose) Synthetase in Isolated Working Hearts," J. Mol. Cell Cardiol. 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microalbuminuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. An indole-type or indoline-type piperidine compound of the disclosure can also be used to treat or prevent pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The indole-type or indoline-type piperidine compounds of the disclosure can also be used to treat or prevent pain associated with nerve injury (i.e., neuropathic pain). Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia, or by heat-, cold-, or mechano-allodynia.

Chronic neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

The indole-type or indoline-type piperidine compounds of the disclosure can be used to treat or prevent a migraine including, but not limited to, migraine without aura ("common migraine"), migraine with aura ("classic migraine"), migraine without headache, basilar migraine, familial hemiplegic migraine, migrainous infarction, and migraine with prolonged aura.

The indole-type or indoline-type piperidine compounds of the disclosure can be used to treat or prevent a sleep disorder including, but not limited to, insomnia, hypersomnia, sleep deprivation, sleep apnea, dysomnia, delayed sleep phase syndrome (DSPS), advanced sleep phase syndrome (ASPS), non-24-hour sleep-wake syndrome (e.g., circadian rhythm sleep disorder), situational circadian rhythm sleep disorders (e.g., jet lag, shift work sleep disorders), hypopnea, irregular sleep wake rhythm, nightmares, night terror, parasomnia, restless leg syndrome (RLS), nocturnal mycolonus/periodic limb movement disorder (PLMD), rapid eye movement (REM) sleep disorder, somnambulism/sleep walking, somniloquy/sleep talking, and somniphobia. For example, U.S. Pat. No. 8,003,669 discloses a class of ORL-1 agonists said to be therapeutic agents for circadian rhythm sleep disorder and Miyakawa et al. disclose that administration of the ORL-1 receptor agonist known as W-212393 induces phase advance of locomotor activity circadian rhythm in mice ("ORL1 receptor-mediated down-regulation of mPER2 in the suprachiasmatic nucleus accelerates re-entrainment of the circadian clock following a shift in the environmental light/dark cycle," *Neuropharmacol.* 52:1055-1064 (2007)).

Metabolic disorders can be caused by an abnormal metabolic process and can be acquired, e.g., failure of a metabolically important organ such as the liver or disease of an endocrine organ, or congenital, e.g., an inherited enzyme abnormality. A congenital metabolic disorder can be caused by a defect in a single gene; some of the more well-known inborn metabolic errors include sickle cell anemia, hypothyroidism, Tay-Sachs disease, phenylketonuria, and cystic fibrosis. The indole-type or indoline-type piperidine compounds can be used to treat or prevent a metabolic disorder including, but not limited to, anorexia nervosa, bulimia, and obesity. For example, U.S. Pat. No. 7,241,770 discloses a class of hydronopol derivative ORL-1 agonists said to be therapeutic agents for metabolic disorders.

A renal disorder may be acute or chronic. An acute renal disorder can be caused by impaired blood flow to the kidneys due to, e.g., blood loss, heart attack, or liver failure; kidney damage due to, e.g., blood clots, hemolytic uremic syndrome, or vasculitis; or urine blockage due to, e.g., bladder cancer, an enlarged prostate, or kidney stones. A chronic renal disorder can be caused by, e.g., diabetes mellitus, hypertension, or polycystic kidney disease. The indole-type or indoline-type piperidine compounds of the disclosure can be used to treat or prevent a renal disorder including, but not limited to, those renal disorders characterized by the syndrome of inappropriate antidiuretic hormone secretion (SIADH) or by imbalances of water retention and/or water excretion or salt excretion. For example, U.S. Pat. No. 6,869,960 discloses a class of spiropiperidine ORL-1 ligands said to be therapeutic agents for renal disorders.

Cardiovascular disorders represent the leading cause of death in the United States, responsible for about 27% of yearly deaths. Cardiovascular disorders can be caused by tobacco use, alcohol abuse, obesity, diabetes mellitus, high cholesterol, high blood pressure, and other factors. The indole-type or indoline-type piperidine compounds of the disclosure can be used to treat or prevent a cardiovascular disorder including, but not limited to, myocardial infarction, arrhythmias, bradycardia, hypertension, hypotension, thrombosis, anemia, arteriosclerosis, and angina pectoris. For example, U.S. Pat. No. 7,241,770 discloses a class of hydronopol derivative ORL-1 agonists said to be therapeutic agents for cardiovascular disorders.

According to the disclosure, some of the indole-type or indoline-type piperidine compounds are agonists at the ORL-1 receptor, some of the indole-type or indoline-type piperidine compounds are partial agonists at the ORL-1 receptor, and some of the indole-type or indoline-type piperidine compounds of the disclosure are antagonists at the ORL-1 receptor. In another embodiment, an indole-type or indoline-type piperidine compound of the disclosure is an agonists at the ORL-1 receptor and an agonist at a µ, κ and/or δ opioid receptor, particularly at a µ opioid receptor. In another embodiment, an indole-type or indoline-type piperidine compounds of the disclosure is a partial agonist at the ORL-1 receptor and an agonist at a μ, κ and/or δ opioid receptor, particularly at a μ opioid receptor. In another embodiment, an indole-type or indoline-type piperidine compounds of the disclosure is an antagonist at the ORL-1 receptor and an agonist at a μ, κ and/or δ opioid receptor, particularly at a μ opioid receptor. In another embodiment, a indole-type or indoline-type piperidine compounds of the disclosure is an agonist at the ORL-1 receptor and an antagonist at μ, κ and/or δ opioid receptor, particularly at μ opioid receptor. In another embodiment, an indole-type or indoline-type piperidine compound of the disclosure is a partial agonist at the ORL-1 receptor and an antagonist at μ, κ and/or δ opioid receptor, particularly at a μ opioid receptor. In another embodiment, an indole-type or indoline-type piperidine compound of the disclosure is an antagonist at the ORL-1 receptor and an antagonist at a μ, κ and/or δ opioid receptor, particularly at a opioid receptor.

The disclosure also provides methods for inhibiting ORL-1 receptor function in a cell, comprising contacting a cell capable of expressing the ORL-1 receptor with an amount of an indole-type or indoline-type piperidine compound of the disclosure effective to inhibit ORL-1 receptor function in the cell. This method can be adapted for use in vitro as part of an assay to select compounds that can be useful for treating or preventing a Condition in an animal. Alternatively, this method can be adapted for use in vivo, (i.e., in an animal such as a human) by contacting a cell in the animal with an effective amount of an indole-type or indoline-type piperidine compound of the disclosure. In one embodiment, the method is useful for treating or preventing pain in an animal in need of such treatment or prevention. In another embodiment, the method is useful for treating or preventing a memory disorder, obesity, constipation, depression, dementia, Parkinsonism, a sleep disorder, a metabolic disorder, a renal disorders, or a cardiovascular disorder (each being a "Condition") in an animal.

The present disclosure also relates to methods for activating ORL-1 receptor function in a cell, comprising contacting a cell capable of expressing the ORL-1 receptor with an amount of an indole-type or indoline-type piperidine compound of the disclosure effective to activate ORL-1 receptor function in the cell. This method can be adapted for use in vitro as part of an assay to select compounds useful for treating or preventing, pain, anxiety, cough, diarrhea, high blood pressure, epilepsy, anorexia/cachexia, urinary incontinence, or drug abuse. Alternatively, the method can be adapted for use in vivo (i.e., in an animal such as a human), by contacting a cell in the animal with an effective amount of an indole-type or indoline-type piperidine compound of the disclosure. In one embodiment, the method is useful for treating or preventing pain in an animal in need of such treatment or prevention. In another embodiment, the method is useful for treating or preventing anxiety, cough, diarrhea, high blood pressure, epilepsy, anorexia/chachexia, urinary incontinence, or drug abuse in an animal in need of such treatment or prevention.

Examples of tissue comprising cells capable of expressing the ORL-1 receptor include but are not limited to brain, spinal cord, vas deferens, and gastrointestinal tract tissue. Methods for assaying cells that express the ORL-1 receptor are known in the art; for example, see Shimohigashi et al., "Sensitivity of Opioid Receptor-like Receptor ORL1 for Chemical Modification on Nociceptin, a Naturally Occurring Nociceptive Peptide," *J. Biol. Chem.* 271(39):23642-23645 (1996); Narita et al., "Identification of the G-protein Coupled ORL1 Receptor in the Mouse Spinal Cord by [$^{35}$S]-GTPγS Binding and Immunohistochemistry," *Brit. J. Pharmacol.* 128:1300-1306 (1999); Milligan, "Principles: Extending the Utility of [$^{35}$S]GTPγS Binding Assays," *TIPS* 24(2):87-90 (2003); and Lazareno, "Measurement of Agonist-stimulated [$^{35}$S]GTPγS Binding to Cell Membranes," *Methods in Molecular Biology* 106:231-245 (1999).

4.5 Therapeutic/Prophylactic Administration and Compositions

Due to their activity, the indole-type or indoline-type piperidine compounds of the disclosure are advantageously useful in human and veterinary medicine. As described above, the indole-type or indoline-type piperidine compounds of the disclosure are useful for treating or preventing a Condition in an animal in need thereof. The indole-type or indoline-type piperidine compounds of the disclosure can be administered to any animal requiring modulation of the opioid and/or ORL-1 receptors.

When administered to an animal, the indole-type or indoline-type piperidine compounds of the disclosure can be administered as a component of a composition that comprises a pharmaceutically acceptable carrier or excipient. The compositions, which comprise an indole-type or indoline-type piperidine compounds of the disclosure, can be administered orally. An indole-type or indoline-type piperidine compound of the disclosure can also be administered by any other convenient route, for example, by infusion or bolus injection, by absorption through epithelial or mucocutaneous linings (e.g., oral, rectal, and intestinal mucosa, etc.) and can be administered together with a second therapeutically active agent. Administration can be systemic or local. Various delivery systems are known, e.g., encapsulation in liposomes, microparticles, microcapsules, multiparticulates, capsules, etc., and can be used to administer an indole-type or indoline-type piperidine compounds of the disclosure.

Methods of administration include, but are not limited to, intradermal, intramuscular, intraperitoneal, parenteral, intravenous, subcutaneous, intranasal, epidural, oral, sublingual, intracerebral, intravaginal, transdermal, transmucosal, rectal, by inhalation, or topical, particularly to the ears, nose, eyes, or skin. The method of administration is left to the discretion of the practitioner. In some instances, administration will result in the release of an indole-type or indoline-type piperidine compound of the disclosure into the bloodstream. In other instances, administration will result in only local release of an indole-type or indoline-type piperidine compound of the disclosure.

In specific embodiments, it can be desirable to administer an indole-type or indoline-type piperidine compounds of the disclosure locally. This can be achieved, for example and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce an indole-type or indoline-type piperidine compound of the disclosure into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, an indole-type or indoline-type piperidine compound of the disclosure can be formulated as a suppository, with traditional binders and excipients such as triglycerides.

When an indole-type or indoline-type piperidine compound of the disclosure is incorporated for parenteral administration by injection (e.g., continuous infusion or bolus injection), the formulation for parenteral administration can be in the form of a suspension, solution, emulsion in an oily or aqueous vehicle, and such formulations can further comprise pharmaceutically necessary additives such as one or more stabilizing agents, suspending agents, dispersing agents, and the like. An indole-type or indoline-type piperidine compound of the disclosure can also be in the form of a powder for reconstitution as an injectable formulation.

In another embodiment, an indole-type or indoline-type piperidine compound of the disclosure can be delivered in a vesicle, in particular a liposome (see Langer, "New Methods of Drug Delivery," Science 249:1527-1533 (1990); and Treat et al., "Liposome Encapsulated Doxorubicin Preliminary Results of Phase I and Phase II Trials," pp. 317-327 and 353-365 in Liposomes in the Therapy of Infectious Disease and Cancer (1989)).

In yet another embodiment, an indole-type or indoline-type piperidine compound of the disclosure can be delivered in a controlled-release system or sustained-release system (see, e.g., Goodson, "Dental Applications," in *Medical Applications of Controlled Release*, Vol. 2, *Applications and Evaluation, Langer and Wise*, eds., CRC Press, Chapter 6, pp. 115-138 (1984), hereafter "Goodson"). Other controlled- or sustained-release systems discussed in the review by Langer, Science 249:1527-1533 (1990) can be used. In one embodiment, a pump can be used (Langer, Science 249: 1527-1533 (1990); Sefton, "Implantable Pumps," in CRC Crit. Rev. Biomed. Eng. 14(3):201-240 (1987); Buchwald et al., "Long-term, Continuous Intravenous Heparin Administration by an Implantable Infusion Pump in Ambulatory Patients with Recurrent Venous Thrombosis," Surgery 88:507-516 (1980); and Saudek et al., "A Preliminary Trial of the Programmable Implantable Medication System for Insulin Delivery," New Engl. J. Med. 321:574-579 (1989)). In another embodiment, polymeric materials can be used (see Goodson; Smolen et al., "Drug Product Design and Performance," *Controlled Drug Bioavailability* Vol. 1, John Wiley & Sons, New York (1984); Langer et al., "Chemical and Physical Structure of Polymers as Carriers for Controlled Release of Bioactive Agents: A Review," *J. Macromol. Sci. Rev. Macromol. Chem.* C23(1):61-126 (1983); Levy et al., "Inhibition of Calcification of Bioprosthetic Heart Valves by Local Controlled-Release Diphosphonate," Science 228:190-192 (1985); During et al., "Controlled Release of Dopamine from a Polymeric Brain Implant: In Vivo Characterization," Ann. Neurol. 25:351-356 (1989); and Howard et al., "Intracerebral drug delivery in rats with lesion-induced memory deficits," J. Neurosurg. 71:105-112 (1989)). In yet another embodiment, a controlled- or sustained-release system can be placed in proximity of a target of an indole-type or indoline-type piperidine compound of the disclosure, e.g., the spinal column, brain, or gastrointestinal tract, thus requiring only a fraction of the systemic dose.

Pharmaceutical compositions of the disclosure can preferably further comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when an indole-type or indoline-type piperidine compound of the disclosure is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, EtOH, and the like. The compositions, if desired, can also contain minor amounts of wetting or emulsifying agents, or pH buffering agents. Specific examples of pharmaceutically acceptable carriers and excipients that can be used to formulate oral dosage forms are described in the *Handbook of Pharmaceutical Excipients*, (Amer. Pharmaceutical Ass'n, Washington, D.C., 1986), incorporated herein by reference.

Pharmaceutical compositions of the disclosure can take the form of solutions, suspensions, emulsions, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described by Radebough et al., "Preformulation," pp. 1447-1676 in *Remington's Pharmaceutical Sciences* Vol. 2 (Gennaro, ed., 19$^{th}$ Ed., Mack Publishing, Easton, Pa., 1995), incorporated herein by reference.

In one embodiment, the indole-type or indoline-type piperidine compounds of the disclosure are formulated in accordance with routine procedures as a composition adapted for oral administration to human beings. An indole-type or indoline-type piperidine compound of the disclosure to be orally delivered can be in the form of tablets, capsules, gelcaps, caplets, lozenges, aqueous or oily solutions, suspensions, granules, powders, emulsions, syrups, or elixirs, for example. When an indole-type or indoline-type piperidine compound of the disclosure is incorporated into oral tablets, such tablets can be compressed, tablet triturates, enteric-coated, sugar-coated, film-coated, multiply compressed, or multiply layered. Techniques and compositions for making solid oral dosage forms are described in *Pharmaceutical Dosage Forms: Tablets* (Lieberman et al., eds., 2$^{nd}$ Ed., Marcel Dekker, Inc., 1989 & 1990). Techniques and compositions for making tablets (compressed and molded), capsules (hard and soft gelatin) and pills are also described by King, "Tablets, Capsules, and Pills," pp. 1553-1593 in *Remington's Pharmaceutical Sciences* (Osol, ed., 16$^{th}$ Ed., Mack Publishing, Easton, Pa., 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in *Pharmaceutical Dosage Forms: Disperse Systems* (Lieberman et al., eds., 2$^{nd}$ Ed., Marcel Dekker, Inc., 1996&1998).

When an indole-type or indoline-type piperidine compound of the disclosure is to be injected parenterally, it can be, e.g., in the form of an isotonic sterile solution. Alternatively, when an indole-type or indoline-type piperidine compound of the disclosure is to be inhaled, it can be formulated into a dry aerosol or can be formulated into an aqueous or partially aqueous solution.

An orally administered indole-type or indoline-type piperidine compound of the disclosure can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, when in tablet or pill form, the compositions can be coated to delay disintegration and absorption in the gastrointestinal tract thereby providing a sustained action over an extended period of time. Selectively permeable membranes surrounding an osmotically active driving compounds are also suitable for orally administered compositions. In these latter platforms, fluid from the environment surrounding the capsule is imbibed by the driving compounds, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the indole-type or indoline-type piperidine compounds of the disclosure can be formulated for intravenous administration. In certain embodiments, compositions for intravenous administration comprise sterile isotonic aqueous buffer. Where necessary, the compositions can also include a solubilizing agent. An indole-type or indoline-type piperidine compound of the disclosure for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where an indole-type or indoline-type piperidine compound of the disclosure is to be administered by infusion, it can be dispensed, for example, with an infusion bottle containing sterile pharmaceutical grade water or saline. When an indole-type or indoline-type piperidine compound of the disclosure is administered by injection, an ampule of sterile water for injection or saline can be provided so that the ingredients can be mixed prior to administration.

An indole-type or indoline-type piperidine compound of the disclosure can be administered by controlled-release or sustained-release means or by delivery devices that are known to those in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide controlled- or sustained-release of one or more active ingredients using, for example, hydropropylmethyl cellulose, ethylcellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known to those in the art, including those described herein, can be readily selected for use with the active ingredients of the disclosure. The disclosure thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained-release counterparts. In one embodiment, a controlled- or sustained-release composition comprises a minimal amount of an indole-type or indoline-type piperidine compound of the disclosure to treat or prevent the Condition or a symptom thereof in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the indole-type or indoline-type piperidine compound of the disclosure, and can thus reduce the occurrence of adverse side effects.

Controlled- or sustained-release compositions can initially release an amount of an indole-type or indoline-type piperidine compound of the disclosure that promptly produces the desired therapeutic or prophylactic effect, and gradually and continually release other amounts of the indole-type or indoline-type piperidine compounds of the disclosure to maintain this level of therapeutic or prophylactic effect over an extended period of time. To maintain a constant level of the indole-type or indoline-type piperidine compounds of the disclosure in the body, the indole-type or indoline-type piperidine compounds of the disclosure can be released from the dosage form at a rate that will replace the amount of the indole-type or indoline-type piperidine compounds of the disclosure being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the indole-type or indoline-type piperidine compounds of the disclosure that is effective for the treatment or prevention of a Condition can be determined by standard clinical techniques. In addition, in vitro and/or in vivo assays can optionally be employed to help identify optimal dosage ranges. The precise dose to be employed will also depend on, e.g., the route of administration and the seriousness of the Condition, and can be decided according to the judgment of a practitioner and/or each animal's circumstances. In other examples thereof, variations will necessarily occur depending upon the weight and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts, however, range from about 0.01 mg/kg of body weight to about 3000 mg/kg of body weight of the animal per day, although they are, in certain embodiments, from about 0.01 mg/kg of body weight to about 2500 mg/kg of body weight of the animal per day or from about 0.01 mg/kg of body weight to about 1000 mg/kg of body weight of the animal per day. In another embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of an indole-type or indoline-type piperidine compound of the disclosure, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 hr until the Condition is abated. In another embodiment, an effective dosage amount is administered about every 12 hr until the Condition is abated. In another embodiment, an effective dosage amount is administered about every 8 hr until the Condition is abated. In another embodiment, an effective dosage amount is administered about every 6 hr until the Condition is abated. In another embodiment, an effective dosage amount is administered about every 4 hr until the Condition is abated. The effective dosage amounts described herein refer to total amounts administered; that is, if more than one indole-type or indoline-type piperidine compound of the disclosure is administered, the effective dosage amounts correspond to the total amount administered.

Where a cell capable of expressing the ORL-1 receptor, the µ-opioid receptor, the κ-opioid receptor and/or the δ-opioid receptor is contacted with an indole-type or indoline-type piperidine compound of the disclosure in vitro, the amount effective for inhibiting or activating that receptor function in a cell will, in certain embodiments, range from about $10^{-12}$ mol/L to about $10^{-4}$ mol/L, in one embodiment, from about $10^{-12}$ mol/L to about $10^{-5}$ mol/L, in another embodiment, from about $10^{-12}$ mol/L to about $10^{-6}$ mol/L, and in another embodiment, from about $10^{-12}$ mol/L to about $10^{-9}$ mol/L of a solution or suspension of a pharmaceutically acceptable carrier or excipient. In one embodiment, the volume of solution or suspension comprising the indole-type or indoline-type piperidine compounds of the disclosure will be from about 0.01 µL to about 1 mL. In another embodiment, the volume of solution or suspension will be about 200 µL.

An indole-type or indoline-type piperidine compound of the disclosure has a binding affinity ($K_i$) for the human ORL-1 receptor of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment. The binding affinity $K_i$ can be measured in ways known to the art, e.g., by an assay utilizing membranes from recombinant HEK-293 cells expressing the ORL-1 receptor.

In certain embodiments, an indole-type or indoline-type piperidine compound of the disclosure has a $K_i$ (nM) of about 300 or less for binding to ORL-1 receptors. In one embodiment, an indole-type or indoline-type piperidine compound of the disclosure has a $K_i$ (nM) of about 100 or less. In another embodiment, an indole-type or indoline-type piperidine compound of the disclosure has a $K_i$ (nM) of about 35 or less. In another embodiment, an indole-type or indoline-type piperidine compound of the disclosure has a $K_i$ (nM) of about 20 or less. In another embodiment, an indole-type or indoline-type piperidine compound of the disclosure has a $K_i$ (nM) of about 15 or less. In another embodiment, an indole-type or indoline-type piperidine compound of the disclosure has a $K_i$ (nM) of about 10 or less. In another embodiment, an indole-type or indoline-type piperidine compound of the disclosure has a $K_i$ (nM) of about 4 or less. In another embodiment, an indole-type or indoline-type piperidine compound of the disclosure has a $K_i$ (nM) of about 1 or less. In another embodiment, an indole-type or indoline-type piperidine compound of the disclosure has a $K_i$ (nM) of about 0.4 or less. In another embodiment, an indole-type or indoline-type piperidine compound of the disclosure has a $K_i$ (nM) of about 0.1 or less.

ORL-1 GTP $EC_{50}$ is the concentration of a compound providing 50% of the maximal response for the compound at an ORL-1 receptor. In one embodiment, an indole-type or indoline-type piperidine compound of the disclosure has an ORL-1 GTP $EC_{50}$ (nM) of about 5000 or less to stimulate ORL-1 receptor function, or about 1000 or less, or about 100 or less, or about 80 or less, or about 50 or less, or about 35 or less, or about 15 or less, or about 10 or less, or about 4 or less, or about 1 or less, or about 0.4 or less, or about 0.1 or less.

ORL-1 GTP Emax (%) is the maximal effect elicited by a compound relative to the effect elicited by nociceptin, a standard ORL-1 agonist. In certain embodiments, an indole-type or indoline-type piperidine compound of the disclosure acting as an agonist has an ORL-1 GTP Emax (%) of about 50% or greater, or about 75% or greater, or about 85% or greater, or about 95% or greater, or about 100% or greater. In certain embodiments, an indole-type or indoline-type piperidine compound of the disclosure acting as a partial agonist has an ORL-1 GTP Emax (%) of less than about 10%, or less than about 20%, or less than about 30%, or less than about 40%, or less than about 50%.

In certain embodiments, an indole-type or indoline-type piperidine compound of the disclosure has a binding affinity ($K_i$) for the human µ-opioid receptor of about 1000 nM or less, about 500 nM or less, about 100 nM or less, about 50 nM or less, or about 20 nM or less, or about 5 nM or less.

In certain embodiments, an indole-type or indoline-type piperidine compound of the disclosure has a $K_i$ (nM) for the human µ-opioid receptor of about 3000 or less for binding to a human µ-opioid receptor, or about 1000 or less, or about 650 or less, or about 525 or less, or about 250 or less, or about 100 or less, or about 10 or less, or about 1 or less. In one embodiment, an indole-type or indoline-type piperidine compound of the disclosure has substantially no activity.

µ GTP $EC_{50}$ is the concentration of a compound providing 50% of the maximal response for the compound at a human µ-opioid receptor. In certain embodiments, an indole-type or indoline-type piperidine compound of the disclosure has a µ GTP $EC_{50}$ (nM) of about 20,000 or less to stimulate human µ-opioid receptor function, or about 10,000 or less, or about 5000 or less, or about 4100 or less, or about 3100 or less, or about 2000 or less, or about 1000 or less, or about 100 or less, or about 10 or less, or about 1 or less, or about 0.4 or less.

µ GTP Emax (%) is the maximal effect elicited by a compound relative to the effect elicited by DAMGO, a standard µ agonist. In certain embodiments, an indole-type or indoline-type piperidine compound of the disclosure has a µ GTP Emax (%) of about 10% or greater, or about 20% or greater, or about 50% or greater, or about 65% or greater, or about 75% or greater, or about 88% or greater. In other embodiments, an indole-type or indoline-type piperidine compound of the disclosure has a GTP Emax (%) of about 10% or less, or about 5% or less, or about 2% or less.

In one embodiment, an indole-type or indoline-type piperidine compound of the disclosure has a $K_i$ (nM) of about 20,000 or less for binding to a human κ-opioid receptor. In another embodiment, an indole-type or indoline-type piperidine compound of the disclosure has substantially no activity. In certain embodiments, an indole-type or indoline-type piperidine compound of the disclosure that binds to the human κ-opioid receptor has a $K_i$ (nM) of about 10,000 or less, or about 5000 or less, or about 1000 or less, or about 500 or less, or about 300 or less, or about 100 or less, or about 50 or less, or about 20 or less, or about 15 or less.

κ GTP $EC_{50}$ is the concentration of a compound providing 50% of the maximal response for the compound at a human κ-opioid receptor. In certain embodiments, an indole-type or indoline-type piperidine compound of the disclosure has a κ GTP $EC_{50}$ (nM) of about 20,000 or less to stimulate human κ-opioid receptor function, or about 10,000 or less, or about 5000 or less, or about 2000 or less, or about 1500 or less, or about 800 or less, or about 500 or less, or about 300 or less, or about 100 or less, or about 50 or less, or about 25 or less.

κ GTP Emax (%) is the maximal effect elicited by a compound relative to the effect elicited by U69,593. In certain embodiments, an indole-type or indoline-type piperidine compound of the disclosure has a κ GTP Emax (%) of about 10% or greater, or about 15% or greater, or about 30% or greater, or about 40% or greater, or about 45% or greater, or about 75% or greater, or about 90% or greater. In other embodiments, an indole-type or indoline-type piperidine compound of the disclosure has a κ GTP Emax (%) of about 10% or less, or about 5% or less, or about 2% or less.

In one embodiment, an indole-type or indoline-type piperidine compound of the disclosure has a $K_i$ (nM) of about 20,000 or less for binding to a human δ-opioid receptor. In another embodiment, an indole-type or indoline-type piperidine compound of the disclosure has substantially no activity. In other embodiments, an indole-type or indoline-type piperidine compound of the disclosure that binds to the human δ-opioid receptor has a $K_i$ (nM) of about 10,000 or less, or about 9000 or less, or about 7500 or less, or about 6500 or less, or about 5000 or less, or about 3000 or less, or about 2500 or less, or about 1000 or less, or about 500 or less, or about 350 or less, or about 250 or less, or about 100 or less.

δ GTP $EC_{50}$ is the concentration of a compound providing 50% of the maximal response for the compound at a human δ-opioid receptor. In certain embodiments, an indole-type or indoline-type piperidine compound of the disclosure has a δ GTP $EC_{50}$ (nM) of about 20,000 or less to stimulate human δ-opioid receptor function, or about 10,000 or less, or about 1000 or less, or about 100 or less, or about 90 or less, or about 50 or less, or about 25 or less or less.

δ GTP Emax (%) is the maximal effect elicited by a compound relative to the effect elicited by met-enkephalin. In certain embodiments, an indole-type or indoline-type piperidine compound of the disclosure has a δ GTP Emax (%) of about 10% or greater, or about 30% or greater, or about 50% or greater, or about 75% or greater, or about 90% or greater, or about 100% or greater. In other embodiments, an indole-type or indoline-type piperidine compound of the disclosure has a δ GTP Emax (%) of about 10% or less, or about 5% or less, or about 2% or less.

The indole-type or indoline-type piperidine compounds of the disclosure can be assayed in vitro or in vivo for the desired therapeutic or prophylactic activity prior to use in humans. Animal model systems can be used to demonstrate safety and efficacy.

The methods for treating or preventing a Condition in an animal in need thereof can further comprise co-administering a second therapeutic agent to the animal being administered an indole-type or indoline-type piperidine compound of the disclosure (i.e., a first therapeutic agent). The second therapeutic agent is preferably administered in an effective amount.

It is well within the skilled artisan's purview to determine the second therapeutic agent's optimal effective-amount range. An indole-type or indoline-type piperidine compound of the disclosure and the second therapeutic agent combined can act either additively or synergistically to treat the same Condition, or they may act independently of each other such that the indole-type or indoline-type piperidine compound of the disclosure treats or prevents a first Condition and the second therapeutic agent treats or prevents a second condition, which may or may not be the same as the first Condition. In one embodiment, where a second therapeutic agent is administered to an animal for treatment of a Condition (e.g., pain), the minimal effective amount of the indole-type or indoline-type piperidine compound of the disclosure will be less than its minimal effective amount would be where the second therapeutic agent is not administered. In this embodiment, the indole-type or indoline-type piperidine compound of the disclosure and the second therapeutic agent can act synergistically to treat or prevent a Condition. In one embodiment, an indole-type or indoline-type piperidine compound of the disclosure is administered concurrently with a second therapeutic agent as a single composition comprising an effective amount of an indole-type or indoline-type piperidine compound of the disclosure and an effective amount of the second therapeutic agent. Alternatively, a composition comprising an effective amount of an indole-type or indoline-type piperidine compound of the disclosure and a second composition comprising an effective amount of the second therapeutic agent are concurrently administered. In another embodiment, an effective amount of an indole-type or indoline-type piperidine compound of the disclosure is administered prior or subsequent to administration of an effective amount of the second therapeutic agent. In this embodiment, the indole-type or indoline-type piperidine compound of the disclosure is administered while the second therapeutic agent exerts its therapeutic effect, or the second therapeutic agent is administered while the indole-type or indoline-type piperidine compound of the disclosure exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-II inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts or solvates thereof, or any mixture thereof.

In certain embodiments, the opioid agonist is codeine, hydromorphone, hydrocodone, oxycodone, dihydrocodeine, dihydromorphine, morphine, tramadol, oxymorphone, pharmaceutically acceptable salts or solvates thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroxprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable salt or solvate thereof, or any mixture thereof. Other suitable non-opioid analgesics include the following, non-limiting, chemical classes of analgesic, antipyretic, nonsteroidal anti-inflammatory drugs; salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable salt or solvate thereof; or any mixture thereof. For a more detailed description of the NSAIDs, see Insel, "Analgesic-Antipyretic and Anti-inflammatory Agents and Drugs Employed in the Treatment of Gout," pp. 617-657 in *Goodman & Gilman's The Pharmacological Basis of Therapeutics* (Goodman et al., eds., $9^{th}$ Ed., McGraw-Hill, New York 1996), and Hanson, "Analgesic, Antipyretic and Anti-Inflammatory Drugs," pp. 1196-1221 in *Remington: The Science and Practice of Pharmacy Vol. II* (Gennaro, ed., $19^{th}$ Ed., Mack Publishing, Easton, Pa., 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable salt or solvate thereof, or any mixture thereof.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable salt or solvate thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenyl-hydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabatrin, zonisamide, a pharmaceutically acceptable salt or solvate thereof, or any mixture thereof.

Examples of useful $Ca^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexiline, a pharmaceutically acceptable salt or solvate thereof, or any mixture thereof.

Examples of useful therapeutic agents for treating or preventing UI include, but are not limited to, propantheline, imipramine, hyoscyamine, oxybutynin, dicyclomine, a pharmaceutically acceptable salt or solvate thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable salt or solvate thereof; or any mixture thereof.

Examples of useful therapeutic agents for treating or preventing diarrhea include, but are not limited to, diphenoxylate, loperamide, a pharmaceutically acceptable salt or solvate thereof, or any mixture thereof.

Examples of useful therapeutic agents for treating or preventing epilepsy include, but are not limited to, carbamazepine, ethosuximide, gabapentin, lamotrigine, phenobarbital, phenytoin, primidone, valproic acid, trimethadione, benzodiazepines, γ vinyl GABA, acetazolamide, felbamate, a pharmaceutically acceptable salt or solvate thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable salt or solvate thereof, or any mixture thereof.

Examples of non-steroidal anti-inflammatory agents, 5-lipoxygenase inhibitors, anti-emetics, β-adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

A pharmaceutical composition of the disclosure may be prepared by admixing an indole-type or indoline-type piperidine compound of the disclosure or a pharmaceutically acceptable salt or solvate thereof with a pharmaceutically acceptable carrier or excipient. Admixing can be accomplished using known methods for admixing a compound and a pharmaceutically acceptable carrier or excipient. The indole-type or indoline-type piperidine compound of the disclosure is preferably present in the composition in an effective amount.

4.6 Kits

The disclosure further provides kits that can simplify the handling and administration of an indole-type or indoline-type piperidine compound of the disclosure to an animal.

A typical kit of the disclosure comprises a unit dosage form of an indole-type or indoline-type piperidine compound of the disclosure. In one embodiment, the unit dosage form comprises a first container, which can be sterile, containing an effective amount of an indole-type or indoline-type piperidine compound of the disclosure and a pharmaceutically acceptable carrier or excipient. The kit can further comprise a label or printed instructions instructing the use of the indole-type or indoline-type piperidine compound of the disclosure to treat or prevent a Condition. The kit can further comprise a unit dosage form of a second therapeutic agent, for example, a second container containing an effective amount of the second therapeutic agent and a pharmaceutically acceptable carrier or excipient. In another embodiment, the kit comprises a container containing an effective amount of an indole-type or indoline-type piperidine compound of the disclosure, an effective amount of a second therapeutic agent and a pharmaceutically acceptable carrier or excipient. Examples of second therapeutic agents include, but are not limited to, those listed above.

Kits of the disclosure can further comprise a device that is useful for administering the unit dosage forms. Examples of such a device include, but are not limited to, a syringe, a drip bag, a patch, an inhaler, and an enema bag.

5. EXAMPLES

The following Examples are set forth to assist in understanding the claimed invention and should not be construed as specifically limiting. Variations of the claimed invention that would be within the purview of those skilled in the art, including the substitution of equivalents now known or later developed, as well as changes in formulation or changes in experimental design, are considered to fall within the scope of the claimed invention.

Certain Examples below relate to the synthesis of illustrative indole-type or indoline-type piperidine compound of the disclosure.

Example 1: Synthesis of 2-(1-((1R,1'R,3R,3'R,5S,5'S)-[3,9'-bi(9'-azabicyclo[3.3.1]nonan)]-3'-yl)-1H-indol-3-yl)acetic acid (7)

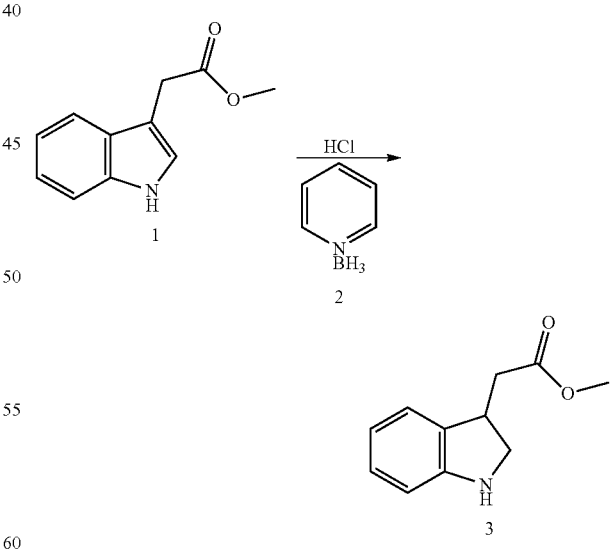

A suspension of methyl 2-(1H-indol-3-yl) acetate (1) (3 g, 15.86 mmol) in MeOH (50 ml) was cooled to 0° C. 12 N HCl (7.93 ml, 95 mmol) was added dropwise, keeping the reaction mixture below 25° C. After cooling to 0° C., borane-pyridine complex (2) (6.55 ml, 63.4 mmol) was added dropwise. The reaction mixture was stirred at room temperature for 1 hour. After cooling to 0° C., water (20 ml) was added slowly. The mixture was basified to pH 8.0 with 5N NaOH and then extracted with EtOAc. The organic layer was washed with saturated NaHCO₃, brine and dried over anhydrous Na₂SO₄, filtered and concentrated in vacuo. The crude methyl 2-(indolin-3-yl) acetate (3) was used to the next step.

5'S)-[3,9'-bi(9'-azabicyclo[3.3.1]nonan)]-3'-yl)-1H-indol-3-yl)acetate(6) came out at 30% (10% NH4 MeOH/DCM).

(5) MS: (m/e): 437.2 (M+1)

(6) MS: (m/e): 435.4 (M+1)

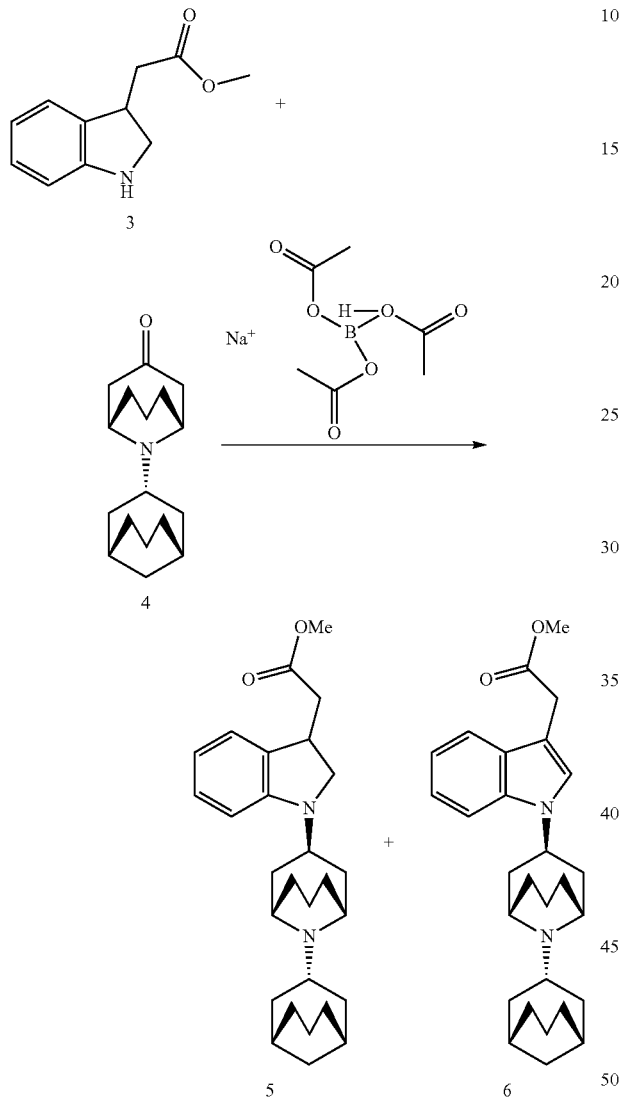

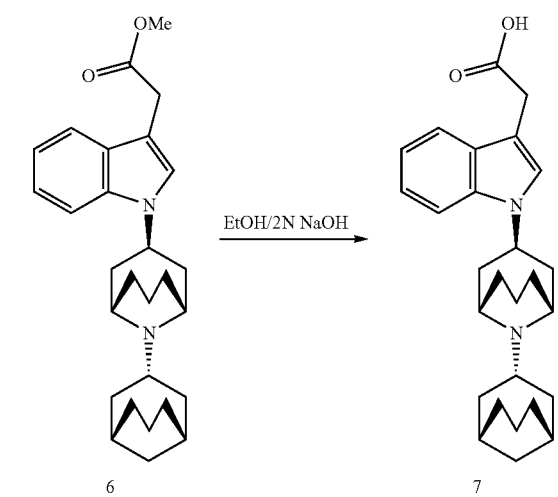 [SMILES: COC(=O)Cc1cn([C@H]2C[C@H]3CCC[C@@H](C2)N3[C@H]2C[C@@H]3CCC[C@@H](C3)C2)c2ccccc12 ; O=C(O)Cc1cn([C@H]2C[C@H]3CCC[C@@H](C2)N3[C@H]2C[C@@H]3CCC[C@@H](C3)C2)c2ccccc12]

Methyl 2-(1-((1R, 'R,3R,3'R,5 S,5'S)-[3,9'-bi(9'-azabicyclo[3.3.1]nonan)]-3'-yl)-1H-indol-3-yl)acetate (6) (150 mg, 0.345 mmol) was dissolved in EtOH (6 ml) and 2N NaOH (1.5 ml), and the reaction mixture was stirred at room temperature for 1 hour. The mixture was concentrated and the crude was dissolved with MeOH, and then subjected to PREP HPLC directly. The desired fraction was collected and freeze-dried to give 2-(1-((1R,1'R,3R,3'R,5S,5'S)-[3,9'-bi(9'-azabicyclo[3.3.1]nonan)]-3'-yl)-1H-indol-3-yl)acetic acid (7).

(7): ¹HNMR (CD3OD) δ 7:44-7:51 (d, J=10.52 Hz, 1H), 7:31-7:41 (t, J=8.33 Hz, 1H), 7:05-7:16 (t, J=7.89 Hz, 1H), 6:92-7:04 (m, 1H), 6:03-5:17 (br, 1H), 4:04-4:34 (br, 3H), 3:62-3:71 (br, 2H), 2:46-2:65 (br, 2H), 1:95-2:36 (br, 9H), 1:43-1:89 (br, 14H), ppm; MS: (m/e): 421.2 (M+1).

To a stirred solution of methyl 2-(indolin-3-yl)acetate (3) (3.2 g, 16.7 mmol) in HOAc (20 ml) was added (1R,1'R,3R,5S,5'3S)-9'-aza[3,9'-bi(bicyclo[3.3.1]nonan)]-3'-one (4) (4.8 g, 18.5 mmol) in one portion at room temperature. The reaction mixture stirred for 3 hours at room temperature and cooled to 0° C. and sodium triacetoxyborohydride was added at 0° C. The reaction mixture was stirred at room temperature for three days. The mixture was cooled and diluted with H₂O and basified to pH~11.0 using 5N NaOH, and then extracted with EtOAc. The organic layer washed with brine and dried over Na₂SO₄, filtered and concentrated in vacuo. The residue was purified by ISCO 5% to 30% MeOH/DCM. methyl 2-(1-((1R,1'R,3R,3'R,5S,5'S)-[3,9'-bi(9'-azabicyclo[3.3.1]nonan)]-3'-yl)indolin-3-yl)acetate (5) came out at 10% whereas methyl 2-(1-((1R,1'R,3R,3'R,5S, Example 2: Synthesis of 2-(1-((1R,1'R,3R,3'R,5S, 5'S)-[3,9'-bi(9'-azabicyclo[3.3.1]nonan)]-3'-yl)-1H-indol-3-yl)-2-oxoacetic acid (7)

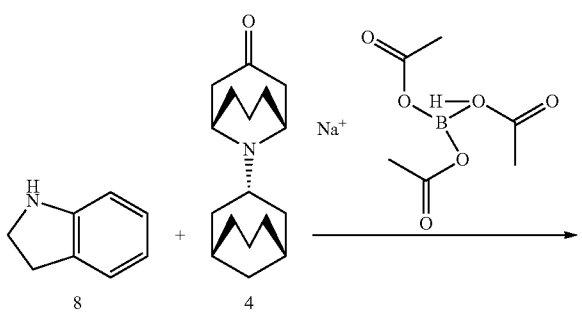

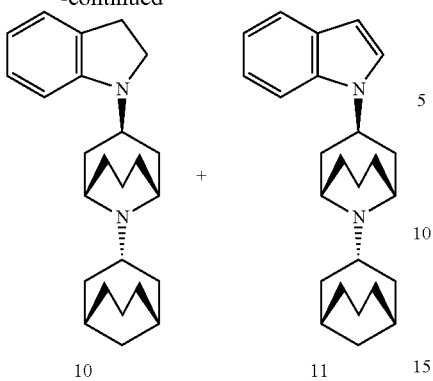

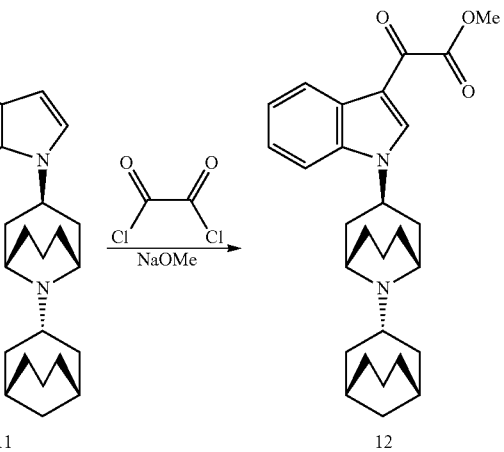

To a stirred solution of indoline (8) (2 g, 16.78 mmol) in HOAc (20 ml) was added (1R,1'R,3R,5S,5'S)-9'-aza[3,9'-bi(bicyclo[3.3.1]nonan)]-3'-one (4) (4.8 g, 18.5 mmol) in one portion at room temperature. The reaction mixture stirred for 3 hours at room temperature and cooled to 0° C. and sodium triacetoxyborohydride (5.34 g, 25.3 mmol) was added at 0° C. The reaction mixture was stirred at room temperature for three days. The mixture was cooled and diluted with H₂O and basified to pH 11.0 using 5N NaOH, and then extracted with EtOAc. The organic layer was washed with brine and dried over Na₂SO₄, filtered and concentrated in vacuo. The residue was purified by ISCO 5% to 30% MeOH/DCM. (1R,1'R,3R,3'R,5S,5'S)-3'-(indolin-1-yl)-9'-aza-3,9'-bi(bicyclo[3.3.1]nonane) (10) came out at 10% whereas (1R,1'R,3R,3'R,5S,5'S)-3'-(1H-indol-1-yl)-9'-aza-3,9'-bi(bicyclo[3.3.1]nonane) (11) came out at 30% (10% NH4 MeOH/DCM).

(10) MS: (m/e): 365.4 (M+1)

(11) MS: (m/e): 363.6 (M+1)

To a solution of (1R,1'R,3R,3'R,5S,5'S)-3'-(1H-indol-1-yl)-9'-aza-3,9'-bi(bicyclo[3.3.1]nonane) (11) (0.310 g, 0.855 mmol) in DCM (12 ml) was added oxalyl chloride (0.119 g, 0.941 mmol) with ice bath cooling and stir at ambient temperature for 3 hours. The solution was cooled at −70° C. and sodium methoxide (0.092 g, 1.710 mmol) was added slowly; the reaction mixture was stirred at ambient temperature for 1 hour and then evaporated in vacuo. The solid was extracted with chloroform and dried with Na₂SO₄ and evaporated in vacuo. The crude product was purified by ISCO 10% to 70% EtOAc/Hex to obtain methyl 2-(1-((1R,1'R,3R,3'R,5S,5'S)-[3,9'-bi(9'-azabicyclo[3.3.1]nonan)]-3'-yl)-1H-indol-3-yl)-2-oxoacetate (12).

(12) MS: (m/e): 449.4 (M+1)

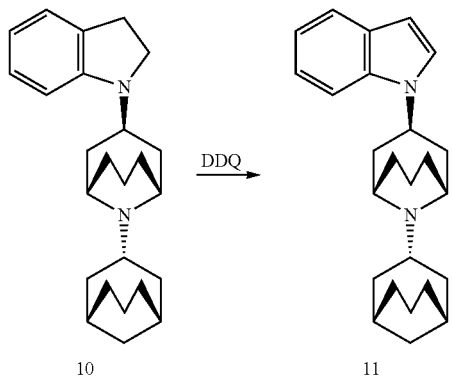

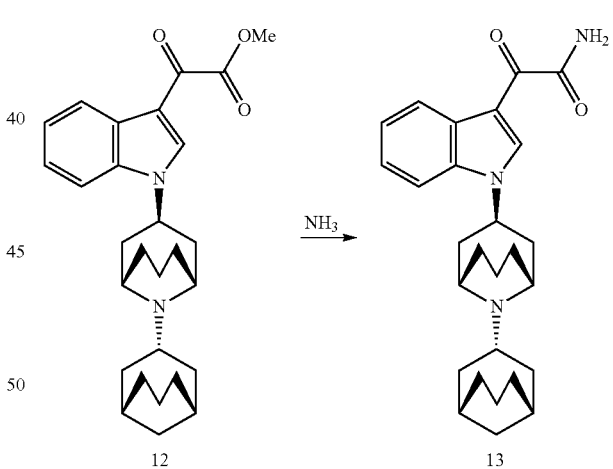

To a solution of (1R,1'R,3R,3'R,5S,5'S)-3'-(indolin-1-yl)-9'-aza-3,9'-bi(bicyclo[3.3.1]nonane) (10) (400 mg, 1.097 mmol) in dry chlorobenzene (30 ml) was added DDQ (747 mg, 3.29 mmol) and then the mixture was refluxed for 2 hours under stirring. The reaction mixture was evaporated in vacuo and the residue was subjected to ISCO for purification using EtOAc/Hex and 5 to 30% MeOH/DCM to give 1R,1'R,3R,3'R,5S,5'S)-3'-(1H-indol-1-yl)-9'-aza-3,9'-bi(bicyclo[3.3.1]nonane) (11)

A solution of methyl 2-(1-((1R,1'R,3r,3'R,5S,5'S)-[3,9'-bi(9'-azabicyclo[3.3.1]nonan)]-3'-yl)-1H-indol-3-yl)-2-oxoacetate (12) (45 mg, 0.100 mmol) in 7N ammonia methanol was stirred at 70° C. for two hours. The reaction mixture was concentrated in vacuo and the crude was dissolved in MeOH and subjected to PREP HPLC. The desired fraction was collected and dried in a freeze drier to give 2-(1-((1R,1'R,3R,3'R,5S,5'S)-[3,9'-bi(9'-azabicyclo[3.3.1]nonan)]-3'-yl)-1H-indol-3-yl)-2-oxoacetamide (13).

(13): ¹HNMR (CD3OD) δ 8:79-8:90 (br, 1H), 8:13-8:33 (d, J=9.21 Hz, 1H), 7:47-7:60 (d, J=8.11 Hz, 1H), 7:12-7:34 (m, 2H), 5:105:32 (br, 1H), 4:04-4:38 (br, 3H), 2:57-2:78

(br, 2H), 2:19-2:35 (br, 3H), 1:96-2:19 (br, 7H), 1:45-1:91 (br, 13H), ppm; MS: (m/e): 434.2 (M+1).

Example 3: Synthesis of 2-(1-((1R,1'R,3R,3'R,5S,5'S)-[3,9'-bi(9'-azabicyclo[3.3.1]nonan)]-3'-yl)-1H-indol-3-yl)-2-oxoacetamide (14)

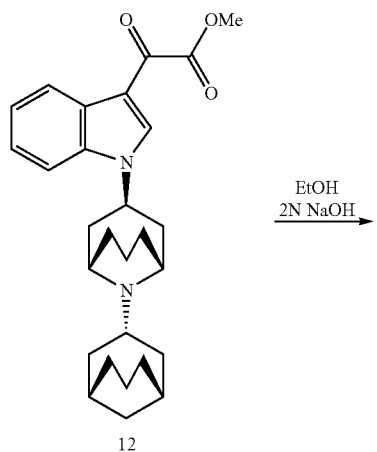

12

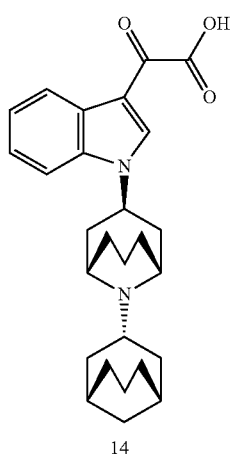

14

Methyl 2-(1-((1R,1'R,3R,3'R,5 S,5'S)-[3,9'-bi(9'-azabicyclo[3.3.1]nonan)]-3'-yl)-1H-indol-3-yl)-2-oxoacetate (12) (160 mg, 0.357 mmol) was dissolved in EtOH (6 ml) and 2N NaOH (1.5 ml), and the reaction mixture was stirred at room temperature for 1 hour. The mixture was concentrated and the crude was dissolved with MeOH, and then subjected to PREP HPLC directly. The desired fraction was collected and dried on freeze drier to yield the desire product of 2-(1-((1R,1'R,3R,3'R,5S,5'S)-[3,9'-bi(9'-azabicyclo[3.3.1]nonan)]-3'-yl)-1H-indol-3-yl)-2-oxoacetic acid (14).

(14): $^1$HNMR (CD3OD) δ 8:57-8:68 (br, 1H), 8:15-8:28 (d, J=9.43 Hz, 1H), 7:48-7:63 (d, J=8.33 Hz, 1H), 7:17-7:36 (m, 2H), 5:05-5:29 (br, 1H), 4:10-4:38 (br, 3H), 2:59-2:78 (br, 2H), 2:24-2:39 (br, 3H), 2:02-2:20 (br, 6H), 1:41-1:88 (br, 13H), ppm; MS: (m/e): 435.3 (M+1).

Example 4: Synthesis: 2-(1-((1R,3r,5S)-9-cyclodecyl-9-azabicyclo[3.3.1]nonan-3-yl)-1H-indol-3-yl)-2-oxoacetic acid (19)

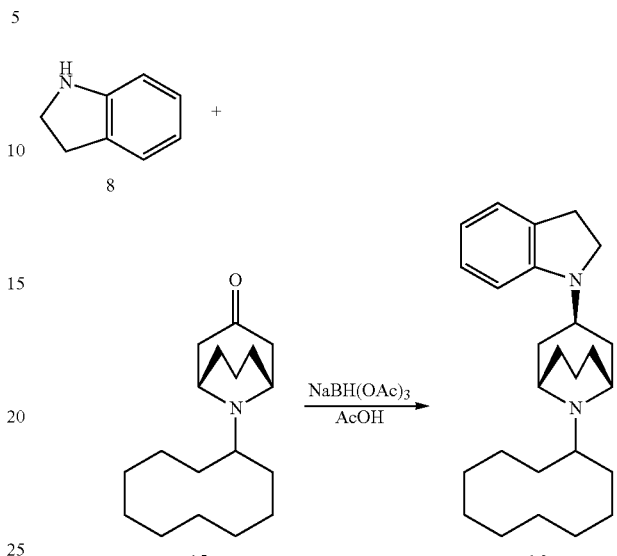

Indoline (8) (1.0 eq) (1.55 g, 12.59 mmol) was stirred as solution in AcOH at room temperature under nitrogen; an exotherm was observed. After cooling to room temperature, (1R,5S)-9-cyclodecyl-9-azabicyclo[3.3.1]nonan-3-one (15) (1.1 eq) (3.84 g, 13.85 mmol) was added in one portion. Next, NaBH(OAc)$_3$ (1.5 eq) (4.0 g, 18.9 mmol) was added at room temperature in portions over 10-15 minutes. The reaction mixture was stirred overnight at room temperature. The reaction was diluted with DI H$_2$O and EtOAc. 5N NaOH was added dropwise to adjust the pH to 10-11, keeping the reaction mixture in ice water. The layers were separated and the aqueous layer was extracted. The combined organic layer was extracted with NaCl and dried with (MgSO$_4$)$_2$. The filtrate was concentrated and purified by column using 5% to 40% EtOAc/Hex then 5% MeOH/DCM to get the desire intermediate 1-((1R,3r,5S)-9-cyclodecyl-9-azabicyclo[3.3.1]nonan-3-yl)indoline (16).

(16) MS: (m/e): 381.4 (M+1)

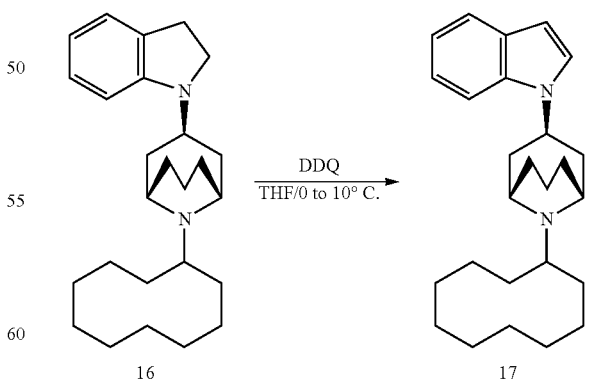

A solution of the 1-((1R,3r,5S)-9-cyclodecyl-9-azabicyclo[3.3.1]nonan-3-yl)indoline (16) (410 mg, 1.077 mmol) in THF was stirred at 0-5° C. under nitrogen A solution of DDQ (269 mg, 1.19 mmol) in THF was added dropwise to the reaction, keeping the temperature below 10° C. The dark thick solution was allowed to warm to room temperature and stirred for about two days. To the mixture EtOAc and water were added, then 5N NaOH was added drop wise addition until the pH of the solution was 10-11. The organic solvent was extracted and dried with (MgSO4)2. The filtrate was evaporated and crude 1-((1R,3r,5S)-9-cyclodecyl-9-azabicyclo[3.3.1]nonan-3-yl)-1H-indole (17) was taken to the next step.

(17) MS: (m/e): 379.2 (M+1)

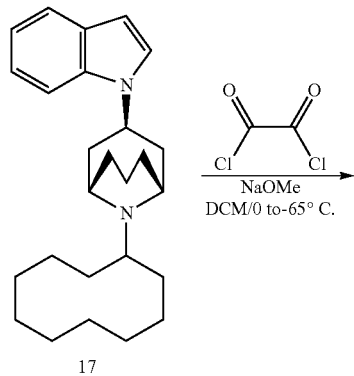

To a solution of 1-((1R,3r,5S)-9-cyclodecyl-9-azabicyclo[3.3.1]nonan-3-yl)-1H-indole (17) (0.3 g, 0.79 mmol) in dichlormethane, oxalyl chloride (0.11 g, 0.87 mmol) was added at 0° C. and stirred at ambient temperature for 1 hour and cooled at −65° C. Next, sodium methoxide (0.09 g 1.59 mmol) was added slowly and the reaction was stirred at room temperature overnight. The organic solvent was evaporated and purified and crude was purified by column using 10% to 40% EtOAc/Hex, then 5% MeOH/DCM to get desired intermediate methyl 2-(1-((1R,3r,5S)-9-cyclodecyl-9-azabicyclo[3.3.1]nonan-3-yl)-1H-indol-3-yl)-2-oxoacetate (18).

(18) MS: (m/e): 465.2 (M+1)

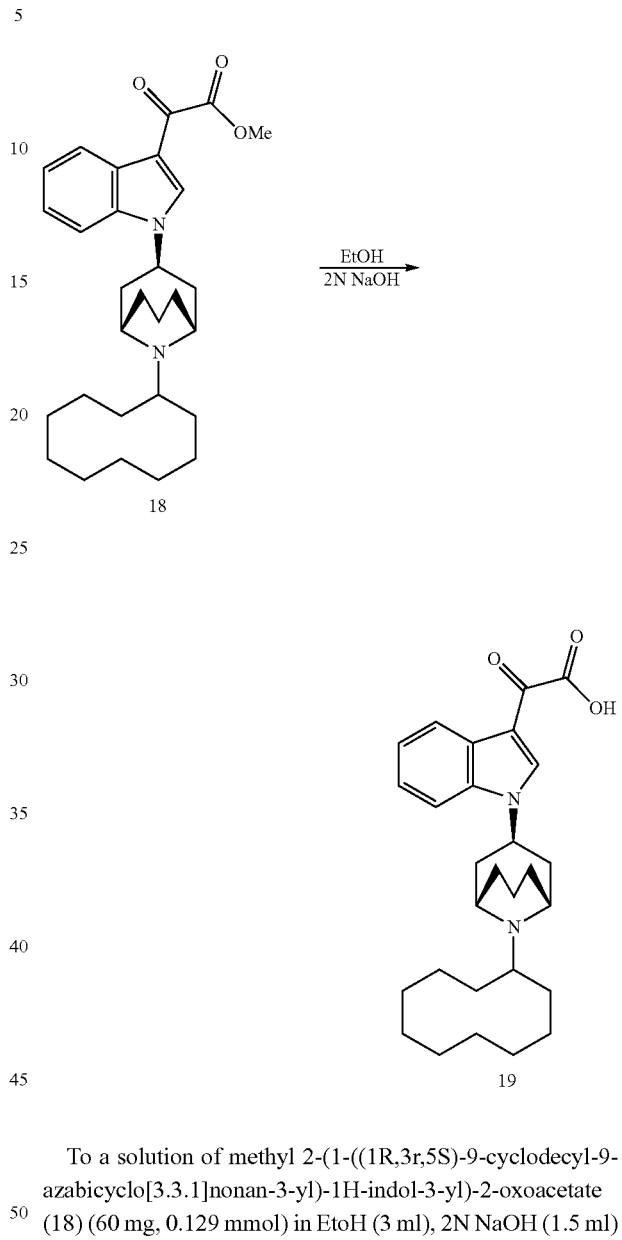

To a solution of methyl 2-(1-((1R,3r,5S)-9-cyclodecyl-9-azabicyclo[3.3.1]nonan-3-yl)-1H-indol-3-yl)-2-oxoacetate (18) (60 mg, 0.129 mmol) in EtoH (3 ml), 2N NaOH (1.5 ml) was added and the reaction mixture was allowed to stir for 1 hour at room temperature. Product formation was observed by LC/MS. The mixture was concentrated and the crude was dissolved in DCM/MeOH (1:1), and then taken to prep HPLC for purification to separate the desired product 2-(1-((1R,3r,5S)-9-cyclodecyl-9-azabicyclo[3.3.1]nonan-3-yl)-1H-indol-3-yl)-2-oxoacetic acid (19).

(19): $^1$HNMR (CD3OD) δ: 8:44-8:66 (br, 1H), 8:08-8:34 (d, J=9.21 Hz, 1H), 7:43:7-:73 (br, 1H), 7:00-7:38 (m, 2H), 5:06-5:43 (br, 1H), 4:06-4:441 (br, 2H), 3:76-3:97 (br, 1H), 2:50-2:92 (br, 2H), 2:17-2:-37 (br, 3H), 1:99-2:18 (br, 2H), 1:82-2:00 (br, 4H), 1:69-1:83 (br, 3H), 1:25-1:68 (br, 14H), ppm; MS: (m/e): 453.3 (M+1).

Example 5: Synthesis of 2-(1-((1R,3r,5S)-9-cyclodecyl-9-azabicyclo[3.3.1]nonan-3-yl)-1H-indol-3-yl)acetic acid (23)

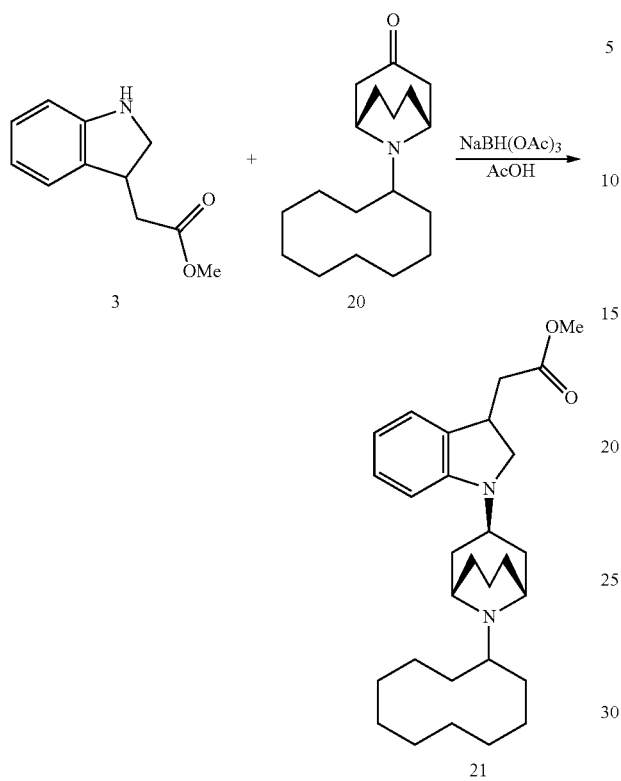

To a stirred solution of (1R,5S)-9-cyclodecyl-9-azabicyclo[3.3.1]nonan-3-one (20) (3.0 g, 10.81 mmol) in THF (150 ml) was added methyl 2-(indolin-3-yl)acetate (3) (2.3 g, 11.89 mmol) in one portion at room temperature. The reaction mixture stirred for 3 hours at room temperature and sodium triacetoxyborohydride (6.88 g, 32.4 mmol) was added at 0° C. The reaction mixture was stirred at room temperature for three days. The mixture was cooled and diluted with H$_2$O and basified to pH 11.0 using 5N NaOH, and then extracted with EtOAc. The organic layer was washed with brine and dried over Na$_2$SO$_4$, filtered and concentrated in vacuo. The residue was purified by ISCO 5% to 30% MeOH/DCM to obtain the desired intermediate methyl 2-(1-((1R,3r,5S)-9-cyclodecyl-9-azabicyclo[3.3.1]nonan-3-yl)indolin-3-yl)acetate (21).

(21) MS: (m/e): 452.4 (M+1)

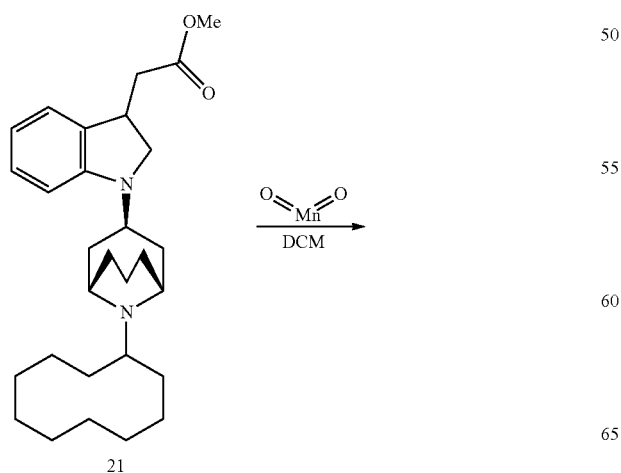

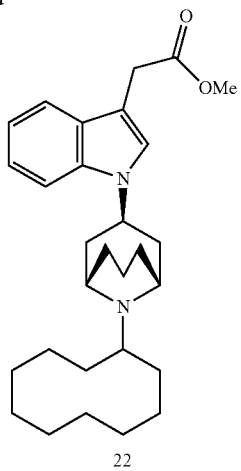

To a solution of methyl 2-(1-((1R,3r,5S)-9-cyclodecyl-9-azabicyclo[3.3.1]nonan-3-yl)indolin-3-yl)acetate (21) (500 mg, 1.1 mmol) in dichloromethane (50 ml) was added MnO$_2$ (960 mg, 11.0 mmol). The reaction mixture was stirred in a sealed vial overnight at 75° C. The material was filtered through celite and evaporated. The crude intermediate methyl 2-(1-((1R,3r,5S)-9-cyclodecyl-9-azabicyclo[3.3.1]nonan-3-yl)-1H-indol-3-yl)acetate (22) was taken to the next step.

(22) MS: (m/e): 451.4 (M+1)

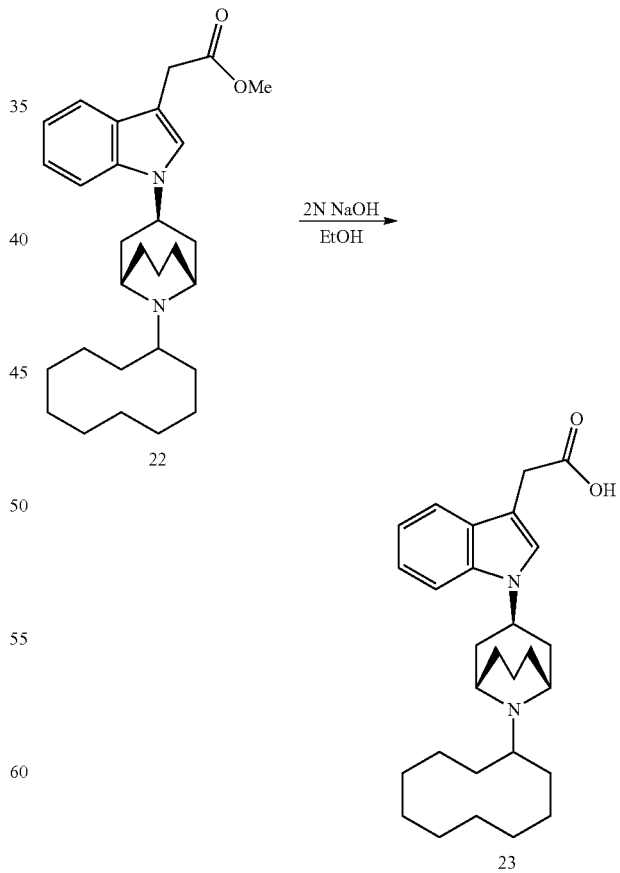

To a solution of methyl 2-(1-((1R,3r,5S)-9-cyclodecyl-9-azabicyclo[3.3.1]nonan-3-yl)-1H-indol-3-yl)acetate (22)

(100 mg, 0.2 mmol) in EtOH (3 ml), 2N NaOH (1.5 ml) was added and the reaction mixture was allowed to stir for 1 hour at room temperature. Product formation was observed by LC/MS. The mixture was concentrated and the crude was dissolved in DCM/MeOH (1:1), and then taken to prep HPLC for purification, to provide 2-(1-((1R,3r,5S)-9-cyclodecyl-9-azabicyclo[3.3.1]nonan-3-yl)-1H-indol-3-yl)acetic acid (23).

(23): $^1$HNMR (CD3OD) δ: 7:42-7:52 (br, 1H), 7:30-7:39 (d, J=9.21 Hz, 2H), 7:05-7:16 (t, J=9.21 Hz, 1H), 6:87-7:05 (t, J=9.21 Hz, 1H), 4:95-5:25 (br, 1H), 4:03-4:19 (br, 2H), 3:77-3:90 (br, 1H), 3:57-3:70 (br, 2H), 2:47-2:77 (br, 2H), 1:12-2:33 (br, 26H), ppm; MS: (m/e): 437.3 (M+1).

Example 6: In vitro ORL-1 Receptor Binding Assay

ORL-1 Receptor Binding Assay Procedures: Membranes from recombinant HEK-293 cells expressing the human opioid receptor-like receptor (ORL-1) (Receptor Biology) were prepared by lysing cells in ice-cold hypotonic buffer (2.5 mM MgCl$_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets resuspended in hypotonic buffer to a final concentration 1-3 mg/mL. Protein concentrations were determined using the BioRad protein assay reagent with bovine serum albumen as a standard. Aliquots of the ORL-1 receptor membranes were stored at −80° C.

Radioligand binding assays (screening and dose-displacement) used 0.1 nM [$^3$H]-nociceptin (NEN; 87.7 Ci/mmole) with 10-20 μg membrane protein in a final volume of 500 μL binding buffer (10 mM MgCl$_2$, 1 mM EDTA, 5% DMSO, 50 mM HEPES, pH 7.4). Non-specific binding was determined in the presence of 10 nM unlabeled nociceptin (American Peptide Company). All reactions were performed in 96-deep well polypropylene plates for 1 h at about 25° C. Binding reactions were terminated by rapid filtration onto 96-well Unifilter GF/C filter plates (Packard) presoaked in 0.5% polyethylenimine (Sigma-Aldrich). Harvesting was performed using a 96-well tissue harvester (Packard) followed by three filtration washes with 500 μL ice-cold binding buffer. Filter plates were subsequently dried at 50° C. for 2-3 hours. Fifty μL/well scintillation cocktail (BetaScint; Wallac) was added and plates were counted in a Packard Top-Count for 1 min/well. The data from screening and dose-displacement experiments were analyzed using Microsoft Excel and the curve fitting functions in GraphPad PRISM™, v. 3.0, respectively, or an in-house function for one-site competition curve-fitting.

ORL-1 Receptor Binding Data: An indole-type or indoline-type piperidine compound of the disclosure has a binding affinity (K$_i$) for the human ORL-1 receptor of about 1000 nM or less in one embodiment, or about 500 nM or less in another embodiment. In certain embodiments, an indole-type or indoline-type piperidine compound of the disclosure has a K$_i$ (nM) of about 300 or less for binding to ORL-1 receptors. In one embodiment, an indole-type or indoline-type piperidine compound of the disclosure has a K$_i$ (nM) of about 100 or less. In another embodiment, an indole-type or indoline-type piperidine compound of the disclosure of the disclosure has a K$_i$ (nM) of about 35 or less. In another embodiment, an indole-type or indoline-type piperidine compound of the disclosure of the disclosure has a K$_i$ (nM) of about 20 or less. In another embodiment, an indole-type or indoline-type piperidine compound of the disclosure of the disclosure has a K$_i$ (nM) of about 15 or less. In another embodiment, an indole-type or indoline-type piperidine compound of the disclosure of the disclosure has a K$_i$ (nM) of about 10 or less. In another embodiment, an indole-type or indoline-type piperidine compound of the disclosure of the disclosure has a K$_i$ (nM) of about 4 or less. In another embodiment, an indole-type or indoline-type piperidine compound of the disclosure of the disclosure has a K$_i$ (nM) of about 1 or less. In another embodiment, an indole-type or indoline-type piperidine compound of the disclosure of the disclosure has a K$_i$ (nM) of about 0.4 or less. In another embodiment, an indole-type or indoline-type piperidine compound of the disclosure of the disclosure has a K$_i$ (nM) of about 0.1 or less.

Example 7: In Vitro ORL-1 Receptor Functional Assay

ORL-1 Receptor [$^{35}$S]GTPγS Binding Assay Procedures: Membranes from recombinant HEK-293 cells expressing the human opioid receptor-like (ORL-1) (Receptor Biology) were prepared by lysing cells in ice-cold hypotonic buffer (2.5 mM MgCl$_2$, 50 mM HEPES, pH 7.4) (10 mL/10 cm dish) followed by homogenization with a tissue grinder/Teflon pestle. Membranes were collected by centrifugation at 30,000×g for 15 min at 4° C., and pellets resuspended in hypotonic buffer to a final concentration of 1-3 mg/mL. Protein concentrations were determined using the BioRad protein assay reagent with bovine serum albumen as a standard. Aliquots of the ORL-1 receptor membranes were stored at −80° C.

Functional binding assays were conducted as follows. ORL-1 membrane solution was prepared by sequentially adding final concentrations of 0.066 μg/μL ORL-1 membrane protein, 10 g/mL saponin, 3 μM GDP and 0.20 nM [35S]GTPγS to binding buffer (100 mM NaCl, 10 mM MgCl$_2$, 20 mM HEPES, pH 7.4) on ice. The prepared membrane solution (190 μL/well) was transferred to 96-shallow well polypropylene plates containing 10 μL of 20× concentrated stock solutions of agonist/nociceptin prepared in DMSO. Plates were incubated for 30 min at about 25° C. with shaking. Reactions were terminated by rapid filtration onto 96-well Unifilter GF/B filter plates (Packard) using a 96-well tissue harvester (Packard) and followed by three filtration washes with 200 μL ice-cold binding buffer (10 mM NaH$_2$PO$_4$, 10 mM Na$_2$HPO$_4$, pH 7.4). Filter plates were subsequently dried at 50° C. for 2-3 hours. Fifty μL/well scintillation cocktail (BetaScint; Wallac) was added and plates were counted in Packard Top-Count for 1 min/well. Data are analyzed using the sigmoidal dose-response curve fitting functions in GraphPad PRISM v. 3.0, or an in-house function for non-linear, sigmoidal dose-response curve-fitting.

ORL-1 Receptor Functional Data: ORL-1 GTP EC$_{50}$ is the concentration of a compound providing 50% of the maximal response for the compound at an ORL-1 receptor. In one embodiment, an indole-type or indoline-type piperidine compound of the disclosure has an ORL-1 GTP EC$_{50}$ (nM) of about 5000 or less to stimulate ORL-1 receptor function. In another embodiment, an indole-type or indoline-type piperidine compound of the disclosure has an ORL-1 GTP EC$_{50}$ (nM) of about 1000 or less. In another embodiment, an indole-type or indoline-type piperidine compound of the disclosure has an ORL-1 GTP EC$_{50}$ (nM) of about 100 or less. In another embodiment, an indole-type or indoline-type piperidine compound of the disclosure has an ORL-1 GTP EC$_{50}$ (nM) of about 80 or less. In another embodiment, an indole-type or indoline-type piperidine compound of the disclosure has an ORL-1 GTP $EC_{50}$ (nM) of about 50 or less. In another embodiment, an indole-type or indoline-type piperidine compound of the disclosure has an ORL-1 GTP $EC_{50}$ (nM) of about 35 or less. In another embodiment, an indole-type or indoline-type piperidine compound of the disclosure has an ORL-1 GTP $EC_{50}$ (nM) of about 15 or less. In another embodiment, an indole-type or indoline-type piperidine compound of the disclosure has an ORL-1 GTP $EC_{50}$ (nM) of about 10 or less. In another embodiment, an indole-type or indoline-type piperidine compound of the disclosure has an ORL-1 GTP $EC_{50}$ (nM) of about 4 or less. In another embodiment, an indole-type or indoline-type piperidine compound of the disclosure has an ORL-1 GTP $EC_{50}$ (nM) of about 1 or less. In another embodiment, an indole-type or indoline-type piperidine compound of the disclosure has an ORL-1 GTP $EC_{50}$ (nM) of about 0.4 or less. In another embodiment, an indole-type or indoline-type piperidine compound of the disclosure has an ORL-1 GTP $EC_{50}$ (nM) of about 0.1 or less.

ORL-1 GTP Emax (%) is the maximal effect elicited by a compound relative to the effect elicited by nociceptin, a standard ORL-1 agonist. In one embodiment, an indole-type or indoline-type piperidine compound of the disclosure has an ORL-1 GTP Emax (%) of about 50% or greater. In another embodiment, an indole-type or indoline-type piperidine compound of the disclosure has an ORL-1 GTP Emax (%) of about 75% or greater. In another embodiment, an indole-type or indoline-type piperidine compound of the disclosure has an ORL-1 GTP Emax (%) of about 85% or greater. In another embodiment, an indole-type or indoline-type piperidine compound of the disclosure has an ORL-1 GTP Emax (%) of about 95% or greater. In another embodiment, an indole-type or indoline-type piperidine compound of the disclosure has an ORL-1 GTP Emax (%) of about 100% or greater. In another embodiment, an indole-type or indoline-type piperidine compound of the disclosure has an ORL-1 GTP Emax (%) of about 110% or greater. In certain embodiments, an indole-type or indoline-type piperidine compound of the disclosure acting as a partial agonist has an ORL-1 GTP Emax (%) of less than about 10%. In one embodiment, partial agonist indole-type or indoline-type piperidine compound of the disclosure has an ORL-1 GTP Emax (%) of less than about 20%. In another embodiment, partial agonist Indole-type or indoline-type piperidine compound of the disclosure has an ORL-1 GTP Emax (%) of less than about 30%. In another embodiment, partial agonist Indole-type or indoline-type piperidine compound of the disclosure has an ORL-1 GTP Emax (%) of less than about 40%. In another embodiment, partial agonist indole-type or indoline-type piperidine compound of the disclosure has an ORL-1 GTP Emax (%) of less than about 50%. In some embodiments, an indole-type or indoline-type piperidine compound of the disclosure acting as an antagonist has an ORL-1 GTP Emax (%) of less than about 5%, for example, less than about 2%, such as around 1%.

Example 8: In Vitro Mu-Opioid Receptor Binding Assays

μ-Opioid Receptor Binding Assay Procedures: Radioligand binding assays are conducted using freshly thawed membranes expressing human μ-receptors (Perkin Elmer, Shelton, Conn.). Radioligand dose-displacement binding assays for human μ-opioid receptors use 0.2 nM[$^3$H]-diprenorphine (NEN, Boston, Mass.), with 5-20 mg membrane protein/well in a final volume of 500 μL binding buffer (10 mM $MgCl_2$, 1 mM EDTA, 5% DMSO, 50 mM HEPES, pH 7.4). Reactions are carried out in the absence or presence of increasing concentrations of unlabeled naloxone. All reactions are conducted in 96-deep well polypropylene plates for 1-2 hr at about 25° C. Binding reactions are terminated by rapid filtration onto 96-well Unifilter GF/C filter plates (Packard, Meriden, Conn.) presoaked in 0.5% polyethylenimine using a 96-well tissue harvester (Brandel, Gaithersburg, Md.) followed by performing three filtration washes with 500 μL of ice-cold binding buffer. Filter plates are subsequently dried at 50° C. for 2-3 hours. BetaScint scintillation cocktail (Wallac, Turku, Finland) is added (50 μL/well), and plates are counted using a Packard Top-Count for 1 min/well. The data are analyzed using the one-site competition curve fitting functions in GraphPad PRISM v. 3.0 (San Diego, Calif.), or an in-house function for one-site competition curve-fitting.

μ-Opioid Receptor Binding Data: In certain embodiments, an indole-type or indoline-type piperidine compound of the disclosure has a $K_i$ (nM) of about 3000 or less for binding to μ-opioid receptors, or about 1000 or less, or about 650 or less, or about 525 or less, or about 250 or less, or about 100 or less, or about 10 or less, or about 1 or less, or about 0.1 or less.

Example 9: In Vitro Mu-Opioid Receptor Functional Assays

μ-Opioid Receptor Functional Assay Procedures: [$^{35}$S] GTPγS functional assays are conducted using freshly thawed membranes expressing human μ-receptors. Assay reactions are prepared by sequentially adding the following reagents to binding buffer (100 mM NaCl, 10 mM $MgCl_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; NEN). The prepared membrane solution (190 μL/well) is transferred to 96-shallow well polypropylene plates containing 10 μL of 20× concentrated stock solutions of the agonist DAMGO ([D-Ala2, N-methyl-Phe4 Gly-ol5]-enkephalin) prepared in DMSO. Plates are incubated for 30 min at about 25° C. with shaking. Reactions are terminated by rapid filtration onto 96-well Unifilter GF/B filter plates (Packard, Meriden, Conn.) using a 96-well tissue harvester (Brandel, Gaithersburg, Md.) followed by three filtration washes with 2001 μL of ice-cold wash buffer (10 mM $NaH_2PO_4$, 10 mM $Na_2HPO_4$, pH 7.4). Filter plates are subsequently dried at 50° C. for 2-3 hr. BetaScint scintillation cocktail (Wallac, Turku, Finland) is added (50 L/well) and plates are counted using a Packard Top-Count for 1 min/well. Data are analyzed using the sigmoidal dose-response curve fitting functions in GraphPad PRISM v. 3.0, or an in-house function for non-linear, sigmoidal dose-response curve-fitting.

μ-Opioid Receptor Functional Data: μ GTP $EC_{50}$ is the concentration of a compound providing 50% of the maximal response for the compound at a μ-opioid receptor. In certain embodiments, an indole-type or indoline-type piperidine compound of the disclosure has a μ GTP $EC_{50}$ (nM) of about 5000 or less, or about 4100 or less, or about 3100 or less, or about 2000 or less, or about 1000 or less, or about 100 or less, or about 10 or less, or about 1 or less, or about 0.4 or less, or about 0.1 or less.

μ GTP Emax (%) is the maximal effect elicited by a compound relative to the effect elicited by DAMGO, a standard μ agonist. In certain embodiments, an indole-type or indoline-type piperidine compound of the disclosure has a μ GTP Emax (%) of about 10% or greater, or about 20% or greater, or about 50% or greater, or about 65% or greater, or about 75% or greater, or about 88% or greater, or about 100% or greater. In other embodiments, an indole-type or indoline-type piperidine compound of the disclosure has a μ GTP Emax (%) of about 10% or less, or about 5% or less, or about 2% or less.

Example 10: In Vitro Kappa-Opioid Receptor Binding Assays

κ-Opioid Receptor Binding Assay Procedures: Membranes from recombinant HEK-293 cells expressing the human kappa opioid receptor (kappa) (cloned in house) are prepared by lysing cells in ice cold hypotonic buffer (2.5 mM $MgCl_2$, 50 mM HEPES, pH 7.4) (10 mL/10 cm dish) followed by homogenization with a tissue grinder/Teflon pestle. Membranes are collected by centrifugation at 30,000×g for 15 min at 4° C. and pellets resuspended in hypotonic buffer to a final concentration of 1-3 mg/mL. Protein concentrations are determined using the BioRad protein assay reagent with bovine serum albumen as a standard. Aliquots of kappa receptor membranes are stored at −80° C.

Radioligand dose displacement assays use 0.4-0.8 nM [$^3$H]-U69,593 (NEN; 40 Ci/mmole) with 10-20 μg membrane protein (recombinant kappa opioid receptor expressed in HEK 293 cells; in-house prep) in a final volume of 200 μL binding buffer (5% DMSO, 50 mM Trizma base, pH 7.4). Non-specific binding is determined in the presence of 101 μM unlabeled naloxone or U69,593. All reactions are performed in 96-well polypropylene plates for 1 h at a temperature of about 25° C. Binding reactions are determined by rapid filtration onto 96-well Unifilter GF/C filter plates (Packard) presoaked in 0.5% polyethylenimine (Sigma-Aldrich). Harvesting is performed using a 96-well tissue harvester (Packard) followed by five filtration washes with 200 μL ice-cold binding buffer. Filter plates are subsequently dried at 50° C. for 1-2 hours. Fifty μL/well scintillation cocktail (MicroScint20, Packard) is added and plates counted in a Packard Top-Count for 1 min/well.

κ-Opioid Receptor Binding Data: In one embodiment, an indole-type or indoline-type piperidine compound of the disclosure has substantially no activity at a κ-opioid receptor. In certain embodiments, an indole-type or indoline-type piperidine compound of the disclosure has a Ki (nM) of about 20,000 or less, or about 10,000 or less, or about 5000 or less, or about 500 or less, or about 300 or less, or about 100 or less, or about 50 or less, or about 20 or less, or about 15 or less, or about 10 or less.

Example 11: In Vitro Kappa-Opioid Receptor Functional Assays

κ-Opioid Receptor Functional Assay Procedures: Functional [$^{35}$S]GTPγS binding assays are conducted as follows. Kappa opioid receptor membrane solution is prepared by sequentially adding final concentrations of 0.026 μg/μL kappa membrane protein (in-house), 10 μg/mL saponin, 3 μM GDP and 0.20 nM [$^{35}$S]GTPγS to binding buffer (100 mM NaCl, 10 mM $MgCl_2$, 20 mM HEPES, pH 7.4) on ice. The prepared membrane solution (190 μL/well) is transferred to 96-shallow well polypropylene plates containing 10 μL of 20× concentrated stock solutions of agonist prepared in DMSO. Plates are incubated for 30 min at a temperature of about 25° C. with shaking. Reactions are terminated by rapid filtration onto 96-well Unifilter GF/B filter plates (Packard) using a 96-well tissue harvester (Packard) and followed by three filtration washes with 200 μL ice-cold binding buffer (10 mM $NaH_2PO_4$, 10 mM $Na_2HPO_4$, pH 7.4). Filter plates are subsequently dried at 50° C. for 2-3 hours. Fifty μL/well scintillation cocktail (MicroScint20, Packard) is added and plates counted in a Packard Top-Count for 1 min/well.

κ-Opioid Receptor Functional Data: κ GTP $EC_{50}$ is the concentration of a compound providing 50% of the maximal response for the compound at a κ-opioid receptor. In certain embodiments, an indole-type or indoline-type piperidine compound of the disclosure has a κ GTP $EC_{50}$ (nM) of about 20,000 or less, or about 10,000 or less, or about 5000 or less, or about 2000 or less, or about 1500 or less, or about 800 or less, or about 500 or less, or about 300 or less, or about 100 or less, or about 50 or less, or about 10 or less.

κ GTP Emax (%) is the maximal effect elicited by a compound relative to the effect elicited by U69,593. In certain embodiments, an indole-type or indoline-type piperidine compound of the disclosure has a κ GTP Emax (%) of about 10% or greater, or about 15% or greater, or about 30% or greater, or about 40% or greater, or about 45% or greater, or about 75% or greater, or about 90% or greater, or about 100% or greater. In other embodiments, an indole-type or indoline-type piperidine compound of the disclosure has a κ GTP Emax (%) of about 10% or less, or about 5% or less, or about 2% or less.

Example 12: In Vitro Delta-Opioid Receptor Binding Assays

δ-Opioid Receptor Binding Assay Procedures: Radioligand dose-displacement assays use 0.2 nM [$^3$H]-Naltrindole (NEN; 33.0 Ci/mmole) with 10-20 μg membrane protein (recombinant delta opioid receptor expressed in CHO-K1 cells; Perkin Elmer) in a final volume of 500 μL binding buffer (5 mM $MgCl_2$, 5% DMSO, 50 mM Trizma base, pH 7.4). Non-specific binding is determined in the presence of 251M unlabeled naloxone. All reactions are performed in 96-deep well polypropylene plates for 1 h at a temperature of about 25° C. Binding reactions are determined by rapid filtration onto 96-well Unifilter GF/C filter plates (Packard) presoaked in 0.5% polyethylenimine (Sigma-Aldrich). Harvesting is performed using a 96-well tissue harvester (Packard) followed by five filtration washes with 500 μL ice-cold binding buffer. Filter plates are subsequently dried at 50° C. for 1-2 hours. Fifty μL/well scintillation cocktail (MicroScint20, Packard) is added and plates counted in a Packard Top-Count for 1 min/well.

δ-Opioid Receptor Binding Data: In one embodiment, an indole-type or indoline-type piperidine compound of the disclosure has substantially no activity at a δ-opioid receptor. In certain embodiments, an indole-type or indoline-type piperidine compound of the disclosure has a Ki (nM) of about 20,000 or less, or about 10,000 or less, or about 7500 or less, or about 6500 or less, or about 5000 or less, or about 3000 or less, or about 2500 or less, or about 1000 or less, or about 500 or less, or about 350 or less, or about 250 or less, or about 100 or less, or about 10 or less.

Example 13: In vitro Delta-Opioid Receptor Functional Assays

δ-Opioid Receptor Functional Assay Procedures: Functional [$^{35}$S]GTPγS binding assays are conducted as follows using membranes expressing human δ-opioid receptors. Delta opioid receptor membrane solution is prepared by sequentially adding final concentrations of 0.026 μg/μL delta membrane protein (Perkin Elmer), 10 µg/mL saponin, 3 M GDP and 0.20 nM [$^{35}$S]GTPγS to binding buffer (100 mM NaCl, 10 mM MgCl$_2$, 20 mM HEPES, pH 7.4) on ice. The prepared membrane solution (190 µL/well) is transferred to 96-shallow well polypropylene plates containing 10 µL of 20× concentrated stock solutions of agonist prepared in DMSO. Plates are incubated for 30 min at a temperature of about 25° C. with shaking. Reactions are terminated by rapid filtration onto 96-well Unifilter GF/B filter plates (Packard) using a 96-well tissue harvester (Packard) and followed by three filtration washes with 200 µL ice-cold binding buffer (10 mM NaH$_2$PO$_4$, 10 mM Na$_2$HPO$_4$, pH 7.4). Filter plates are subsequently dried at 50° C. for 1-2 hours. Fifty µL/well scintillation cocktail (MicroScint20, Packard) is added and plates counted in a Packard Top-count for 1 min/well.

δ-Opioid Receptor Functional Data: δ GTP EC$_{50}$ is the concentration of a compound providing 50% of the maximal response for the compound at a δ receptor. In certain embodiments, an indole-type or indoline-type piperidine compound of the disclosure has a δ GTP EC$_{50}$ (nM) of about 20,000 or less, or about 10,000 or less, or about 100 or less, or about 1000 or less, or about 90 or less, or about 50 or less, or about 25 or less, or about 10 or less.

δ GTP Emax (%) is the maximal effect elicited by a compound relative to the effect elicited by met-enkephalin. In certain embodiments, an indole-type or indoline-type piperidine compound of the disclosure has a δ GTP Emax (%) of about 10% or greater, or about 30% or greater, or about 50% or greater, or about 75% or greater, or about 90% or greater, or about 100% or greater, or about 110% or greater. In other embodiments, an indole-type or indoline-type piperidine compound of the disclosure has a δ GTP Emax (%) of about 10% or less, or about 5% or less, or about 2% or less.

Example 14: Cytochrome P450 1A2, 2C9, 2D6, and 3A4

Cytochrome P450 1A2 (CYP1A2), 2C9 (CYP2C9), 2D6 (CYP2D6), and 3A4 (CYP3A4) are enzymes of the cytochrome P450 super family known to be involved in metabolizing and eliminating many drugs, e.g., orally-administered opiates, particularly at lower concentrations. Indole-type or indoline-type piperidine compound of the disclosure were tested for the extent to which they inhibited production of reference metabolites for these enzymes.

For example, using commercially available pooled human hepatic microsome and employing, as an indicator, the O-demethylation of dextromethorphan ((4bR,8aS,9R)-3-methoxy-11-methyl-6,7,8,8a,9,10-hexahydro-5H-9,4b-(epiminoethano)phenanthrene) as a typical substrate metabolism reaction for human CYP2D6, Indole-type or indoline-type piperidine compound of the disclosure were tested for the extent to which they inhibited reference metabolite production by CYP2D6. The reaction conditions were as follows: 5 mol/L dextromethorphan substrate, 15 minute reaction time, 37° C. reaction temperature, 0.2 mg protein/mL pooled human hepatic microsome enzyme, andindole-type or indoline-type piperidine compound of the disclosure concentrations of 1, 5, 10, and 20 mol/L (four concentrations for each compound). Similar reactions were performed for the other CYP enzymes.

The substrate, human hepatic microsome, or an indole-type or indoline-type piperidine compound of the disclosure in 50 mmol/L HEPES buffer as a reaction solution was added to a 96-well plate at the concentrations as described above, cofactor NADPH was added to initiate metabolism reactions as a marker and, after incubation at 37° C. for 15 minutes, a 1:1 MeOH:MeCN (vol.:vol.) solution was added to stop the reaction. Following centrifugation at 3000 rpm for 15 minutes, the amount of dextrorphan ((4bR,8aS,9R)-11-methyl-6,7,8,8a,9,10-hexahydro-5H-9,4b-(epiminoethano)phenanthren-3-ol, the CYP2D6 metabolite) present was determined quantitatively by LC/MS/MS.

As a control, addition of only DMSO (a solvent for Indole-type or indoline-type piperidine compound of the disclosure) to a reaction system was adopted (i.e., 100% metabolite production). At each concentration of an indole-type or indoline-type piperidine compound of the disclosure added, the activity (%) was calculated from the amount of dextrorphan present. The IC$_{50}$ was determined by reverse presumption by a logistic model using a concentration and an inhibition rate.

A "low" value of CYP1A2, CYP2C9, CYP2D6, or CYP3A4 IC$_{50}$, e.g., about 1 M or less, is an indicator that undesirable drug-drug interactions are possible. In contrast, a "high" value of CYP1A2, CYP2C9, CYP2C19, CYP2D6, or CYP3A4 IC$_{50}$, e.g., about 17-20 µM or greater, is an indicator of the absence of undesirable drug-drug interactions.

In certain embodiments, an indole-type or indoline-type piperidine compound of the disclosure has a CYP1A2, CYP2C9, CYP2D6, or CYP3A4 IC$_{50}$ of about 15M or greater, or of about 16 µM or greater, or of about 17 µM or greater, or of about 17.5 µM or greater, or of about 18 µM or greater, or of about 18.5 µM or greater, or of about 19 µM or greater, or of about 20 µM or greater, Example 15: Efficacy of Receptor Binding and Activity Response The following Table (Table 22) provides, for several indole-type piperidine compound of the disclosure, results on the efficacy of binding and activity response to the ORL-1 receptor, and CYP1A2, CYP2C9, CYP2D6, and CYP3A4 response. Table 22 indicates that compounds of the disclosure have very high affinity for the ORL-1 receptor. Additionally, compounds of the disclosure are highly selective for the ORL-1 receptor relative to the µ-opioid receptor, δ-opioid receptor and κ-opioid receptor. For instance, compound 23 has a K$_i$ of well over 20 µM for the µ-opioid receptor, δ-opioid receptor and κ-opioid receptor. Hence, compound 23 is more selective for the ORL-1 receptor than the µ-opioid receptor, δ-opioid receptor and the κ-opioid receptor by several orders of magnitude.

In Table 22, binding efficacy to the ORL-1 receptor was determined by the procedure in Example 6. Activity response to the ORL-1 receptor was determined by the procedure in Example 7. Also in Table 22, Cytochrome P450 (i.e., CYP1A2, CYP2C9, CYP2D6, and CYP3A4) response, in the form of IC$_{50}$, was determined by the procedure in Example 14.

TABLE 22

Efficacy of Receptor Binding, Activity Response, and Cytochrome P450 Response of Selected Indole-Type Piperidine Compounds of the Disclosure

| Compound No. | Compound | ORL-1 $K_i$* | GTPγS $EC_{50}$ | $E_{max}$ | Cytochrome P450° |
|---|---|---|---|---|---|
| 13 | [structure] | 1.0 ± 0.35 | >20 | — | CYP1A2: >20<br>CYP2C9: >20<br>CYP2D6: >20<br>CYP3A4: >20 |
| 7 | [structure] | 3.02 ± 0.66 | >20 | 0.33 ± 0.67 | CYP1A2: >20<br>CYP2C9: >20<br>CYP2D6: 14.6<br>CYP3A4: >20 |
| 14 | [structure] | 3.98 ± 0.94 | >20 | 9 ± 8 | CYP1A2: >20<br>CYP2C9: >20<br>CYP2D6: >20<br>CYP3A4: >20 |

TABLE 22-continued

Efficacy of Receptor Binding, Activity Response, and Cytochrome P450 Response of Selected Indole-Type Piperidine Compounds of the Disclosure

| Compound No. | Compound | ORL-1 $K_i$* | GTPγS^ $EC_{50}$ | $E_{max}$ | Cytochrome P450° |
|---|---|---|---|---|---|
| 11 | | 1.73 ± 0.4 | 1.23 ± 0.36 | 23.5 ± 1.26 | CYP1A2: >20<br>CYP2C9: >20<br>CYP2D6: >20<br>CYP3A4: >20 |
| 23 | | 25.47 ± 5.35 | 46.99 ± 11.66 | 74.33 ± 2.85 | CYP1A2: >20<br>CYP2C9: >20<br>CYP2D6: 1.15<br>CYP3A4: >20 |
| 19 | | 5.84 ± 0.66 | 24.82 ± 6.11 | 100 ± 5.51 | CYP1A2: >20<br>CYP2C9: >20<br>CYP2D6: 3.25<br>CYP3A4: >20 |

*$K_i$ [Average ± Std Deviation] (nM)
^GTPγS ($EC_{50}$: μM, $E_{max}$: %) [mean ± SEM]
°$IC_{50}$ (μM)

Example 16: In Vivo Assays for Prevention or Treatment of Pain

Test Animals: Each experiment uses rats weighing between 200-260 g at the start of the experiment. The rats are group-housed and have free access to food and water at all times, except prior to oral administration of an indole-type or indoline-type piperidine compound of the disclosure when food is removed for 16 hours before dosing. A control group acts as a comparison to rats treated with an indole-type or indoline-type piperidine compound of the disclosure. The control group is administered the carrier for the indole-type or indoline-type piperidine compound of the disclosure. The volume of carrier administered to the control group is the same as the volume of carrier andindole-type or indoline-type piperidine compound of the disclosure administered to the test group.

Acute Pain: To assess the actions of an indole-type or indoline-type piperidine compound of the disclosure for the treatment or prevention of acute pain, the rat tail flick test is used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of an indole-type or indoline-type piperidine compound of the disclosure. Data are expressed as tail flick latency(s) and the percentage of the maximal possible effect (% MPE), i.e., 20 seconds, is calculated as follows:

$$\% \ MPE = \frac{[(\text{post administration latency}) - (\text{pre-administration latency})]}{(20 \ \text{s pre-administration latency})} \times 100$$

The rat tail flick test is described in D'Amour et al., "A Method for Determining Loss of Pain Sensation," *J. Pharmacol. Exp. Ther.* 72:74-79 (1941).

Inflammatory Pain: To assess the actions of an indole-type or indoline-type piperidine compound of the disclosure for the treatment or prevention of inflammatory pain, the Freund's complete adjuvant ("FCA") model of inflammatory pain is used. FCA-induced inflammation of the rat hind paw is associated with the development of persistent inflammatory mechanical hyperalgesia and provides reliable prediction of the anti-hyperalgesic action of clinically useful analgesic drugs (Bartho et al., "Involvement of capsaicin-sensitive neurons in hyperalgesia and enhanced opioid antinociception in inflammation," *Naunyn-Schmiedeberg's Archives of Pharmacol.* 342:666-670 (1990)). The left hind paw of each animal is administered a 50 µL intraplantar injection of 50% FCA. 24 hour post injection, the animal is assessed for response to noxious mechanical stimuli by determining the PWT, as described below. Rats are then administered a single injection of 1, 3, 10 or 30 mg/kg of either an indole-type or indoline-type piperidine compound of the disclosure; 30 mg/kg of a control selected from Celebrex, indomethacin, and naproxen; or carrier. Responses to noxious mechanical stimuli are then determined 1, 3, 5 and 24 hours post administration. Percentage reversal of hyperalgesia for each animal is defined as:

$$\% \ Reversal = \frac{[(\text{post administration} \ PWT) - (\text{pre-administration} \ PWT)]}{[(\text{baseline} \ PWT) - (\text{pre-administration} \ PWT)]} \times 100$$

Neuropathic Pain: To assess the actions of an indole-type or indoline-type piperidine compound of the disclosure for the treatment or prevention of neuropathic pain, either the Seltzer model or the Chung model is used.

In the Seltzer model, the partial sciatic nerve ligation model of neuropathic pain is used to produce neuropathic hyperalgesia in rats (Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anesthesia. Following induction of anesthesia, the left thigh of the male, 6-7 week old Jcl:SD rat is shaved. The sciatic nerve is exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. The wound area is then dusted with antibiotic powder. Sham treatment involved an identical surgical procedure except that the sciatic nerve is not manipulated or ligated.

Following surgery, animals are weighed and placed on a warm pad until they recovered from anesthesia. Animals are then returned to their home cages until behavioral testing began. The animal is assessed for response to noxious mechanical stimuli by determining PWT for the rear paw of the animal, as described below, prior to surgery (baseline), then immediately prior to and 1, 3, and 5 hours after oral drug-in-vehicle administration (for day 1). Thus, the 24 hour time point is the start of the next day when drug-in-vehicle was again orally administered (24 hours after the prior administration). On days 4 and 7, PWT response is determined 1, 3, and 5 hours thereafter. Percentage reversal of neuropathic hyperalgesia at each of the specified times after administration is defined as:

$$\% \ Reversal = \frac{[(\text{post administration} \ PWT) - (\text{pre-administration} \ PWT)]}{[(\text{baseline} \ PWT) - (\text{pre-administration} \ PWT)]} \times 100$$

Additionally, 10 mg/kg of pregabalin (Kemprotec, Ltd., Middlesbrough, UK), an anticonvulsant accepted for relief of particular neuropathic pain, in vehicle and the vehicle alone (0.5% weight/volume methylcellulose (400 cP, Wako Pure Chemical Industries, Ltd.)/aqueous solution) are orally administered as controls. Eight rats that underwent partial ligation of the left sciatic nerve are used for each treatment group except for pregabalin, where six rats are treated. Dunnett's test is conducted for the % reversal; values with $p<0.05$ are considered to be statistically significant.

Additionally, as a control the rats undergo sham surgery in which an identical surgical procedure is followed with regard to the right thigh but the sciatic nerve is neither manipulated nor ligated.

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anesthesia. Following induction of anesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered an indole-type or indoline-type piperidine compound of the disclosure for the left rear paw of the animal. The animal can also be assessed for response to noxious thermal stimuli or for tactile allodynia, as described below. The Chung model for neuropathic pain is described in Kim, "An Experimental Model for Peripheral Neuropathy Produced by Segmental Spinal Nerve Ligation in the Rat," Pain 50(3):355-363 (1992).

Response to Mechanical Stimuli as an Assessment of Mechanical Hyperalgesia: The paw pressure assay was used to assess mechanical hyperalgesia. For this assay, hind paw withdrawal thresholds (PWT) to a noxious mechanical stimulus were determined using an analgesymeter (Model 37215, commercially available from Ugo Basile of Italy) as described in Stein, "Unilateral Inflammation of the Hindpaw in Rats as a Model of Prolonged Noxious Stimulation: Alterations in Behavior and Nociceptive Thresholds," Pharmacol. Biochem. Behavior 31:451-455 (1988). The maximum weight that could be applied to the hind paw was set at 250 g and the end point was taken as complete withdrawal of the paw. PWT was determined once for each rat at each time point and either only the affected (ipsilateral) paw was tested, or both the ipsilateral and contralateral (non-injured) paw were tested.

Response to Thermal Stimuli as an Assessment of Thermal Hyperalgesia: The plantar test is used to assess thermal hyperalgesia. For this test, hind paw withdrawal latencies to a noxious thermal stimulus are determined using a plantar test apparatus (commercially available from Ugo Basile of Italy) following the technique described by Hargreaves et al., "A New and Sensitive Method for Measuring Thermal Nociception in Cutaneous Hyperalgesia," Pain 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal and licking of the paw are considered nociceptive behavioral responses.

6. EQUIVALENTS

The claimed invention is not to be limited in scope by the specific embodiments disclosed in the Examples, which are intended as illustrations of a few aspects of the claimed invention. Embodiments that are functionally equivalent to those described herein are within the scope of the claimed invention. Indeed, various modifications of the claimed invention, in addition to those shown and described herein, may become apparent to those skilled in the art and are intended to fall within the scope of the following claims.

Lastly, the entire disclosures of all publications and documents cited herein (including are expressly incorporated herein by reference for all purposes.

What claimed is:
1. A compound of the structure:

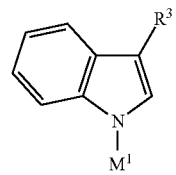

or a pharmaceutically acceptable salt or solvate thereof, wherein $M^1$ is selected from the group consisting of:

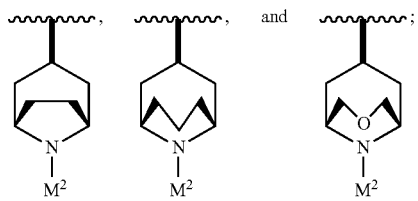

and
$M^2$ is selected from the group consisting of:

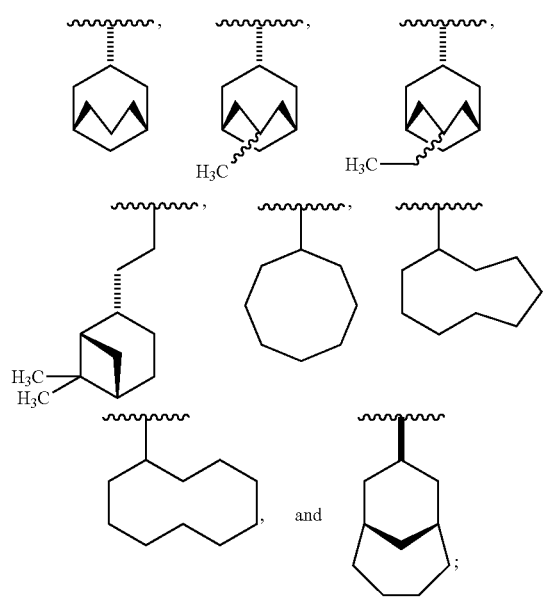

$R^3$ is:
(a) —X, —($C_1$-$C_6$)alkyl-X, -(5- or 6-membered)heterocycle-X, or -(5- or 6-membered)heterocycle-($C_1$-$C_6$)alkyl-X; or (b) —(CH₂)_d—C(=Y)CN, —(CH₂)_d—C(=Y)X, —(CH₂)_d—C(=Y)T³, —(CH₂)_d—C(=Y)YX, —(CH₂)_d—C(=Y)C(=Y)YX, —(CH₂)_d—C(=Y)YT³, —(CH₂)_d—C(=Y)N(T¹)(T²), —(CH₂)_d—C(=Y)N(R⁹)CN, —(CH₂)_d—C(=Y)N(R⁹)X, —(CH₂)_d—C(=Y)N(R⁹)YH, —(CH₂)_d—C(=Y)N(R⁹)YX, —(CH₂)_d—C(=Y)N(R⁹)YCH₂X, —(CH₂)_d—C(=Y)N(R⁹)YCH₂CH₂X, or —(CH₂)_d—C(=Y)N(R⁹)S(=O)₂T³;

X is selected from:
(a) —H, —(C₁-C₆)alkyl, —(C₂-C₆)alkenyl, —(C₂-C₆)alkynyl, —(C₁-C₆)alkoxy, —(C₃-C₇)cycloalkyl, —(C₆-C₁₄)bicycloalkyl, —(C₈-C₂₀)tricycloalkyl, —(C₅-C₁₀)cycloalkenyl, —(C₇-C₁₄)bicycloalkenyl, —(C₈-C₂₀)tricycloalkenyl, -(5- or 6-membered)heterocycle, and -(7- to 10-membered)bicycloheterocycle, each of which is unsubstituted or substituted with 1, 2, or 3 independently selected R⁸ groups; and
(b) -phenyl, -naphthalenyl, —(C₁₄)aryl, and -(5- or 6-membered)heteroaryl, each of which is unsubstituted or substituted with 1, 2, or 3 independently selected R⁷ groups;

each Y is independently O or S;
each R⁷ is independently —(C₁-C₄)alkyl, —(C₂-C₆)alkenyl, —(C₂-C₆)alkynyl, —OR⁹, —SR⁹, —C(halo)₃, —CH(halo)₂, —CH₂(halo), —CN, -halo, —N₃, —NO₂, —CH=N(R⁹), —N(R⁹)₂, —N(R⁹)OH, —N(R⁹)S(=O)R¹², —N(R⁹)S(=O)₂R¹², —N(R⁹)C(=O)R¹², —N(R⁹)C(=O)N(T¹)(T²), —N(R⁹)C(=O)OR¹², —C(=O)R⁹, —C(=O)N(T¹)(T²), —C(=O)OR⁹, —OC(=O)R⁹, —OC(=O)N(T¹)(T²), —OC(=O)OR⁹, —S(=O)R⁹, or —S(=O)₂R⁹;
each R⁸ is independently —(C₁-C₄)alkyl, —(C₂-C₆)alkenyl, —(C₂-C₆)alkynyl, -(5- or 6-membered)heteroaryl, —(C₁-C₆)alkyl-C(=O)OR⁹, —N(R⁹)(C₁-C₆)alkyl-C(=O)OR⁹, —OR⁹, —SR⁹, —C(halo)₃, —CH(halo)₂, —CH₂(halo), —CN, =O, =S, -halo, —N₃, —NO₂, —CH=N(R⁹), —N(R⁹)₂, —N(R⁹)OH, —N(R⁹)S(=O)R¹², —N(R⁹)S(=O)₂R¹², —N(R⁹)C(=O)R¹², —N(R⁹)C(=O)N(T¹)(T²), —N(R⁹)C(=O)OR¹², —C(=O)R⁹, —C(=O)N(T¹)(T²), —C(=O)OR⁹, —OC(=O)R⁹, —OC(=O)N(T¹)(T²), —OC(=O)OR⁹, —S(=O)R⁹, or —S(=O)₂R⁹;
each R⁹ is independently —H, —(C₁-C₆)alkyl, —(C₂-C₆)alkenyl, —(C₂-C₆)alkynyl, —(C₃-C₈)cycloalkyl, —(C₅-C₈)cycloalkenyl, -phenyl, -benzyl, -(3- to 7-membered)heterocycle, —C(halo)₃, —CH(halo)₂, or —CH₂(halo);
each R¹² is independently —H or —(C₁-C₄)alkyl;
each T¹ and T² is independently —H or —(C₁-C₁₀)alkyl;
each T³ is independently —H or —(C₁-C₁₀)alkyl; and
each d is, independently, an integer selected from 0, 1, 2, and 3.

2. The compound of claim 1 or a pharmaceutically acceptable salt or solvate thereof, wherein M¹ is

3. The compound of claim 1 or a pharmaceutically acceptable salt or solvate thereof, wherein M² is

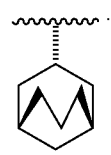

4. The compound of claim 1, wherein the compound is of the following formula:

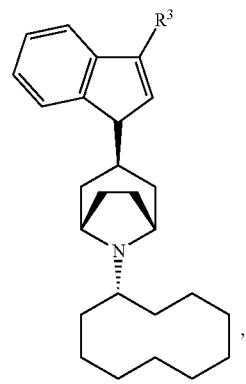

or a pharmaceutically acceptable salt or solvate thereof.

5. The compound of claim 1 or a pharmaceutically acceptable salt or solvate thereof, wherein R³ is selected from the group consisting of —H, —C(=O)C(=O)OH, —C(=O)C(=O)NH₂, —CH₂C(=O)OH, —CH₂C(=O)NH₂, —CF₂C(=O)OH, and —CF₂C(=O)NH₂.

6. A compound selected from:

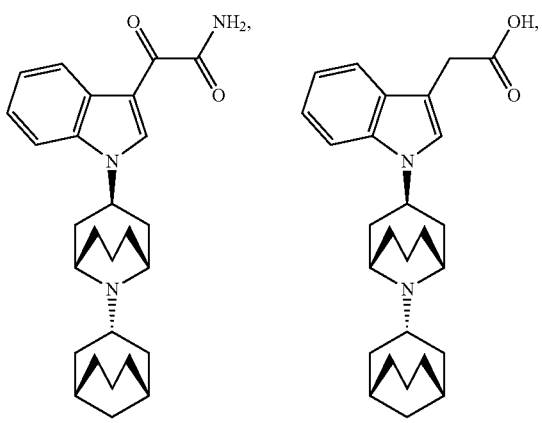

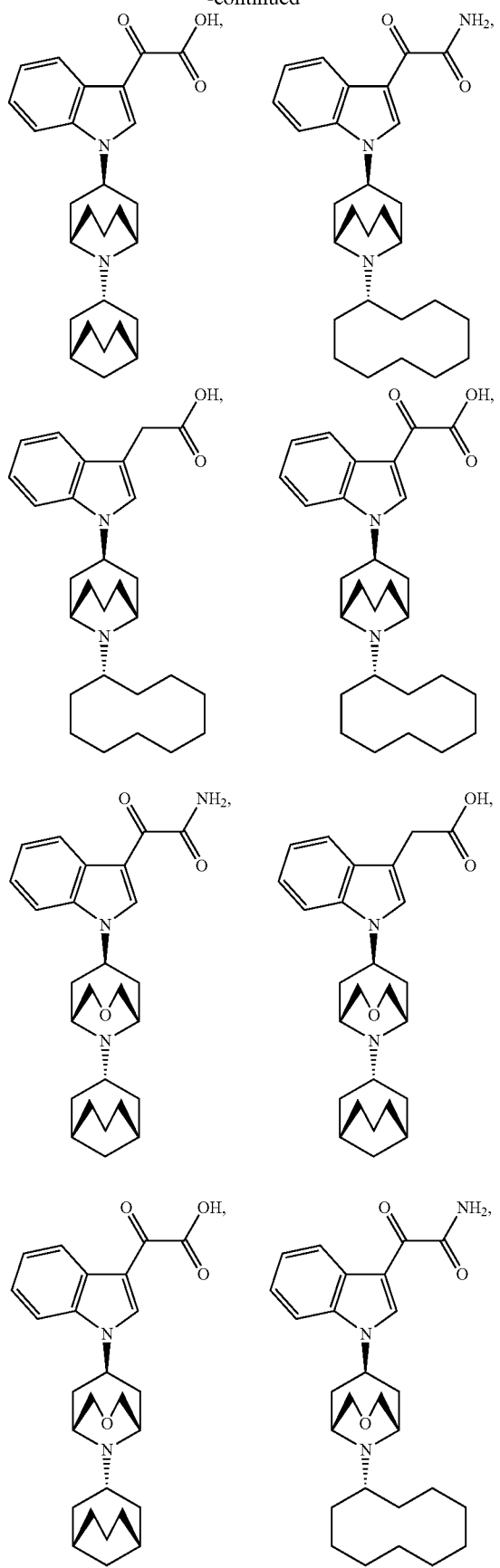
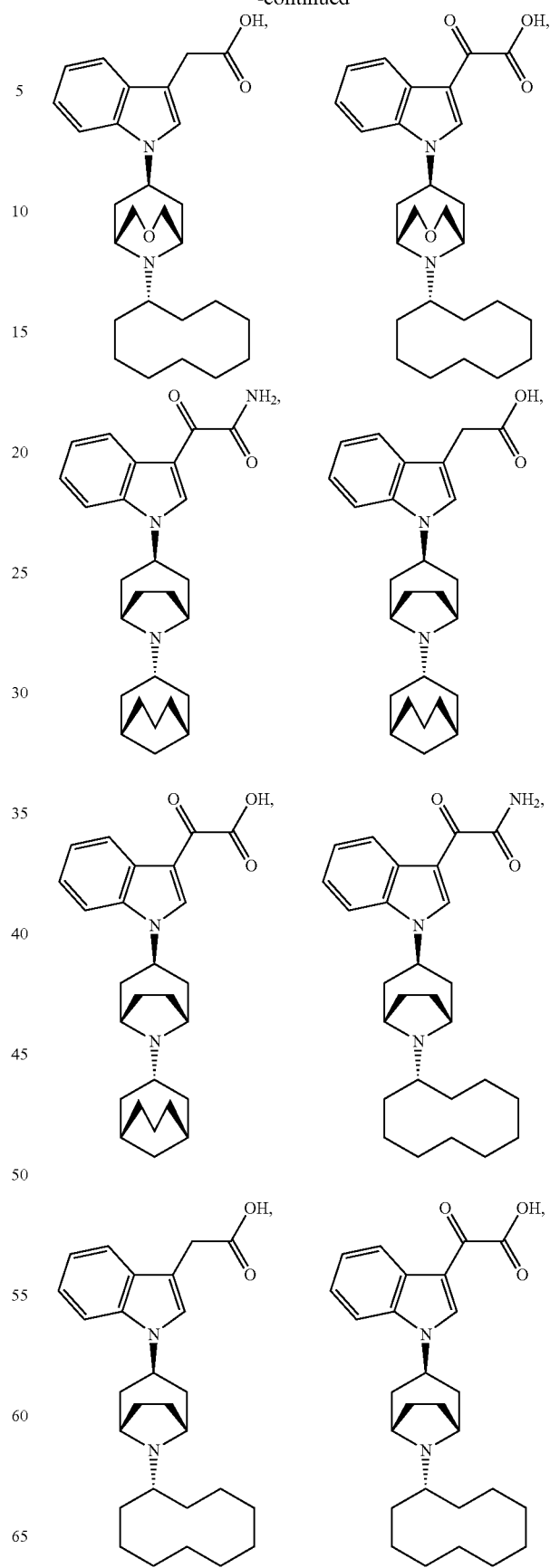

-continued

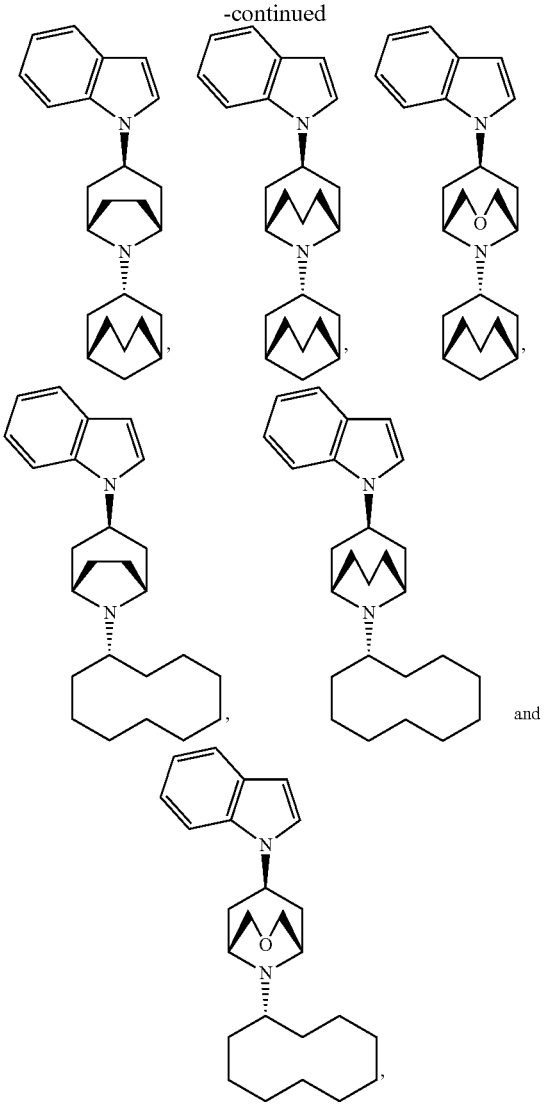

or a pharmaceutically acceptable salt or solvate thereof.

7. A pharmaceutical composition comprising an effective amount of the compound of claim 1 or a pharmaceutically acceptable salt or solvate thereof and a pharmaceutically acceptable carrier or excipient.

8. A method for modulating ORL-1 receptor function in a cell, comprising contacting a cell capable of expressing the ORL-1 receptor with an effective amount of the compound of claim 1 or a pharmaceutically acceptable salt or solvate thereof.

9. The method of claim 8, wherein the composition or the compound or the pharmaceutically acceptable salt or solvate of the compound acts as an agonist at the ORL-1 receptor.

10. A method for treating pain in an animal, comprising administering to an animal in need thereof an effective amount of the compound of claim 1 or a pharmaceutically acceptable salt or solvate thereof.

11. The compound of claim 1 or a pharmaceutically acceptable salt or solvate-thereof, wherein $R^3$ is selected from the group consisting of —H, —(CH$_2$)$_d$—C(=Y)T$^3$, —(CH$_2$)$_d$—C(=Y)YX, —(CH$_2$)$_d$—C(=Y)C(=Y)YX, and —(CH$_2$)$_d$—C(=Y)YT$^3$.

12. The compound of claim 1 or a pharmaceutically acceptable salt or solvate thereof, $R^3$ is selected from the group consisting of —H, —C(=O)C(=O)OH, —C(=O)C(=O)NH$_2$, —CH$_2$C(=O)OH, and —CH$_2$C(=O)NH$_2$.

13. A pharmaceutical composition comprising an effective amount of the compound of claim 6 or a pharmaceutically acceptable salt or solvate thereof and a pharmaceutically acceptable carrier or excipient.

* * * * *